United States Patent
Davicioni et al.

(10) Patent No.: US 9,617,604 B2
(45) Date of Patent: Apr. 11, 2017

(54) SYSTEMS AND METHODS FOR EXPRESSION-BASED CLASSIFICATION OF THYROID TISSUE

(71) Applicant: GenomeDx Biosciences, Inc., Vancouver (CA)

(72) Inventors: Elai Davicioni, Vancouver (CA); Sam Michael Wiseman, Vancouver (CA)

(73) Assignee: GENOMEDX BIOSCIENCES, INC., Vancouver, BC (CA)

( * ) Notice: Subject to any disclaimer, the term of this patent is extended or adjusted under 35 U.S.C. 154(b) by 0 days.

(21) Appl. No.: 14/926,349

(22) Filed: Oct. 29, 2015

(65) Prior Publication Data

US 2016/0076108 A1  Mar. 17, 2016

Related U.S. Application Data

(63) Continuation of application No. 13/258,429, filed as application No. PCT/CA2010/000621 on Apr. 29, 2010, now Pat. No. 9,206,482.

(60) Provisional application No. 61/173,738, filed on Apr. 29, 2009.

(51) Int. Cl.
C12Q 1/68 (2006.01)

(52) U.S. Cl.
CPC ...... *C12Q 1/6886* (2013.01); *C12Q 2600/112* (2013.01); *C12Q 2600/158* (2013.01)

(58) Field of Classification Search
None
See application file for complete search history.

(56) References Cited

U.S. PATENT DOCUMENTS

| | | |
|---|---|---|
| 3,687,808 A | 8/1972 | Merigan, Jr et al. |
| 5,143,854 A | 9/1992 | Pirrung et al. |
| 5,288,514 A | 2/1994 | Ellman |
| 5,384,261 A | 1/1995 | Winkler et al. |
| 5,538,848 A | 7/1996 | Livak et al. |
| 5,677,195 A | 10/1997 | Winkler et al. |
| 5,846,717 A | 12/1998 | Brow et al. |
| 5,985,557 A | 11/1999 | Prudent et al. |
| 5,994,069 A | 11/1999 | Hall et al. |
| 6,001,567 A | 12/1999 | Brow et al. |
| 6,090,543 A | 7/2000 | Prudent et al. |
| 6,136,182 A | 10/2000 | Dolan et al. |
| 7,319,011 B2 | 1/2008 | Riggins et al. |
| 9,074,258 B2 | 7/2015 | Davicioni et al. |
| 9,206,482 B2 | 12/2015 | Davicioni et al. |
| 2003/0194734 A1 | 10/2003 | Jatkoe |
| 2005/0042222 A1 | 2/2005 | Yamamoto et al. |
| 2007/0031873 A1 | 2/2007 | Wang et al. |
| 2007/0037186 A1 | 2/2007 | Jiang et al. |
| 2008/0044824 A1 | 2/2008 | Giordano et al. |
| 2008/0145841 A1 | 6/2008 | Libutti et al. |
| 2012/0115743 A1 | 5/2012 | Davicioni et al. |
| 2012/0172243 A1 | 7/2012 | Davicioni et al. |
| 2015/0329915 A1 | 11/2015 | Davicioni et al. |

FOREIGN PATENT DOCUMENTS

| | | |
|---|---|---|
| WO | WO-9015070 A1 | 12/1990 |
| WO | WO-9210092 A1 | 6/1992 |
| WO | WO-9309668 A1 | 5/1993 |
| WO | WO-9322684 A1 | 11/1993 |
| WO | WO-2005085471 A2 | 9/2005 |
| WO | WO-2005100608 A2 | 10/2005 |
| WO | WO-2006047484 A2 | 5/2006 |
| WO | WO-2006127537 A2 | 11/2006 |
| WO | WO-2009143603 A1 | 12/2009 |
| WO | WO-2010056374 A2 | 5/2010 |
| WO | WO-2010099598 A1 | 9/2010 |

OTHER PUBLICATIONS

US 5,962,233, 10/1999, Livak et al. (withdrawn)
Aldred et al. Papillary and follicular thyroid carcinomas show distinctly different microarray expression profiles and can be distinguished by a minimum of five genes. J Clin Oncol. 2004;22(17):3531-9.
Ausubel, et al. Current Protocols in Molecular Biology. Wiley & Sons, New York, 1995.
Cerutti et al. Diagnosis of suspicious thyroid nodules using four protein biomarkers. Clin Cancer Res. 2006;12(11 Pt 1):3311-8.
Cibas, et al. The Bethesda System for Reporting Thyroid Cytopathology. Am J Clin Pathol. Nov. 2009;132(5):658-65. doi: 10.1309/AJCPPHLWMI3JV4LA.
Dougherty. The fundamental role of pattern recognition for gene-expression/microarray data in bioinformatics. Pattern recognition. 2005; 38:2226-2228.
Endocrine website. http://www.endocrineweb.com/noduleus.html.
Englisch, et al. Chemically Modified Oligonucleotides as Probes and Inhibitors. Angew. Chem. Int. Ed. Eng. 1991; 30:613-629.
Finley et al. Advancing the molecular diagnosis of thyroid nodules: defining benign lesions by molecular profiling. Thyroid. 2005;15(6):562-8.
Finley et al. Discrimination of benign and malignant thyroid nodules by molecular profiling. Ann Surg. 2004;240(3):425-36; discussion 436-7.
Fodor, et al. Light-directed, spatially addressable parallel chemical synthesis. Science. Feb. 15, 1991;251(4995):767-73.
Fontaine, et al. Increasing the number of thyroid lesions classes in microarray analysis improves the relevance of diagnostic markers. PLoS One. Oct. 29, 2009;4(10):e7632. doi: 10.1371/journal.pone.0007632.

(Continued)

*Primary Examiner* — Nancy Treptow
(74) *Attorney, Agent, or Firm* — Wilson, Sonsini, Goodrich, Rosati, PC

(57) ABSTRACT

A system for classifying thyroid nodule tissue as malignant or benign is provided that is based on the identification of sets of gene transcripts, which are characterized in that changes in expression of each gene transcript within a set of gene transcripts can be correlated to with either malignant or benign thyroid nodule disease. The thyroid classification system provides for sets of "thyroid classifying" target sequences and further provides for combinations of polynucleotide probes and primers derived there from. These combinations of polynucleotide probes can be provided in solution or as an array. The combination of probes and the arrays can be used for diagnosis. The invention further provides further methods of classifying thyroid nodule tissue.

11 Claims, 6 Drawing Sheets

(56) References Cited

OTHER PUBLICATIONS

Fryknas et al. Molecular markers for discrimination of benign and malignant follicular thyroid tumors. Tumour Biol. 2006;27(4):211-20.

Fujarewicz, et al. A multi-gene approach to differentiate papillary thyroid carcinoma from benign lesions: gene selection using support vector machines with bootstrapping. Endocr Relat Cancer. Sep. 2007;14(3):809-26.

Gait. Oligoribonucleotides. in Antisense Research and Applications. Crooke, S. T. and Lebleu, B., ed., CRC Press. 1993; Ch 16 289-302.

Griffith, et al. Biomarker panel diagnosis of thyroid cancer: a critical review. Expert Rev Anticancer Ther. Sep. 2008;8(9):1399-413. doi: 10.1586/14737140.8.9.1399.

Griffith et al. Meta-analysis and meta-review of thyroid cancer gene expression profiling studies identifies important diagnostic biomarkers. J Clin Oncol. 2006;24(31):5043-51.

Hamada, et al. Diagnostic usefulness of PCR profiling of the differentially expressed marker genes in thyroid papillary carcinomas. Cancer Lett. Jun. 28, 2005;224(2):289-301. Epub Nov. 18, 2004.

Intarnational Search Report for PCT/CA2010/000621, completed Jul. 14, 2010.

International Search Report for PCT/CA2010/000266, mailed Jul. 12, 2010.

Kanehisa. Use of statistical criteria for screening potential homologies in nucleic acid sequences. Nucleic Acids Res. Jan. 11, 1984;12(1 Pt 1):203-13.

Kasraeian, et al. A comparison of fine-needle aspiration, core biopsy, and surgical biopsy in the diagnosis of extremity soft tissue masses. Clin Orthop Relat Res. Nov. 2010;468(11):2992-3002. doi: 10.1007/s11999-010-1401-x.

Kebebew et al. Diagnostic and extent of disease multigene assay for malignant thyroid neoplasms. Cancer. 2006;106(12):2592-7.

Koshkin, et al. LNA (locked nucleic acids): An RNA mimic forming exceedingly stable LNA: LNA duplexes. J. Am. Chem. Soc. 1998; 120:13252-13253.

Koshkin, et al. LNA (locked nucleic acids): synthesis of the adenine, cytosine, guanine 5-methylcytosine, thymine and uracil bicyclonucleoside monomers, oligomerisation, and unprecedented nucleic acid recognition. Tetrahedron. 1998; 54(14):3607-3630.

Kroschwitz. The Concise Encyclopedia of Polymer Science and Engineering, (1990) pp. 858-859. John Wiley & Sons.

Kumar, et al. The first analogues of LNA (locked nucleic acids): phosphorothioate-LNA and 2'-thio-LNA. Bioorg Med Chem Lett. Aug. 18, 1998;8(16):2219-22.

Martin. A New Access to 2'-O-Alkylated Ribonucleosides and Properties of 2'-O-Alkylated Oligoribonucleotides. Helv. Chim. Acta. 1995; 78:486-504. (in German with English abstract).

Mazzanti, et al. Using gene expression profiling to differentiate benign versus malignant thyroid tumors. Cancer Res. Apr. 15, 2004;64(8):2898-903.

Mineva, et al. Differential expression of alphaB-crystallin and Hsp27-1 in anaplastic thyroid carcinomas because of tumor-specific alphaB-crystallin gene (CRYAB) silencing. Cell Stress Chaperones. Autumn 2005;10(3):171-84.

Nielsen, et al. Sequence-selective recognition of DNA by strand displacement with a thymine-substituted polyamide. Science. Dec. 6, 1991;254(5037):1497-500.

Notice of allowance dated Mar. 27, 2015 for U.S. Appl. No. 13/254,571.

Notice of allowance dated Jul. 30, 2015 for U.S. Appl. No. 13/258,429.

Office action dated Jan. 16, 2015 for U.S. Appl. No. 13/258,429.

Office action dated Mar. 11, 2014 for U.S. Appl. No. 13/254,571.

Office action dated Apr. 8, 2014 for U.S. Appl. No. 13/258,429.

Office action dated Sep. 11, 2013 for U.S. Appl. No. 13/258,429.

Office action dated Dec. 4, 2014 for U.S. Appl. No. 13/254,571.

Prasad et al. Identification of genes differentially expressed in benign versus malignant thyroid tumors. Clin Cancer Res. 2008;14(11):3327-37.

Puskas, et al. Gene profiling identifies genes specific for well-differentiated epithelial thyroid tumors. Cell Mol Biol (Noisy-le-grand). Sep. 5, 2005;51(2):177-86.

Robinson, et al. A comparison of Affymetrix gene expression arrays. BMC Bioinformatics. Nov. 15, 2007;8:449.

Sanghvi. Heterocyclic base modifications in nucleic acids and their applications in antisense oligonucleotides. in Antisense Research and Applications. Crooke, S. T. and Lebleu, B., ed., CRC Press. 1993; Ch 15 274-285.

Shibru, et al. Does the 3-gene diagnostic assay accurately distinguish benign from malignant thyroid neoplasms? Cancer. Sep. 1, 2008;113(5):930-5. doi: 10.1002/cncr.23703.

Singh, et al. LNA (locked nucleic acids): synthesis and high-affinity nucleic acid recognition. Chem. Commun. 1998; 4:455-456.

Singh, et al. Synthesis of 2'-amino-LNA: A novel conformationally restricted high-affinity oligonucleotide analogues with a handle. J. Bio. Chem. 1998; 63:10035-10039.

Written Opinion of the International Searching Authority for PCT/CA2010/000621, mailed Aug. 11, 2010.

Yukinawa, et al. A multi-class predictor based on a probabilistic model: application to gene expression profiling-based diagnosis of thyroid tumors. BMC Genomics. Jul. 27, 2006;7:190.

SEQUENCE LISTING

<160> NUMBER OF SEQ ID NOS: 659

<210> SEQ ID NO 1
<211> LENGTH: 71
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Affymetrix ID 3420365

<400> SEQUENCE: 1
attctttgga gttgcgtcat taggagcttt acagtaagat atcttactag ccaatattag    60
cctgccacag g                                                         71

<210> SEQ ID NO 2
<211> LENGTH: 92
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Affymetrix ID 3696401

<400> SEQUENCE: 2
gggcaaccta ggcacactca gtataaaaac gcagagatcc atccgaatgg gaggcattgg    60
ggtctggaaa ccagaaatgc aggacggcca gt                                  92

<210> SEQ ID NO 3
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Affymetrix ID 3577628

<400> SEQUENCE: 3
ctgcctctcg ctcctcaacc cctccc                                         26

<210> SEQ ID NO 4
<211> LENGTH: 122
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Affymetrix ID 3415760

<400> SEQUENCE: 4
tggagctgtc atcactcaac aaaaaaccga ggccctcaat ccaccttcag gccccgcccc    60
atgggcccct caccgctggt tggaaagagt gttggtgttg gctggggtgt caataaagct   120
gt                                                                  122

<210> SEQ ID NO 5
<211> LENGTH: 647
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:

<223> OTHER INFORMATION: Affymetrix ID 2537615

<400> SEQUENCE: 5

```
agcctgtgag tatcccggcc ttccatccca gcactctcct gcaaaaatgc agaacaaaca      60
ttaataacgt ctgaattctg actgctccag taacagcaca cacttgatac aagacagaag     120
ggcctggaca ggagctcttt tcacaaagga ccgctggcga gatgagccat ccttcttgct     180
tgtcatgctg gagggaagtt tctggcttcc ggacaaatgc ttgtttgcag gaggccacag     240
aggatccacg tggcaaaggt tcctactcac agagtgggat ctgcaatccg caggcagggt     300
ccttcaggaa gaagccgtgc tgagcacaca ggtccctgcg accacagatg aacagaacgc     360
ctggccttgc ccctggtgtc agtcagacta attaggggcc caggggactt gctggcactg     420
cccttgctgt ggctggaaaa gctatttaaa ttcacaaaga gcctcacttc caggccaggt     480 cctttggtt ccatgcgtgg gagccaggtg caaagacgaa tgtgctctca gcagaacgac      540
cctgggctct gcttatctcc gaggacagga tctaatctca cactgaattt cagaagggag     600
accgatcatg ttggcaatgc cccctcctg tatgcaagta agtgact                    647
```

<210> SEQ ID NO 6
<211> LENGTH: 130
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Affymetrix ID 2727648

<400> SEQUENCE: 6

```
aagcccatga gtccttgaaa atatttttta tatatacagt aacttatgt gtaaatacat       60 aagcggcgta agtttaaagg atgttggtgt tccacgtgtt ttattcctgt atgttgtcca     120
attgttgaca                                                            130
```

<210> SEQ ID NO 7
<211> LENGTH: 228
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Affymetrix ID 3367706

<400> SEQUENCE: 7

```
ttttgcctgc acattctgag agagccattt ggcaaacaac aataataaat ttacatttgg      60
atggtgtatt tcactcagag aactttcata tgtattatct catttggggc tcacaacaat     120
tctttaacca gggtatgtat tactaataat aattaacaat agccagcatt tacagtgttt     180
atatgtcaac tgctgttcat tattgcctcc ttttgacaga gaccaaca                  228
```

<210> SEQ ID NO 8
<211> LENGTH: 82
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Affymetrix ID 2828473

<400> SEQUENCE: 8

```
tgctcccacg cctgcttctt aaggtccctg ctcggccggt gtaaatatgt ttcaccctgt    60
ccctctaata aagctcctct gc                                              82

<210> SEQ ID NO 9
<211> LENGTH: 305
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Affymetrix ID 2414960

<400> SEQUENCE: 9
gacaacccgg gatcgtttgc aagtaactga atccattgcg acattgtgaa ggcttaaatg    60
agtttagatg ggaaatagcg ttgttatcgc ctgggttta aattatttga tgagttccac   120
ttgtatcatg gcctacccga ggagaagagg agtttgttaa ctgggcctat gtagtagcct   180
catttaccat cgtttgtatt actgaccaca tatgcttgtc actgggaaag aagcctgttt   240
cagctgcctg aacgcagttt ggatgtcttt gaggacagac attgcccgga aactcagtct   300
attta                                                                305

<210> SEQ ID NO 10
<211> LENGTH: 437
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Affymetrix ID 2526829

<400> SEQUENCE: 10
acgcccagga ctatttgaac tgatgaaata tccaaatgtc cagtcctata gcctacttac    60
acctaagtga acactacagc gaagtgttca gtgaacagac cttgagaagg tctgtaatta   120
gatgataagg aagggtcacc ttgccccatg gcctctcgaa gccctccatt ccacctgtga   180
gtgtgactca gctggatttc gagtgggatg aagttgctgc aacagctgga tatttctcgc   240
atccacctga gagtatgtct ctggagggca catgataatc cttgctgtgg tgctgtggat   300
tgccatttat gcctcacaac aaccctggaa ggtagtttgc tccttttaaa agcaatttct   360
tgtcatacaa cgtactgcat atctttaaag tgatgggttt ttacatatgt gtgacttggg   420
agaccatcac cgcattc                                                   437

<210> SEQ ID NO 11
<211> LENGTH: 105
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Affymetrix ID 2526817

<400> SEQUENCE: 11
cttcaaggac aaatcgtaaa ggtagtgttt tagacttctg cacacaaatg gaaattcagg    60
tagaatatct ttcttttcta gaatcatcta tcttactcaa aaagg                   105

<210> SEQ ID NO 12
<211> LENGTH: 215
<212> TYPE: DNA
```

<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Affymetrix ID 2598305

<400> SEQUENCE: 12
gtctgaatgc ccacgacatg tcttttgcaa ttacacatag ggaaagtgaa cttgttggtt    60
agtttatgtc ttgagctgag ccctttacga acatctttt tccttctcag tgccaagcga   120
ggaatttaca gagaaagaag ttgtgaaacc accatagtta gttgctgtgc tttgaatttc   180
ttttgctcaa atggcctcag cgaaatctta tttgc                              215

<210> SEQ ID NO 13
<211> LENGTH: 739
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Affymetrix ID 2338243

<400> SEQUENCE: 13
tctcctcggg taggccatga tacaagtgga actcatcaaa taatttaaac ccaaggcgat    60
aacaacgcta tttcccatct aaactcattt aagccttcac aatgtcgcaa tggattcagt   120
tacttgcaaa cgatcccggg ttgtcataca gatacttgtt ttttacacat aacgctatgc   180
catcccttcc ttcactgccc cagtcaggtt tcctgttgtt ggaccgaaag gggatacatt   240
ttagaaatgc ttccttcaag acagaagtga gaaagaaagg agaccctgag gccaggatct   300
attaaacctg gtgtgtgcgc aaaagggagg gggaaggcag gaatttgaaa ggataaacgt   360
ctcctttgcg ccgaggaatc aggaagcgtg actcacttgg gtctgggacg ataccgaaat   420
ccggtacccc accccatccc ctgccccgcc gggtacctac aagctcggtt cctttctcaa   480
ctcccccagt tccttgatct ccaccttctt gtacttcccc gactttctcc ggttggtgat   540
caccaggacg gccatgccgg cgacgagggc caccacgacc accacgatga cggcgatgag   600
gccggcggtg aggcgcttca tggagaactt cgggggaatc tcgtccaggt aatagatgag   660
cgtgcgctcc acctgcaggg gttctccgcg cacgcgcaag tccaggccgc cgcggccctg   720
gaatagagac tcgcccttg                                                739

<210> SEQ ID NO 14
<211> LENGTH: 169
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Affymetrix ID 2598348

<400> SEQUENCE: 14
gaatcgtgtc tttctcattg gctcaatgta gtctccgtag agtctagaat gcttcagcac    60
ctggcacact gcttaacaaa tggtgaatga aaaaaaaaaa aagaaaagtc attctttttc   120
ttctttcacc ctatgtccat aatctggcca tttgcagaac ttgatgtcc               169

<210> SEQ ID NO 15
<211> LENGTH: 865
<212> TYPE: DNA

<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Affymetrix ID 2598349

<400> SEQUENCE: 15

```
gtcttctata ctcagccagg ttatcaatca aatatgaggg caaaataata ttttcagaca      60
gattttaggc agtttatctt ccatatatcc ttttctttaa gggtatttgt agatacactc     120
cagaaaaaca agagtgaaat atgaaggaag ttgtggggtc cagcaaacag tgcttccaaa     180
tcagacccct gatagaggtg gaaaactttg caatgcaaca actgcgtagc tggcttagag     240
gacagccaat acagatggaa cagaaagatg aggatgggat tgagggatca gggattgagg     300
tctccaagaa taaaaaggga cttcatgaaa aaagtaggct tgtggataat taatcacagg     360
ggcaaataat gcagttaaaa taacaacatg acaatcaggt ggaggaatgt ataataaacc     420
caaatgtggc tggtagagt ggctcacacc tgtaatccca gcactttggg aggccaagcc      480
gggcagatta cctgaggtca ggagttcgag accagcttgg ccaacatggc gaaacccgt      540
ctctactaaa aatacaaaaa ttagccaggc ttggggcgc acgcctgtag tcccagctcc      600
tcaggagctg aggtaggaga atcacttgaa cccaggaggc aaaggttgca gggagttgag     660
ccaagatcgc gccattgcac cctagcctgg gcaacagagc gagattctgt ttcaaaaaac     720
ccccaagtgt attataaggc aataattcct atacgaagca aactaaaatg cagcaatatt     780
aaggtataaa aacaaagagg aataattcca ttgaaccttg attctggaaa ctttgatcca     840
cccagcagtc atgatgttag actca                                           865
```

<210> SEQ ID NO 16
<211> LENGTH: 131
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Affymetrix ID 2598307

<400> SEQUENCE: 16

```
ttgacaaacc atcccagatg caagtgaccg atgttcagga caacagcatt agtgtcaagt      60
ggctgccttc aagttcccct gttactggtt acagagtaac caccactccc aaaaatggac     120
caggaccaac a                                                          131
```

<210> SEQ ID NO 17
<211> LENGTH: 541
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Affymetrix ID 2562439

<400> SEQUENCE: 17

```
ccgtcctta aagtgctgca gtatggccag acgtggtggc tcacacctgc aatcccagca       60
ccttaggagg ccgaggcagg aggatccttg aggtcaggag ttcgagacca gcctcgccaa     120
catggtgaaa ccccatttct actaaaaata caaaaaatta gccaagtgtg gtggcatatg     180
cctgtaatcc caactactca gaaggccgag gcaggagaat tacttgaacg caggagaatc     240
```

```
actgcagccc aggaggcaga ggttgcagtg agccgagatt gcaccactgc actccagcct      300
gggtgacaga gcaagactcc atctcagtaa ataaataaat aaataaaaag cgctgcagta      360
gctgtggcct caccctgaag tcagcgggcc caggcctacc tcactctctc ccttggcaga      420
gaagcagacg tccatagctc ctctccctca caagcgctcc cagcctgccc tccagctgct      480
gctctcccct cccagtctct actcactggg atgaggttag gtcatgagga caccaaaaac      540
c                                                                      541

<210> SEQ ID NO 18
<211> LENGTH: 60
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Affymetrix ID 3577632

<400> SEQUENCE: 18
gggtcaactg gcatcacta aggtcttcag caatggggct gacctctccg gggtcacaga       60

<210> SEQ ID NO 19
<211> LENGTH: 56
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Affymetrix ID 2401582

<400> SEQUENCE: 19
ggggcaaggc tctggcacaa aacctcctcc tcccaggcac tcatttatat tgctct          56

<210> SEQ ID NO 20
<211> LENGTH: 393
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Affymetrix ID 2598368

<400> SEQUENCE: 20
gccaccgcgc ttagcctgtt tttagttttc taaagcaagg tccctattga aaggcaggcc      60 ataacagtg atgactaaga aaaatcctgg aagagcctga gaaggaaaaa gatgaaatat      120
aatgccagag aatgaagtta gtcaaggaa cagtgtgaaa acaataaata aatagataaa      180
tgaaaatgtt atttgacaga gagatgaaac tagactaaac cattcagctg cctttccact      240
gtaacaaatg taatttcatc tttcagaagt gtaatacctt gcagcaccag agctgaatat      300
gaacatatta ccaaaaatag attaccaggc atagatagca ttcctttttt aagtttgaat      360
tgaccacttg cgactctcga cctgatgtat gta                                   393

<210> SEQ ID NO 21
<211> LENGTH: 86
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Affymetrix ID 2598282
```

<400> SEQUENCE: 21
tttaaactcc ttattcccag cagcagtatt ctacattcta accaggttct cccagctttg    60
agacgtctca gacttaccag ttctcc                                         86

<210> SEQ ID NO 22
<211> LENGTH: 221
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Affymetrix ID 3549675

<400> SEQUENCE: 22
ccaggaactt ggtgatgata tcgtgggtga gttcattttc caggtgctgt agtttcccct    60
catcaggcag gaagaagatg gcggtggcat tgcccaggta tttcatcagc agcacccagc   120
tggacagctt cttacagtgc tggatgttaa acatgcctaa acgcttcatc ataggcacct   180
tcacggtggt cacctggtcc acgtggaagt cctcttcctc g                       221

<210> SEQ ID NO 23
<211> LENGTH: 260
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Affymetrix ID 2526824

<400> SEQUENCE: 23
tgtctccacg gccagtgaca gcatacacag tgatggtata atcaactcca ggtttaaggc    60
cgctgatggt agctgtagac ttgctcccag gcacagtgaa ctcctggaca gggctatttc   120
ctcctgtatg aaaaagggtt agttcagagt gtgaggggtt tagagctact tgggtattac   180
tgattaattg aattaccaca tttatagcag catgtaaatc acatcttctt gcttattccc   240
ttttaaagag cgctatcttg                                               260

<210> SEQ ID NO 24
<211> LENGTH: 65
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Affymetrix ID 2598340

<400> SEQUENCE: 24
tgatgcccct cctgacacga ctgtggacca agttgatgac acctcaattg ttgttcgctg    60
gagca                                                                65

<210> SEQ ID NO 25
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Affymetrix ID 2598328

<400> SEQUENCE: 25
gcaaaccctg acactggagt gctcac                                            26

<210> SEQ ID NO 26
<211> LENGTH: 60
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Affymetrix ID 3460512

<400> SEQUENCE: 26
gtaccaccag ccctaatcag catcaaacaa aaatatcccc aagagtattc tatgagttga       60

<210> SEQ ID NO 27
<211> LENGTH: 389
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Affymetrix ID 2598278

<400> SEQUENCE: 27
ggagcgggga tgtcaagttc atttatgtga ctctttggct caacttacat aatctttgtt       60
ttgatatcac agttgtctaa ttattttact ttgtagctta aggcaggctg aattgttgat      120
aaaatggaaa aagtagtata ttgttatata agcttctgag gtgtgttttg ttgtataagc      180
cctggaggtt aaaaagtcat cccttatgta tagtagttaa aggcataaaa ctgtgacttt      240
tagatattcc acagaaccag acttatttga tgtggataat aaccaatgat ttagcatttt      300
gtttgctttt gttttatttt atccgggttc attttttact cttcccatgt acatgaaaca      360
ggtggtggcg tgtagagatc agctgatcc                                        389

<210> SEQ ID NO 28
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Affymetrix ID 3976357

<400> SEQUENCE: 28
cttccagtcc cgtcaccttg cctgcct                                           27

<210> SEQ ID NO 29
<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Affymetrix ID 3335899

<400> SEQUENCE: 29
ggcacttcag gtccgtgggc cgtatctgtc acaataaat                              39

<210> SEQ ID NO 30
<211> LENGTH: 143

```
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Affymetrix ID 2598367

<400> SEQUENCE: 30
atgcaacgat caggacacaa ggacatccta tagaattgga gacacctgga gcaagaagga    60
taatcgagga aacctgctcc agtgcatctg cacaggcaac ggccgaggag agtggaagtg   120
tgagaggcac acctctgtgc aga                                           143

<210> SEQ ID NO 31
<211> LENGTH: 150
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Affymetrix ID 2598338

<400> SEQUENCE: 31
gacagacgtg aaggtcacca tcatgtggac accgcctgag agtgcagtga ccggctaccg    60
tgtggatgtg atccccgtca acctgcctgg cgagcacggg cagaggctgc ccatcagcag   120
gaacaccttt gcagaagtca ccgggctgtc                                    150

<210> SEQ ID NO 32
<211> LENGTH: 112
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Affymetrix ID 2598326

<400> SEQUENCE: 32
gcccacacat atggatgacc actagcaagt gtaatgatct caatatttat ttctcattca    60
gttgggtttc cttgtatttg ccacattagt gtttaccctg ttcctaatgg ca           112

<210> SEQ ID NO 33
<211> LENGTH: 105
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Affymetrix ID 2598299

<400> SEQUENCE: 33
caagaagggc tcgtgtgaca gatgctactg agaccaccat caccattagc tggagaacca    60
agactgagac gatcactggc ttccaagttg atgccgttcc agcca                   105

<210> SEQ ID NO 34
<211> LENGTH: 179
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Affymetrix ID 3549673
```

```
<400> SEQUENCE: 34
ggtgggattc accactttc ccatgaagag gggagacttg gtatttgtt caatcattaa      60 gaagacaaag ggtttgttga acttgacctc ggggggata gacatgggta tggcctctaa   120
aaacatggcc ccagcagctt cagtccctt ctcgtcgatg gtcagcacag ccttatgca    179

<210> SEQ ID NO 35
<211> LENGTH: 139
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Affymetrix ID 2598346

<400> SEQUENCE: 35
tggaaggaag ctaccatacc aggccactta aactcctaca ccatcaaagg cctgaagcct    60
ggtgtggtat acgagggcca gctcatcagc atccagcagt acggccacca agaagtgact   120
cgctttgact tcaccacca                                                139

<210> SEQ ID NO 36
<211> LENGTH: 125
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Affymetrix ID 2598372

<400> SEQUENCE: 36
ccatgaaggg ggtcagtcct acaagattgg tgacacctgg aggagaccac atgagactgg    60
tggttacatg ttagagtgtg tgtgtcttgg taatggaaaa ggagaatgga cctgcaagcc   120
catag                                                               125

<210> SEQ ID NO 37
<211> LENGTH: 82
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Affymetrix ID 2598281

<400> SEQUENCE: 37
tcaacgaagg cttgaaccaa cctacggatg actcgtgctt tgacccctac acagtttccc    60
attatgccgt tggagatgag tg                                            82

<210> SEQ ID NO 38
<211> LENGTH: 84
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Affymetrix ID 2598374

<400> SEQUENCE: 38
atcaacagtg ggagcggacc tacctaggca atgcgttggt ttgtacttgt tatggaggaa    60
```

```
gccgaggttt taactgcgag agta                                             84
```

<210> SEQ ID NO 39
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Affymetrix ID 2598329

<400> SEQUENCE: 39

```
cattgtctcc accaacaaac ttgcatctgg ag                                    32
```

<210> SEQ ID NO 40
<211> LENGTH: 54
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Affymetrix ID 2598352

<400> SEQUENCE: 40

```
gctcaagtgg tcctgtcgaa gtatttatca ctgagactcc gagtcagccc aact            54
```

<210> SEQ ID NO 41
<211> LENGTH: 69
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Affymetrix ID 2400179

<400> SEQUENCE: 41

```
gaaatttatt actagcttgc tacccacgat gaaatcaaca acctgtatct ggtatcaggc      60
cgggagaca                                                              69
```

<210> SEQ ID NO 42
<211> LENGTH: 1102
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Affymetrix ID 2324040

<400> SEQUENCE: 42

```
cagctggtgt gccttaagag aatccctata aataacagaa aagcactcc aagcattcct       60 gtacgtggac tcagagcaca gagaaaagaa actaaaatgc cttttggcat ttcaagatat     120
ttggcactct tgtgattaca ttttttaca gtccattaaa gagaataaac tgacataata     180
ttagagaaat aaacaggctg ctcacacaac agactgcaag gggaagttag aaaaagctca    240
agcatttttt tctttgtttt tcgtgtgtgt gtgtgtgtgt gtgtgtgtgt gtgtgtgttt    300
ttctgacata aaaaatgtgt ccatttgcat taacttgggc agatagcttg cagcaacaaa    360
gaaacacaag ctttacaact cattttaaaa taaaatcttt tctatgtatc attccttaga    420
aaagttctct tcttgttta aacacattcc tgataacttc taaagatgac caaaataaaa    480
cagaatatct acagagatca ttttctgaat tttttgtaca tccaaggata acaacataaa    540
```

```
aaaaataaaa ctggacagca tttcacatcc aagtgcacag aaccatttt gcaagattaa       600 ataatgtaaa cattgggaac agccaaatca gcgaagaatg ccaacacctc aaaacacctg       660
gtgttgccgc ttcattaagt ggttcaaaat ccagatctat aattgcgcaa tattcaccgt       720
atataaaaag aaatggatat taattttgac aaatagctgc aactgagact tcttttatt       780 tctttatatg tgtatatagt gaattttat tattttaaa atttatta ttttttatt         840 tttattttg cagaggagcc cagagccttc tcctcctcct cctcctcctc tcgcctcatc       900
tgtctcccgg cctgatacca gatacaggtt gttgatttca tcgtgggtag caagctagta      960
ataaatttca aagtgctttc tcttttcatg cttttgccca ataactgtta ccgccgttct     1020
tattctctcc cttaactcat tgtctttggg ggagttagac accaggaggt gccttgtcgg     1080
tcatattttt cagcacgtca tc                                              1102

<210> SEQ ID NO 43
<211> LENGTH: 339
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Affymetrix ID 2375629

<400> SEQUENCE: 43
taggataggg gacacgatta cgttcctaag tgaaggtttc aagctgggct ttgcaggggg        60
tataattagt atggtcactg tgtcttgtag gatgtttggc tccttggtga tagagcttgc      120
caaaatggtg tcctttgata aggagggctg ggggcaggg agttgaagaa attcccttgc      180
caggcttggg gatctgtaaa catttccatt aatcaacaag tgtgtactaa tcccgagtct      240
tacattgcga tgcctcacta tccccacagc cccatcccta cctctctgcc caccagggct      300
gagctcaaat ctgtgtgttg tggacctctg cataggccc                             339

<210> SEQ ID NO 44
<211> LENGTH: 90
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Affymetrix ID 2598342

<400> SEQUENCE: 44
tccaagcaca gccacttctg tgaacatccc tgacctgctt cctggccgaa aatacattgt        60
aaatgtctat cagatatctg aggatgggga                                        90

<210> SEQ ID NO 45
<211> LENGTH: 47
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Affymetrix ID 3577630

<400> SEQUENCE: 45
ccgtgcataa ggctgtgctg accatcgacg agaaagggac tgaagct                     47
```

```
<210> SEQ ID NO 46
<211> LENGTH: 603
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Affymetrix ID 2526820

<400> SEQUENCE: 46
gcctctgctc aaattagacc taatggaact gaaatgtgca gtctttctct ttctctcttt    60
cttttttaaa tttgagaagc aagttgtagg aagtagaatc cagactaatc atatcagtgt   120
cataagtatg agaattacag aggtttggct caacagtttt tcatggtttg aaatggtaaa   180
aatagataaa acacacatgt tcattttga aattttccta tatcaggaat acacattttc    240
ttgaaattaa ctgaaactgg atgcaaaagt aagacattat ttagctctaa gttgtagaaa   300
ccaaataaag ataaatgtga gaggtttctc tccctccttt aaaaaaggaa acattttaaa   360
attcaacaga aggtataaaa gaagagcaat gatagctctt cttttacatt ttaacatctt   420
gtttgaattt ttaaaaggtg aataacaagg ctttatattg agtggctgta gtaaagaaaa   480
aaaataaaac caaactctgc agtgcatgtt aaattatttc tcctattaaa gaatacaata   540
tatacactat gctgttagat aaaaaaaatc acaagaaatg catcaaaaca tggagaacct   600
ttt                                                                 603

<210> SEQ ID NO 47
<211> LENGTH: 65
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Affymetrix ID 2598358

<400> SEQUENCE: 47
catctttggt gcagcacaac ttcgaattat gagcaggacc agaaatactc tttctgcaca    60
gacca                                                               65

<210> SEQ ID NO 48
<211> LENGTH: 148
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Affymetrix ID 2598321

<400> SEQUENCE: 48
ttgggtaccg catcacagta gttgcggcag gagaaggtat ccctattttt gaagattttg    60
tggactcctc agtaggatac tacacagtca cagggctgga gccgggcatt gactatgata   120
tcagcgttat cactctcatt aatggcgg                                      148

<210> SEQ ID NO 49
<211> LENGTH: 181
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
```

<223> OTHER INFORMATION: Affymetrix ID 2598302

<400> SEQUENCE: 49

```
ctattcctgc accaactgac ctgaagttca ctcaggtcac acccacaagc ctgagcgccc      60
agtggacacc acccaatgtt cagctcactg gatatcgagt gcgggtgacc cccaaggaga     120
agaccggacc aatgaaagaa atcaaccttg ctcctgacag ctcatccgtg gttgtatcag     180
g                                                                      181
```

<210> SEQ ID NO 50
<211> LENGTH: 192
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Affymetrix ID 3536718

<400> SEQUENCE: 50

```
tcagcactta gtccagattc tggggagaag tttgatgatg gtccttgaat atttagcact      60
tagaagtgct aggaggatgc ctcactaagt tacgtaagaa gcagaagagg acgagtaccg     120
cctgatggat tgaccccgaa aactagctgt gtccaagtag aataggtgtc tcgctctgtt     180
aagcggtctt ta                                                          192
```

<210> SEQ ID NO 51
<211> LENGTH: 34
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Affymetrix ID 2598289

<400> SEQUENCE: 51

```
cttcatggac cagagatctt ggatgttcct tcca                                   34
```

<210> SEQ ID NO 52
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Affymetrix ID 3976358

<400> SEQUENCE: 52

```
agtccctgcg gtcccagata gcctga                                            26
```

<210> SEQ ID NO 53
<211> LENGTH: 82
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Affymetrix ID 3335898

<400> SEQUENCE: 53

```
aagctgcgct gtgactttga ggtccttgtg gttccctggc agaactcctc tcagctccta      60
aagcacaact gtgtgcagat gt                                                82
```

<210> SEQ ID NO 54
<211> LENGTH: 88
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Affymetrix ID 2598296

<400> SEQUENCE: 54
ttacaaccag gcactgacta caagatctac ctgtacacct tgaatgacaa tgctcggagc    60 tccctgtgg tcatcgacgc ctccactg                                       88

<210> SEQ ID NO 55
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Affymetrix ID 2598271

<400> SEQUENCE: 55
tgttaattgc ccaattgagt gcttcatgcc tt                                  32

<210> SEQ ID NO 56
<211> LENGTH: 353
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Affymetrix ID 2526809

<400> SEQUENCE: 56
ttcctacagt attgcgggcc agacacttaa gtgaaagcag aagtgtttgg gtgactttcc    60
tacttaaaat tttggtcata tcatttcaaa acatttgcat cttggttggc tgcatatgct   120
ttcctattga tcccaaacca aatcttagaa tcacttcatt taaaatactg agcggtattg   180
aatacttcga agcagaacag gcaatgtgca gccctcattt atgagaaaac cctcaggaaa   240
ctcccagggt gatgcttgga gaagctgtga gttgagctga agctggagaa cttcctccag   300
agcaaagggc ttaagaaaga aagaagaact ctaagctggg tctgctaaca tca          353

<210> SEQ ID NO 57
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Affymetrix ID 2598277

<400> SEQUENCE: 57
gatggtgcca tgacaatggt gtgaacta                                       28

<210> SEQ ID NO 58
<211> LENGTH: 38
<212> TYPE: DNA
<213> ORGANISM: Artificial Sequence
<220> FEATURE:

<223> OTHER INFORMATION: Description of Artificial Sequence: Synthetic
      oligonucleotide
<220> FEATURE:
<223> OTHER INFORMATION: Affymetrix ID 2598280

<400> SEQUENCE: 58
aaactgttgt gccagtgctt aggctttgga agtggtca                              38

<210> SEQ ID NO 59
<211> LENGTH: 101
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Affymetrix ID 2562441

<400> SEQUENCE: 59
ttgattgaaa gtcctagggt gattctattt ctgctgtgat ttatctgctg aaagctcagc     60
tggggttgtg caagctaggg acccattcct gtgtaataca a                        101

<210> SEQ ID NO 60
<211> LENGTH: 559
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Affymetrix ID 2598320

<400> SEQUENCE: 60
acatagatgg tgttgcatgc tgccaccagt tactccggtt aaatatggat gtttcatggg     60
ggaagtcagc aattggccaa agattcagat agggtggatt gggggggataa ggaatcaaat   120 gcatctgcta aactgattgg agaaaaaacac atgcaagtat tcttcagtac actctcattt   180
aaaccacaag tagatataaa gctagagaaa tacagatgtc tgctctgtta aatataaaat   240
agcaaatgtt cattcaattt gaagacctag aatttttcgt cttaaatacc aaacacgaat   300
accaaattgc gtaagtacca attaattata agaaatatat caccaaaatg taccatcatg   360
atcttccttc taccctttga taaactctac catgctcctt ctttgtagct aaaaacccat   420
caaaatttag ggtagagtgg atgggcattg ttttgaggta ggagaaaagt aaacttggga   480
gcattctagg ttttgttgct gtcactaggt aaagaaacac ctctttaacc acagtctggg   540
gacaagcatg caacatttt                                                 559

<210> SEQ ID NO 61
<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Affymetrix ID 3460465

<400> SEQUENCE: 61
cagtatgttc attctgctct tgtgactaca gtctttttg                            39

<210> SEQ ID NO 62
<211> LENGTH: 222
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Affymetrix ID 2598313

<400> SEQUENCE: 62
ccaactggca ttgactttc tgatattact gccaactctt ttactgtgca ctggattgct    60
cctcgagcca ccatcactgg ctacaggatc cgccatcatc ccgagcactt cagtgggaga   120
cctcgagaag atcgggtgcc ccactctcgg aattccatca ccctcaccaa cctcactcca   180
ggcacagagt atgtggtcag catcgttgct cttaatggca ga                      222

<210> SEQ ID NO 63
<211> LENGTH: 84
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Affymetrix ID 2598354

<400> SEQUENCE: 63
tgacatcact tacaatgtga acgacacatt ccacaagcgt catgaagagg ggcacatgct    60
gaactgtaca tgcttcggtc aggg                                          84

<210> SEQ ID NO 64
<211> LENGTH: 67
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Affymetrix ID 2598286

<400> SEQUENCE: 64
caagaagctc tctctcagac aaccatctca tgggccccat tccaggacac ttctgagtac    60
atcattt                                                             67

<210> SEQ ID NO 65
<211> LENGTH: 77
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Affymetrix ID 2526813

<400> SEQUENCE: 65
tttccgttcc caagacatgt gcagctcatc atctggccat tttctccctg acggtcccac    60
ttctctccaa tcttgta                                                  77

<210> SEQ ID NO 66
<211> LENGTH: 480
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Affymetrix ID 2598332

<400> SEQUENCE: 66

```
ctacattcta ttactttggg cattgaatag taactataaa tgcagaataa aaatatctat      60
ggattgaatg ggaaccaact aattgaacat gaagccaagg aaatgatttc tttatgagtg     120
ttggctgcag aagattaaag tactttgca gacggaatcg ctcttttctt aaattactct     180
tgaaattcct cagaggagaa aaatactaac aataattttt ggtcatgtct atccttttgc     240
tcaacatttt aaaggaagtg gtcttaaatc tcccacatat ctacatcaca ataacaacct     300
ctattcacaa accgattcct attaaataca tttccattta cattacagag aattatgaga     360
ctccttattt ctagctgaac atcatttgtt attttcaact cgacattttg aattatagaa     420
gcacctaaca taagtacttt ttcagcatat attctaacca tggactagtt tgcaattttc     480
```

<210> SEQ ID NO 67
<211> LENGTH: 145
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Affymetrix ID 2598356

<400> SEQUENCE: 67

```
ggaaatctgc acaaccaatg aagggggtcat gtaccgcatt ggagatcagt gggataagca     60
gcatgacatg ggtcacatga tgaggtgcac gtgtgttggg aatggtcgtg gggaatggac    120
atgcattgcc tactcgcagc ttcga                                          145
```

<210> SEQ ID NO 68
<211> LENGTH: 35
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Affymetrix ID 2598267

<400> SEQUENCE: 68

```
gttctgcttc gaagtattca ataccgctca gtatt                                35
```

<210> SEQ ID NO 69
<211> LENGTH: 75
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Affymetrix ID 2598365

<400> SEQUENCE: 69

```
tttccgcaaa tccatctttc ctttgacatg ccatttgagg ataatttgca gtgtttcagc     60
taataaccta agata                                                      75
```

<210> SEQ ID NO 70
<211> LENGTH: 821
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Affymetrix ID 3270357

```
<400> SEQUENCE: 70
ggccacctgc tatacagttg ttaaatctta aatatgcttt ttaaaaattg gaataatgta      60
ttaaggtcaa ataatatccc ataaaatata tatttctgct aatattagta aatatcttaa     120
tttttcatta gattcatatc atttaatttc acatattcaa cacctttaaa tgttgtaatc     180
ttaatatgcg aagtgtgcct ctgcaagata ctaacacaaa gctcatgtta agaaaacagt     240
tgaggactca gaagtcagtt cgaaaatgca ctttcctaac agtgaattca caaccctgaa     300
cagcagcatt tttggaaggc aaactgttcg tgatggtaca atgtaaatgg ggacttctgt     360
aaagttctca gtttcggtcc atgtggttta tctttacatt ttaaagatca aagaagtctt     420
tacaacctga atccaggtct aaaacacact agagtagctg gtgactataa ataatatttt     480
aaaatgctgt gtctacacca tcaagactgt gtctacacta tcttggctga acgagaagag     540
atgtaaatgc tgggtggtcc cgttgaccca cggcgttggg tacaacaaaa ccagccatcg     600
gagttacacc ccaaagcacc atttgctgtc cagctgcctg tcgtttggcc cagaccaccc     660
tcagaaaaaa accagctgcc tctcccattc tcccctcccg ttctgccaca gcggcctggg     720
ctggtccagt gctatgcctg gaggctcaac acaaaacttc ccatccaaac attcagatga     780
actgagcgtc ttacacacgc agtacagagg agcacacatt a                        821

<210> SEQ ID NO 71
<211> LENGTH: 65
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Affymetrix ID 2598301

<400> SEQUENCE: 71
gtgagtgtct atgctcttaa ggacactttg acaagcagac cagctcaggg agttgtcacc      60
actct                                                                 65

<210> SEQ ID NO 72
<211> LENGTH: 110
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Affymetrix ID 2598371

<400> SEQUENCE: 72
gacttcctat gtggtcggag aaacgtggga gaagccctac caaggctgga tgatggtaga      60
ttgtacttgc ctgggagaag gcagcggacg catcacttgc acttctagaa                110

<210> SEQ ID NO 73
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Affymetrix ID 2685324

<400> SEQUENCE: 73
tttcaaactg ggttattcac tgctgcacgt cag                                  33
```

```
<210> SEQ ID NO 74
<211> LENGTH: 230
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Affymetrix ID 3536724

<400> SEQUENCE: 74
ggtcattgtc tttcctgtct cagtagtaat caatcactgc ttatcttcaa aaacccagag      60 tagggggatgg ggcagttagt ggggacagag ggcagatggg taagattcag agcacaggct    120
agtgtgacgg aagtttaaac ttgtgagtta aatagggttt ggcaatctag ctggatagca    180
tccctgcccc ttgaagagat gtttttgtgg cgccacacta ctgacttagg               230

<210> SEQ ID NO 75
<211> LENGTH: 89
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Affymetrix ID 3451841

<400> SEQUENCE: 75
gcacagctgt gccaatgata ccatttgctt caatttggat ggcggatatg attgtcgatg      60
tcctcatgga aagaattgca caggggact                                        89

<210> SEQ ID NO 76
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Affymetrix ID 2598270

<400> SEQUENCE: 76
ctgacagaga agattcccga gagtaa                                            26

<210> SEQ ID NO 77
<211> LENGTH: 164
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Affymetrix ID 2598288

<400> SEQUENCE: 77
cacccaccct gggtatgaca ctggaaatgg tattcagctt cctggcactt ctggtcagca      60
acccagtgtt gggcaacaaa tgatctttga ggaacatggt tttaggcgga ccacaccgcc    120
cacaacggcc accccataa ggcataggcc aagaccatac ccgc                       164

<210> SEQ ID NO 78
<211> LENGTH: 94
<212> TYPE: DNA
<213> ORGANISM: Artificial Sequence
<220> FEATURE:
<223> OTHER INFORMATION: Description of Artificial Sequence: Synthetic
``` oligonucleotide
<220> FEATURE:
<223> OTHER INFORMATION: Affymetrix ID 2827683

<400> SEQUENCE: 78
tttcagcaag ccagttttgg agtgactgca agaagtatga tgtgactgtg tttcagtata     60
ttggagaact tgtcgctac ctttgcaaac aatc                                  94

<210> SEQ ID NO 79
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Affymetrix ID 2598324

<400> SEQUENCE: 79
gtgtccctat ctctgatacc atcatcccag                                      30

<210> SEQ ID NO 80
<211> LENGTH: 1027
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Affymetrix ID 2598303

<400> SEQUENCE: 80
caaactcggg catttcatag cagcatgatt ctgagcacac gtgggtaaga cctttcttct     60
ctggttagat atcatatgct ggtgtataat tagcttaaat gattgtgatt tagacaccta   120
ggaaataatc aatagggcaa ttgctttcca taatacttta tcttcttgtg ctttatttct   180
gaagcagagt agaatgctaa agatgtatcc tagtgacagc ataaacccta gaggtgacag   240
tctgtattat tgcttttcgc ttctcttttc tgcttctgtt gggagccagt tttcttctta   300
cgccgcatta cagagagaac gtcaaattta gcagccatat ctgccatagg gtccaaataa   360
agagacaata aaaacattat tctctctttt ttggatggaa tactgcgtga aatggttatc   420
catacaaaga tactttatgt agaatagaaa aaggaggccg ggtgcagtgg ctcacacatg   480
taatcctagt gctttgggag gctaagccgg gagcactgat tgaggccagg agttcatgat   540
cagcctgggc aatgaagtga gaccccgtct ctacaaaaaa atatgaaaaa attagcgagg   600
tgtggtgaca catgcctgta gtcccagcta ctcaagaggc tgaggtagag gatcacttga   660
gcctacgagt tcaaggctgc agtgagctat gataactcca ctgcactgcc gcctggatga   720
cacagagaga ccgtttctaa attaattaat taacaatttt aagaaagaaa aagggccatt   780 gcttatttt ccatacaaaa gtaaaataaa tcataatggc caataagcca atgtaacttt   840 ttttttaag ggaaagcaaa acttgtaaaa cctaaaatct cttagagttt tggcatttac   900
ccaaatgttt tcagtgattc tgagaattgg tggatataaa acacatttct cagcaaacac   960
tttcttcatt ttgcatccct tactgtacgt actttcttgt actgaatctt tgcttgacca  1020
gggaacc                                                            1027

<210> SEQ ID NO 81
<211> LENGTH: 34
<212> TYPE: DNA
<213> ORGANISM: Artificial Sequence

```
<220> FEATURE:
<223> OTHER INFORMATION: Description of Artificial Sequence: Synthetic
      oligonucleotide
<220> FEATURE:
<223> OTHER INFORMATION: Affymetrix ID 2562442

<400> SEQUENCE: 81
ctctgctgct tgagagctat tgctttgtta agat                                  34

<210> SEQ ID NO 82
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Affymetrix ID 2598363

<400> SEQUENCE: 82
tctggcccct tcaccgatgt tcgtgcagct gtttaccaac cgcagcct                   48

<210> SEQ ID NO 83
<211> LENGTH: 76
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Affymetrix ID 2598273

<400> SEQUENCE: 83
gctgtgacaa ctgccgcaga cctggggtg aacccagtcc cgaaggcact actggccagt       60
cctacaacca gtattc                                                      76

<210> SEQ ID NO 84
<211> LENGTH: 243
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Affymetrix ID 2598304

<400> SEQUENCE: 84
tgatcgccct aaaggactgg cattcactga tgtggatgtc gattccatca aaattgcttg      60
ggaaagccca caggggcaag tttccaggta cagggtgacc tactcgagcc ctgaggatgg     120
aatccatgag ctattccctg cacctgatgg tgaagaagac actgcagagc tgcaaggcct    180
cagaccgggt tctgagtaca cagtcagtgt ggttgccttg cacgatgata tggagagcca    240
gcc                                                                  243

<210> SEQ ID NO 85
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Affymetrix ID 3020344

<400> SEQUENCE: 85
gagccgagtg gagggcgcga gccagatgcg gggcgacagc tgacttgctg agaggaggcg      60
```
gggaggcgcg gagcgcgcgt gtggtccttg cgccgctgac                                100

<210> SEQ ID NO 86
<211> LENGTH: 382
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Affymetrix ID 2325319

<400> SEQUENCE: 86
aggaggtttt gtgccagagc cttgcccccct cactcactct tgggggtcct gatgaactct    60
tggaccctgt ggaagataag agttagagac ctcggcctcc tggtcagtgg agcccttggc   120
ctcatgcctg gtgggctaag cgggcccagc tggggtttga ggtaggggag gccttggctt   180
ggccccagca gctccagggc cctgagttcc tgccagaggc tggagagcag gcagctgctg   240
cttttcctgg tccttggtag gggagggtcc tcaggcttgc gtgccaaagc ctgaaggatt   300
ctgcttctgc cagcgccaga gatcctcacc tgcaacacgg cgaggtgtgt gctcagggcc   360
cacggtggaa tgcagagcct cc                                             382

<210> SEQ ID NO 87
<211> LENGTH: 158
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Affymetrix ID 3460510

<400> SEQUENCE: 87
tgtatgccca taagatgcta tcatcggagg cactgacccc ccaagtgacc cctgacagtc    60
ccctcacctc tcccacaaga cttccaaagg atcgcccctc caagccattg ttatgtgtga   120
cctcatggca acttcccgac atgagtttag ctgcaggc                            158

<210> SEQ ID NO 88
<211> LENGTH: 106
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Affymetrix ID 2598339

<400> SEQUENCE: 88
tattcgccat cagtagaagg tagcagcaca gaactcaacc ttcctgaaac tgcaaactcc    60
gtcaccctca gtgacttgca acctggtgtt cagtataaca tcacta                  106

<210> SEQ ID NO 89
<211> LENGTH: 76
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Affymetrix ID 3371816

<400> SEQUENCE: 89

```
acctgcttac agacatcact tttaagtcct tgtggatgt gggcacagtg aagagcaata      60
aagagtgtga ggttcc                                                    76

<210> SEQ ID NO 90
<211> LENGTH: 63
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Affymetrix ID 2400181

<400> SEQUENCE: 90
ttgttattga agatgatagg attgatgacg tgctgaaaaa tatgaccgac aaggcacctc    60
ctg                                                                  63

<210> SEQ ID NO 91
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Affymetrix ID 3536743

<400> SEQUENCE: 91
atacaagtac tggttgaacc tgaccacttc aag                                 33

<210> SEQ ID NO 92
<211> LENGTH: 66
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Affymetrix ID 3536736

<400> SEQUENCE: 92
cactttgaga aactcaggga tggggttagt caaagaggac ttgtgtttgc attaacctcc    60
agggag                                                               66

<210> SEQ ID NO 93
<211> LENGTH: 84
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Affymetrix ID 3634838

<400> SEQUENCE: 93
caccgtaaga cctacagtac ggaggagtac caccacaggc tgcagacgtt tgccagcaac    60
tggaggaaga taaacgccca caac                                           84

<210> SEQ ID NO 94
<211> LENGTH: 54
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
```

<223> OTHER INFORMATION: Affymetrix ID 3976359

<400> SEQUENCE: 94

```
gcctgcacag tgtccaccct gttcccactc ccatctttct tccggacaat gaaa            54
```

<210> SEQ ID NO 95
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Affymetrix ID 2598268

<400> SEQUENCE: 95

```
tgttagcaga cccagcttag agttctt                                          27
```

<210> SEQ ID NO 96
<211> LENGTH: 67
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Affymetrix ID 3451865

<400> SEQUENCE: 96

```
atgatttatg agtgcgctgc gggtggagtg aagtgtcatg gtcgtcgtta tgataacgct      60
ggaaaga                                                               67
```

<210> SEQ ID NO 97
<211> LENGTH: 523
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Affymetrix ID 2526825

<400> SEQUENCE: 97

```
aggtaagccc tcaacccagg attgcatgca ttgtgtcctt tttaaaactt ttaacagaat      60
acattccttt taaataaaat ttggaaaata cagaaaagta aagagaagaa aaaataaaaa     120
tcacttattt ccaccactga taatatgttt gtgaatttac aatccttta tttcctcagc     180 tctgccgttc cccctctagt tgtagtatat aaacaacttt ttatttgggt tttagaacaa     240
attatatcat ctatatctta cgtattttct tggaaaaaac aagggctccg ttgaatggac     300
ttgccaaagt ttctttaatt ctttgttcac tgttgggctt tcaggttatc cacaacagaa     360
tctgatttaa tcagagtgta aaatagcatt ttactgctgt acctgtctct ccgtaagtga     420
tcctgtaata tctcactgtg acagcaggag catcccagct gatcagtagg ctggtggggg     480
tcgcagcaac aacttccagg tccctcggaa catcagaaac tag                       523
```

<210> SEQ ID NO 98
<211> LENGTH: 60
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Affymetrix ID 2721993

```
<400> SEQUENCE: 98
ttcttcaaca tctccggcat cttgctgtgg tacccgatcc cgttcactcg cctgcccatc    60

<210> SEQ ID NO 99
<211> LENGTH: 269
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Affymetrix ID 2827693

<400> SEQUENCE: 99
tcatatgctt tcttaggaag agtgagaggg gggtatatga ttctttatga aatggggaaa    60
gggagctaac attaattatg catgtactat atttccttaa tatgagagat aattttttaa   120
ttgcataaga attttaattt cttttaattg atataaacag tagttgatta ttcttttat   180 ctatttggag attcagtgca taactaagta ttttccttaa tactaaagat tttaaataat   240
aaatagtggc tagcggtttg gacaatcac                                     269

<210> SEQ ID NO 100
<211> LENGTH: 479
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Affymetrix ID 2598309

<400> SEQUENCE: 100
tctgttgtgg ataacctgaa agcccaacag tgaacaaaga attaaagaaa ctttggcaag    60
tccattcaac ggagcccttg ttttttccaa gaaaatacgt aagatataga tgatataatt   120
tgttctaaaa cccaaataaa aagttgttta tatactacaa ctagaggggg aacggcagag   180
ctgaggaaat aaaaggattg taaattcaca aacatattat cagtggtgga ataagtgat    240 ttttatttt tcttctcttt acttttctgt attttccaaa tttatttaa aaggaatgta    300 ttctgttaaa agttttaaaa aggacacaat gcatgcaatc ctgggttgag ggcttacctt   360
ctcccacttc taatgctact ctactactca gtgacatttt aaagctgaaa tgttaaaaca   420
gcgctaactg taattttctc tcaatgttta tacacttacc aaggtttgct acatgcata    479

<210> SEQ ID NO 101
<211> LENGTH: 334
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Affymetrix ID 2722006

<400> SEQUENCE: 101
tccaccatcc cagcaagtca ggatatcaga cagtcctccc ctgaccctcc cccttgtaga    60
tatcaattcc caaacagagc caaatactct atatctatag tcacagccct gtacagcatt   120
tttcataagt tatatagtaa atggtctgca tgatttgtgc ttctagtgct ctcatttgga   180
aatgaggcag gcttcttcta tgaaatgtaa agaaagaaac cactttgtat attttgtaat   240
accacctctg tggccatgcc tgccccgccc actctgtata tatgtaagtt aaacccgggc   300
```

```
aggggctgtg gccgtctttg tactctggtg attt                                334
```

<210> SEQ ID NO 102
<211> LENGTH: 134
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Affymetrix ID 2598330

<400> SEQUENCE: 102

```
gaggcaccac gagaagtgac ttcagactca ggaagcatcg ttgtgtccgg cttgactcca    60
ggagtagaat acgtctacac catccaagtc ctgagagatg acaggaaag agatgcgcca    120 attgtaaaca aagt                                                      134
```

<210> SEQ ID NO 103
<211> LENGTH: 351
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Affymetrix ID 2598283

<400> SEQUENCE: 103

```
tgagttgata tagggcacag gtttcctgat gtcttttccc agaccctctc catctcacca    60
tgctgctgtc ctcttgagtg attaaatact gaaacgatta cctataaaga aaatacccct   120
tctgcagaca tggggacagt tggcttttgc tcctgatata aaatgctacc aacattgtgc   180
atttctgtct gcagagaatg ttattccaat gttatttcca ttttttttcca atgttatttc   240 cattttttt tctgactata caggttaaaa gcttctatag aggttaaaag atcattaact   300
cttctttgta gcacctggga aatccttta aatcaatagc gtgccacctg g             351
```

<210> SEQ ID NO 104
<211> LENGTH: 29
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Affymetrix ID 2685316

<400> SEQUENCE: 104

```
tactttactt ggcggagcag tttgcaggg                                      29
```

<210> SEQ ID NO 105
<211> LENGTH: 385
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Affymetrix ID 3666402

<400> SEQUENCE: 105

```
tctgacgtta gagtggtggc ttccttagcc tttcaggatg gaggaatgtg ggcagtttga    60
cttcagcact gaaaacctct ccacctgggc cagggttgcc tcagaggcca agtttccaga   120
```

```
agcctcttac ctgccgtaaa atgctcaacc ctgtgtcctg ggcctgggcc tgctgtgact      180
gacctacagt ggactttctc tctggaatgg aaccttctta ggcctcctgg tgcaacttaa      240 ttttttttt taatgctatc ttcaaaacgt tagagaaagt tcttcaaaag tgcagcccag       300
agctgctggg cccactggcc gtcctgcatt tctggtttcc agaccccaat gcctcccatt      360
cggatggatc tctgcgtttt tatac                                            385
```

<210> SEQ ID NO 106
<211> LENGTH: 366
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Affymetrix ID 2685306

<400> SEQUENCE: 106

```
aaatttgct gtgtgggtca cacaaggtct acattacaaa agacagaatt cagggatgga       60
aaggagaatg aacaaatgtg ggagttcata gttttccttg aatccaactt ttaattacca     120
gagtaagttg ccaaaatgtg attgttgaag tacaaaagga actatgaaaa ccagaacaaa     180
ttttaacaaa aggacaacca cagagggata tagtgaatat cgtatcattg taatcaaaga     240
agtaaggagg taagattgcc acgtgcctgc tggtactgtg atgcatttca agtggcagtt     300
ttatcacgtt tgaatctacc attcatagcc agatgtgtat cagatgtttc actgacagtt     360
tttaac                                                                 366
```

<210> SEQ ID NO 107
<211> LENGTH: 437
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Affymetrix ID 2526814

<400> SEQUENCE: 107

```
gtagggtca aagcacgagt catccgtagg ttggttcaag ccttcgttga ctatgaagaa       60
aaggaagaaa aagcaaaaag agacatctta ttaatcgatt tggaccataa gaagaaaatc     120
gaatgactgt atacaatgac ttaatctaaa acaagaattc caggaggatt aagaggcatt     180
catctgttct atcaaggcat taactgctct aaaaaaccat ggttagatgt gacacctgtc     240
acaggcaccc gacaggaagc ccatcttta tttttcccct gcttctaaga taattgccat      300
ttctgttgaa actacttcat agaacatgga acagatcttg aggcaattga agctagtgga     360
gaactttagt gggatgcaaa gactaatgat gcctctccat tggtacctga gtgaccttgg     420
gccagctatt taatacc                                                     437
```

<210> SEQ ID NO 108
<211> LENGTH: 138
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Affymetrix ID 2598344

<400> SEQUENCE: 108

```
acaggagaga cgactccctt ttctcctctt gtggccactt ctgaatctgt gaccgaaatc    60
acagccagta gctttgtggt ctcctgggtc tcagcttccg acaccgtgtc gggattccgg   120
gtggaatatg agctgagt                                                 138
```

<210> SEQ ID NO 109
<211> LENGTH: 152
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Affymetrix ID 2491742

<400> SEQUENCE: 109

```
tcatgaccta acctcatccc agtgagtaga gactgggagg ggagagcagc agctggaggg    60
caggctggga gcgcttgtga gggagaggag ctatggacgt ctgcttctct gccaagggag   120
agagtgaggt aggcctgggc ccgctgactt ca                                 152
```

<210> SEQ ID NO 110
<211> LENGTH: 168
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Affymetrix ID 2598318

<400> SEQUENCE: 110

```
ctgacctgcg attcaccaac attggtccag acaccatgcg tgtcacctgg gctccacccc    60
catccattga tttaaccaac ttcctggtgc gttactcacc tgtgaaaaat gaggaagatg   120
ttgcagagtt gtcaatttct ccttcagaca atgcagtggt cttaacaa                168
```

<210> SEQ ID NO 111
<211> LENGTH: 58
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Affymetrix ID 3839605

<400> SEQUENCE: 111

```
agagggaga tgtttagagg tgtggagggc ggcagaggtt tgaacagtgc agacaagg       58
```

<210> SEQ ID NO 112
<211> LENGTH: 126
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Affymetrix ID 2598325

<400> SEQUENCE: 112

```
cctacaaacg gccagcaggg aaattctttg gaagaagtgg tccatgctga tcagagctcc    60
tgcactttTg ataacctgag tcccggcctg gagtacaatg tcagtgttta cactgtcaag   120
gatgac                                                              126
```

```
<210> SEQ ID NO 113
<211> LENGTH: 127
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Affymetrix ID 2451595

<400> SEQUENCE: 113
caaaggacac cattttggca agctctatca ccaaggagcc aaacatccta caagacacag        60
tgaccatact aattataccc cctgcaaagc ccagcttgaa accttcactt aggaacgtaa       120
tcgtgtc                                                                 127

<210> SEQ ID NO 114
<211> LENGTH: 103
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Affymetrix ID 2721980

<400> SEQUENCE: 114
actgttcggg ctgccatccc cattatcatg ggggccaaca ttggaacgtc aatcaccaac        60
actattgttg cgctcatgca ggtgggagat cggagtgagt tca                         103

<210> SEQ ID NO 115
<211> LENGTH: 70
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Affymetrix ID 2721989

<400> SEQUENCE: 115
tgcatggttg actggctacc tggccatcct cgtcgggca ggcatgacct tcatcgtaca         60
gagcagctct                                                              70

<210> SEQ ID NO 116
<211> LENGTH: 155
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Affymetrix ID 2722000

<400> SEQUENCE: 116
gatgtctaat cctgcgccta gctgggttgg tcagtagaac ctattttcag actcaaaaac        60
catcttcaga aagaaaaggc ccagggaagg aatgtatgag aggctctccc agatgaggaa       120
gtgtactctc tatgactatc aagctcaggc ctctc                                  155

<210> SEQ ID NO 117
<211> LENGTH: 31
<212> TYPE: DNA
<213> ORGANISM: Artificial Sequence
<220> FEATURE:
<223> OTHER INFORMATION: Description of Artificial Sequence: Synthetic
      oligonucleotide
```

<220> FEATURE:
<223> OTHER INFORMATION: Affymetrix ID 3087187

<400> SEQUENCE: 117
ctatgatgag gggacagacg tttttcagca g                              31

<210> SEQ ID NO 118
<211> LENGTH: 31
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Affymetrix ID 2526818

<400> SEQUENCE: 118
atgtactcag aagtgtcctg gaatggggcc c                              31

<210> SEQ ID NO 119
<211> LENGTH: 79
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Affymetrix ID 2598331

<400> SEQUENCE: 119
tctattccac cttacaacac cgaggtgact gagaccacca ttgtgatcac atggacgcct     60
gctccaagaa ttggttttta                                               79

<210> SEQ ID NO 120
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Affymetrix ID 2721991

<400> SEQUENCE: 120
gaatcggcgt gataaccatt gagagggctt atccactcac                         40

<210> SEQ ID NO 121
<211> LENGTH: 41
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Affymetrix ID 2400180

<400> SEQUENCE: 121
ggagagaata agaacggcgg taacagttat tggcaaaaag c                       41

<210> SEQ ID NO 122
<211> LENGTH: 79
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Affymetrix ID 2598287

<400> SEQUENCE: 122
aggaaatcca aattggtcac atccccaggg aagatgtaga ctatcacctg tacccacacg    60
gtccgggact caatccaaa                                                 79

<210> SEQ ID NO 123
<211> LENGTH: 90
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Affymetrix ID 2584026

<400> SEQUENCE: 123
tggtatactg atgaagacca tggaatagct agcagcacag cacaccaaca tatatatacc    60
cacatgagcc acttcataaa acaatgtttc                                     90

<210> SEQ ID NO 124
<211> LENGTH: 110
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Affymetrix ID 3536744

<400> SEQUENCE: 124
tgcagtgaat gatgctcact tgttgcagta caatcatcgg gttaaaaaac tcaatgaaat    60
cagcaaactg ggaatttctg gtgacataga cctcaccagt gcttcatata              110

<210> SEQ ID NO 125
<211> LENGTH: 110
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Affymetrix ID 2598284

<400> SEQUENCE: 125
cactctgaca ggcctcacca gaggtgccac ctacaacgtc atagtggagg cactgaaaga    60
ccagcagagg cataaggttc gggaagaggt tgttaccgtg ggcaactctg              110

<210> SEQ ID NO 126
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Affymetrix ID 2598294

<400> SEQUENCE: 126
tgatgcacca tccaacctgc gtttcctggc caccacaccc aattccttgc tggtatcatg    60
gcagccgcca cgtgccagga ttaccggcta catcatcaag                         100

<210> SEQ ID NO 127
<211> LENGTH: 71
<212> TYPE: DNA

<213> ORGANISM: Artificial Sequence
<220> FEATURE:
<223> OTHER INFORMATION: Description of Artificial Sequence: Synthetic
    oligonucleotide
<220> FEATURE:
<223> OTHER INFORMATION: Affymetrix ID 3451875

<400> SEQUENCE: 127
ctgaaaggca taactgcatg gagaattcca tctgcagaaa tctgaatgac agggctgttt    60
gtagctgtcg a                                                         71

<210> SEQ ID NO 128
<211> LENGTH: 70
<212> TYPE: DNA
<213> ORGANISM: Artificial Sequence
<220> FEATURE:
<223> OTHER INFORMATION: Description of Artificial Sequence: Synthetic
    oligonucleotide
<220> FEATURE:
<223> OTHER INFORMATION: Affymetrix ID 2598308

<400> SEQUENCE: 128
tgggagcaag tctacagcta ccatcagcgg ccttaaacct ggagttgatt ataccatcac    60
tgtgtatgct                                                           70

<210> SEQ ID NO 129
<211> LENGTH: 81
<212> TYPE: DNA
<213> ORGANISM: Artificial Sequence
<220> FEATURE:
<223> OTHER INFORMATION: Description of Artificial Sequence: Synthetic
    oligonucleotide
<220> FEATURE:
<223> OTHER INFORMATION: Affymetrix ID 3825011

<400> SEQUENCE: 129
cggaggacgc gacctcagtt gtcctgccct gtggaatggg ctcaaggttc ctgagacacc    60
cgattcctgc ccaaacagct g                                              81

<210> SEQ ID NO 130
<211> LENGTH: 337
<212> TYPE: DNA
<213> ORGANISM: Artificial Sequence
<220> FEATURE:
<223> OTHER INFORMATION: Description of Artificial Sequence: Synthetic
    polynucleotide
<220> FEATURE:
<223> OTHER INFORMATION: Affymetrix ID 3464873

<400> SEQUENCE: 130
tcagcagttt ctcttggcag catcagctgg gctgctttct ttgtgtgtgg ccccaggtgt    60
caaaatgaca ccagctgtct gtactagaca aggttaccaa gtgcggaatt ggttaatact   120
aacagagaga tttgctccat tctctttgga ataacaggac atgctgtata gatacaggca   180
gtaggtttgc tctgtaccca tgtgtacagc ctacccatgc agggactggg attcgaggac   240
ttccaggcgc atagggtaga accaaatgat agggtaggag catgtgttct ttagggcctt   300
gtaaggctgt ttccttttgc atctggaact gactata                            337

<210> SEQ ID NO 131
<211> LENGTH: 144
<212> TYPE: DNA
<213> ORGANISM: Artificial Sequence
<220> FEATURE:
<223> OTHER INFORMATION: Description of Artificial Sequence: Synthetic

```
        polynucleotide
<220> FEATURE:
<223> OTHER INFORMATION: Affymetrix ID 3263765

<400> SEQUENCE: 131
tgcagagtcc tacagctggt tcaaggcagc atcaggctca gaaccccttt ctctcagctc    60
tctgttgtga ttatttcagg accttgttct gttttccaca tggcctctaa tctagacacc   120
tgacctggtg ggagtaacct ttca                                          144

<210> SEQ ID NO 132
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Affymetrix ID 2562440

<400> SEQUENCE: 132
ctgcaccaat gctaataaag tcctattctc tt                                  32

<210> SEQ ID NO 133
<211> LENGTH: 67
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Affymetrix ID 3536745

<400> SEQUENCE: 133
accttacatg tgtaaaggtt tcatgttcac tgtgagtgaa aatttttaca ttcatcaata    60
tccctct                                                              67

<210> SEQ ID NO 134
<211> LENGTH: 76
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Affymetrix ID 2598290

<400> SEQUENCE: 134
ccgggaaccg aatatacaat ttatgtcatt gccctgaaga ataatcagaa gagcgagccc    60
ctgattggaa ggaaaa                                                    76

<210> SEQ ID NO 135
<211> LENGTH: 317
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Affymetrix ID 2526822

<400> SEQUENCE: 135
ggcctcaatc agtgctcccg gcttagcctc ccaaagcact aggattacat gtgtgagcca    60
ctgcacccgg cctcctttt ctattctaca taaagtatct ttgtatggat aaccatttca   120
cgcagtattc catccaaaaa agagagaata atgtttttat tgtctcttta tttggaccct  180
```

```
atggcagata tggctgctaa atttgacgtt ctctctgtaa tgcggcgtaa gaagaaaact    240
ggctcccaac agaagcagaa aagagaagcg aaaagcaata atacagactg tcacctctag    300
ggtttatgct gtcacta                                                   317
```

<210> SEQ ID NO 136
<211> LENGTH: 102
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Affymetrix ID 2526816

<400> SEQUENCE: 136

```
ttcccgaacc ttatgcctct gctggtcttt cagtgcctcc actatgacgt tgtaggtggc    60
acctctggtg aggcctgtca gagtggcact ggtagaagtt cc                       102
```

<210> SEQ ID NO 137
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Affymetrix ID 2584027

<400> SEQUENCE: 137

```
tccaaagccc tggtcgatgt tggagtggat ttc                                 33
```

<210> SEQ ID NO 138
<211> LENGTH: 354
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Affymetrix ID 3329530

<400> SEQUENCE: 138

```
gaaagtccaa tctctccagt gagtaacgtt aaaaccatta cacatgagca tgggagaatc    60
gcttccatta gtttaggaca gagagatttt gcttttaca gagtaaatca gtgctcaaat     120
agatacttcc tcaaatatgt cctttctaca ttctgaacag cccaagtgca ataagatcct    180
tccccctttc caatcaagaa aatgccactt ttctacttgc tcttcctccc cagacgtgag    240
tctaaggacc caaagtgctc actcctttac tgcttgttaa gtgtaatgtg gggaggctca    300
gaactggggc tgacgctact gagagcaagg ctaagggcct ggtatctctc tcta          354
```

<210> SEQ ID NO 139
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Affymetrix ID 3020368

<400> SEQUENCE: 139

```
ggcaagtgga gggtcaacac ccatgggtgg ct                                  32
```

<210> SEQ ID NO 140
<211> LENGTH: 54
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Affymetrix ID 3451912

<400> SEQUENCE: 140

```
atggagtctc gggtcttact gagaacattc tgtttgatct tcggtctcgg agca         54
```

<210> SEQ ID NO 141
<211> LENGTH: 141
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: Affymetrix ID 3917691

<400> SEQUENCE: 141

```
agcttccgaa catggacaca gagtaagacc agccatagac caaaacagga aggaaaaaaa    60
aaaagaggct cattgaaaca tgaatcgcca ccctctcctc acacattctt aaaatacacg   120
gagattctca gacatggaag a                                             141
```

<210> SEQ ID NO 142
<211> LENGTH: 306
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: Affymetrix ID 3420343

<400> SEQUENCE: 142

```
gaggagtttt acattgcagc ttagaagcct ttcttccaat agcagagatt tggtgtcatg    60
tggtgttcat cagtttgaaa agaagtattt ctgctgtttg cctcaagatg tacatacaga   120
gatgtgctga ttctcagaac ttctatagaa ttccattagc cagtcctgcc aattgaaatt   180
tggcatttaa ttatttgcat ttttctattc ttgcctagga aaggagctcg tcacatacct   240
agtttagtga tggaaagtat ttggagaaag ttttagagag tggggctcag gctcaagaat   300
acaatg                                                             306
```

<210> SEQ ID NO 143
<211> LENGTH: 197
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: Affymetrix ID 3343460

<400> SEQUENCE: 143

```
gcatatttgc ctagtaaggc tagtagaacc acatttccca aagtgtgctc cttaaacact    60
catgccttat gattttctac caaaagtaaa aagggttgta ttaagtcaga ggaagatgcc   120
tctccatttt ccctctcttt atcagaggtt cacatgcctg tctgcacatt aaaagctctg   180
ggaagacctg ttgtaaa                                                 197
```

<210> SEQ ID NO 144
<211> LENGTH: 165
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Affymetrix ID 2721982

<400> SEQUENCE: 144
ttcttcaact ggctgtccgt gttggtgctc ttgcccgtgg aggtggccac ccattacctc      60
gagatcataa cccagcttat agtggagagc ttccacttca agaatggaga agatgcccca     120
gatcttctga aagtcatcac taagcccttc acaaagctca ttgtc                    165

<210> SEQ ID NO 145
<211> LENGTH: 96
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Affymetrix ID 2598310

<400> SEQUENCE: 145
ggacctggaa gttgttgctg cgaccccac cagcctactg atcagctggg atgctcctgc       60
tgtcacagtg agatattaca ggatcactta cggaga                               96

<210> SEQ ID NO 146
<211> LENGTH: 177
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Affymetrix ID 3270278

<400> SEQUENCE: 146
ttcctctaca ggaatggggt ttggcagtga tccaaagact cactgttatg acatgttctc      60
agggaagtag gtcatatgtc cccagggtat tcagagaggc ctgtgagtgt gagatgtttg     120
ggctgagcag ggctttcttc ctctcaaggc tccaagggc gggccaacag gtcattt         177

<210> SEQ ID NO 147
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Affymetrix ID 3577627

<400> SEQUENCE: 147
ctggccccct ccctggatga cattaa                                           26

<210> SEQ ID NO 148
<211> LENGTH: 79
<212> TYPE: DNA
<213> ORGANISM: Artificial Sequence
<220> FEATURE:
<223> OTHER INFORMATION: Description of Artificial Sequence: Synthetic
      oligonucleotide

```
<220> FEATURE:
<223> OTHER INFORMATION: Affymetrix ID 2598276

<400> SEQUENCE: 148
tgatgggaag acataccacg taggagaaca gtggcagaag gaatatctcg gtgccatttg    60
ctcctgcaca tgctttgga                                                 79

<210> SEQ ID NO 149
<211> LENGTH: 135
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Affymetrix ID 3907236

<400> SEQUENCE: 149
atcgtgggca tcctctttgc cgtcttcctg atcctactgc tcatgtaccg tatgaagaag    60
aaggatgaag gcagctatga cctgggcaag aaacccatct acaagaaagc ccccaccaat   120
gagttctacg cgtga                                                    135

<210> SEQ ID NO 150
<211> LENGTH: 242
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Affymetrix ID 3464882

<400> SEQUENCE: 150
tcgagtctta aataatccgg ggagaaagac gcccgggtag atttgaggtg cagccttgga    60
gggagggatt agaagccgct agactttttt tcctcccctc tcagtagcac ggagtccgaa   120
ttaattggat tcattcact ggggaggaac aaaaactatc tgggcagctt cattgagaga    180
gattcattga cactaagagc cagcggctgc agctgggtgc agagagaacc tccggcttta   240
ct                                                                  242

<210> SEQ ID NO 151
<211> LENGTH: 186
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Affymetrix ID 2598295

<400> SEQUENCE: 151
tgacttgtat gcaatcagtt tcatgaactc aaaaaacaaa tgtgaggcgt atattttgt     60 attatagatt ccagagaatc ttgtttccgg tttacagtat tctcagattc ttttaagtgt   120
gtttagaacg gctcgggaga aaagtgtggg agtaattttc ttggttattt gccttcttag   180
agactt                                                              186

<210> SEQ ID NO 152
<211> LENGTH: 127
<212> TYPE: DNA
<213> ORGANISM: Artificial Sequence
<220> FEATURE:
<223> OTHER INFORMATION: Description of Artificial Sequence: Synthetic
```

```
            polynucleotide
<220> FEATURE:
<223> OTHER INFORMATION: Affymetrix ID 2477461

<400> SEQUENCE: 152
tttctcaaca gtacttaaat agcggttgga aaacgtagcc ttcattttat gatttttca      60 tatgtggaaa tctattacat gtaatacaaa acaaacatgt agtttgaagg cggtcagatt    120
tctttga                                                              127

<210> SEQ ID NO 153
<211> LENGTH: 107
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Affymetrix ID 2562463

<400> SEQUENCE: 153
cctggagcag gagtgcaacg tcctcccctt gaagctgctc atgccccagt gcaaccaagt     60
gcttgacgac tacttccccc tggtcatcga ctacttccag aaccaga                  107

<210> SEQ ID NO 154
<211> LENGTH: 93
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Affymetrix ID 3907239

<400> SEQUENCE: 154
aactagagga gaatgaggtt atccccaaga gaatctcacc cgttgaagag agtgaggatg     60
tgtccaacaa ggtgtcaatg tccagcactg tgc                                  93

<210> SEQ ID NO 155
<211> LENGTH: 884
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Affymetrix ID 2944958

<400> SEQUENCE: 155
tcgggtcatt tcctagcgcc ggtcacactg gctggcctcc tcccctcaac atctcctcct     60
ccggctgcag agggggcaag gggaaaagag ggaggaaaaa aaagcccaa acggaattc      120 gcctgcgtgg agtctctcag tcccggcgtt cccccaaaac atctgccatc ggccaaattc    180
gtcaccccgg agccttctgt cttcatcacg cgtttaaaaa aagggggga ggggtgcgct    240 gggttctccc ctcctttctt gaccaagaag caaaataaaa caaaaccaag gtggtgatgc    300
aggaaggggg agactccttc aagtctctag aaaactaact cgccttcttg ctggggtgc    360 agacaagtcc ggaagctcgt tggaaggggg aggggtctc ttcaagcaaa ggggagcaaa    420
ctcgaagtcg cttttttttt tttgccatca acaacaacat caataacaac aatcacaggt    480
cgcccctgtc tacccctctt ctcctccgcg tccctccggc tgggcagagt gggtccccgg    540
cccgggaagg tgggggatgg gagcgcgggt ccaaaacgcc gccgcgctcc ttgatccgac    600
```

```
gacgagaacg cgggcgaagc cagccctgct tacttttct  ttcttttttc ccttttctct    660
ttaaactctt cgtctgtcct tttcgtttct ttttttcact ttttttttct cctctcctac    720
cccccccggc ccttctccct gcctgcgcgc ccttcagtag gtgaaaacca ggttggagat    780
gctggactcg agccagtctc ccgagatcat ctcgctcacc tcgggcgtgc agtagtccgg    840
gaactcgaag tgcgagccgg agccgggctc gaagttaaaa tcca                     884
```

<210> SEQ ID NO 156
<211> LENGTH: 236
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Affymetrix ID 2512878

<400> SEQUENCE: 156

```
catcatcttg acagtgcagt tttgagataa tgaaaacaaa aatgagtttt aataagcttt     60
aaatggcatg gtatttgag gtgctaaggt aaagagaaac attgttttat gaagtggctc    120
atgtgggtat atatatgttg gtgtgctgtg ctgctagcta ttccatggtc ttcatcagta    180
taccactaga gagagaaaga aaagaagtta gaattaggaa gtcagtactc ttctta       236
```

<210> SEQ ID NO 157
<211> LENGTH: 662
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Affymetrix ID 3020350

<400> SEQUENCE: 157

```
cgccctggga gccaaagtcc tttcatctgt aaaggaccgg ttcatcaact tctttgtagg     60
caataccata aattcttctt atttcccaga tcatccattg cattcgatat cagtgagaag    120
gctaaaggaa acgaaagatg gttttatgtt tttgacggac cagtcctaca ttgatgtttt    180
acctgagttc agagattctt accccattaa gtatgtccat gcctttgaaa gcaacaattt    240
tatttacttc ttgacggtcc aaagggaaac tctagatgct cagacttttc acacaagaat    300
aatcaggttc tgttccataa actctggatt gcattcctac atggaaatgc ctctggagtg    360
tattctcaca gaaagagaa aaagagatc cacaaagaag gaagtgttta atatacttca    420
ggctgcgtat gtcagcaagc ctggggccca gcttgctaga caaataggag ccagcctgaa    480
tgatgacatt cttttcgggg tgttcgcaca aagcaagcca gattctgccg aaccaatgga    540
tcgatctgcc atgtgtgcat tccctatcaa atatgtcaac gacttcttca acaagatcgt    600
caacaaaaac aatgtgagat gtctccagca ttttacggga cccaatcatg agcactgctt    660
ta                                                                   662
```

<210> SEQ ID NO 158
<211> LENGTH: 114
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Affymetrix ID 3928670

```
<400> SEQUENCE: 158
cataaggtca tgacgtgtct atgtcaaaag ttcttatata tttcttttat aagctgaaag      60
aaggtctatt tttatgtttt taggtctatg aatggaacgt tgtaaatgct tgtc           114

<210> SEQ ID NO 159
<211> LENGTH: 54
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Affymetrix ID 3460452

<400> SEQUENCE: 159
tgcagaaagg aaggtgcagt caatttcggg aaccaggact tgcacttgtg ccct           54

<210> SEQ ID NO 160
<211> LENGTH: 257
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Affymetrix ID 2721987

<400> SEQUENCE: 160
taatgttttt tccaacccag ccatccttcg ttattctaat tactccttac atatactttt     60
gtatatctct gcttctctct tctcaccctc ccaccacatt aattctgagc actatatctt    120
aatactctag gtatgattac cccaaagaat caagttaact taccacctcc cacattctag    180
gcactataca ttcattcata taaccatgtt ttgctgggat tatctggggg atgcagaagg    240
ggctttataa ttagcaa                                                   257

<210> SEQ ID NO 161
<211> LENGTH: 110
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Affymetrix ID 2598357

<400> SEQUENCE: 161
ccttcctata caacaaccac aattacactg attgcacttc tgagggcaga agagacaaca     60
tgaagtggtg tgggaccaca cagaactatg atgccgacca gaagtttggg              110

<210> SEQ ID NO 162
<211> LENGTH: 129
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Affymetrix ID 2722004

<400> SEQUENCE: 162
gtggctaaag tctaacgctc ctctcttggt cagataacaa aagccctccc tgttggatct     60
tttgaaataa aacgtgcaag ttatccaggc tcgtagcctg catgctgcca ccttgaatcc    120
cagggagta                                                           129
```

<210> SEQ ID NO 163
<211> LENGTH: 85
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Affymetrix ID 3420360

<400> SEQUENCE: 163
gatttatggg ccatacatca ccttcctggt tggctttgtt gacaccttgt cacattcttg    60
cttgggcttg aggaattcat tgttc                                         85

<210> SEQ ID NO 164
<211> LENGTH: 104
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Affymetrix ID 2721988

<400> SEQUENCE: 164
gtgaatttcc acctcccgga tcttgctgtg ggcaccatct tgctcatact ctccctgctg    60
gtcctctgtg gttgcctgat catgattgtc aagatcctgg gctc                    104

<210> SEQ ID NO 165
<211> LENGTH: 88
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Affymetrix ID 2721976

<400> SEQUENCE: 165
cctactccac ggctacactg atagatgagc ccactgaggt ggatgacccc tggaacctac    60
ccactcttca ggactcgggg atcaagtg                                      88

<210> SEQ ID NO 166
<211> LENGTH: 107
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Affymetrix ID 3634817

<400> SEQUENCE: 166
gagttccacc atgagctcac ccgtgtctat gacgcaaaga tcaccagcca tgtgccttag    60
tgtccttctt aacagactca aaccacatgg accacgaata ttctttc                 107

<210> SEQ ID NO 167
<211> LENGTH: 521
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Affymetrix ID 2584025

<400> SEQUENCE: 167

```
ctttgcatag attccctgag caggatttta atcttttct aactggactg gttcaaatgt      60
tgttctcttc tttaaaggga tggcaagatg tgggcagtga tgtcactagg gcagggacag    120
gataagaggg attagggaga gaagatagca gggcatggct gggaacccaa gtccaagcat    180
accaacacga gcaggctact gtcagctccc ctcggagaag agctgttcac agccagactg    240
gcacagtttt ctgagaaaga ctattcaaac agtctcagga aatcaaatat gcaaagcact    300
gacttctaag taaaaccaca gcagttgaaa agactccaaa gaatgtaag ggaaactgcc     360
agcaacgcag gcccccaggt gccagttatg ctataggtg ctacaaaaac acagcaaggg     420
tgatgggaaa gcattgtaaa tgtgctttta aaaaaaata ctgatgttcc tagtgaaaga     480
ggcagcttga aactgagatg tgaacacatc agcttgccct g                       521
```

<210> SEQ ID NO 168
<211> LENGTH: 117
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Affymetrix ID 2722002

<400> SEQUENCE: 168

```
cttcctcacg tggacaggtg tgctagtcca ggcagttcac ttgcagtttc cttgtcctca     60
tgcttcgggg atgggagcca cgcctgaact agagttcagg ctggatacat gtgctca       117
```

<210> SEQ ID NO 169
<211> LENGTH: 144
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Affymetrix ID 3312464

<400> SEQUENCE: 169

```
tatgcgacac cactgacact gcttttactg agcatgcaat ccggagaagc tccttttcag     60
cagttttctc tagagcagat caatttaaga agcagttacc atcaatgcaa ttatgtgccc    120
ctgcgctcct gaacgctggt caga                                           144
```

<210> SEQ ID NO 170
<211> LENGTH: 764
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Affymetrix ID 3263773

<400> SEQUENCE: 170

```
agccattacg ggagcacagc atgtgctgac tactgtactt ccagacccct gccctcttgg     60
gactgcccag tccttgcacc tcagagttcg ccttttcatt tcaagcataa ggcaataaat    120
acctgcagca acgtgggaga aagaagttgc tggaccagga gaaaggcag ttatgaagcc     180
aattcatttt gaaggaagca caatttccac cttatttttt gaactttggc agtttcaatg    240
tctgtctctg ttgcttcggg gcataagctg atcaccgtct agttgggaaa gtaaccctac    300
```

```
agggtttgta gggacatgat cagcatcctg atttgaaccc tgaaatgttg tgtagacacc    360
ctcttgggtc caatgaggta gttggttgaa gtagcaagat gttggctttt ctggattttt    420
tttgccatgg gttcttcact gaccttggac tttggcatga ttcttagtca tacttgaact    480
tgtctcattc cacctcttct cagagcaact cttcctttgg gaaaagagtt cttcagatca    540
tagaccaaaa aagtcatacc ttcgaggtgg tagcagtaga ttccaggagg agaagggtac    600
ttgctaggta tcctgggtca gtggcggtgc aaactggttt cctcagctgc ctgtccttct    660
gtgtgcttat gtctcttgtg acaattgttt tcctccctgc ccctggaggt tgtcttcaag    720
ctgtggactt ctgggatttg cagattttgc aacgtggtac tact                    764
```

<210> SEQ ID NO 171
<211> LENGTH: 222
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Affymetrix ID 3460456

<400> SEQUENCE: 171

```
ttctgagatg gagcaccaaa ctggaaaagg gagagatgag cccattgggg caaatcttta    60
aactcttcta ctatttttaa gcgtacttgt gaaaatgttt acctgtatgt atacatacag    120
aaaaacaaat gagtttgaac tatgattatc cattacttta ttttttttaaa aaagatatct    180 tgccaagtct taaggtggtt ctgcgggtaa atcagggtag ca                      222
```

<210> SEQ ID NO 172
<211> LENGTH: 101
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Affymetrix ID 2598373

<400> SEQUENCE: 172

```
acacttaccg agtgggtgac acttatgagc gtcctaaaga ctccatgatc tgggactgta    60
cctgcatcgg ggctgggcga gggagaataa gctgtaccat c                      101
```

<210> SEQ ID NO 173
<211> LENGTH: 694
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Affymetrix ID 3730395

<400> SEQUENCE: 173

```
cccttctttg cagagcccga ggagcctccc ctgtcccctc gggcagatct gttgtgtctc    60
tcttcccacc tggcagcctc agctctgtgc ccctcaccct gctccctctc gccccttctc    120
tcccacccct tccttctgag ccgggccctg gggattgggg agccctcttg ttcctgatga    180
gggtcagctg agggggctga gcatccatca ctcctgtgcc tgctgggtg gctgtggggc     240 gtggcaggag gggcctaggt gggttgggcc tgagaaccag gcacgggtg tggtgtctgc     300 tgggctggag ataagactgg ggagagacac cccaacctcc cagggtggga gctgggccgg    360
```

```
gctgggatgt catctcctgc cgggcggggg agggctctgc ccctggaaga gtccctgtg        420 gggaccaaaa taagttccct aacatctcca gctcctggct ctggtttgga gcaaggggaa       480
gggttgccag agtcctgggg gccccagagg agcaggagtc tgggagggcc cagagttcac       540
cctctagtgg atccaggagg agcagcaccc gagccctgga gtggcccagt acccttccaa       600
gaggccacag tcccagccag gacaaagtat gcggcccatc ctggtgcgac agcgtgggac       660
aatgtgaaca tggactcgaa gacatggccc tttc                                   694
```

<210> SEQ ID NO 174
<211> LENGTH: 162
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Affymetrix ID 2377256

<400> SEQUENCE: 174

```
agttgacact gttcaggttt actgagtatg gatctaatgt gctatggtgg aaatatgaac        60
ttgaccaaga ttgcaggatt aaatggtctc taatttattg tagccaggt ttttcatact        120 aatactttt actttatttg gaagcggact tggattgtac ta                           162
```

<210> SEQ ID NO 175
<211> LENGTH: 74
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Affymetrix ID 3312484

<400> SEQUENCE: 175

```
cctggggttg catttgcaca cactgttaat gaataggga cgaacactgc aacatgaggg         60
tgcgatcagt tatc                                                          74
```

<210> SEQ ID NO 176
<211> LENGTH: 31
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Affymetrix ID 3451913

<400> SEQUENCE: 176

```
agggagacga tggactgagc tgatccgcac c                                       31
```

<210> SEQ ID NO 177
<211> LENGTH: 700
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Affymetrix ID 2400178

<400> SEQUENCE: 177

```
tgttggcatt cttcgctgat ttggctgttc ccaatgttta cattatttaa tcttgcaaaa        60
```

```
atggttctgt gcacttggat gtgaaatgct gtccagtttt attttttta tgttgttatc      120 cttggatgta caaaaaattc agaaaatgat ctctgtagat attctgtttt attttggtca     180
tctttagaag ttatcaggaa tgtgtttaaa acaagaagag aacttttcta aggaatgata     240
catagaaaag atttattttt aaaatgagtt gtaaagcttg tgtttctttg ttgctgcaag     300
ctatctgccc aagttaatgc aaatggacac attttttatg tcagaaaaac acacacacac    360
acacacacac acacacacac acacgaaaaa caaagaaaaa aatgcttgag cttttttctaa   420 cttcccttg cagtctgttg tgtgagcagc ctgtttattt ctctaatatt atgtcagttt     480
attctcttta atggactgta aaaaaatgta atcacaagag tgccaaatat cttgaaatgc    540
caaaaggcat tttagtttct tttctctgtg ctctgagtcc acgtacagga atgcttggag    600
tgtcttttct gttatttata gggattctct taaggcacac cagctgcctg ttttgcatgg    660
tatttgcaaa aatgcctctt gcgtgaggaa atcttttacc                          700
```

<210> SEQ ID NO 178
<211> LENGTH: 62
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Affymetrix ID 2451596

<400> SEQUENCE: 178

```
gggatagtga ggcatcgcaa tgtaagactc gggattagta cacacttgtt gattaatgga      60
aa                                                                      62
```

<210> SEQ ID NO 179
<211> LENGTH: 86
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Affymetrix ID 2827686

<400> SEQUENCE: 179

```
aaaaggatca taaggtgcgt ttggcaattg gaaatggcat acggagtgat gtatggagag      60
aatttttaga cagatttgga aatata                                           86
```

<210> SEQ ID NO 180
<211> LENGTH: 65
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Affymetrix ID 2685329

<400> SEQUENCE: 180

```
gaaatgattt tatatacaac cgtgcatgca tttctgtatt ggtcggctta tctggatgca      60
atttt                                                                  65
```

<210> SEQ ID NO 181
<211> LENGTH: 85
<212> TYPE: DNA
<213> ORGANISM: Artificial Sequence
<220> FEATURE:

<223> OTHER INFORMATION: Description of Artificial Sequence: Synthetic
      oligonucleotide
<220> FEATURE:
<223> OTHER INFORMATION: Affymetrix ID 2584058

<400> SEQUENCE: 181
ggatcactac ttgtgtgatg tgacatgggc aacacaagaa agaatttctt tgcagtggct    60
caggaggatt cagaactatt cggtc                                          85

<210> SEQ ID NO 182
<211> LENGTH: 63
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Affymetrix ID 2598306

<400> SEQUENCE: 182
gcccacagtg gagtatgtgg ttagtgtcta tgctcagaat ccaagcggag agagtcagcc    60
tct                                                                  63

<210> SEQ ID NO 183
<211> LENGTH: 98
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Affymetrix ID 3928671

<400> SEQUENCE: 183
cagaggcttc taatcgtcgc atttactggc tccagtgcaa cacatccatc tgaaaacact    60
cggaagtctg gtgcttggag agggtgccat tgtctctt                            98

<210> SEQ ID NO 184
<211> LENGTH: 269
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Affymetrix ID 3069235

<400> SEQUENCE: 184
tcccagtctg acatacccttt tctaaaatgt tcacagtgca gtgttttgt ggcctaacaa    60 aatttttctc atatcattaa aaataaacat ttttataaaa aatataacac tttaaatgtt   120
tacgtcgaca aaaccagtta gagtaaccta caccacatgc actatacagt agcaagcaca   180
aaattccaca gaatgaagca tcacaaagtt ctgctcaggg tggctattcc atctaggtga   240
aatagctggg attttcaatt gcctttttc                                     269

<210> SEQ ID NO 185
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Affymetrix ID 2562462

```
<400> SEQUENCE: 185
acacagcacc ctatccagac acatac                                              26

<210> SEQ ID NO 186
<211> LENGTH: 264
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Affymetrix ID 2632440

<400> SEQUENCE: 186
ctgccacttg aaatgcatca cagtaccagc aggcacgtgg caatcttacc tccttacttc         60
tttgattaca atgatacgat attcactata tccctctgtg gttgtccttt tgttaaaatt        120
tgttctggtt ttcatagttc cttttgtact tcaacaatca cattttggca acttactctg        180
gtaattaaaa gttggattca aggaaaacta tgaactccca catttgttca ttctcctttc        240
catccctgaa ttctgtcttt tgta                                              264

<210> SEQ ID NO 187
<211> LENGTH: 140
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Affymetrix ID 3420356

<400> SEQUENCE: 187
atccaaggga tatgttgcag gtgtcttaag agtcaggtaa aaggcaagat gattcattat         60
atctgttctt tttgtgatac ccatgtaact acctataagc ttcaaagtga aataaacatt        120
acctcttgta ccttagcccg                                                   140

<210> SEQ ID NO 188
<211> LENGTH: 567
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Affymetrix ID 3263784

<400> SEQUENCE: 188
actgccagag tctaaccagc ggttcatttt agttttgcct caaggtggat ggtctctggt         60
tcccccttga ctagaaatct ggggtgtggg tagcctccca aaaggatggc tctgtaagcg        120
ggtctcacca gcaccttcaa caaaccccg tgtgaagaag gtcagaggcg gggaagcccc        180
tctgcttgtg gcctgacaac atttttatc taaagattct gagtaggtag tggttatttt        240
catttctaaa aagcatactt ttttgtggag gtggaggtgc attttaacat ctctaaaacc        300
tgggtgcatc ttaggatcaa cagtgtctta ggtttgatga aatacaccat ataggctagg        360
cttggtagct catgcctata atcccagcac ttcaggaggc tgaggtagga agatcgcttg        420
aggccaggag ttgaagacca ttctgggcaa catagcaaga actcatctct accaaaaaaa        480
ttataaaatt agccaggcat ggtggtacat gcctgtaggc ccagctactc gggagactga        540
gacggtagga tctcttcagc gtaggaa                                           567
```

<210> SEQ ID NO 189
<211> LENGTH: 404
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Affymetrix ID 3769232

<400> SEQUENCE: 189

```
caacagtgcc atagtgacat ccttaaaatg tctgattcaa gtatactctt agagggatag      60
aaaactactc ctttctcaat aatcaaaata gagttcactt tgtctacatt ttgttttaaaa    120 ataggataac caggaatcta tggctcctcc caaaaatata gtgcccttcc agatatgggc    180
aaaaattctt taaagggaa taaatccgaa gtaaatccaa cagggaatct gcttgcaata     240
gagaagcaac acacatctgg gaatcaaccc cagatattca tggtgagtcc cctccgtctg    300
cattctaatg acatgtgtac attaattaag gagacccagt caataaggac aaatattttg    360
aaggtaaaat gcagcaatca atgtcgtgca ttacctgtgt cttg                      404
```

<210> SEQ ID NO 190
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Affymetrix ID 2377249

<400> SEQUENCE: 190

```
aatgtcccag ctacaatagt cacaccaaca cc                                   32
```

<210> SEQ ID NO 191
<211> LENGTH: 57
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Affymetrix ID 2377248

<400> SEQUENCE: 191

```
agagactcca tcagttcttc aaaaacacac cacagaaaat gtttcagcta caagaac       57
```

<210> SEQ ID NO 192
<211> LENGTH: 95
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Affymetrix ID 3067479

<400> SEQUENCE: 192

```
tgagtgtgaa tgtccaagta atggtgtatg taatggtaca ggcaaatgtg actggatttc    60
cctcaaaaaa gtaactatta aacagtcttg atctc                               95
```

<210> SEQ ID NO 193
<211> LENGTH: 33
<212> TYPE: DNA
<213> ORGANISM: Artificial Sequence
<220> FEATURE:
<223> OTHER INFORMATION: Description of Artificial Sequence: Synthetic
       oligonucleotide
<220> FEATURE:
<223> OTHER INFORMATION: Affymetrix ID 3020359

<400> SEQUENCE: 193
gtagaagcat tgccaggat tgacaaacga tag                                    33

<210> SEQ ID NO 194
<211> LENGTH: 42
<212> TYPE: DNA
<213> ORGANISM: Artificial Sequence
<220> FEATURE:
<223> OTHER INFORMATION: Description of Artificial Sequence: Synthetic
       oligonucleotide
<220> FEATURE:
<223> OTHER INFORMATION: Affymetrix ID 3451874

<400> SEQUENCE: 194
atggttttag ggctcttcga gaggataatg cctactgtga ag                         42

<210> SEQ ID NO 195
<211> LENGTH: 572
<212> TYPE: DNA
<213> ORGANISM: Artificial Sequence
<220> FEATURE:
<223> OTHER INFORMATION: Description of Artificial Sequence: Synthetic
       polynucleotide
<220> FEATURE:
<223> OTHER INFORMATION: Affymetrix ID 2491744

<400> SEQUENCE: 195
ggaatgggtc cctagcttgc acaacccag ctgagctttc agcagataaa tcacagcaga       60
aatagaatca ccctaggact ttcaatcaaa agctggaagt ccaccttaca gaaagacaaa     120
aagaaacccc tttttatatc ttaacaaagc aatagctctc aagcagcaga gcatctcgag     180
gaagaaagct tgcccggtcg ccatcccatc atgccagagc gtgcagtgtc cacccttgac    240
tacgctgggg aattgctgat tttttgaaaa agcttaactt aacaatttct gatgtctatc    300
ttttagagtt ctgtatgttc ccatttttta ttcttctgaa ttttgaattg caagtagctg    360
taaaatccaa tctttgagtg catgggggtg ggtgtgaggc ggggctcagc ttcaaccccc    420
tgtcctgtaa agcagtggct ggttttttcct gagcccagcc ctgggaggtc gtggtaggtg   480
tggaggctgc agagctcctc cagatgctgc cctcgctgtg cctcacacca gagaggatgg    540
aagtgggctc tggtgtcaga ctgtggttga gc                                  572

<210> SEQ ID NO 196
<211> LENGTH: 210
<212> TYPE: DNA
<213> ORGANISM: Artificial Sequence
<220> FEATURE:
<223> OTHER INFORMATION: Description of Artificial Sequence: Synthetic
       polynucleotide
<220> FEATURE:
<223> OTHER INFORMATION: Affymetrix ID 3464875

<400> SEQUENCE: 196
aactcatttt caggccgtgt cgacatcctg ttcctcctaa tgggccgtcc cctgtgactt      60
ccctctctct tttaaaatgc ctgaataccct ccattgttag ctgcacaaca tttggagcat   120
aatttaatag acccttgcag tctggttgtc tgtgtaaaag gcattcacga acatattgca    180
gggtttctgg tattcacatg ccgaggcaaa                                      210

<210> SEQ ID NO 197
<211> LENGTH: 26
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Affymetrix ID 2584067

<400> SEQUENCE: 197
cagtgcctac tctgctctgt ggtggt                                        26

<210> SEQ ID NO 198
<211> LENGTH: 309
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: Affymetrix ID 2722005

<400> SEQUENCE: 198
atgggctttg attagctgtc ctctctccat gcctgcaaag ctccagattt ttggggaaag    60
ctgtacccaa ctggactgcc cagtgaactg ggatcattaa gtacagtcga gcacacgtgt   120
gtgcatgggt caaagggtg tgttccttct catcctagat gccttctctg tgccttccac    180
agcctcctgc ctgattacac cactgccccc gccccaccct cagccatccc aattcttcct   240
ggccagtgcg ctccagcctt atctaggaaa ggaggagtgg gtgtagccgt gcagcaagat   300
tggggcctc                                                          309

<210> SEQ ID NO 199
<211> LENGTH: 101
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: Affymetrix ID 3721357

<400> SEQUENCE: 199
ctccagccgc gacttgatgt ccatgagccg ctggtactcc tgattctgcc gctcactatc    60
agctcgcaca tcgcccagct gggcttcaat accgctgatc a                       101

<210> SEQ ID NO 200
<211> LENGTH: 137
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: Affymetrix ID 3020391

<400> SEQUENCE: 200
tgggcagtga attagttcgc tacgatgcaa gagtacacac tcctcatttg gataggcttg    60
taagtgcccg aagtgtaagc ccaactacag aaatggtttc aaatgaatct gtagactacc   120
gagctacttt tccagaa                                                  137

<210> SEQ ID NO 201
<211> LENGTH: 45

<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Affymetrix ID 3868840

<400> SEQUENCE: 201
gcctctgtcc ctcctactca acctgcttta tctctaggcc ttcct                45

<210> SEQ ID NO 202
<211> LENGTH: 238
<212> TYPE: DNA
<213> ORGANISM: Artificial Sequence
<220> FEATURE:
<223> OTHER INFORMATION: Description of Artificial Sequence: Synthetic
polynucleotide
<220> FEATURE:
<223> OTHER INFORMATION: Affymetrix ID 3306643

<400> SEQUENCE: 202
gcttcacgga cgtgggctga aacccgccc gcgccgcgct gagcagggcc gagggagccg      60
gccagggccc cagaggagtc cggaacggat tcccgtcgct accgaggtct gcgcgtgtaa    120
ggagaggacg tcggagattt gcctcgaggg gtggggtata gatgactgga gaggtcaggc    180
gcgggttggt catcgctgag gctgggtgat gggtggccgg attcgttata ctgttttc     238

<210> SEQ ID NO 203
<211> LENGTH: 137
<212> TYPE: DNA
<213> ORGANISM: Artificial Sequence
<220> FEATURE:
<223> OTHER INFORMATION: Description of Artificial Sequence: Synthetic
polynucleotide
<220> FEATURE:
<223> OTHER INFORMATION: Affymetrix ID 2721994

<400> SEQUENCE: 203
atctctgcca agtatcgctg gttcgccgtc ttctacctga tcatcttctt cttcctgatc     60
ccgctgacgg tgtttggcct ctcgctggcc ggctggcggg tgctggttgg tgtcggggtt    120
cccgtcgtct tcatcat                                                   137

<210> SEQ ID NO 204
<211> LENGTH: 272
<212> TYPE: DNA
<213> ORGANISM: Artificial Sequence
<220> FEATURE:
<223> OTHER INFORMATION: Description of Artificial Sequence: Synthetic
polynucleotide
<220> FEATURE:
<223> OTHER INFORMATION: Affymetrix ID 3329532

<400> SEQUENCE: 204
tatagtcctt ccttactgac tcctaggccc atccccagct gatggagaag ctaagcagaa     60
actgcagcta agacagagat tcaaaaggta attgtggtga ggggttcaca gggtagggga    120
agaacaaccc aaagaactca caggagctaa gaaaacataa gaaaaacatg agcaagagaa    180
agaagcgcct ttttcccctc ctttcctctt gttaaatgat gattgacaca cccgggctca    240
atttccagtt cattacgtaa cactctgagc aa                                  272

<210> SEQ ID NO 205
<211> LENGTH: 77
<212> TYPE: DNA

```
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Affymetrix ID 2377247

<400> SEQUENCE: 205
ttccaaggtc ccaccaacag ttcagaaacc taccacagta aatgttccaa ctacagaagt    60
ctcaccaact tctcaga                                                  77

<210> SEQ ID NO 206
<211> LENGTH: 140
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Affymetrix ID 2558642

<400> SEQUENCE: 206
tctgtaatgt gttaatgtga ttagcagtta ttttccttaa tatctgaatt atacttaaag    60
agtagtgagc aatataagac gcaattgtgt ttttcagtaa tgtgcattgt tattgagttg   120
tactgtacct tatttggaag                                              140

<210> SEQ ID NO 207
<211> LENGTH: 97
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Affymetrix ID 2830378

<400> SEQUENCE: 207
tgcttgcacc cacagtccat agacatccaa ccgcccaatg catatccaac ctcagcaact    60
ttacaatccc caacgccagc ccacaacttg actttta                            97

<210> SEQ ID NO 208
<211> LENGTH: 35
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Affymetrix ID 2477456

<400> SEQUENCE: 208
ttccagttct gcatctgata ccgtctcctt tccct                              35

<210> SEQ ID NO 209
<211> LENGTH: 79
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Affymetrix ID 3451868

<400> SEQUENCE: 209
tgagtgtgct gaagggcgcc attactgtcg tgaaaataca atgtgtgtca acaccccggg    60
```
ttcttttatg tgcatctgc                                                    79

<210> SEQ ID NO 210
<211> LENGTH: 112
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Affymetrix ID 3087225

<400> SEQUENCE: 210
gttttagagc tgtttactca ttagtaaagg accgcaatgt tagtaaagaa aacctatgaa      60
atgtatgtta aagattctta gtattgtaca gggataaagc aaatgcatga aa             112

<210> SEQ ID NO 211
<211> LENGTH: 60
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Affymetrix ID 3020384

<400> SEQUENCE: 211
gcatgtcaac atcgctctaa ttcagagata atctgttgta ccactccttc cctgcaacag      60

<210> SEQ ID NO 212
<211> LENGTH: 56
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Affymetrix ID 2735072

<400> SEQUENCE: 212
tttggtggtg tcaattgctt atttgttttc ccacggttgt ccagcaatta ataaaa          56

<210> SEQ ID NO 213
<211> LENGTH: 101
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Affymetrix ID 2598353

<400> SEQUENCE: 213
gacgttttat caaattggag attcatggga gaagtatgtg catggtgtca gataccagtg      60
ctactgctat ggccgtggca ttggggagtg gcattgccaa c                        101

<210> SEQ ID NO 214
<211> LENGTH: 597
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Affymetrix ID 3385809

<400> SEQUENCE: 214

```
acgttgatga gcctaggcct ttgcagacct cttacagtta ctctgtcaca gcccttcaaa     60
ggttctttga cttcagatta agaatcaatt gcatgtggaa tgcatgtgca aaggaagaga   120
tattcaaggc aattgttacc atgtaccata aaccttgtac ataattttt gtcattttct    180 tttcctctgt ctctatccct tcttctttga cacacaatag acacctagtc aatttattac   240
aaaaaaaatg aatgaatgaa gtggaattca gttgggaaat aggttaaata aattatttag   300
gagatgagga ataggtaaaa agagacaagt acatagttta ttcttttgac ttagaaaact   360
tttgattctt aaattctgca gaattggaga aactggtggg gaaacttcta aaatcattat   420
ttaattacca gagatgtaat agatatagac aaaagcagtt ttcttctttt attattttt    480 catcagttag ttcttagctt aaatagtagt ccaaagctgg tagggacaga gggaattagc   540
tggtggctga atgaggaatt gtatcacttt ttgtgaatca cggtgtaagc acatttg      597
```

<210> SEQ ID NO 215
<211> LENGTH: 70
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Affymetrix ID 2721985

<400> SEQUENCE: 215

```
gttccctcga ctgctaactg cacctcccct tccctctgtt ggacggatgg catccaaaac    60
tggaccatga                                                            70
```

<210> SEQ ID NO 216
<211> LENGTH: 137
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Affymetrix ID 3020363

<400> SEQUENCE: 216

```
agcgcgccgt gatgaatatc gaacagagtt taccacagct ttgcagcgcg ttgacttatt    60
catgggtcaa ttcagcgaag tcctcttaac atctatatcc accttcatta aaggagacct  120
caccatagct aatcttg                                                  137
```

<210> SEQ ID NO 217
<211> LENGTH: 153
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Affymetrix ID 2437139

<400> SEQUENCE: 217

```
actctggtgc acaacggcac ctctgccagg gctaccacaa ccccagccag caagagcact    60
ccattctcaa ttcccagcca ccactctgat actcctacca cccttgccag ccatagcacc  120
aagactgatg ccagtagcac tcaccatagc acg                                153
```

<210> SEQ ID NO 218
<211> LENGTH: 105
<212> TYPE: DNA

<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: Affymetrix ID 3460453

<400> SEQUENCE: 218

```
tttacctgac tcttaagaca cctgcaacat atcccttgga tgttccgcct tgtcacactc    60
ataaccgagg ggaaaaagaa gacaaaggtg aatgctcagt tagcc                    105
```

<210> SEQ ID NO 219
<211> LENGTH: 78
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Affymetrix ID 3020356

<400> SEQUENCE: 219

```
cattgatgcc aataagataa aactagacct cagtggctcc tcctcaactc cacccaatct    60
atttgtctcc aaagtgct                                                  78
```

<210> SEQ ID NO 220
<211> LENGTH: 336
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: Affymetrix ID 2830183

<400> SEQUENCE: 220

```
ggaagtatcc agacaccaat ttttaataaa atgaattccc caaagggagt cttgactgaa    60
ttaaggctgt tgtttatagg aagccagata taatgatgtg aaaaaaacta attttttaata  120 ataatcaccg gcagtaacgg gggcaggggg aaaaagtaca gtgtggtgta tttttttgttt  180 ttttcttttt cacaacatct acaggacaca agagaagcac ttagacactg taaggctggg   240
aaccatgctg taataaccac cagtgtgggt aatcaaaaag ggtctttgac atttaagagg   300
gttggggctc cctgcactgt cagaattcca cgtaaa                              336
```

<210> SEQ ID NO 221
<211> LENGTH: 129
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: Affymetrix ID 2562444

<400> SEQUENCE: 221

```
acctaccacg acctcccagg gctgggctca ggaaaaacca gccactgctt tacaggacag    60
ggggttgaag ctgagccccg cctcacaccc accccatgc actcaaagat tggattttac    120
agctacttg                                                           129
```

<210> SEQ ID NO 222
<211> LENGTH: 110
<212> TYPE: DNA
<213> ORGANISM: Artificial Sequence
<220> FEATURE:
<223> OTHER INFORMATION: Description of Artificial Sequence: Synthetic
polynucleotide
<220> FEATURE:
<223> OTHER INFORMATION: Affymetrix ID 2830181

<400> SEQUENCE: 222
gataagtcta cgtggaaaag cattcagaat ttactaggtt tttgctacat cactatttca    60
tctacaatag ggacaacaaa ctgacactca ggatttgatg ggctctcatt              110

<210> SEQ ID NO 223
<211> LENGTH: 573
<212> TYPE: DNA
<213> ORGANISM: Artificial Sequence
<220> FEATURE:
<223> OTHER INFORMATION: Description of Artificial Sequence: Synthetic
polynucleotide
<220> FEATURE:
<223> OTHER INFORMATION: Affymetrix ID 2764175

<400> SEQUENCE: 223
acacacgtgt gctcgactgt acttaatgat cccagttcac tgggcagtcc agttgggtac    60
agctttcccc aaaaatctgg agctttgcag gcatggagag aggacagcta atcaaagccc   120
atctgtggga aaatggaaaa atgtttggaa agagattcca gtgggtgggt ggatggaaag   180
aaggaagtta acccaggaag tcatcttgca cagaaagtaa ggaggcagag aggggtggag   240
agctattcca ggtgcagata ctccctggga ttcaaggtgg cagcatgcag gctacgagcc   300
tggataactt gcacgtttta tttcaaaaga tccaacaggg agggcttttg ttatctgacc   360
aagagaggag cgttagactt tagccacaat gcttttgaat tgggcttctt agtttgctaa   420
attaagaatc tggggccctt ttggcagaat gctatgctac tcattcctca ctttcttctc   480
ctccatctgc cccactctct gtctcttagg aagacaagag cagcaggtga gcacatgtat   540
ccagcctgaa ctctagttca ggcgtggctc cca                                573

<210> SEQ ID NO 224
<211> LENGTH: 46
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Affymetrix ID 3907240

<400> SEQUENCE: 224
tgacttggaa gactccatga tcggccctga agttgtccat cccttg                   46

<210> SEQ ID NO 225
<211> LENGTH: 31
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Affymetrix ID 3917721

<400> SEQUENCE: 225
gctggggcta tggatgctac acaaaggaac t                                   31

<210> SEQ ID NO 226
<211> LENGTH: 73
<212> TYPE: DNA

<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Affymetrix ID 2442021

<400> SEQUENCE: 226
aggcagaatg tgctaccagt ggtcatgaag acatgcctgt ggagaggatt ctagaagctg    60
aacttgctgt tga                                                      73

<210> SEQ ID NO 227
<211> LENGTH: 640
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Affymetrix ID 3907235

<400> SEQUENCE: 227
tccagctctg attacctttg aagtgttcag aagagacatt gtcttctact gttctgccag    60
gttcttcttg agctttgggc ctcagttgcc ctggcagaaa aatggattca acttggcctt   120
tctgaaggca agactgggat tggatcactt cttaaacttc cagttaagaa tctaggtccg   180
ccctcaagcc catactgacc atgcctcatc cagagctcct ctgaagccag ggggctaacg   240
gatgttgtgt ggagtcctgg ctggaggtcc tcccccagtg gccttcctcc cttcctttca   300
cagccggtct ctctgccagg aaatggggga aggaactaga accacctgca ccttgagatg   360
tttctgtaaa tgggtacttg tgatcacact acgggaatct ctgtggtata tacctggggc   420
cattctaggc tctttcaagt gacttttgga aatcaaccttt ttttatttgg gggggaggat   480
ggggaaaaga gctgagagtt tatgctgaaa tggatttata gaatatttgt aaatctattt   540
ttagtgtttg ttcgtttttt taactgttca ttcctttgtg cagagtgtat atctctgcct   600
gggcaagagt gtggaggtgc cgaggtgtct tcattctctc                         640

<210> SEQ ID NO 228
<211> LENGTH: 62
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Affymetrix ID 3451838

<400> SEQUENCE: 228
aatggattcg ttatgtgtcg acggatggtc tgtgactgtg agaatcccac agttgatctt    60
tt                                                                  62

<210> SEQ ID NO 229
<211> LENGTH: 126
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Affymetrix ID 3769234

<400> SEQUENCE: 229
tcacgattgt caatggctag gattgttcaa cttgccagag cccagagcgg aaacccaaaa    60

```
ttaccagaaa agagattcta ctttgctgag ggttggggat gggcaggtag ctatgccaca    120
cttttt                                                              126

<210> SEQ ID NO 230
<211> LENGTH: 185
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Affymetrix ID 3577636

<400> SEQUENCE: 230
gaccctttga agtcaaggac accgaggaag aggacttcca cgtggaccag gtgaccaccg    60
tgaaggtgcc tatgatgaag cgtttaggca tgtttaacat ccagcactgt aagaagctgt   120
ccagctgggt gctgctgatg aaatacctgg gcaatgccac cgccatcttc ttcctgcctg   180
atgag                                                              185

<210> SEQ ID NO 231
<211> LENGTH: 113
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Affymetrix ID 2377236

<400> SEQUENCE: 231
cgtacaagtt ttcccgagga tactgtaata acgtacaaat gtgaagaaag ctttgtgaaa    60
attcctggcg agaaggactc agtgatctgc cttaagggca gtcaatggtc aga          113

<210> SEQ ID NO 232
<211> LENGTH: 123
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Affymetrix ID 2435391

<400> SEQUENCE: 232
gcagaaatga gcagttcgct cctccctgat aagagttgtc ccaaagggtc gcttaaggaa    60
tctgccccac agcttccccc atagaaggat ttcatgagca gatcaggaca cttagcaaat   120
gta                                                                123

<210> SEQ ID NO 233
<211> LENGTH: 553
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Affymetrix ID 2400186

<400> SEQUENCE: 233
ccctgtctct ccgttctagc tcgtccccca ccccacccttt tcttctttct cctcctctcc    60
ttcctctccc cctctcctct gtctccttcc accgtctccc ctgcctccct gtctttcagt   120
```

```
cctgttttt cagccccgtc tccctctcgg tttctctccc ccaccctccc tccgggtttc    180
ctccccggtg ccctccctcc tctctccctc ccctcccct ccgcccctcg cagccccgcc     240
gctcgcagct cccagtctgc ctccccgaac cggcgccgcc gcccgcactc gccgcaggac    300
cggcccgccc ggctcccggg gtgcgccctc tccgtcccg cgcctccgg gctcgcaggg      360 acgtctcctc cctcccggct cgcggccccg cccggcccgg ccccgccca gagccccagc    420 gcgccgagga tgtgagtcct gctcgcctct ggcggagcag cagccactcg cgcgcggagc    480
cggagcgcag cgcagcgcag ccgcgggcgc tctccgggcc gctcgcgcga gtgccgcgct    540
cttgccctag cgg                                                       553
```

```
<210> SEQ ID NO 234
<211> LENGTH: 238
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Affymetrix ID 2751991

<400> SEQUENCE: 234
ccctagggct agtatgcacc atattgcatt taaaaaaatg tttggaaagc tgttggaaac    60
tttttgtcaa cacgtccaca tttgcagtaa tattctgtgg ctttgaatgt aaatttagga   120
atttatcatg ttcacaaata aaggagagat gaagtttact aataataaaa tgaaactgat    180
aatcagtttt gaatctaagc agttgtttca gaggcggttt catgtgagtc tttgatta     238
```

```
<210> SEQ ID NO 235
<211> LENGTH: 64
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Affymetrix ID 2377265

<400> SEQUENCE: 235
tttaaaagat agaaagatgc tcatcctagt gacagaccaa gagacaatac aacccaaatt    60
ggac                                                                 64
```

```
<210> SEQ ID NO 236
<211> LENGTH: 94
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Affymetrix ID 3464878

<400> SEQUENCE: 236
cttgtggtgt tcttgcgcc gggctgcggt tcttacaagc tgtgaaaact actacggctt     60
ctcaggttag atgattgctt ttctcgttct ggca                                94
```

```
<210> SEQ ID NO 237
<211> LENGTH: 83
<212> TYPE: DNA
<213> ORGANISM: Artificial Sequence
<220> FEATURE:
<223> OTHER INFORMATION: Description of Artificial Sequence: Synthetic
      oligonucleotide
```

<220> FEATURE:
<223> OTHER INFORMATION: Affymetrix ID 3835890

<400> SEQUENCE: 237
cgcgcagcct gcagcgggag accctgtccc cgccccagcc gtcctcctgg ggtggaccct    60
agtttaataa agattcacca agt                                           83

<210> SEQ ID NO 238
<211> LENGTH: 124
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Affymetrix ID 2721999

<400> SEQUENCE: 238
cccattagcg aatgaaattg atgcagtcct acctaactcg attccctttg gcttggtggt    60
aggcctgcag ggcactttta ttccaacccc tggtcactca gtaatctttt actccaggaa   120
ggca                                                                124

<210> SEQ ID NO 239
<211> LENGTH: 126
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Affymetrix ID 3125505

<400> SEQUENCE: 239
ttgcctgtgt caatgaatcc tgttctcact acctgggatt ttccattcac cctcctcctt    60
caccaccccc acccatacac acatattcca gatccaacgg gcagcctcca tcatgtcaca   120
ctcttc                                                              126

<210> SEQ ID NO 240
<211> LENGTH: 81
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Affymetrix ID 2562443

<400> SEQUENCE: 240
tcagcaattc cccagcgtag tcaagggtgg acactgcacg ctctggcatg atgggatggc    60
gaccgggcaa gctttcttcc t                                             81

<210> SEQ ID NO 241
<211> LENGTH: 79
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Affymetrix ID 2453163

<400> SEQUENCE: 241
acttgtaggg aatcacggca ccttaattgt ccaatttggg ttgtattgtc tcttggtctg    60
tcactaggat gagcatctt                                         79

<210> SEQ ID NO 242
<211> LENGTH: 55
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Affymetrix ID 3263752

<400> SEQUENCE: 242
gttctggcaa gtccatatca gctcatgtct agattaccca tgaaatcctc ccatc        55

<210> SEQ ID NO 243
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Affymetrix ID 3825012

<400> SEQUENCE: 243
ggctggtctg atggaactgt gtatttattt                              30

<210> SEQ ID NO 244
<211> LENGTH: 224
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Affymetrix ID 2377237

<400> SEQUENCE: 244
ccgtgtttga tactgatacc tagtagaatt aaaagaaatg aagatttctt gttttaggtg    60
aatatacata cagtcatcca caccttatgt gcccttttgat ttcataaaat atatattggc  120
attatcttgg aggaaaaaaa tctgttactt acatagccct gtattagctt tgagatatat  180
gagtagagat aaagataaag agacccgata acctgacttt gaac                   224

<210> SEQ ID NO 245
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Affymetrix ID 3907194

<400> SEQUENCE: 245
accctgagac ttggctccac cactgatatc ctcctttggg gaaaggct              48

<210> SEQ ID NO 246
<211> LENGTH: 60
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Affymetrix ID 2377268

<400> SEQUENCE: 246
ggcacacgtg tttcacgttg acaggtttgc ttgggacgct agtaaccatg ggcttgctga    60

<210> SEQ ID NO 247
<211> LENGTH: 67
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Affymetrix ID 3343458

<400> SEQUENCE: 247
ttaagttaat cttcacgttt ttgcaaactt tgattttat ttcatctgaa cttgtttcaa    60
agattta                                                             67

<210> SEQ ID NO 248
<211> LENGTH: 572
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Affymetrix ID 2377271

<400> SEQUENCE: 248
ggcagtcctg gaatcacatt cttagcacac ctacacctct tgaaaataga acaacttgca    60
gaattgagag tgattccttt cctaaaagtg taagaaagca tagagatttg ttcgtattta   120
gaatgggatc acgaggaaaa gagaaggaaa gtgatttttt tccacaagat ctgtaatgtt   180
atttccactt ataaggaaa taaaaaatga aaaacattat ttggatatca aaagcaaata    240
aaaacccaat tcagtctctt ctaagcaaaa ttgctaaaga gagatgaacc acattataaa   300
gtaatctttg gctgtaaggc attttcatct ttccttcggg ttggcaaaat attttaaagg   360
taaaacatgc tggtgaacca ggggtgttga tggtgataag ggaggaatat agaatgaaag   420
actgaatctt cctttgttgc acaaatagag tttggaaaaa gcctgtgaaa ggtgtcttct   480
ttgacttaat gtctttaaaa gtatccagag atactacaat attaacataa gaaaagatta   540
tatattattt ctgaatcgag atgtccatag tc                                 572

<210> SEQ ID NO 249
<211> LENGTH: 108
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Affymetrix ID 2359172

<400> SEQUENCE: 249
gctaagtgtc ctgatctgct catgaaatcc ttctatgggg gaagctgtgg ggcagattcc    60
ttaagcgacc ctttgggaca actcttatca gggaggagcg aactgctc                108

<210> SEQ ID NO 250
<211> LENGTH: 2882
<212> TYPE: DNA
<213> ORGANISM: Artificial Sequence
<220> FEATURE:
<223> OTHER INFORMATION: Description of Artificial Sequence: Synthetic
      polynucleotide <220> FEATURE:
<223> OTHER INFORMATION: Affymetrix ID 3733280

<400> SEQUENCE: 250

| | | | | | |
|---|---|---|---|---|---|
| acacggtctg | ttggtcagag | gcccaaaaca | gttatacaga | tgacggtact | ggtcaagatg | 60 |
| ggtcaagcaa | gcggccacaa | gggactgagg | caagcacaat | ggtttcaaag | aaagactgta | 120 |
| agctccatga | ttagcataaa | gcactaacca | tgtctccatg | tgacccgatg | gcacatagat | 180 |
| gttgtagaat | aagttatggg | tttttatgtt | ttgttttgtg | tttttccaaa | acttgaactt | 240 |
| gcaggcaagc | cttggttggg | tatttgattt | atccagaatg | cttctcttta | gggaacaagg | 300 |
| atgtttttaa | tggcataaca | aaggcaagac | tctgccttaa | ttttttgaaaa | gctgctaact | 360 |
| acatgaacac | aaatgtgtat | ttttgttgca | gtgtagtttt | cctttttgtgt | aattttaaag | 420 |
| tcagtgttga | attttattga | aagctcatga | tgcgcttcaa | agtggcaagt | atttggctat | 480 |
| taactgccaa | aacaagagcc | tgattttttg | aggccagtaa | ttcgtttgct | agaattgatt | 540 |
| ttttttctct | ctctcttttgt | tacataaggg | cattatgtaa | cactagccga | atggtagcct | 600 |
| ctgggttgtt | gttttttttct | tttcctccat | gatgttaatg | ggttatctca | aatttttaagt | 660 |
| taaactacct | aaaataaata | ccaaagataa | tgcatatttt | tgcacagtgg | agcttacact | 720 |
| taaaagaaaa | caaagcccca | tgggctgcct | tgaaatcaag | agacaataac | tttgaacctc | 780 |
| agcaagacct | tgaaccgccg | gttcattttg | caccttattc | agaaaataga | gcatcatact | 840 |
| caccgagtct | agtcagtgta | gtgcttttaa | aaattttgtc | ctttcatgta | acttttttat | 900 |
| tttaagagga | agaagaagaa | aggggcacac | acacacaata | ccgacgtcta | tcctttcctg | 960 |
| ctaggcagtg | ctggccaggc | tcatgtgtag | tgtgcgagat | ggtgatgtac | tcttatattt | 1020 |
| ttctgggctt | ttcctttttgc | acattccaaa | attcatttca | taagacaaga | tcttcatagg | 1080 |
| acctccttgg | catcctggca | ttctcaaaac | tgagccatcc | agcatgaaag | ataaatgggt | 1140 |
| ttaaaccctt | gctgctgaat | ttattgcctg | gactgtcagg | acatcaccag | cccaccttca | 1200 |
| ccttagggaa | gatgccacac | ctggcctcca | cacttgctct | tctgatcagt | ctgtctggat | 1260 |
| tgagtcctac | agtgtcagat | agggcggcaa | atgccaaagc | agggaaacag | ggaggtgtgg | 1320 |
| acaagccagt | ttgatgcagc | acttcagatc | aagtgcttag | gaaggagagg | aaacttgcct | 1380 |
| tttttatggc | agaggatagt | aatgaaaatg | tctcagtatt | ttagggtcaa | tgagagccat | 1440 |
| aaaaatataa | cataatcaca | agtaaggag | ataatggtct | aaaacagcta | tttcccttttt | 1500 |
| ctgtgtgcat | acttatgact | gaatgtgagc | taagcatttt | ctcctgtgga | gccctagagc | 1560 |
| aggttactaa | ggaaggacac | attgttttcc | agaagcctcc | cctgcctggc | tgactgcctt | 1620 |
| gctagaaaca | taatttttttt | tttctcactg | aagctcaata | atggaactct | ttttttttttt | 1680 |
| tttttttaatt | taaagttccc | tatttgtgaa | ttctgggatt | actgactttt | cttttttaatt | 1740 |
| ggagtctcaa | aatcaactct | cttatggtat | tatatctctg | tatgccatta | aaaaacagct | 1800 |
| tgttctagaa | tcatgtattt | tgtaaactga | tgtttgtgat | ggtctctggt | tcttgaacag | 1860 |
| ccatatctga | atgccgtgcc | tgcaaaacta | tgacaatttt | tgctgttttc | agccttcaga | 1920 |
| tttgatggct | tgggaaactg | aggtgttatt | ttcaatgaaa | caaagaaaga | gatgttaagc | 1980 |
| aagtggttgt | tttagatcca | aatgtaaagg | caggtttggg | aaggtgttta | aagagttgga | 2040 |
| ggaattgggg | attgagttgt | aaagaaaact | tacagaagag | gcaacaattt | ggttcttgac | 2100 |
| agtgagagga | tattgagggc | ttcagctgct | gctattatga | tgttttgcaa | aggaaaataa | 2160 |
| tcaaaccaaa | gagtattcag | tgatatgtaa | attaaatgaa | gatacagtgg | agaatggggg | 2220 |

```
tgaccacaaa agaggctccc cctaaacaca cagtgctgcc acttaaaaag acttgagaaa    2280
tttgaaaggg ggtgggtatg ggggggggcaa gaaagaggga gggaaatctt tcaacttatt   2340
tctgaaaaag agaaaaaaat ataaaatttc tggtgcacag gtttgttttt tcaagaaaat    2400
tttgcagaag ctatgttttt aaagtgtaca ttttataaag tttatcagat attttcatat    2460
ttaaagccaa atgtaaatag aggtctgtaa agaaaaataa ttgccataga aagtataatt    2520
tcagtgcagt aatttctgag agctagtacc tatatgctac cggttagcat ggttttagca    2580
aatatatacc agccttataa ggttcgtatt gctatgttct tctgttattt atttcagcat    2640
ggactgttca tttgaaacct ttttctagtt attagcgttt taacagttac aagctttaaa    2700
tggcaatttt tttttttttt tttttttttt tttttttttt gtcaagagcc aagacacagg    2760
taatgcacga cattgattgc tgcattttac cttcaaaata tttgtcctta ttgactgggt    2820
ctccttaatt aatgtacaca tgtcattaga atgcagacgg aggggactca ccatgaatat    2880
ct                                                                   2882
```

<210> SEQ ID NO 251
<211> LENGTH: 460
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Affymetrix ID 3020355

<400> SEQUENCE: 251

```
cagacttctg ccttatcagt ggccatccca ccctatgttc ttatctcctc agtctaaaaa    60
gaaaaatggg gacccatcag aatttggata gaagaccctc caggaatttc tgccactgct   120
tattcatggg ttggcacaga cactgattca gtgggcacac agagttcaga atgattcaga   180
gcccagatat gtgccctaag tcacatctcc agcgtccagg gaggactgta aagtgctcgt   240
tatcaggaaa atgaaaccaa gggctcagct actcctgaag tcattaaaac tccttccctt   300
gatttttttt tttttttttt taaatagtat atgtggtaac cgaatctagg atcctggata   360
cattccagtc tgctaattac atatttttt ctaactaaaa tgttccaggc aggttcattt    420
gcatgtgaat tacttgctga gccatgttga cttcctattc                          460
```

<210> SEQ ID NO 252
<211> LENGTH: 29
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Affymetrix ID 2453796

<400> SEQUENCE: 252

```
ggaccggttg ggtcagagtt ccatgctgg                                       29
```

<210> SEQ ID NO 253
<211> LENGTH: 149
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Affymetrix ID 3460455

-continued

```
<400> SEQUENCE: 253
agcgaccata tgttaaacct ccatgtgtgc ctgctctttt cagtcatcta ataaatgatt      60
ctgccattat tgttactctt gtgcaagcac gggcaaatac cacaagcaag acttgaaaac     120
aaatcctcag ttccctgtct ttaacaatg                                       149

<210> SEQ ID NO 254
<211> LENGTH: 53
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Affymetrix ID 3928709

<400> SEQUENCE: 254
cctgccctga cggtcgtccg gccaggcgac actgcacggg acaccctgga gct             53

<210> SEQ ID NO 255
<211> LENGTH: 439
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Affymetrix ID 3351275

<400> SEQUENCE: 255
cccttgacta tttagccaag acataagcta caaattttgc cggaaaaact gtccatacat      60
ttttaactac ttcttcatta ttcttatgga ccatcatcca ggacatctgt ttgaagaaat     120
atccagttat aatattttca aaggttagaa ttgtgaagaa aaaatataaa atgtgattaa     180
aggatatata gccttcagat gtaatttaca gttttaaaat tgcactttaa aactttgctt     240
ttttagacag tataaaaggc agaatgagac agatatgtaa tgaatttcag aactgaggtt     300
catatgtaaa tcatacaatt ttttaaaaaa tagtattgga aaaatatcaa ggtctataca     360
tttaaataca gataatctgt ttgaaaattc cagtttgtta aagaaaaaaa catctgcagt     420
ccagtcgatt aaaaactga                                                  439

<210> SEQ ID NO 256
<211> LENGTH: 153
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Affymetrix ID 3217301

<400> SEQUENCE: 256
gaggagtcaa gagccttgct tgcctgcgtc agcgctgtgc cagcagccac ctctttccag      60
agggctcctc ttctctctct ccatcttatc acagcctctt cttctgacct catccaacgc     120
ttctgcttca acatcaaagg aggacacttt taa                                  153

<210> SEQ ID NO 257
<211> LENGTH: 220
<212> TYPE: DNA
<213> ORGANISM: Artificial Sequence
<220> FEATURE:
<223> OTHER INFORMATION: Description of Artificial Sequence: Synthetic
      polynucleotide
```

```
<220> FEATURE:
<223> OTHER INFORMATION: Affymetrix ID 2377263

<400> SEQUENCE: 257
tgagcatgtg gtcaatctta gagtatgtgc tatgtgcaga tgagaagaat gtatatcctg      60
ttgttcttgg gtgtaatgtt atgtagatgt ctgttaagtc catttggtca agtgtcaagt     120
ttaggtcatg aatatctttg ttagttttct gccttgatta tgtgtctaac attgtcaatg     180
gggtgttgaa gtctcccact atattgtgtg gttatttcca                           220

<210> SEQ ID NO 258
<211> LENGTH: 102
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Affymetrix ID 3976345

<400> SEQUENCE: 258
tggcttctgg catcctgttg ttgctgtggc tgatagcccc cagcagggcc tgcacctgtg      60
tcccacccca cccacagacg gccttctgca attccgacct cg                        102

<210> SEQ ID NO 259
<211> LENGTH: 88
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Affymetrix ID 2377245

<400> SEQUENCE: 259
tcaaggggaa cgtgaccatt atggatatag acagtctgta acgtatgcat gtaataaagg      60
attcaccatg attggagagc actctatt                                        88

<210> SEQ ID NO 260
<211> LENGTH: 109
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Affymetrix ID 2414961

<400> SEQUENCE: 260
gtgagtcacg cttcctgatt cctcggcgca aaggagacgt ttatcctttc aaattcctgc      60
cttccccctc ccttttgcgc acacaccagg tttaatagat cctggcctc                 109

<210> SEQ ID NO 261
<211> LENGTH: 31
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Affymetrix ID 2876911

<400> SEQUENCE: 261
ctgagggtgc acacccgagc cgtgacagag g                                    31
```

```
<210> SEQ ID NO 262
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Affymetrix ID 2764272

<400> SEQUENCE: 262
agtagtaacc actagcattg gacaggattt                                      30

<210> SEQ ID NO 263
<211> LENGTH: 109
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Affymetrix ID 3406425

<400> SEQUENCE: 263
ctcaggaata cagagaatac taaccaaaag aagctactcc gaggtgacgg caaagttaag      60
gataaaaagc atgctcaaag aaaaaatcgg agcagactag aaatcttgt               109

<210> SEQ ID NO 264
<211> LENGTH: 858
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Affymetrix ID 3222204

<400> SEQUENCE: 264
ctaccggatc gccatgactt taacatcttt gttcacattc cctacttaat ccataaatgt      60
agtctactgt ttcaccttct ccccacactc cctcttgtca tatgtactta atgaacactc    120
cccactccca ccccagaaat gagaaggtcg aaatatttct gctttgtatt caaaatcctt    180
tagaccttgt cttgtccata gctcttgtgt gcttacctca tatcatcgtc ccttgtgatc    240
aacctggctg gtccccagct acatttcagc cttctcaaaa gaaatatacc aatgagtata    300
tttccaaaac gtatttaaaa cttttgccat ctcaaaatct caaccatgat cttaacaaac    360
ttacccagtg ggctcgtcat tggaaaacca aatgtgaact tatttatcg gtaatcacta     420 atatcagaga gactctgcaa cacggactaa atccataatt ttctcaagac taatgattcc    480
tacagaaatt aacaacggaa tagtcaaaca tctgtgtttc ccaaagtctt tctagagatt    540
actagctcca cagaatgttc aaaggtccta ctcggtgagg aaattccacg ttcaaataag    600
tttggaaaga ctgagttaaa caaagttaaa gaggatcttt aactgcacgg cttttcagaa    660
caccctaacg tgcatcatct ccaagaagta cttatccagg cagtattttc caaacttatt    720
tgacaaagga tacttttttaa ggaagaggat caaacaggaa tagttcactg tgagcacact   780
ttgggaaact cagctctaaa tctacattga cattgagttt tgtctagtta aggcaatgca    840
agatgaaacc ctgggtcc                                                  858

<210> SEQ ID NO 265
<211> LENGTH: 86
<212> TYPE: DNA
```

```
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Affymetrix ID 3928687

<400> SEQUENCE: 265
ctctctgggg ggatcattcc tgtattatgc tgaccgcttc aagctctaca gtgccttctg    60
cgccagccac acaaaagttc ccaagg                                         86

<210> SEQ ID NO 266
<211> LENGTH: 70
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Affymetrix ID 3067480

<400> SEQUENCE: 266
catactggta gatgcgaaat ttatctgtgc atgaaagggt cacttctgta atagtgcaac    60
agatttggta                                                           70

<210> SEQ ID NO 267
<211> LENGTH: 96
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Affymetrix ID 3451908

<400> SEQUENCE: 267
ccctacagat tgacgtctta acagagttag aacttgggga gtccacgacc ggagtgcgtc    60
aggtcccggg gctgcataat gggacgaaag cctttc                              96

<210> SEQ ID NO 268
<211> LENGTH: 1255
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Affymetrix ID 3928672

<400> SEQUENCE: 268
ttgccgtgtt ctgactgtac ccttccctct tccatgtctg agaatctccg tgtattttaa    60
gaatgtgtga ggagagggtg gcgattcatg tttcaatgag cctctttttt ttttttcttc   120
ctgttttggt ctatggctgg tcttactctg tgtccatgtt cggaagctct agttttgcat   180
agaattatag agatgccaaa ctctttgaaa agagatccaa atttatcgct tgagagaaag   240
aaaagaaaca ctattttttg tattttacct gagatacagg ggcacaaata gatgagaatt   300
ttacagtgtt agtgtatgta tccctgagcc taaaaaatga ggatataacc ttttacagag   360
agagtgaggc gtggtggttt tatatttata tatgaaaggc cagcaagctc atgcgaagga   420 tatactttc  ttccaaaaag cggattttt  tttttaatg tttgaatcta tatttgagat    480
gggagtttgg ttggattaaa catgacaccc cggtgggcgg tgtgtgtgtc tgttgcacat   540
ggcagggagg ggagcctcct tctcatgggg ttgccatggt gatcattggt ttttccatca   600
```

```
aaattgcatc ttcatccata gattaccttc cccttccctg acagtccata accaaacctt      660
taaacagaac aacctcttta aaaacttctc ttgtgtttaa cactttcttc atgccaacga      720
aacagggtaa acatgctcaa acattaaca gtctaaacag atatccaaat actaagaaga       780
aaaacaagtt atagcacttt caattttttt tttttttta aaaaaaggtt tatagctttt       840
tcttttccca tgtcacaatg tccacttcct aagaagggtt taaaatacta tgaaacttt      900 cttttggggg aaaatatcta tttggtgttt gacacatcag taggtacttt aaagacctga     960
attttatagt agctttagga gttatatttt ataaaaatca gttatgactt tatatttcca    1020
gacaatagag agttcagtac atcatgctct tgtgcctctg cctgcttttc ctgcgttccc    1080
accctgtatt cccccccgcct ttcgggtttc cagggcttcg agcttgatct tttgaaagtt   1140
ttattctatt aaattttttgc tatatcttct ggttttctga aaaagcttta gaatggtttc   1200 tataccctt gtatcactgc atttttccat atcatctccg gttcgatcgc gtcca          1255

<210> SEQ ID NO 269
<211> LENGTH: 199
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Affymetrix ID 2437119

<400> SEQUENCE: 269
ctgcaccctg tttgggctgg tgagctggga gttcaggtgg gctgctcaca gcctccttca      60
gaggccccac caatttctcg gacacttctc agtgtgtgga agctcatgtg ggcccctgag     120
ggctcatgcc tgggaagtgt tgtggtgggg gctcccagga ggactggccc agagagccct    180
gagatagcgg ggatcctga                                                  199

<210> SEQ ID NO 270
<211> LENGTH: 370
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Affymetrix ID 3252064

<400> SEQUENCE: 270
cactaacgac ttcagggcag ggctctgata ttccatgaat gtatcaggaa atatatatgt      60
gtgtgtatgt ttgcacactt gtgtgtgggc tgtgagtgta agtgtgagta agagctggtg    120
tctgattgtt aagtctaaat atttccttaa actgtgtgga ctgtgatgcc acacagagtg    180
gtctttctgg agaggttata ggtcactcct ggggcctctt gggtccccca cgtgacagtg    240
cctgggaatg tattattctg cagcatgacc tgtgaccagc actgtctcag tttcactttc    300
acatagatgt ccctttcttg gccagttatc ccttccttt agcctagttc atccaatcct     360
cactgggtgg                                                            370

<210> SEQ ID NO 271
<211> LENGTH: 1017
<212> TYPE: DNA
<213> ORGANISM: Artificial Sequence
<220> FEATURE:
<223> OTHER INFORMATION: Description of Artificial Sequence: Synthetic
      polynucleotide
```

```
<220> FEATURE:
<223> OTHER INFORMATION: Affymetrix ID 2751985

<400> SEQUENCE: 271
actgaaaacc gcctgaaacc tgctgcaact attgttatta actctgtata gctccaaacc      60
tggaacctcc tgatcagttt gaaggacatt gataaactgt gattttacaa taacattatc     120
atctgcagtt actgtttaca agactgcttt taccttaaac tttgtagatg tttacatctt     180
tttgttgtgt tttaagatga tgttggtaat ttgtgccttt agctctgttt tattagacag     240
agttaaagca tgttgtcttc tttgggatta cactcagggg tctgaaaggc agtttgattt     300
ttatttttaa cacacttgaa aaaggttgg agtagccaga cttttcatata taacttggtg     360 attatcaacc tgttgtgtct ttatttaatt ttacatcttt ttgaagcact gccacaggtt     420
attagccaag gtggccttcc ttcacagtca tgctgctttt ttgaaaggtg aatttcaaca     480
catttagtgc ctctttcatt tctcagtata tatttcaaga gcttgtgatg aaatctatag     540
gatggtaatg atggacttgt cacctgtatg gggaatactt ttactactca gaaatgaatt     600
tatgtgctgc catttgctat aaagttgaac tttgtatggc ttgaaaaaga aatgacaata     660
tggaacatcc caaggctgtc ccatagggtt ggaagttgtg tagcattcac tcccttacct     720
actggcattc ccagtgccct ctgtccatac ctacttctag gattgcaaag gagtcttcca     780
actagagaaa aattgtccac tgacatttgg gatttacttt tctccaatac ctgccaatac     840
agaaaactat tatcagttgt tattgttatc ccttgaaagc gagggtgaca aaacaacaa     900 aacaccgtta taaacacatc aaaggttcat tctgactgag gtaagacttt ccaagcccct    960
gttagattag gccttataaa acttgtgtgc attataacct aagctgtgca acctgtg       1017

<210> SEQ ID NO 272
<211> LENGTH: 164
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Affymetrix ID 2830201

<400> SEQUENCE: 272
aagactcaag ttggaagatg caaattcaga ttacaagcta cctcacctgc tacctgccac      60
ctctctggct ctcctacaaa ccagatcatc catgcaacag gtcccacgcc cccatgggca     120
gggcccacac catcagtagg aaaggctttg ctaatgatgg ccta                      164

<210> SEQ ID NO 273
<211> LENGTH: 191
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Affymetrix ID 3126229

<400> SEQUENCE: 273
ggggaaacat agctctactt ggagagttta gtttgaggtg ttgaattcag agtgtgtgga      60
ataataaatg gatgtgtcca gtaagcaatt atgcatactt tgatctggag ccaatgaagg     120
ggccagaaat gcagatctga acagtcatta acaaaaaatt ggtaatttaa gccatgcaag     180
tagatgatgt c                                                          191
```

<210> SEQ ID NO 274
<211> LENGTH: 154
<212> TYPE: DNA
<213> ORGANISM: Artificial Sequence
<220> FEATURE:
<223> OTHER INFORMATION: Description of Artificial Sequence: Synthetic
polynucleotide
<220> FEATURE:
<223> OTHER INFORMATION: Affymetrix ID 3252057

<400> SEQUENCE: 274
tgtttaggga gcgatgggct gcaaaggtaa atagatggta ggggctatag gtggagtaaa    60
ggctcagatt tgcatggaag agaataaggg ccttccctgg tagagatact ttatggttcc   120
cctctctggc agactcccag tggacagata aatc                               154

<210> SEQ ID NO 275
<211> LENGTH: 301
<212> TYPE: DNA
<213> ORGANISM: Artificial Sequence
<220> FEATURE:
<223> OTHER INFORMATION: Description of Artificial Sequence: Synthetic
polynucleotide
<220> FEATURE:
<223> OTHER INFORMATION: Affymetrix ID 3222218

<400> SEQUENCE: 275
gaaacacttg gcttctaggg cagtaagtcc acagtatgtc atttgcagtt gaaatgtgga    60
gccagcattt atgtgaagcc tcttggtcct catctcaact attgtccact gtatttttta   120
ttcataatat tcccccttct ttcataattc tgaccccctc tctctttaat ttagctactg   180
attttatttg tggaagttgt accttttact cacttggcta gcatttattt aataaaggga   240
tctggatggg gcacacgtag catccactac tgacatggcc acagtactgc ctctctgagt   300
t                                                                   301

<210> SEQ ID NO 276
<211> LENGTH: 32
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Affymetrix ID 3217284

<400> SEQUENCE: 276
agtacaacgc tgtggccgac acactggaga tc                                 32

<210> SEQ ID NO 277
<211> LENGTH: 28
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Affymetrix ID 3401511

<400> SEQUENCE: 277
tgggcgctca ataaacacac atgagaac                                      28

<210> SEQ ID NO 278
<211> LENGTH: 123
<212> TYPE: DNA
<213> ORGANISM: Artificial Sequence

```
<220> FEATURE:
<223> OTHER INFORMATION: Description of Artificial Sequence: Synthetic
      polynucleotide
<220> FEATURE:
<223> OTHER INFORMATION: Affymetrix ID 3020380

<400> SEQUENCE: 278
aacagtattc ttgaatgtta taccccagcc caaaccattt caactgagtt tgctgttaaa      60
ttgaaaattg acttagccaa ccgagagaca agcatcttca gttaccgtga agatcccatt     120
gtc                                                                   123

<210> SEQ ID NO 279
<211> LENGTH: 41
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Affymetrix ID 3371817

<400> SEQUENCE: 279
tcaccttgcc tggcttggag tcatgactaa tcctgcacct g                          41

<210> SEQ ID NO 280
<211> LENGTH: 82
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Affymetrix ID 2377242

<400> SEQUENCE: 280
caaattattt ggctcgactt ctagtttttg tcttatttca ggcagctctg tccagtggag      60
tgacccgttg ccagagtgca ga                                               82

<210> SEQ ID NO 281
<211> LENGTH: 326
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Affymetrix ID 2558708

<400> SEQUENCE: 281
gagaggccat tgtaggttta ttgattggcc tagttttaat attattgtgt ctcagggaat      60
agggaggcct gaggagaagg agagagatgg agaaatgact gataaatgtg tgttctgact     120
gctccattga tcagctaagt ttgctgtctt ctacgggtgt ggttcatggc accccgaaac     180
aattacaata gtaacatcaa agatcactga gcacctgtca ccataacaga tattataata     240
ataatgaatt gtgattatta ccaaaatgtg acacagagac acgaagtgag cgcttgctgt     300
tggatagatg ccacaaactt taaatt                                          326

<210> SEQ ID NO 282
<211> LENGTH: 60
<212> TYPE: DNA
<213> ORGANISM: Artificial Sequence
<220> FEATURE:
<223> OTHER INFORMATION: Description of Artificial Sequence: Synthetic
      oligonucleotide
```

<220> FEATURE:
<223> OTHER INFORMATION: Affymetrix ID 3351271

<400> SEQUENCE: 282
ctgcatcccg gcagctcttc agatgcttgc acaccttgtt tacagctccc ggtaacgaca       60

<210> SEQ ID NO 283
<211> LENGTH: 88
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Affymetrix ID 2466609

<400> SEQUENCE: 283
cgacaagtgt ggcttcccag agagcgtgga gaatggggac tttgtgcact gtgaggagtc       60
tgggaggcgc gtgctggtgt attcctgc                                          88

<210> SEQ ID NO 284
<211> LENGTH: 34
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Affymetrix ID 2537610

<400> SEQUENCE: 284
ggaggttgca cagattgcgg gggatttggg gaga                                   34

<210> SEQ ID NO 285
<211> LENGTH: 75
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Affymetrix ID 3727592

<400> SEQUENCE: 285
atggagaaaa tgtcccgacc gctcccsctg aatcccacct ttatcccgcc tccctacggc       60
gtgctcaggt ccctg                                                        75

<210> SEQ ID NO 286
<211> LENGTH: 74
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Affymetrix ID 3367674

<400> SEQUENCE: 286
atggtggagg atggtagttt cgtcctgggg aaggagggat ttattcatat gcaacatcag       60
taatgccttt caga                                                         74

<210> SEQ ID NO 287
<211> LENGTH: 89
<212> TYPE: DNA
<213> ORGANISM: Artificial Sequence
<220> FEATURE:

```
<223> OTHER INFORMATION: Description of Artificial Sequence: Synthetic
      oligonucleotide
<220> FEATURE:
<223> OTHER INFORMATION: Affymetrix ID 2537568

<400> SEQUENCE: 287
tccaactttc acgagaagat taagaaaatc cacaaacaat acctgttgtt gcaagctcct    60
gtgatgggcc tgtatttgtt cgccaggca                                      89

<210> SEQ ID NO 288
<211> LENGTH: 125
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Affymetrix ID 2466585

<400> SEQUENCE: 288
cgctattctg acctcctgat ggcatgggga caatacatcg accacgacat cgcgttcaca    60
ccacagagca ccagcaaagc tgccttcggg ggaggggctg actgccagat gacttgtgag   120
aacca                                                               125

<210> SEQ ID NO 289
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Affymetrix ID 3095405

<400> SEQUENCE: 289
cttattttac acatccgaag aaacaccatc aca                                 33

<210> SEQ ID NO 290
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Affymetrix ID 3933538

<400> SEQUENCE: 290
agttcatatc tggagcctga tgtcttaacg aataaaggtc ccatgctc                 48

<210> SEQ ID NO 291
<211> LENGTH: 149
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Affymetrix ID 2763591

<400> SEQUENCE: 291
aagacgtccc tgctcggagc ttctcaaata tctgaccaca acgatgacc ctcctcacac     60 caaacccaca gagaacagaa acagcagcag agacaaatgc acctccaaaa agaagtccca   120
cacacagtcg cagtcacaac acttacaag                                     149
```

<210> SEQ ID NO 292
<211> LENGTH: 62
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Affymetrix ID 2466562

<400> SEQUENCE: 292
gtccctggaa ggcaattaag gcgcccattt cagaagagtt acagccgtga aaattactca    60
gc                                                                    62

<210> SEQ ID NO 293
<211> LENGTH: 29
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Affymetrix ID 3662208

<400> SEQUENCE: 293
gctgtgtttg caaaggggcg tcagagaag                                       29

<210> SEQ ID NO 294
<211> LENGTH: 114
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Affymetrix ID 2466570

<400> SEQUENCE: 294
tgctgagcat cattgcaaac atgtctggat gtctcccta catgctgccc ccaaaatgcc      60
caaacacttg cctggcgaac aaatacaggc ccatcacagg agcttgcaac aaca          114

<210> SEQ ID NO 295
<211> LENGTH: 662
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Affymetrix ID 2466631

<400> SEQUENCE: 295
ctcctgggaa gagcactcct ggcttcctgc agggccggtg ggaggaggaa agtgattctg     60
agggagaggc tggagcctta aggaccaaca aggcaaagtg acttgtctca tcctccagag   120
attcaccaac acatgagcct cagaccccag gcttctgcct ccagcagccg ccctgccgca   180
cactgctctt actcctcctt ataccctcac tcacggggaa cacagcccag tgatcccgga   240
ggaaactcac tccctccctg actcaacaag gcagtctcgg gggcaccgtt agccacgcga   300
ccctgtaaag ctgccgtcct catttcacat gtgaagcagc tgaattccag agtgctgggt   360
cccagcccag gcagccctca gcctcacgca aggcaatagt taggagtcct tcggcattga   420
aagcaaactc agacacatct gacctggagt tctacctgca ctaagagaag agagtggtaa   480
ctaattcatg gataaaacag accatcgagg cagcactgaa tgatctcacc cacgaatgac   540

```
aacagtggca caggagggct atgaacattt tgcttcagga tgttttattt cgctctactg    600
ttatgtagag aaagcatggt ttgcttttta aactttttgt gacccaaaaa taccagactg    660
tt                                                                   662

<210> SEQ ID NO 296
<211> LENGTH: 811
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Affymetrix ID 3367675

<400> SEQUENCE: 296
gttagtgttc gccaaaggac agccaagctt tcttttaaaa agtgataaaa gtcttatttt     60
aatatgcttt aagctgaaag aaaaaaaaat aagaaacagg cagtgtttta aaaaccaaca    120
cagatttgca caactgttta agagtattgt ttgaaatatt ttaattttca atgttttgtt    180
gttgttgttt tcttggtaat gcttcttttt tgcagatgtg gtcccaattt atagcaatct    240
tctcaacaga agtaggcatg gaaaagactt cttttcatac tctcactata aagaaagctg    300
cattgagaag aaaatggctg tcatttaaag gatggtttaa ctagtgagat tcctattgtg    360
gttatacaag gtctcattgt ttgtttgttt cttttaaatt atttcagctt taaaaataca    420
gaaatggaat ctgtcaagag caggtatttc atacggttaa aaaaatgaac atgcagactc    480
cttttcaata tgggtttata tatataagta tttttgtgt attatgacta cgttaggagt    540
ttattattgt caaggacagt acaactgcaa agggatgctg tatagcaaca catcagaagt    600
cggaaggaac tgacacattc tctcagagct caaggtctta aagagcttga gttaaatcta    660
ggtacagtta caggcatgta tagacttaaa tggatgcaat ggaagctaac taaaataagg    720
cttagttgtc ctttctattt aaatacccca agttgtcttc ttacttcctc tcccctctcc    780
cattttgcac tgtgtgtcga tgcaatcttc g                                   811

<210> SEQ ID NO 297
<211> LENGTH: 76
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Affymetrix ID 3367709

<400> SEQUENCE: 297
gttctgcatt gctgataccg ctagtggttt taaaaataga aatcaaaata agaaccctga     60
tattaaggat tcacag                                                     76

<210> SEQ ID NO 298
<211> LENGTH: 37
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Affymetrix ID 2466600

<400> SEQUENCE: 298
cccaggccac acaagactca cggctctccc tggtctc                              37
```

<210> SEQ ID NO 299
<211> LENGTH: 274
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Affymetrix ID 3367737

<400> SEQUENCE: 299
gagctaccca gtctacgcta ttttgttaat agcatctcaa acagcccaag gcaggtaggc      60
agggaatata atgggaagat gaattttata gagggaacaa gaggagaaat gggcgtattt     120
gtgaaggaga gagggaaaaa gtaggaggga atatatagca gatgtgtttg tgagatcata     180
actcttcctt gtcagttacg atgtcctgac cttgggcttg actttagcac cgggagcagg     240
tcagcatccc tagacttcag tcaacaggga gatg                                 274

<210> SEQ ID NO 300
<211> LENGTH: 81
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Affymetrix ID 3018629

<400> SEQUENCE: 300
tctgggtgtt tacgtgtata gtgtccatca ttctggggct ggatctcggt ttactagctg      60
gccttatatt tggactgttg a                                                81

<210> SEQ ID NO 301
<211> LENGTH: 52
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Affymetrix ID 3132624

<400> SEQUENCE: 301
catctgcagt gtctccctaa actcaataga acagtatcat gcccatctga aa              52

<210> SEQ ID NO 302
<211> LENGTH: 157
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Affymetrix ID 3018633

<400> SEQUENCE: 302
ctggaggaac ttgatatccc aaccaaggaa atagagattc aagtggattg gaactctgag      60
cttccagtca aagtgaacgt tcccaaagtg ccaatccata gccttgtgct tgactgtgga     120
gctatatctt tcctggacgt tgttggagtg agatcac                              157

<210> SEQ ID NO 303
<211> LENGTH: 204
<212> TYPE: DNA

```
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Affymetrix ID 3367689

<400> SEQUENCE: 303
ctgcatctct tgagaccttg ttagaagtgc aagttctttg gctccatcct atagccacag      60
aaccttggag tggcttcaag tgactgatgt ctaaagtttg agaaacattg cattacagga    120
tgctactttt ccagacttgg ttcttacatt ccataaatat ttatcaagta ctcaataagt    180
ggcagggact attggagata cagc                                           204

<210> SEQ ID NO 304
<211> LENGTH: 44
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Affymetrix ID 3693001

<400> SEQUENCE: 304
ccctgctccc aagtacaaat agagtgaccc gtaaaatcca ggat                       44

<210> SEQ ID NO 305
<211> LENGTH: 173
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Affymetrix ID 3018617

<400> SEQUENCE: 305
acctttccca gtggtgagtt taatggtggg atctgttgtt ctgagcatgg ccccgacga       60 acactttctc gtatccagca gcaatggaac tgtattaaat actactatga tagacactgc    120
agctagagat acagctagag tcctgattgc cagtgccctg actctgctgg ttg           173

<210> SEQ ID NO 306
<211> LENGTH: 109
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Affymetrix ID 3018618

<400> SEQUENCE: 306
tggtggcttg cagattggat tcatagtgag gtacttggca gatcctttgg ttggtggctt      60
cacaacagct gctgccttcc aagtgctggt ctcacagcta aagattgtc                109

<210> SEQ ID NO 307
<211> LENGTH: 121
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Affymetrix ID 2763563
```

```
<400> SEQUENCE: 307
ccacaggttc catagaacta atatcctgtc tctctctctc tctctctctc tctcttttt      60 ttttcttttt cctttttgcca tggaatctgg gtgggagagg atactgcggg caccagaatg   120
c                                                                     121

<210> SEQ ID NO 308
<211> LENGTH: 112
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Affymetrix ID 3862190

<400> SEQUENCE: 308
catccaccag gaacgaagat ttcctgaaga agacctggtc cctctggagg ttgcagtggc    60
tgaaggatgc atcatgtgct cctaccctgc tctaccgctt ttctgggtca ca           112

<210> SEQ ID NO 309
<211> LENGTH: 239
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Affymetrix ID 2721305

<400> SEQUENCE: 309
ctggaagctc acatctaaag gcatgaaaag gtttcctttt atcaactgac ccaaacatca    60
taccccaata gtgcaaagtt ccctctctgc tgctttgaat gttgacagcc caactgttgt  120
tctcggagtc gtttagcaaa aaattgattt tgttgcactg gaagaattat tctgctacat  180
ctcttttaaa aaagaaaaaa atccacatta ctaaagcacc agttcggtta ccaaaattg   239

<210> SEQ ID NO 310
<211> LENGTH: 106
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Affymetrix ID 2466569

<400> SEQUENCE: 310
cctgagccaa caagcggagt gattgcccga gcagcagaga taatggaaac atcaatacaa    60
gcgatgaaaa gaaaagtcaa cctgaaaact caacaatcac agcatc                 106

<210> SEQ ID NO 311
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Affymetrix ID 3367712

<400> SEQUENCE: 311
gtgaagggat tcaggatata cggtgcacct tg                                   32
```

```
<210> SEQ ID NO 312
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Affymetrix ID 3833280

<400> SEQUENCE: 312
tgtgacccag aaaagcggta gagcagggta ggagcacatg atgca              45

<210> SEQ ID NO 313
<211> LENGTH: 1859
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Affymetrix ID 3018642

<400> SEQUENCE: 313
taataatgtt cacgtgggcc ctggcatatc tctgttcagt tagagtgagt gctgacccaa    60
cagcctctgt ggtcaagcga gtcacgaatg attaatcata agaaaaatc agttttgac    120 tgacctggat atccatgagc tgcactgatc accatgtaag gtcacattta gtaaatgctg   180
aaataaaatg attaatgcat ttatcaataa agcctttga aaatactttg gataataaat    240
tggagtttta aaaatgcaaa tttgcttagt atctaataat gaagtgttat tacatatagc   300
cggaattgag gatctctttg atcctggaaa tggtttacct aaaagctaca gaaccaggcc   360
aatatatttt gaaatattga tgcagacaaa tgaaataata agagatttt catggtttat    420 aaaaatcttt tttgatatga taataatcat gatcacaact gagatcaaaa aaatatatga   480
cagattattt tgtttaaaaa tgcagttta attatcttag tctatagaaa tgatcattgc    540
atggaggcat gtataggtat gatctgtgta aaatctgaca taaaaacagt gctattctga   600
gtgaaaattt ttttgatgtg cttacataac catggtgatt aaaatgagtt tatatttttt   660
ctcaaaaatt ttagcagtgt gtaaagtaag taatctttaa ctgaactctg accacttaaa   720
aaaaaatcta aaaattgaac tacctatagt agtctgtgtt taaagtgaat ttttaaagac   780
aaagcattct aaatgaactc aatataaaaa cattcatttg gaatgtacat actgaaaaat   840
acaggttttt ttgaccaaaa gttttatat cttttctttt tatttatttt tttcctaagt    900
gccaacaatt ttctagatat tatatacaac acaggctttg atcttgggga cttttcccat   960
atatttcaca ctggagtgaa tgaagttgta cttcatttct agagaaaagt tatacccagg   1020
tccccaattg agaatgtctt gcttgattga aaacgacatc atcccttggt atactccagg   1080
gattggtttc aggacccctg catttaccaa aatttgtgca cactcaagtc ctgcagtcac   1140
ccctgcctaa agatagaatg gcttctctgt ttttcttctg aaatacaacc agaaacaatg   1200
tgtctatttc tgaaagaata ggattaatga tcatacaaat gggttaatcc tgaattctgg   1260
ttgtaaatct ggttacagca taactaggat tataatgctg cctcattttc acagcactac   1320
ttgcttatat tgacaacaaa tcatctcgct aaagagtgaa tgtaggccag gcgcggtggc   1380
tcatgcctgt aatcccagca ctttgggagg ccgaggcggg tggatcacga ggtcaggaga   1440
tcgagaccat cctggctaac atggtaaaac cccgtctcta ctaaaaatag aaaaaaagaa   1500
attagcctag cgtggtggct ggcgggcgcc tgtagtccca gctatttggg aggctaaggc   1560
```

```
aggagaatgg cgtgaacccg ggaggcggag cttgcagtga gccgaggtcg tgccactgca    1620
ctccagcctg ggcgacagag caagactccg tctcaaaaaa aaaaaaaaaa aaaaaaaag     1680 agtgaatgta atagtcttgc agaaaatgaa tgaataccct tgttcaataa aggaaatatg    1740
cactgctcac tttttgaag gaaatgccaa agttacgttt tacaacaagg ctagagtttg     1800
taaattctgg gttcatttgt gatgacataa gtcagcaaac tgcgggaata ctgtctctt     1859
```

<210> SEQ ID NO 314
<211> LENGTH: 513
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Affymetrix ID 3367697

<400> SEQUENCE: 314

```
agtgcttgtt aacccagtgc ctcagcccctt cttagacatg aatcagaacc tttggtggta    60
gagcaggaaa ttggcacttt agcacccagg gtgattttta tgcctactaa agtgtgagaa    120
caactgactt tgaagctgta ggtgtttggg ttggtggcgt atttatccct agaattgctc    180
cgtgtaattt gatgatgagg acatcttct gtttcttttcc tccaaaatgg aaggcaaact    240
aaattaaaat ccagttaatt caggttctga gttgattggg acatggataa ttgtgatctt    300
tttgctgatt tctaaaatat tttcccttca ttatctgttg gatttcaagt gcattctgct    360
ctgtgttata gaatgagggt tgatgtgaaa cttagggaga ctccaattat atacatggtt    420
caattactgg ttccataatt tagggtgtcc tcttttccca ttgactttca ctttcttcgt    480
acttaaatgg caaggttgta ctctctgatc tca                                 513
```

<210> SEQ ID NO 315
<211> LENGTH: 103
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Affymetrix ID 3018616

<400> SEQUENCE: 315

```
tatgccctac tagctgcagt tcctgtcgga tatggtctct actctgcttt tttccctatc    60
ctgacatact ttatctttgg aacatcaaga catatctcag ttg                      103
```

<210> SEQ ID NO 316
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Affymetrix ID 3367743

<400> SEQUENCE: 316

```
aaatgcacag cggtattgat gagtagatcc ttg                                  33
```

<210> SEQ ID NO 317
<211> LENGTH: 131
<212> TYPE: DNA
<213> ORGANISM: Artificial Sequence
<220> FEATURE:

<223> OTHER INFORMATION: Description of Artificial Sequence: Synthetic
      polynucleotide
<220> FEATURE:
<223> OTHER INFORMATION: Affymetrix ID 2537609

<400> SEQUENCE: 317
gttggattta tggaggttgc acagaaagga gatctgggga ggttgcacac agagtggggg    60
ggatttgggg aggtttcaca aagctagggg catttgagga gaatgcacac agtggggcga   120
tttggggacg t                                                        131

<210> SEQ ID NO 318
<211> LENGTH: 96
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Affymetrix ID 3933539

<400> SEQUENCE: 318
atgcgaggct cggagcaccc ttgcccggct gtgattgctg ccaggcactg ttcatctcag    60
cttttctgtc cctttgctcc cggcaagcgc ttctgc                              96

<210> SEQ ID NO 319
<211> LENGTH: 81
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Affymetrix ID 2586066

<400> SEQUENCE: 319
taccaaagga agttatgagt gtgtctgtgc tgatggcttc acgtctatga gtgaccgccc    60
tggaaaacga tgtgcagctg a                                              81

<210> SEQ ID NO 320
<211> LENGTH: 142
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Affymetrix ID 3132617

<400> SEQUENCE: 320
tgaccagaat aaggagggtc caatcaacat attattgtgg agatagcctt ttttttttt    60 ttctggcttc tacctaattt atttataata aagacaagct aggctacctc ataggattct   120
ggtgtggatt cgctaattaa ta                                            142

<210> SEQ ID NO 321
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Affymetrix ID 2727647

<400> SEQUENCE: 321

```
ttctttgcag tggcttaatg tttgaa                                       26
```

<210> SEQ ID NO 322
<211> LENGTH: 2123
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Affymetrix ID 3067233

<400> SEQUENCE: 322

```
ggagctggag ctatcctacc tcatcagtgt tttgtcttct gttgggatga actttgttaa    60
aactaatgca tggttaagat gaaaggcaga aggaagggtt tgataaacca gaacattctc   120
gcctgattgt tagtgttctg aagtaaatac agaagaggct ccaaaataca gacctctgta   180
catcaacctt ccgtaatcca cctgccttgc atatgcagac catgacaatt ctacgagctc   240
ctggaaacag aactcagaac tcctccccag agaaccctga tgcaaattct ctgaaatggt   300
agtcagcatg tgcgttttcc tgagaagtga atgagtcaac agctttcaac agatcttcaa   360
aggcttactt cacccaatga agttaagaac cactaaagaa gaaacctaaa aggaaaatcc   420
aggtcatgaa ctttgcaatt tttattcaca tacagagaag aggggaggaa tctcttgtgt   480
atgtttttact tatgtatacc actggttctt aataaagggc ttttttttgcc tccagaggtc   540
aatgcctgga gacatttttg gttgtcacac ctagggagat gctattggga tctagtgagt   600
agagaccaga gatgctgcta acatcctac aatgaagttt gctatcactc caaggttttg   660
catgcgactt aaactgtaca tttattaatc aattgctaca tgtactaaaa tatgtatctc   720
tctccatata tgtatatatg cgtgtatttt ttcattattg ttggatgtat agctcaactc   780
cactacaaca gaggaaagta tttgttttaa agtagaatct gaatatactc actctgtata   840
ccctcatcca taccttcaag atctggtgaa aacactatct cttgcaagaa cattctttga   900
tgctgttcag aattaatcca gaccctttc tgtattctct taataccttta tctgatcctc   960
tcttaagtta cttctcacta tctaccttag taacacaatt ttatttacat acaagttctc  1020
tctccctcac tagacaaaaa cttcttgagg gcaagcactg tgtctccttt caaccattat  1080
tatcttctct catgtttttt gaacagattt atctatagcc caaacatacc ttttcaaaaa  1140
actaaaaatt actttacata tttgatctaa ggctttgttt ttctccatta agagcatgct  1200
gtggatatct ttgcaagtga gtgcataagg attttttctta accttggaga tggctgtcta  1260
ggatttcaga atatcaactc atatttgtag ctccatggca actcacctac acaactcaca  1320
actctttatt gaaggcattc tgtaccaata taaatatagt ccatatccca ttctaatatg  1380
gatttctgct ccttgttgct tgctattttg aacacttttta gtctggtcca gtcaggccta  1440
taaccacttt tgcatcagaa cttggcaatg gtttgctggt tcagaggatt aaggagtggg  1500
gtaaggctgg cagaaggaca gaagagaaaa gacttgagta acaacaggag gcaaaagagt  1560
aacttagctt ggctaataga attcttattt gaaatgcatc tctctatata agagtttggt  1620
tcaataatca caatataata agtcctgcat gtatctggat gaagataatt gcttttttct  1680
gttcaatgct tttccatagc agaaatagct ggggcagaac aaaatggtat ctctgttaca  1740
ggattctata agggtataga actgcttttc tcataggtaa aaggcagacc gtttgaattt  1800
ggcttttaa aaacagaaga gtaggaggaa ataacagctt gctctctcca ccctatttaa  1860
ttgtgatatt aaacacctta gattactcac ttgggcttta taaggcaacc ttctcctgtt  1920
```

```
tcacacagag gtgggtggtt cttatttatc agacttttaa aatattcagg acttctttcc    1980
aaagaaatag atgcatcact taaaaataaa tatcagacaa tattattgat actttacagt    2040
acttatttag cagttaatac ttttttaaaa ggcattttct tatttatcat ttaggcattt    2100
gcagtgtaag acaaactccc ttg                                            2123
```

<210> SEQ ID NO 323
<211> LENGTH: 378
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Affymetrix ID 2763565

<400> SEQUENCE: 323

```
cacatgttta ttcatgggtg tcagctttgc ttttcctgga gtctcttggt gatggagtgt     60
gcgtgtgtgc atgtatgtgt gtgtgtatgt atgtgtgtgg tgtgtgtgct tggtttaggg    120
gaagtatgtg tgggtacatg tgaggactgg gggcacctga ccagaatgcg caagggcaaa    180
ccatttcaaa tggcagcagt tccatgaaga cacgcttaaa acctagaact tcaaaatgtt    240
cgtattctat tcaaaaggaa atatatatat atatatatat atatatatat atatatataa    300
attaaaaagg aaagaaaact aacaaccaac caaccaacca accaaccaca aaccacccta    360
aaatgacagc cgctgatg                                                  378
```

<210> SEQ ID NO 324
<211> LENGTH: 75
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Affymetrix ID 3018631

<400> SEQUENCE: 324

```
gaagaacctc aaggagtgaa gattcttaga ttttccagtc ctattttcta tggcaatgtc     60 gatggttttta aaaaa                                                    75
```

<210> SEQ ID NO 325
<211> LENGTH: 60
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Affymetrix ID 2586118

<400> SEQUENCE: 325

```
atgccgccga atcctcaaat ggctgtagca acaacatgaa tgcctgtcag cagatttgcc     60
```

<210> SEQ ID NO 326
<211> LENGTH: 150
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Affymetrix ID 2466608

<400> SEQUENCE: 326

```
agccacgtct tcacggatgc acagaggcgt gagctggaga agcactccct gtctcgggtc      60
atctgtgaca acactggcct caccagggtg cccatggatg ccttccaagt cggcaaattc     120
cccgaagact ttgagtcttg tgacagcatc                                      150
```

<210> SEQ ID NO 327
<211> LENGTH: 246
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Affymetrix ID 2586111

<400> SEQUENCE: 327

```
gtcattgtca atgcagccgt tcatgctttt ggcttgactc tctatggcca gtatatttac      60
tggactgact tgtacacaca aagaatttac cgagctaaca aatatgacgg gtcaggtcag     120
attgcaatga ccacaaattt gctctcccag cccaggggaa tcaacactgt tgtgaagaac     180
cagaaacaac agtgtaacaa tccttgtgaa cagtttaatg ggggctgcag ccatatctgt     240
gcacca                                                                246
```

<210> SEQ ID NO 328
<211> LENGTH: 249
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Affymetrix ID 3367703

<400> SEQUENCE: 328

```
aggcccatga gagacgagcg aattttcagg gtattgagtg ccttgctaca ttcacactgt      60
atgtgccgtt caagattact attgaaggga aaatcacaag gtattggttt ttaaggaggg     120
tattcgtatt taaggctatt tgctgtagga attaccttct acagagtttg aactctgttc     180
tgaaaagtct gagagaaata gaaacagttc ataggaaatt ttgaagtttg gctagcctgt     240
aaaccacag                                                             249
```

<210> SEQ ID NO 329
<211> LENGTH: 118
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Affymetrix ID 2586171

<400> SEQUENCE: 329

```
gtgacctgcc agcagggcta tttcaagtgc cagagtgagg gacaatgcat ccccaactcc      60
tgggtgtgtg accaagatca agactgtgat gatggctcag atgaacgtca agattgct      118
```

<210> SEQ ID NO 330
<211> LENGTH: 284
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:

-continued

<223> OTHER INFORMATION: Affymetrix ID 2331562

<400> SEQUENCE: 330

```
ctgccctttt gaggcctcca tgagggccaa atgtgccatg ggacacttag tgccatgcct    60
gcgcagacct gtggaataaa cagcaattct gagcaggctc attttaaagg gacttgcaaa   120
tttgggcgtt ccttgtgtgc cttcctcata aacccactc ctcccagaat atgcttagag    180
gtgctgctgt atttacctga gagctatgct tttcatcaaa aacctaaacg tgatcatctc   240
ttggatgagg tgtggccctg cacactcgcc tgctcgtgga agga                    284
```

<210> SEQ ID NO 331
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Affymetrix ID 3108614

<400> SEQUENCE: 331

```
atctgagcca gtcaccataa atatccaaga cctactttcc                          40
```

<210> SEQ ID NO 332
<211> LENGTH: 116
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Affymetrix ID 2537604

<400> SEQUENCE: 332

```
gtgaaggact taccacctgc aaatcaccgt cgaggtgaga cctgcgaagc ctccgatcag    60
cagagcagcc agcgacatgg agatccaagt cacccgaggg agcctcccgg agtctg       116
```

<210> SEQ ID NO 333
<211> LENGTH: 74
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Affymetrix ID 2466626

<400> SEQUENCE: 333

```
atctcggaga caggcggagg aactcccgag ctgagatgcg gaaagcacca ggccgtaggg    60
acctcaccgc agcg                                                     74
```

<210> SEQ ID NO 334
<211> LENGTH: 139
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Affymetrix ID 3018640

<400> SEQUENCE: 334

```
ttcgggaggt ctctatgagc aaggaataca agacaaaact tcctcaatgc attgactatt    60
tcttcagact caaaacactc attctttttt ctattaagcc attgaaagag aagcactaag   120
```
actgcttcta ggctttatt                                              139

<210> SEQ ID NO 335
<211> LENGTH: 58
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Affymetrix ID 2466621

<400> SEQUENCE: 335
atctcaacct ggcttcgaat gttcaagtct gacacatcgc aaaggctaca cccaaaca        58

<210> SEQ ID NO 336
<211> LENGTH: 138
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Affymetrix ID 2586151

<400> SEQUENCE: 336
aagactgtag ttcatggagg ctccctcatt cctcatccct tggagtaag cttatttgaa       60 ggtcaggtgt tctttacaga ttggacaaag atggccgtgc tgaaggcaaa caagttcaca     120
gagaccaacc cacaagtg                                                   138

<210> SEQ ID NO 337
<211> LENGTH: 44
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Affymetrix ID 2466629

<400> SEQUENCE: 337
atctagtacc atgtcgtagt tactctcagg catggatgaa taaa                       44

<210> SEQ ID NO 338
<211> LENGTH: 362
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Affymetrix ID 3367739

<400> SEQUENCE: 338
aggcctggtg ctcattctct atgagaccct tccaatgtct aacatgagtc tttcatagta      60
ggactaaacc tctttgaaaa ctattgtata gtcaagatag aaaggaggtt agagctctgt    120
tgactgtttt taccactcct ggaagaattg aactcggggc atgtccaagt cacaagctct    180
ttttttagga attgttttac atgagcattt aaaaaaaaat agtaggacac cccaaataca    240
cacacccccc caccctggaa tttacaaacg ctaaccaaac aaagggtct ttccattgac     300 tgcctggata ttagtgtaaa tactaggatg ttgctttgca agtatattct ggagagcgag    360
tc                                                                   362

<210> SEQ ID NO 339
<211> LENGTH: 35
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Affymetrix ID 3811356

<400> SEQUENCE: 339
ggaggatgga aaggctcgct caatcaagaa aattc                              35

<210> SEQ ID NO 340
<211> LENGTH: 114
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Affymetrix ID 3108604

<400> SEQUENCE: 340
ggaaagatgt ctgccaagct atagaccatg gctgtgaaca catttgtgtg aacagtgatg    60
actcatacac gtgcgagtgc ttggagggat tccggctcgc tgaggatggg aaac         114

<210> SEQ ID NO 341
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Affymetrix ID 2466601

<400> SEQUENCE: 341
atgcattctg gcacatggaa gaaaca                                        26

<210> SEQ ID NO 342
<211> LENGTH: 77
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Affymetrix ID 2466566

<400> SEQUENCE: 342
gaaagcctga ggagtctcgt gtctctagcg tcttggagga aagcaagcgc ctggtggaca   60
ccgccatgta cgccacg                                                  77

<210> SEQ ID NO 343
<211> LENGTH: 130
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Affymetrix ID 2586065

<400> SEQUENCE: 343
gctctccttt gttgctactg cctgacaatg tccgaattcg aaaatataat ctctcatctg   60

```
agaggttctc agagtatctt caagatgagg aatatatcca agctgttgat tatgattggg    120
atcccaagga                                                           130
```

```
<210> SEQ ID NO 344
<211> LENGTH: 87
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Affymetrix ID 3095521

<400> SEQUENCE: 344
agtcttccag agttttcggg agctaattaa ttatgtgatt tcctctcctc tgagaactgt    60
tttgctggcg tgtcaccaag ttgtcac                                        87
```

```
<210> SEQ ID NO 345
<211> LENGTH: 54
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Affymetrix ID 2586168

<400> SEQUENCE: 345
caacatgtga gcagcttact tgtgacaatg gggcctgcta taacaccagt caga          54
```

```
<210> SEQ ID NO 346
<211> LENGTH: 84
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Affymetrix ID 2466628

<400> SEQUENCE: 346
ttcatgttcc caaaatcacc gtacgactct tttccaaaca caggcaaatc cgaaatcagc    60
aggacgactg ttttcccaac acgg                                           84
```

```
<210> SEQ ID NO 347
<211> LENGTH: 86
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Affymetrix ID 2466564

<400> SEQUENCE: 347
cgctcgctgt gctgtctgtc acgctggtta tggcctgcac agaagccttc ttccccttca    60
tctcgagagg gaaagaactc ctttgg                                         86
```

```
<210> SEQ ID NO 348
<211> LENGTH: 786
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
```

<223> OTHER INFORMATION: Affymetrix ID 3160700

<400> SEQUENCE: 348

| | | | | | |
|---|---|---|---|---|---|
| tttgggcttt | atcagaactc | ctttctaagg | agcactagaa | tgagaaatca | tgttgttcga | 60 |
| tcgtttcaca | tctgtatatc | agctctaaag | cagagatgta | ttatggtgat | actccaaggt | 120 |
| ggcatagcca | ttcatttaca | acttccagat | ttgagctgcc | tggagggaat | ccatatcagc | 180 |
| tctgcataag | attatataca | aagctgtcac | tcacaaaagg | ctggatgtgc | tttcatccaa | 240 |
| ctggaaggct | ttattcttcc | aagttcattc | atactcaaag | aggccagtac | tttgccatcc | 300 |
| ttgcacttct | gttatcaggg | cccaaataac | agtggcaagc | taccaactaa | gttgtatttt | 360 |
| aataaagatt | ccatgggttg | aacaagccac | gttgcagaaa | aagagcttcc | cctaacctgg | 420 |
| gttgttgcag | agtaaatccc | acgacataag | ctggtatcag | tggttcgggg | gaaatagttc | 480 |
| cattctatga | ctcttgtctc | ctcctccagg | aggactgttc | taactagtaa | tcttggccct | 540 |
| attcattaca | tcctctgctt | gtcattctgc | taatttatga | agatagttta | ttatagtctg | 600 |
| tacttcagtt | ctcatcttgt | aaataatgct | taacataaac | ttgtacttac | actgaaatcc | 660 |
| aaaatagtca | tgtttctgca | gtattctgta | gccaacttaa | acctgtgctt | tcatgtttaa | 720 |
| gaaatgagaa | attgtgccaa | agatagcaga | agagtagata | agtgctcagt | attgacgacc | 780 |
| tacatc | | | | | | 786 |

<210> SEQ ID NO 349
<211> LENGTH: 164
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Affymetrix ID 3325106

<400> SEQUENCE: 349

| | | | | | |
|---|---|---|---|---|---|
| ggcctgacag | ggaccagaaa | atatggcttt | ggtgttgctg | tttattagca | atgctgagac | 60 |
| cagttgtaat | aggagccgag | cagtgtgtgg | gtgataaagt | gtgggtgtc | aagaagcggc | 120 |
| agcaaccaga | aattagactg | acaagagcca | gcactcgctg | gata | | 164 |

<210> SEQ ID NO 350
<211> LENGTH: 393
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Affymetrix ID 2721311

<400> SEQUENCE: 350

| | | | | | |
|---|---|---|---|---|---|
| ctgcctggag | accttgatct | tgacctggaa | tatggtgatc | gggaacacga | cctgtgtcga | 60 |
| gaaaaggacc | ttgaacgaga | gcgcatcctt | tggggtcttt | gagaaaataa | ggatttgggt | 120 |
| ggtgacacag | aatctctaca | tggagagtta | aaagaagaac | aagaaggaga | cacattgaac | 180 |
| aatgaatagg | attgcgtgcc | atcccaaggg | tagctcagtt | tatcactttc | atcttcgctg | 240 |
| tcatcaaaca | ggccatccat | ggctagtcct | gaatttataa | acataggtag | tttggagaat | 300 |
| tgttcattac | tgaaatcact | gtccctcagt | tcaccggtct | tgtctgcttc | gtcgtcaaaa | 360 |
| acagcttgac | tgggatgacc | gaagtgcttg | ttc | | | 393 |

<210> SEQ ID NO 351
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Affymetrix ID 3018619

<400> SEQUENCE: 351
tgctggattg ctcaccattg tcgtctgtat ggcagttaag gaattaaatg atcggtttag      60
acacaaaatc ccagtcccta ttcctataga agtaattgtg                          100

<210> SEQ ID NO 352
<211> LENGTH: 93
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Affymetrix ID 2586130

<400> SEQUENCE: 352
acagactgct ctacttcatg gactcctatc ttgattacat ggactttgt gattataatg       60 gacaccatcg gagacaggtg atagccagtg att                                  93

<210> SEQ ID NO 353
<211> LENGTH: 111
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Affymetrix ID 3018636

<400> SEQUENCE: 353
tgcgggttct ttgacgacaa cattagaaag gacacattct ttttgacggt ccatgatgct      60
atactctatc tacagaacca agtgaaatct caagagggtc aaggttccat t              111

<210> SEQ ID NO 354
<211> LENGTH: 61
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Affymetrix ID 3108616

<400> SEQUENCE: 354
aaaacacgat caatgcaaat gtgaaaacct tataatgttc agaaccttg caaacgaaga       60 a                                                                     61

<210> SEQ ID NO 355
<211> LENGTH: 89
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Affymetrix ID 3862193

<400> SEQUENCE: 355

```
atggtctccg agtggatctc ccagctgaga agttagcatc tgtgtccgtg agtcgtacac    60
ctgatggctc cctgctagtc cgccagaag                                      89
```

<210> SEQ ID NO 356
<211> LENGTH: 619
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Affymetrix ID 2586039

<400> SEQUENCE: 356

```
tgtgttctct cactagctgc aagacaaca ttttatttg tgatgtctat gaggaaatcc      60
catatcatta agtgccagtg tcctgcattg agtttgtggt taattaaatg agctcttctg   120
ctgatggacc ctggagcaat ttctcccctc acctgacatt caaggtggtc acctgcccta   180
gtagttggag ctcagtagct gaatttctga accaaatct gtgtcttcat aaaataaggt    240
gcaaaaaaaa aaaataccag ttaagtaaag cctcaactgg gttttgttt ctatgaaaat    300 atcattataa tcactattta tttcctaagt tgaacctgaa tagaaaggga aaccattctt   360
attaagcttt ttattaggcc ctgtggctaa atgtgtacat ttatattaga atgtactgta   420
cagtccagat cttttcttta attcttattg gtttttttt tttttttttt tttagagatg    480
gagtcttgct atattgccaa ggctgatctt gaagtcctgg gctcaagtga tcctcccacc   540
tcagcctcct gagtggttgg ggttacgggc gtgagccact gtgcctggct tccagctctc   600
ctcttaaata gtgggtata                                                619
```

<210> SEQ ID NO 357
<211> LENGTH: 211
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Affymetrix ID 3833286

<400> SEQUENCE: 357

```
tcagggagg gtttaaagct tcagagcccg tggtcatatt tagaaagatc tttaccactg     60
ccacgtggag ggtggaccag agggagcaaa ggtaggagct gggagggacc caggtgggag   120
aggaccagct ggaccaaggg agggccatgg ggacggggaa aggagtgggt acaagagaca   180
ttgaagagac tgagtggact agctgtggtg g                                  211
```

<210> SEQ ID NO 358
<211> LENGTH: 58
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Affymetrix ID 2586132

<400> SEQUENCE: 358

```
tgagcatcta ctgttctggt ctgactgggg ccaccaccct cgcatcgagc gagccagc     58
```

<210> SEQ ID NO 359
<211> LENGTH: 165

```
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Affymetrix ID 2763561

<400> SEQUENCE: 359
tcctattatg tgttcaagga ccacatgtgt tctctatttt gcctttaaat ttttgtgaac    60 caatttaaa tacattctcc tttttgccct ggattgttga catgagtgga atacttggtt   120
tcttttctta cttatcaaaa gacagcacta cagatatcat attga                  165

<210> SEQ ID NO 360
<211> LENGTH: 99
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Affymetrix ID 2466620

<400> SEQUENCE: 360
ctccgggagg ctccctcggg tgacttggat ctccatgtcg ctggctgctc tgctgatcgg    60
aggcttcgca ggtctcacct cgacggtgat ttgcaggtg                          99

<210> SEQ ID NO 361
<211> LENGTH: 125
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Affymetrix ID 2586145

<400> SEQUENCE: 361
ttcacgattg tactgggtag atgcctattt tgataaaatt gagcacagca cctttgatgg    60
tttagacaga agaagactgg gccatataga gcagatgaca catccgtttg gacttgccat   120
cttg                                                                125

<210> SEQ ID NO 362
<211> LENGTH: 108
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Affymetrix ID 3018615

<400> SEQUENCE: 362
gcctttggtg tgctaaagac tcttgtgccc atcttggagt ggctccccaa ataccgagtc    60
aaggaatggc tgcttagtga cgtcatttcg ggagttagta ctgggcta                108

<210> SEQ ID NO 363
<211> LENGTH: 222
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Affymetrix ID 4023363
```

<400> SEQUENCE: 363
tcaggtaagc ggtaggtgga atccagatt tcctcttgag gaaaagtcct aggaatcaca    60
acagaaggga ctttgcagtc ctcattaaca catggacaaa gagcagacaa ctactacgtt   120
acaagggatt caactagtca ctgttgtgaa atgtcatatc catgttgatg acagccctgg   180
cgcctgctca actcccctc tagagttttg cggttacttc cg                      222

<210> SEQ ID NO 364
<211> LENGTH: 105
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Affymetrix ID 2537578

<400> SEQUENCE: 364
tctcgagcag tgaaacaatg gaacaattta atttaaaatt aaggactagc agaaactccc    60
gctatcattg ttggtactta gtactatctc agttagacca aagtc                   105

<210> SEQ ID NO 365
<211> LENGTH: 493
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Affymetrix ID 2763557

<400> SEQUENCE: 365
tggtaaccga actggtgctt tagtaatgtg gatttttttc ttttttaaaa gagatgtagc    60
agaataattc ttccagtgca acaaaatcaa ttttttgcta aacgactccg agaacaacag   120
ttgggctgtc aacattcaaa gcagcagaga gggaactttg cactattggg gtatgatgtt   180
tgggtcagtt gataaaagga aaccttttca tgcctttaga tgtgagcttc cagtaggtaa   240
tgattatgtg tcctttcttg atggctgtaa tgagaacttc aatcactgta gtctaagacc   300
tgatctatag atgacctaga atagccatgt actataatgt gatgattcta aatttgtacc   360
tatgtgacag acattttcaa taatgtgaac tgctgatttg atggagctac tttaagattt   420
gtaggtgaaa gtgtaatact gttggttgaa ctatgctgaa gagggaaagt gagcgattag   480 ttgagcccctt gcc                                                    493

<210> SEQ ID NO 366
<211> LENGTH: 61
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Affymetrix ID 2586159

<400> SEQUENCE: 366
tgggatttta gattgcccag gaagagaaga tgaaaacaac actagtaccg gaaaatactg    60
t                                                                   61

<210> SEQ ID NO 367
<211> LENGTH: 166

```
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Affymetrix ID 3862199

<400> SEQUENCE: 367
atctgcactc gcacctgcca gggatcctgt gcggctctct ccggcctcac gggctgcacc      60
acccgctgtt ttgagggctg tgagtgcgac gaccgcttcc tgctttccca gggtgtctgc    120
atccctgtcc aagattgtgg ctgcacccat aatggccgat acttgc                    166

<210> SEQ ID NO 368
<211> LENGTH: 122
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Affymetrix ID 3811391

<400> SEQUENCE: 368
ggtgggcatt tttcctgggc tgttcctacc aatagacttg ctgctggttt catgttagtt      60
aggtggcaca ccaagagggg actcagaaag aacagaagat cagaacttgc tggtgtcaga    120
ca                                                                   122

<210> SEQ ID NO 369
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Affymetrix ID 3046252

<400> SEQUENCE: 369
gagcccggag ccgcttgatt gtgttgct                                        28

<210> SEQ ID NO 370
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Affymetrix ID 2466563

<400> SEQUENCE: 370
ttggaacttg taaagtggcc caagagtggc tgtaatttgg gccattat                  48

<210> SEQ ID NO 371
<211> LENGTH: 157
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Affymetrix ID 2721641

<400> SEQUENCE: 371
gaggtctcac cttcgccttt gctgaagtct ccccgcagcc ctctccaccc agaggtctcc      60
```

```
ctataccgag acccaccatc cttccatcct gaggaccgcc ccaaccctcg gagccccca        120 ctcagtaggt ctgaaggcct ccatttgtac cgaaaca                                157
```

<210> SEQ ID NO 372
<211> LENGTH: 176
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Affymetrix ID 3108607

<400> SEQUENCE: 372

```
gagggcttaa ctgcagcacc tgtgaaaaca ctttcggttt taattgacag taaattcatt        60
atcagccaag aggctagggt gatcgtaggc tgaacagcaa tgtctgcatg agggaggtgg       120
agagagctgt gctctgctct gtgctggaga attacattca gttctgggca tggtac          176
```

<210> SEQ ID NO 373
<211> LENGTH: 279
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Affymetrix ID 2721309

<400> SEQUENCE: 373

```
tttaagcgtg tcttcatgga actgctgcca tttgaaatgg tttgcccttg cgcattctgg        60
tcaggtgccc ccagtcctca catgtaccca cacatacttc ccctaaacca agcacacaca       120
ccacacacat acatacacac acacatacat gcacacacgc acactccatc accaagagac       180
tccaggaaaa gcaaagctga cacccatgaa taaacatgtg cttactggat atcattctgt       240
ctcttgcctc ttcagcagct gtgttcatgt aaaccattg                               279
```

<210> SEQ ID NO 374
<211> LENGTH: 175
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Affymetrix ID 2586135

<400> SEQUENCE: 374

```
cacgagtgtg ttcaagagcc ctttggggct aaatgcctat gtccattggg attcttactt        60
gccaatgatt ctaagacctg tgaagacata gatgaatgtg atattctagg ctcttgtagc       120
cagcactgtt acaatatgag aggttctttc cggtgctcgt gtgatacagg ctaca           175
```

<210> SEQ ID NO 375
<211> LENGTH: 200
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Affymetrix ID 2537607

<400> SEQUENCE: 375

-continued

```
atttgaggag gttgctcgca gtagggggat tgaggaggt tgcacacagt gggggattt        60 ttgggggtg cacacagtgg gggactagag gaggttgcac acagtgggag ggatttgggg      120
aggctggaca cagtgggggg atttgaggag gttgcacata gtgggggaga ttttgcgagg    180
ttgcacatag ggagattttg                                                  200

<210> SEQ ID NO 376
<211> LENGTH: 53
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Affymetrix ID 3018628

<400> SEQUENCE: 376
cctgaaaggg atgtttatgc agctgtgtga cattcctcgt ctgtggagac aga             53

<210> SEQ ID NO 377
<211> LENGTH: 133
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Affymetrix ID 2466583

<400> SEQUENCE: 377
gtgctgcgtg caatcccttc agatcctccc agcctcccct tgatgtagca atcactgttt      60
ctgccctatg gcttaggagc caaggctcag ggagattgaa atctcttagt gagtggaacc    120
ctgcagattt aaa                                                         133

<210> SEQ ID NO 378
<211> LENGTH: 127
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Affymetrix ID 2586149

<400> SEQUENCE: 378
ccaagttgct attcgtggga tcccgttcac cttgtctacc caggaagatg tcatggttcc     60
agtttcgggg aatccttctt tctttgtcgg gattgatttt gacgcccagg acagcactat   120
cttttttt                                                               127

<210> SEQ ID NO 379
<211> LENGTH: 41
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Affymetrix ID 3662230

<400> SEQUENCE: 379
gattttacgg gtcactctat ttgtacttgg gagcagggct g                          41

<210> SEQ ID NO 380
<211> LENGTH: 98
```

```
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Affymetrix ID 2586140

<400> SEQUENCE: 380
gagacatgcc aacctagtca gtttaattgc cccaatcatc gatgtattga cctatcgttt    60
gtctgtgatg gtgacaagga ttgtgttgat ggatctga                           98

<210> SEQ ID NO 381
<211> LENGTH: 242
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Affymetrix ID 3367740

<400> SEQUENCE: 381
agcgaatttg cctgagactc ctgacccta gttcaatttg ctttacattg tattgcttgc     60
ctccattctg aaatatttct ttaaaatttc tgtagttttt tttttttttc ccacacctca   120
ccccactagc cctttacatt cagctgggaa ataggcctaa ttgggactaa ttgtccagct   180
actgctagat ccattgtctt gcctgttgct agtgaaacgt gtgctgcatg ctacaggact   240
ca                                                                 242

<210> SEQ ID NO 382
<211> LENGTH: 180
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Affymetrix ID 2466598

<400> SEQUENCE: 382
aagcagtcga gagtcagaaa gttcagagga gcctgtgcca ggggctacgc ggctgtttcc    60
caccgtcggt gacaaggatc gcatctccag gtctcttcgt cctggtctcc ccgtgtgctg   120
gggtcctggc ttcccgtcac cttcacgccc atcattttcc caagtgtgga cctttcagtc   180

<210> SEQ ID NO 383
<211> LENGTH: 388
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Affymetrix ID 3367691

<400> SEQUENCE: 383
tttaattaag gtagtgcagg ggctggttcc atattaaaca tggtgatggg gatttaagat    60
aataatgcta ccatcagtac atctaaaatt gtttaatgtt ttactgcaaa tattttttag   120
ctagaagaaa ttaaacaagt ggggaagatt ctcagaaacc aacacagccc aaaatgtgca   180
gataaagaac caaaaaataa cgtagaaagg agcaagatta taataaatat ttttaatgag   240
ttaatttatt tcctcttttt aagtcttaac ttgtaacatt atttgaaatc acagtaaatg   300
```

```
tacattttat ttcttgtttc agccctgagg tgagtttatt tggaatgttt gttttaaatg    360
gatttagcca tcatggaatt aggtcatc                                       388
```

<210> SEQ ID NO 384
<211> LENGTH: 46
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Affymetrix ID 3367679

<400> SEQUENCE: 384

```
gagctgttaa acacggttca gaggcgagtc cggcccaagc tccatg                    46
```

<210> SEQ ID NO 385
<211> LENGTH: 240
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Affymetrix ID 2763590

<400> SEQUENCE: 385

```
caaaatgtcg tggtcttaga agcccaaaga ccccttgaaa tgggcagttg atttaaaaca    60
tgccagcttc tactttaacc ttgtggtgga agtaggcata ttataacaca ccaattataa   120
acatatacct cttttttttt ttcactttca ttttcccaac ttttcctttt aactgcagag   180
tgggagccag tgattctgc tttgaaccat gattaattcg tgtaggtatg ctgttattgc    240
```

<210> SEQ ID NO 386
<211> LENGTH: 79
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Affymetrix ID 2586102

<400> SEQUENCE: 386

```
tgcatcccaa gcgaatggat ctgtgacggt gataatgact gtggggatat gagtgacgag    60 gataaaggc accagtgtc                                                   79
```

<210> SEQ ID NO 387
<211> LENGTH: 182
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Affymetrix ID 3367693

<400> SEQUENCE: 387

```
ggccgaatta attggtgtga ttccattctc aatttaagaa atcaaggtta aatgacttgc    60
ccacaattgc attgagctgg aactagggca taggtctgct gtctccagat ctccagctga   120
cttcccaccg cagcctgtca gtcagtgaaa ttaatctgca gtcattcgca gacacctgaa   180
aa                                                                   182
```

-continued

```
<210> SEQ ID NO 388
<211> LENGTH: 97
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Affymetrix ID 2586067

<400> SEQUENCE: 388
atatatgcga gcaaaattgt acccaattaa atgaaggagg atttatctgc tcctgtacag    60
ctgggttcga aaccaatgtt tttgacagaa cctcctg                            97

<210> SEQ ID NO 389
<211> LENGTH: 87
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Affymetrix ID 3095516

<400> SEQUENCE: 389
tgctcagttc accaatttat cttgcttcct acttggctca aaccaacaca aagcaaaacc    60
ctccacagct ggtcacggcc tcattct                                       87

<210> SEQ ID NO 390
<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Affymetrix ID 2466573

<400> SEQUENCE: 390
atgaaatata agcccgacca ttccgaaact gccaactaa                          39

<210> SEQ ID NO 391
<211> LENGTH: 395
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Affymetrix ID 3145950

<400> SEQUENCE: 391
ctatggccag tgttctacag aagtaagact gtgcaaactt tatcgtatag tcaaatgaga    60
ttgcacacta aggcaggatg aggcagaagc aagttgtgtc cacagtatat tacaaaatac   120
cttgcatagc ttattcattc tcacctggta aattcatctt agaattctga aggattttt    180 tcctagataa atttatacaa gttagtgtat acttcttgtc tttgttctgt ggcaaaccag   240
gtttctcagt actgattgtt ttacttcaca acattattga tttaacaata gcctgagctt   300
tggggctctg cactgcgttc attgtaatcc gtgatacaat gactacaaat gtgtcgcgat   360
ttctaatctt catctgtatc tcaggcgatt ttcca                              395

<210> SEQ ID NO 392
<211> LENGTH: 65
<212> TYPE: DNA
```

```
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Affymetrix ID 2586043

<400> SEQUENCE: 392
ggataataag aattatggaa gtcccataaa cccttctgag atagttccag agacaaaccc    60
aactt                                                                65

<210> SEQ ID NO 393
<211> LENGTH: 85
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Affymetrix ID 3104982

<400> SEQUENCE: 393
tcccacagaa tgttgtagag ttcaatgcga acttcagtcc aggtcaacgt cccttggctt    60
atgctctctc ataaactctc gtgga                                          85

<210> SEQ ID NO 394
<211> LENGTH: 1000
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Affymetrix ID 2336909

<400> SEQUENCE: 394
cctcaattct aggtgaccaa cgggagggct tctcaaggct tagctctccc tgagacccag    60
ctggctttta cccttgacct gtgtccctag ctgaatcact agctcagatt tttctgatct   120
aagcaaacaa ctcccagctg aggaatgcag gccacagcac ccaatcaaga caaattgtta   180
ttatcagaaa atgaagcaac acttgagctg ttcaggccag ttccctgttg aagaaacagt   240
tccctgttga agaaagtaga gcctgacact gctcccactt tggagaccac attccctgca   300
cacggtcttt gagagagcag ttgcactcta caggcacact tctgaggtac ggtatctctc   360
tccagccact ctgataccaa gtaattcaag ctggcattcc ttctattagg gaaattcatt   420
ttacccaatt tgcatttatg gaattgatca tttaagacac taaattagtt tttagaacca   480
attatgggaa gaattccagt tgttaggaag agatgaggag ttggaagagg agggattaga   540
aacaggagga ggcagtcatc ctctccttgc caaaagattt aaacctgtcc acattggtgg   600
tgatgatggg tgagtttcca tggtaacaca tccctaattt taccagggaa gaggagagta   660
ctcactttac catctttgaa tatatttcat agaaatctag ctctctgtac cctgaaatct   720
tccactagcc tcacttttca acagagtcat ctagaaggga gggttggctt cccaaaagca   780
taaccttgac caaccaaac ataggcacc agcaatgctg tcattcagtt atgcagaagc    840
tcatttgtga aattctgttt ctctgatttc ttcgcaagtc tcttaatggt catttgtgtt   900
agattacatc aaactgatgg atagccattg gtattcatct attttaactc tgtgtcttta   960
catatttgtt tatgatggcc acagcctaaa gtacacacgg                        1000

<210> SEQ ID NO 395
```

```
<211> LENGTH: 333
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Affymetrix ID 3108620

<400> SEQUENCE: 395
cggattacaa tgaacgcagt gcagagcccc aaagctcagg ctattgttaa atcaataatg      60
ttgtgaagta aacaatcag tactgagaaa cctggtttgc cacagaacaa agacaagaag     120
tatacactaa cttgtataaa tttatctagg aaaaaaatcc ttcagaattc taagatgaat    180
ttaccaggtg agaatgaata agctatgcaa ggtattttgt aatatactgt ggacacaact    240
tgcttctgcc tcatcctgcc ttagtgtgca atctcatttg actatacgat aaagtttgca    300
cagtcttact tctgtagaac actggccata gga                                 333

<210> SEQ ID NO 396
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Affymetrix ID 3095473

<400> SEQUENCE: 396
atgttgttac agatcccgtt gcgttccaaa aatgaa                               36

<210> SEQ ID NO 397
<211> LENGTH: 492
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Affymetrix ID 2763580

<400> SEQUENCE: 397 gcagggcag atttgttctt ccacagattc agaccagtgc tacctgagag agactttgga      60
ggcaagcaag caggtctctc cttgcagcac aagaaaacag ctccaagacc aggaaatccg    120
agccgagctg aacaagcact tcggtcatcc cagtcaagct gttttttgacg acgaagcaga   180 caagaccggt gaactgaggg acagtgattt cagtaatgaa caattctcca aactaccctat 240 gtttataaat tcaggactag ccatggatgg cctgtttgat gacagcgaag atgaaagtga    300
taaactgagc tacccttggg atggcacgca atcctattca ttgttcaatg tgtctccttc   360
ttgttcttct tttaactctc catgtagaga ttctgtgtca ccacccaaat ccttattttc    420
tcaaagaccc caaaggatgc gctctcgttc aaggtccttt tctcgacaca ggtcgtgttc    480
ccgatcacca ta                                                        492

<210> SEQ ID NO 398
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Affymetrix ID 3367742
```

<400> SEQUENCE: 398
aacgcaccat gcctgcttcc atcttt                                            26

<210> SEQ ID NO 399
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Affymetrix ID 3662219

<400> SEQUENCE: 399
ctacaactcc gactcatttg ctacattc                                          28

<210> SEQ ID NO 400
<211> LENGTH: 279
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Affymetrix ID 2331563

<400> SEQUENCE: 400
ctgaaaagtc ttgagcaaac agttgccgct ctccaccccc tgcttttta aaaaaatttt        60 ttctcacgta agaaaatgtt atctgtgtgc tggggaaaat tttgaaaata acaaaaacca      120
gaatacaaac acccataatc aatcacagag ataaccactg ttcataattc cttccagtct      180
tcttacttgg cacatataca tttgtctttc tttatatatg acatatggat attttacaaa      240
gttaggatcc tactctatgc actgcttggt gatcggatc                             279

<210> SEQ ID NO 401
<211> LENGTH: 265
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Affymetrix ID 3727624

<400> SEQUENCE: 401
gcttgtgatg acgaatcctg ctctaaaata cacaaggagc tttcttgttt cttattaggc       60
ctcagaaaga agtcagttaa cgtcacccaa aagcacaaaa tggattttag tcaaatattt      120
attggatgat acagtgtttt ttaggaaaag catctgccac aaaaatgttc acttcgaaat      180
tctgagttcc tggaatggca cgttgctgcc agtgccccag acagttcttt tctaccctgc      240
gggcccgcac gttttatgag gttga                                           265

<210> SEQ ID NO 402
<211> LENGTH: 79
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Affymetrix ID 2586061

<400> SEQUENCE: 402

```
cttcaagttt tgggagtag cgtctatgac tgtttcaaga attataacat gcccttgaga      60
tcatatagaa ccaaccatt                                                  79

<210> SEQ ID NO 403
<211> LENGTH: 222
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Affymetrix ID 2997517

<400> SEQUENCE: 403
aacgcttgga tagcaacagt ccgtcctaga ggcatttagg tttagtctat tagagatgga      60
gcgagactac tgatttcacc atttgtgctt tcagctaaga ggctgggagc gtgggtggaa     120
atgaagaagg cagttctggc ctggggcagg gagaggaaac cccagactag ctggtgagga     180
gggaagattt gtcacgatca cagtgcagac gcaaagtggg ca                        222

<210> SEQ ID NO 404
<211> LENGTH: 210
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Affymetrix ID 2586088

<400> SEQUENCE: 404
agggccacca tcgacacacg gtgtatgatg gggcactgcc tcacccttc gctattacca       60 tttttgaaga cactatttat tggacagatt ggaatacaag gacagtggaa aagggaaaca    120
aatatgatgg atcaaataga cagacactgg tgaacacaac acacagacca tttgacatcc    180
atgtgtacca tccatatagg cagcccattg                                     210

<210> SEQ ID NO 405
<211> LENGTH: 702
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Affymetrix ID 3992449

<400> SEQUENCE: 405
agctgggacc caccgtgtag acacacgaca tgcaagagtt gcagcggctg ctccaactca      60
ctgctcaccc tcttctgtga gcaggaaaag aaccctactg acatgcatgg tttaacttcc    120
tcatcagaac tctgcccttc cttctgttct tttgtgcttt caaataacta acacgaactt    180
ccagaaaatt aacatttgaa cttagctgta attctaaact gacctttccc cgtactaacg    240
tttggtttcc ccgtgtggca tgttttctga gcgttcctac tttaaagcat ggaacatgca    300
ggtgatttgg gaagtgtaga aagacctgag aaaacgagcc tgtttcagag gaacatcgtc    360
acaacgaata cttctggaag cttaacaaaa ctaaccctgc tgtcctttt attgttttta     420 attaatattt ttgttttaat tgatagcaaa atagtttatg ggtttggaaa cttgcatgaa    480 aatatttag cccccctcaga tgttcctgca gtgctgaaat tcatcctacg gaagtaaccg    540
caaaactcta gaggggagt tgagcaggcg ccagggctgt catcaacatg gatatgacat     600
```

-continued ttcacaacag tgactagttg aatcccttgt aacgtagtag ttgtctgctc tttgtccatg    660
tgttaatgag gactgcaaag tcccttctgt tgtgattcct ag                      702

<210> SEQ ID NO 406
<211> LENGTH: 115
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Affymetrix ID 2586155

<400> SEQUENCE: 406
gattgccaga tatggggaat tgtgaccag aagtgtgaaa gccgacctgg ccgtcacctg     60
tgccactgtg aagaagggta tatcttggag cgtggacagt attgcaaagc taatg        115

<210> SEQ ID NO 407
<211> LENGTH: 97
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Affymetrix ID 2586139

<400> SEQUENCE: 407
ctcaattcaa gtgtgccagt ggggataaat gtattggcgt cacaaatcgt tgtgatggtg    60
tttttgattg cagtgacaac tcggatgaag caggctg                            97

<210> SEQ ID NO 408
<211> LENGTH: 38
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Affymetrix ID 3126609

<400> SEQUENCE: 408
atgacagtgt tgatcggatg ggatgtatgg cagttgga                           38

<210> SEQ ID NO 409
<211> LENGTH: 108
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Affymetrix ID 2586113

<400> SEQUENCE: 409
ttacagtgac tacctcaacc agatgattaa ttccatggct gaagatgggt ctaaccgcac    60
tgtgatagcc cgcgttccaa accaagagc aattgtgtta gatccctg                 108

<210> SEQ ID NO 410
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:

<223> OTHER INFORMATION: Affymetrix ID 2586160

<400> SEQUENCE: 410
aatggtcttg cccagagtcg ggacgatgca tctccattta ta                42

<210> SEQ ID NO 411
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Affymetrix ID 2608611

<400> SEQUENCE: 411
atgagtctgg ccgaggttca gtgtcac                                 27

<210> SEQ ID NO 412
<211> LENGTH: 107
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Affymetrix ID 2586152

<400> SEQUENCE: 412
gcattcatgg atggcagcaa ccgtaaagac ttggtgaaaa caaagctggg atggcctgct    60
ggggtaactc tggatatgat atcgaagcgt gtttactggg ttgactc                107

<210> SEQ ID NO 413
<211> LENGTH: 348
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Affymetrix ID 2466574

<400> SEQUENCE: 413
tgacgtctac atccacctgc aaagcctgcc cctgggtcct gcagtagagc ctgaaccttt    60
ctttggtttg atgcttcctg attcataaat catgatcact caaaaaaaac tctttaaaaa   120
atgtattgtg cctaagttta cattttaaca acctcaagac cagggcctca gccggcagca   180
gtgagttcct gctcggccct tctgaaaggc cctgctgctg tcttgggcgc ctctgcccca   240
gctgctgggc gggctccact gacgctcctg ggagaatctc tgctgaccac acaatgacat   300
tggcactggg agctgtgatc tggggacact tagatctgag ctggtttc              348

<210> SEQ ID NO 414
<211> LENGTH: 93
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Affymetrix ID 2763558

<400> SEQUENCE: 414
atatttcaaa tgaacacgtg caccccatca tcactggagg caaatttcag catagatctg    60
taggattttt agaagaccgt gggccattgc ctt                                93

<210> SEQ ID NO 415
<211> LENGTH: 319
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Affymetrix ID 3662224

<400> SEQUENCE: 415
cactggctac tggttcgaga attgctatct gatgttcaat cacagaggaa gaggagttaa      60
gtggcccagg agtcaggacc atgcttgccc gcaggtgccc tttgtgaaga gggcatttca    120
gaaggcagcg tgggtcatgt gcaagtttgg gtgtcacata accagattca cagcccactt    180
cacaccttcc tggctgtgta gctggcacaa gtcacttaac ctctctgtgc ctccatttcc    240
tcacttgtag aaagcagatt ataaatatat gtagggatta aatgtgatag tgccctggta    300
cctggctcgg gcttaataa                                                  319

<210> SEQ ID NO 416
<211> LENGTH: 77
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Affymetrix ID 3367741

<400> SEQUENCE: 416
ctcaaggcaa agttaccata acggtggatg agtacagctc aaaccccacc caggcattca      60
cgcactacaa catcaac                                                     77

<210> SEQ ID NO 417
<211> LENGTH: 108
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Affymetrix ID 2466582

<400> SEQUENCE: 417
ggcgcctcca acacggccct ggcacgatgg ctccctccag tctatgagga cggcttcagt      60
cagccccgag gctggaaccc cggcttcttg tacaacgggt tcccactg                  108

<210> SEQ ID NO 418
<211> LENGTH: 43
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Affymetrix ID 3108615

<400> SEQUENCE: 418
agaagacaat cttttacggt ctacacaaaa gctttcccat tca                        43

<210> SEQ ID NO 419
<211> LENGTH: 72
<212> TYPE: DNA

```
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Affymetrix ID 2721643

<400> SEQUENCE: 419
ggaagccagc ccgtgcaacg gaagccaggc caactgcccc gcgtcttcag ctgtttcgca    60
tccaccgcca cc                                                        72

<210> SEQ ID NO 420
<211> LENGTH: 202
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Affymetrix ID 2586153

<400> SEQUENCE: 420
ggtttaaata tccaagaggt tctcaatgtt tctgttgaaa ccccagagaa cctggctgtg    60
gactgggtta ataataaaat ctatctagtg gaaaccaagg tcaaccgcat agatatggta   120
aatttggatg gaagctatcg ggttacccct ataactgaaa acttggggca tcctagagga   180
attgccgtgg acccaactgt tg                                            202

<210> SEQ ID NO 421
<211> LENGTH: 165
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Affymetrix ID 2537572

<400> SEQUENCE: 421
ctgcagtttt gttctattgg tcaaaatata ttctgacaaa aatgtatttg aagtgcatga    60
taaggtaaag gtgtgttgaa tattttgatt tcacacttag ttccgagtgt actgtgttaa   120
gcaaggtgcc cctaagttga agggtgtag gcacaattaa cagtc                    165

<210> SEQ ID NO 422
<211> LENGTH: 109
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Affymetrix ID 2586068

<400> SEQUENCE: 422
ccttgtacag aatatgaata taagtgtggc aatgggcatt gcattccaca tgacaatgtg    60
tgtgatgatg ccgatgactg tggtgactgg tccgatgaac tgggttgca              109

<210> SEQ ID NO 423
<211> LENGTH: 105
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
```

<223> OTHER INFORMATION: Affymetrix ID 2586143

<400> SEQUENCE: 423
tgggtgccat tattcgagtc aggaaagcag atggtggaga atgacagtt atccgaagtg    60 gcattgctta catactgcat ttgaaatcgt atgatgtcaa catcc                  105

<210> SEQ ID NO 424
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Affymetrix ID 3893028

<400> SEQUENCE: 424
ttaatgactg gctacagagt aacaaaa                                        27

<210> SEQ ID NO 425
<211> LENGTH: 76
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Affymetrix ID 3367676

<400> SEQUENCE: 425
gttatggcat catgaccgac ggttacacaa cgtacatcaa tgcctcgacg tgtacagtca    60
gctttcaacc gaccaa                                                    76

<210> SEQ ID NO 426
<211> LENGTH: 99
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Affymetrix ID 2586172

<400> SEQUENCE: 426
agtgcgcatt ttcgctgtgg aagtgggcat tgcatccctg cagactggag gtgtgatggg    60
accaaagact gttcagatga cgcggatgaa attggctgc                           99

<210> SEQ ID NO 427
<211> LENGTH: 142
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Affymetrix ID 3142383

<400> SEQUENCE: 427
acctggactg aagttcgcat tgaactctac aacattctgt gggatatatt gttcaaaaag    60
atattgttgt tttccatgat ttagcaagca actaattttc tcccaagctg attttattca   120
atatggttac gttggttaaa ta                                            142

<210> SEQ ID NO 428
<211> LENGTH: 384

```
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Affymetrix ID 3367677

<400> SEQUENCE: 428
cctgaggagt aatccttata ttactcattt tattccctag aactcaatag ttaacacaag     60
gctttgaaat gaaatcccta ttttaaaagg aggaaaaaag ttttctttta ttctccctag    120
taaagaaatc acagcccttc ttcaacaagt ttagcattta aataaagaaa aaaaaattgc    180
tcttagttga aggagaagat tctaccattt aaagaaaata gagtaaaatt gggcagtagc    240
ttctgaaagt cattatatct gaggaggctc aactgaattt catctcactg cccactgaca    300 aaaattttt gttttccttg cctgacagcc ctacattcca tcactctcat ttgtatatat    360
tacagtaaat gtgacacgct ctcc                                           384

<210> SEQ ID NO 429
<211> LENGTH: 82
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Affymetrix ID 2763566

<400> SEQUENCE: 429
atgacagagg gatggcgaat acctcatggg acagcgcgtc cttccctaaa gactattgca     60
agtcatactt aggaatttct cc                                              82

<210> SEQ ID NO 430
<211> LENGTH: 295
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Affymetrix ID 3763228

<400> SEQUENCE: 430
cgggacattt tctccatcgc gatgcactca aattttttcc ccttaaaaaa agaaataaga     60
aagaaacaac cgcccctaa aatgttgctg agcttttcct ccgtcctttg ccaaaagtac    120
tcgctctcaa ggcggtggag aaaagggaag aaaaaaatta cttatatctt tataaataca    180
tctgcataaa aatatatatt aaaaaaaaac tttcgggttt ccagtgcaga cggtcccagg    240
agagcgcgcc aagtgcccgc gggctccccg gcgacgtgca ggatgctctc acctg         295

<210> SEQ ID NO 431
<211> LENGTH: 91
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Affymetrix ID 3108580

<400> SEQUENCE: 431
tgtgcctcat ctaatcacgg atgtcagcac gagtgtgtta acacagatga ttcctattcc     60
```

```
tgccactgcc tgaaaggctt taccctgaat c                                      91
```

<210> SEQ ID NO 432
<211> LENGTH: 71
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Affymetrix ID 2608485

<400> SEQUENCE: 432

```
cctggttgat gatcgttgtg ttgtacagcc agaaaccggg gaccttaaca atccacctaa       60
gaaattcaga g                                                            71
```

<210> SEQ ID NO 433
<211> LENGTH: 202
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Affymetrix ID 2331560

<400> SEQUENCE: 433

```
ctcttcagtg cccagtgtgt aacctggcat ggtttgggtg tgctaggagt ttgtgaaatg       60
aatgttttca agacgcaaac gctgctatgc ccatcaggtg tgcacagcag gcctgaggat      120
catgatgaga ctccctttt atgcagcaaa gcacaaagtg tgacagtcgt ggccttcctg       180
gtggccagac ttctagcaac tt                                              202
```

<210> SEQ ID NO 434
<211> LENGTH: 250
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Affymetrix ID 2763602

<400> SEQUENCE: 434

```
gtctggacca ctttgcaaca tttgttcaaa ctgaaaattt tgacaaagac attctgttca       60
caaagagcca acaaatgttc tgtgtttcga tacatttgga ggttacaaaa tgttgcctgg      120
tcttggcaga taactaagtc tggggaccca catagtgcaa gccatgccct gtttaatttg      180
tctttcaatg gcaaatgtgt ttcttctgtg attcagcata agggatgata ccctccaata      240
ggactgtgtg                                                            250
```

<210> SEQ ID NO 435
<211> LENGTH: 410
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Affymetrix ID 3811360

<400> SEQUENCE: 435

```
taggcccgtt ttcacgtgga gcatgggagc cacgacccct cttaagacat gtatcactgt       60
agagggaagg aacagaggcc ctgggcccctt cctatcagaa ggacatggtg aaggctggga    120
```

```
acgtgaggag aggcaatggc cacggcccat tttggctgta gcacatggca cgttggctgt    180
gtggccttgg cccacctgtg agtttaaagc aaggctttaa atgactttgg agagggtcac    240
aaatcctaaa agaagcattg aagtgaggtg tcatggatta attgacccct gtctatggaa    300
ttacatgtaa aacattatct tgtcactgta gtttggtttt atttgaaaac ctgacaaaaa    360
aaaagttcca ggtgtggaat atgggggtta tctgtacatc ctggggcatt              410
```

<210> SEQ ID NO 436
<211> LENGTH: 136
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Affymetrix ID 2586150

<400> SEQUENCE: 436

```
accaatccgt gtaaagataa caatgggggc tgtgagcagg tctgtgtcct cagccacaga    60
acagataatg atggtttggg tttccgttgc aagtgcacat tcggcttcca actggataca    120
gatgagcgcc actgca                                                     136
```

<210> SEQ ID NO 437
<211> LENGTH: 65
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Affymetrix ID 2586050

<400> SEQUENCE: 437

```
tgtgctgttg acaatcctct tgatcgtcgt aattggagct ctggcaattg caggattctt    60
ccact                                                                 65
```

<210> SEQ ID NO 438
<211> LENGTH: 125
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Affymetrix ID 2586041

<400> SEQUENCE: 438

```
ggaaagtgtt gctgcgacac cacctccatc accttcgctc cctgctaagc ctaagcctcc    60
ttcgagaaga gacccaactc caacctattc tgcaacagaa gacactttta aagacaccgc    120
aaatc                                                                 125
```

<210> SEQ ID NO 439
<211> LENGTH: 239
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Affymetrix ID 3811354

<400> SEQUENCE: 439

```
tgtattgaaa gcttttgtta tcaagatttt catactttta ccttccatgg ctcttttaa      60 gattgatact tttaagaggt ggctgatatt ctgcaacact gtacacataa aaaatacggt    120
aaggatactt tacatggtta aggtaaagta agtctccagt tggccaccat tagctataat    180
ggcactttgt ttgtgttgtt ggaaaaagtc acattgccat taaactttcc ttgtctgtc     239

<210> SEQ ID NO 440
<211> LENGTH: 851
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Affymetrix ID 3088273

<400> SEQUENCE: 440
agcggtccct acttctgagg agaaaatgtg gtttctgact tttaggtaca tcacgatatc     60
accagtctga atgagtttcc ttttctgtaa agcagaaagt gtcattttct tttcctccag    120
tgttcagttg ctcctcttcg aaaatactct tcagagaaag tatctgtacg tctgtattag    180
tacaaaccat tccttcccta tgtctcaatg cctgacattc agtgcctgac agaatcagca    240
tttggcatgt ccttggatat ggcatcaatt tgatgctttg aactgaaagt tctcataatg    300
catctcaaag tatcttctta aaaaatataa aaatgtaggc caacttgtgc tctcttgtaa    360
ggcttgcaaa gtggtaatta aataagcaga ctataactca caagggaaaa aaagtgcatt    420
tttaaataaa agaaaaaaac ggagacagtt aaaaggacaa ccaaaaagat aagcagatta    480
tttttggtta atcttgggga aaatatgaca cgatatttat ggtttctttt cttttctggt    540 ccatttttatt ttacttaatg tactcactag tatcataata agcctatctc ctctcctgcc    600
ttctgatatt ttagcattcc tagaaactag agccctgctg ataggctcat tcatatgagg    660
agaaatatgc ttgcctttca tgctaatgaa ttttttacaa aactgctctt aaatcatgaa    720
tatttcaatg agcacacaaa acaacaggtc tcagtgtgtt gtaaacacca tcaaaacctc    780
cacaccatta ggcttataat ctcacaagca ttctgccttt gtcagacact tcacagggtg    840
caactgggtt a                                                         851

<210> SEQ ID NO 441
<211> LENGTH: 116
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Affymetrix ID 3046251

<400> SEQUENCE: 441
cagcgtgggg aacgagaaac tctttgcctg tagggaccct tctagctgca aacttaaaaa     60
tgtatgtggc aagatgcaac ccaagcaccg agcaggattc cagacgagtt ataatc        116

<210> SEQ ID NO 442
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Affymetrix ID 2336897
```

```
<400> SEQUENCE: 442
cagagtcaag cggaacatcc tggccatggg                                       30

<210> SEQ ID NO 443
<211> LENGTH: 88
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Affymetrix ID 3108574

<400> SEQUENCE: 443
gcctcagaaa accacggatg tgaacatgag tgtgtaaatg ctgatggctc ctacctttgc      60
cagtgccatg aaggatttgc tcttaacc                                         88

<210> SEQ ID NO 444
<211> LENGTH: 109
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Affymetrix ID 3354771

<400> SEQUENCE: 444
taattatcgg actaccaggt tcctggctga ggaggggttt tataaattcc ataactggtt      60
tgatgaccga gcctggtacc ctttgggacg aatcattgga ggaacaatt                  109

<210> SEQ ID NO 445
<211> LENGTH: 89
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Affymetrix ID 3367705

<400> SEQUENCE: 445
ctctagaaat cactcttagt tacagagacc gtcgcttcaa ggctgcagtc aaagtagttg      60
gtgtcaagtt tgagattggt cggaagcta                                        89

<210> SEQ ID NO 446
<211> LENGTH: 237
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Affymetrix ID 3791751

<400> SEQUENCE: 446
cagcgcctta ttttgtgatc acagagaatg caattaatac tttggctgcc ttggtatgta     60
gaccaaacct tctgccacag tgttttgcag tgctgttgtc cagggcagct ctgccaatct     120
tttcattcca acagaaacga tgccagactt ctcggtgcta agcaaagtat aatgaggcgg     180
aagaggtggc tggaaccctc agtgagggaa tgtgctcctg ggatgattct ctacaaa       237

<210> SEQ ID NO 447
<211> LENGTH: 96
```

```
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Affymetrix ID 2514350

<400> SEQUENCE: 447
acagagagtc aggtatgcta tttgctatgg gaaagtgtat attcctgcca tggttcctgt      60
tgtgcagact atacccacta tttaagagga gagctg                                96

<210> SEQ ID NO 448
<211> LENGTH: 122
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Affymetrix ID 2586107

<400> SEQUENCE: 448
ctgatcgcac ttgccagtct ggatacacaa aatgtcataa ttcaaatatt tgtattcctc      60
gcgtttattt gtgtgacgga gacaatgact gtggagataa cagtgatgaa aaccctactt    120
at                                                                   122

<210> SEQ ID NO 449
<211> LENGTH: 87
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Affymetrix ID 3108602

<400> SEQUENCE: 449
gggaccacgg ttgtgaacat tcgtgtgtaa gcagtgaaga ttcgtttgtg tgccagtgct      60
ttgaaggtta tatactccgt gaagatg                                          87

<210> SEQ ID NO 450
<211> LENGTH: 700
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Affymetrix ID 2980482

<400> SEQUENCE: 450
gtctccttcg catctctgtt ctctatcctc tttcttcccc cttttctatt tgttttggt       60 ttattttccc atgtttcttt tcgcaaatac agcaagtgtg tatattgagt caaatctctt    120
cctcctttct tacacaaaat tagcacatta aatatatagt actgcacctt actttttctc    180
tcactatgtc ctagagattg ctctacgcgt tgtatggcgt ttttcatagt tattcactgt    240
gtgtggatac cacagtgtat tcaactgtca cctgatgaca gacatttgca ttctttgcaa    300
tcctttgtaa atacaaacaa tgctgcaatg tacatgtcat tccacatatt ctccaaggta    360
tagttaggac agatcccaga agtggaattt ctgggtcaat gggcaagtgc attttttgctg   420 attattatcc agtttccttc tgttgagttc cattttgcat taccaccagc agtgtttgag    480
```

```
aatgactgtt tctccataga actagaactt ttacagtgaa ttttatccta acttttcttc    540
aatctccttt tacttttact ttctatttta aagaatataa ttcagatttc tctagtggtc    600
atgagtctgt gtgtagtgtg agaatctaga gacaactgtt ctaaggcggc atgagaatgg    660
gcagctcagc tcagagttta gacctcatct gtttccagtg                         700
```

```
<210> SEQ ID NO 451
<211> LENGTH: 56
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Affymetrix ID 3126512

<400> SEQUENCE: 451
atcaagtagg gtttccaagg agtctggttg ggaaggtggt accattgcct tcaaaa        56
```

```
<210> SEQ ID NO 452
<211> LENGTH: 233
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Affymetrix ID 3913484

<400> SEQUENCE: 452
ctgtagccag tcattaatct gaaggtttaa tatatcattt tattgggatg agatcatagt    60
ctttacacaa atgctatgta aacaagttac tgaatatttt tcacctcgtg gagttgtaca   120
caacctttta tatatacaca ccctaccttc tctcaaatgc tgggcttaca ggtttattag   180
ctagggcctt ttgaggtatg ctgtcaggcg acagcccgat gagggtgctc gct          233
```

```
<210> SEQ ID NO 453
<211> LENGTH: 104
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Affymetrix ID 2763571

<400> SEQUENCE: 453
cctaccgtta tacctgtgat gcttttgctg ctcttgaaaa tggatacact ttgcgcaggt    60
caaacgaaac tgactttgag ctgtactttt gtggacgcaa gcaa                   104
```

```
<210> SEQ ID NO 454
<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Affymetrix ID 2980481

<400> SEQUENCE: 454
gagacttttg cagtttcggc tgattcagat agtcattgg                          39
```

```
<210> SEQ ID NO 455
<211> LENGTH: 133
```

```
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Affymetrix ID 2608604

<400> SEQUENCE: 455
ttgtgctatg aaatagcagg tcttgttcat tttttgtaac tattttttg gtacccatta      60 accatcccca cctgtcccct gtcttggaga attgatgcct gagataaatg ggtagccaga    120
tgcacctgta ctc                                                       133

<210> SEQ ID NO 456
<211> LENGTH: 139
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Affymetrix ID 2586064

<400> SEQUENCE: 456
ttgtgtatta cactgtgcga ggggagggct ctaggtttgg tgctatcaaa cgtgcctaca     60
tccccaactt tgaatccggc cgcaataatc ttgtgcagga agttgacctg aaactgaaat   120
acgtaatgca gccagatgg                                                 139

<210> SEQ ID NO 457
<211> LENGTH: 29
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Affymetrix ID 3018621

<400> SEQUENCE: 457
tgaacttcca cctgtgagct tgttctcgg                                       29

<210> SEQ ID NO 458
<211> LENGTH: 1094
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Affymetrix ID 3126626

<400> SEQUENCE: 458
acggccacct tgtatcttgt cactgctcac tgatatattt cctgcctctc cctaccacga     60
aatggaacca catttccaaa tcctaattg ctttcctcct atcaaagaaa agatgtgctg    120
ttggctctcc atgctcctgt cccctgatgc tagctctctg tgctcccct cccctgacac    180 tagctctctg tgctcccct ccccgacctg tgcttttgtc tccacctgtt cctgtctccc   240
acctctggcc cttctgctca ctcctcccca gctgtcactc cttgaagctg tgttggtgtc   300
cacactctct ctacctagca tactttcttc tcatcactga ccagggagct tcaaacctca   360
cctcaatggt agtgtgttcc tgtactctag cttgaggacc agtgcctggc tcttataagg   420
caccaaacaa aagaatgaat gagcgagtga atgaatggaa aagtgaataa agggatgtct   480
```

-continued

| | |
|---|---|
| cctacctgaa gatggctcca cttagtcctc tggcaccacc cacattcttc ttatgggcac | 540 |
| gtgtcattgc attgtcatta ttgtttgcgc agtcgtctcc tgaactcacc cctgagcagg | 600 |
| gcgcagaact ttcctttccc attttggtga tccagctcct tctggagcat ctggggtaa | 660 |
| aaactgtttg tagacacata agcttatagg ccctttgcag ttccgctagt ctgtgaagca | 720 |
| tgactagcaa ataacataaa atagtagctg acgcaatcat ttttggaagg aagcagatgt | 780 |
| tataagtaaa taataatata aaactctaat gtactaactg gcaagttgc tcctatttga | 840 |
| aaagccagag aaaagtaaca gtttggattt tataaagtgg ccttcctttg gatgtgtttt | 900 |
| agacttttaa aatattttcg ttgaatggaa tgagggggtgc cataaagtct gtaagctttt | 960 |
| aatcagtgtc acctttcact gcttcaattt taatttatac tcctgggcca ccattggttt | 1020 |
| tctgcagatg aggctactcc aggaggttca tactggcaca tgaatgggta tccggtgatg | 1080 |
| catgccttcc agta | 1094 |

<210> SEQ ID NO 459
<211> LENGTH: 49
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Affymetrix ID 2649002

<400> SEQUENCE: 459
gtatttgacc acctgctacg tggaagatat tatgctagac acaagttag    49

<210> SEQ ID NO 460
<211> LENGTH: 113
<212> TYPE: DNA
<213> ORGANISM: Artificial Sequence
<220> FEATURE:
<223> OTHER INFORMATION: Description of Artificial Sequence: Synthetic
polynucleotide
<220> FEATURE:
<223> OTHER INFORMATION: Affymetrix ID 2763573

<400> SEQUENCE: 460

| | |
|---|---|
| ccgtgtgatt tatgtcggta aaatcagacc tgacacaaca cggacagaac tgagggaccg | 60 |
| ttttgaagtt tttggtgaaa ttgaggagtg cacagtaaat ctgcgggatg atg | 113 |

<210> SEQ ID NO 461
<211> LENGTH: 501
<212> TYPE: DNA
<213> ORGANISM: Artificial Sequence
<220> FEATURE:
<223> OTHER INFORMATION: Description of Artificial Sequence: Synthetic
polynucleotide
<220> FEATURE:
<223> OTHER INFORMATION: Affymetrix ID 3396651

<400> SEQUENCE: 461

| | |
|---|---|
| tgagccacgc tgtttccaag gaattgtact aggtgctgca atgcaaaggg ttatgacaaa | 60 |
| actgtctgta aatgtaggat ctgaattggt ctttgatagt tttcctgatt tgagaaagaa | 120 |
| gtctctattt ggctaattta gggagctaag agaatggaca aggtctgctt atgtccttct | 180 |
| ggcagcctag catagctttt gcctccctca aatcagttat aagtcaaaac aaataaggca | 240 |
| catttttaa aaaaattccc cccttttaatt gaccaaagta aagccatgac atttcatttg | 300 |
| gtaacctgtt tagaattata aaaatcattt catttggccc agcccatact gcccaagaca | 360 |

```
aaacttccag caattctga tgccatccag ttttgttctt acaaactgca tattaaaaaa    420
aaaaaaaaaa aaaaatcttc aacgtcctaa atgtgatgtg ctcagtgcga agcatatcag    480
agctggacgt gacatttatg t                                              501
```

<210> SEQ ID NO 462
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Affymetrix ID 3893026

<400> SEQUENCE: 462

```
gtcggggaga aatcaggctc tcgaagctca taa                                 33
```

<210> SEQ ID NO 463
<211> LENGTH: 157
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Affymetrix ID 3046250

<400> SEQUENCE: 463

```
ctcgatgctc gattttgagg aagtctggtt tctagaggat gtgcattaag tgacagtcag    60
ctcgttagag tcaatgtcca tttcgccttg gcctcttctc tcccccacta gtgtcacttt   120
acatgagcga agtgctggca cctgttggta agaatga                            157
```

<210> SEQ ID NO 464
<211> LENGTH: 246
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Affymetrix ID 2586114

<400> SEQUENCE: 464

```
tgtgcctttg ggaccctgca aagtgatggc aagaattgtg ccatttcaac agaaaatttc    60
ctcatctttg ccttgtctaa ttccttgaga agcttacact tggaccctga aaccatagc    120 ccaccttttcc aaacaataaa tgtggaaaga actgtcatgt ctctagacta tgacagtgta   180
agtgatagaa tctacttcac acaaaattta gcctctggag ttggacagat ttcctatgcc   240
accctg                                                              246
```

<210> SEQ ID NO 465
<211> LENGTH: 511
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Affymetrix ID 3573880

<400> SEQUENCE: 465

```
gtttctccca taggctgtgt ttacatggag ctatcggttt agccttttaa gcttcattag    60
cttgtctatt attgaaatag tttccaagaa attttagata ttatcataac atctgggtct   120
```

```
actcaaacac ttattgtttg aaagacttat gtcttggacc tatcaaaaac tgactttatt    180
tattgcttag tgaaaatact agtgggatca acaatgattt tcttgaatgg gcatgaatgg    240
agatgcccgc acagtaatgt agaaatgttt catacagcta ttaaaatgta actgacctcc    300
ttagaggcag attagtaact gttcctactt tgtatagcta agtgacagtc acttaactta    360
catgactttc ttttttcaca ttgggtctct ggtcctgtgt cttcacctca tttatagcac    420
gtctccttga tttttggtag tatcaacttc ccagtgatct gttcagttaa gttcttctcc    480
cgttaaccag gaagtgctta ttctctcatc a                                    511
```

<210> SEQ ID NO 466
<211> LENGTH: 175
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: Affymetrix ID 2586101

<400> SEQUENCE: 466

```
ctcggattcc gagtttctct gtgtaaatga cagacctccg gacaggaggt gcattcccca     60
gtcttgggtc tgtgatggcg atgtggattg tactgacggc tacgatgaga atcagaattg    120
caccaggaga acttgctctg aaaatgaatt cacctgtggt tacggactgt gtatc          175
```

<210> SEQ ID NO 467
<211> LENGTH: 134
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: Affymetrix ID 3126515

<400> SEQUENCE: 467

```
acaagacctt gttttgggac tggtgtgtgt actgtattcc tgactgtctg caaggactca     60
aatccatctg cgtttcctgc accagtggag gctgtttatc agtgatggga tgggctccac    120
actccacggt ggct                                                       134
```

<210> SEQ ID NO 468
<211> LENGTH: 250
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: Affymetrix ID 2608689

<400> SEQUENCE: 468

```
gtgggaattt ctgactgaga ccaacatctg atatttgttt gcatactgta ggtgtaaact     60
gctggaaaaa aactggtatt attttttaaaa agggttgcac agccaaatgt taaagctgaa    120
gaagtgacgt tattttagaa gtcttttttt ttttttttcc ttctctgcaa tcagatttct    180
cagcctggta cattatgaac agcttagtgc tgttgagtaa tttatatcag gatgattagg    240
aaagcttttc                                                            250
```

<210> SEQ ID NO 469
<211> LENGTH: 390

```
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Affymetrix ID 4023359

<400> SEQUENCE: 469
aggctcgttt tctcaggtct ttctacactt cccaaatcac ctgcatgttc catgctttaa      60
agtaggaacg ctcagaaaac atgccacacg gggaaaccaa acgttagtac ggggaaaggt     120
cagtttagaa ttacagctaa gttcaaatgt taattttctg gaagttcgtg ttagttattt     180
gaaagcacaa aagaacagaa ggaagggcag agttctgatg aggaagttaa accatgcatg     240
tcagtagggt tctttttcctg ctcacagaag agggtgagca gtgagttgga gcagccgctg     300
caactcttgc atgtcgtgtg tctacacggt gggtcccagc tgaggcatga gaggcatctc     360
agtgggggtt ttatctccta tgcttcttgc                                      390

<210> SEQ ID NO 470
<211> LENGTH: 78
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Affymetrix ID 3046202

<400> SEQUENCE: 470
gaggtgcttg aactcgcttt ctccatcttg tatgactcaa actgccaact gaacttcatc      60
gctcctgaca agcatgag                                                    78

<210> SEQ ID NO 471
<211> LENGTH: 79
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Affymetrix ID 2586075

<400> SEQUENCE: 471
agtgcacaga gagcgagttt cgatgtgtca atcagcagtg cattccctcg cgatggatct      60
gtgaccatta caacgactg                                                   79

<210> SEQ ID NO 472
<211> LENGTH: 420
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Affymetrix ID 3046247

<400> SEQUENCE: 472
cagattaccc tgcttgctgc tagcagaaac ccaaacccac tgcagtctcc catcacattg      60
accattcatt tgtcagcagt gcccctgggt gggaatcagg ctgacagcct tccaaaacct     120
cccctcctgt ccctgcttcc cccacacccc tgcctcaagg gacatctgtg atgcactgga     180
aggtgaccta aacatttggc cagaacccta attctgatac ttctggttct gtgaccccca     240
```

```
ttaattccct tactttccaa acctccaatt cctcacctgt gaatgaggaa ggtgcacctg      300
ggctgcagca ttgctgtgaa gatgaagcaa gtgcttgagg ctctgtgaga tcctgctgtg      360
tggggtctgc tgtccagatc atgaagaact cttgcccctc aggaacttgt atgtagatgc      420

<210> SEQ ID NO 473
<211> LENGTH: 109
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Affymetrix ID 2608629

<400> SEQUENCE: 473
ttttatgacc ggatgaaggt ggcccagcaa gaaatcaaag caacagtgac agtgaacacc       60
agtgacttgg gaaataaaaa gaaagacgat gaggtagaca gggatgccc                 109

<210> SEQ ID NO 474
<211> LENGTH: 496
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Affymetrix ID 3126548

<400> SEQUENCE: 474
ctgtgctatc tctgtcctgt acatgttggc ctgcacccca aaaggtgacg aggagcagct       60
ggcactgccc agggccaaca gccccacggg gaaggagggg taccaggccg tccttcagga      120
gtgggaggag cagcaccgca actacgtgag cagcctgaag cggcagatcg cacagctcaa      180
ggaggagctg caggagagga gtgagcagct caggaatggg cagtaccaag ccagcgatgc      240
tgctggcctg ggtctggaca ggagccccccc agagaaaaacc caggccgacc tcctggcctt     300
cctgcactcg caggtggaca aggcagaggt gaatgctggc gtcaagctgg ccacagagta      360
tgcagcagtg cctttcgata gctttactct acagaaggtg taccagctgg agactggcct      420
tacccgccac cccgaggaga agcctgtgag gaaggacaag cgggatgagt tggtggaagc      480
cattgaatca gccttg                                                      496

<210> SEQ ID NO 475
<211> LENGTH: 745
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Affymetrix ID 3046198

<400> SEQUENCE: 475
tggcatcttg ctcaccgccc tgattctgtt cctcggctcc actgcttcag gtcacttccc       60
atggctgcag tccactggtg ggacaagagc aaagcccact gccagtaaga aggccaaagg      120
gcccttccat cctagccctc tgcaggcatg cccttccttc ccttgggcag gaaagccagc      180
agccccagac tgcccaaaaa cttgcccacc agaccaaggg cagtgcccca aggcccctgt      240
ctggaggaaa tggcctagct atttgatgag aagaccaaac cccacatcct cctttcccct      300
ctctctagaa tcatctcgca ccaccagtta cacttgaatt aagatctgcg ctcaaatctc      360
```

-continued

| | |
|---|---|
| ctcccacctc tctccctgct tttgccttgc tctgttcctc tttggtccca agagcagcag | 420 |
| ccgcagcctc ctcgtgatcc tccctagcat aaatttccca aacagtccac aggtcccatg | 480 |
| cccactttgc gtctgcactg tgatcgtgac aaatcttccc tcctcaccag ctagtctggg | 540 |
| gtttcctctc cctgccccag gccagaactg ccttcttcat ttccacccac gctcccagcc | 600 |
| tcttagctga aagcacaaat ggtgaaatca gtagtctcgc tccatctcta atagactaaa | 660 |
| cctaaatgcc tctaggacgg actgttgcta tccaagcgtt tggtgttacc ttctcctggg | 720 |
| aggtcctgct gcaactcaag ttcca | 745 |

<210> SEQ ID NO 476
<211> LENGTH: 1168
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Affymetrix ID 3573882

<400> SEQUENCE: 476

| | |
|---|---|
| gaggtaggta ccatggccat tcagcacagc cttgatttcc tcccaaagta ggtgagctat | 60 |
| agtgaagaat aggtgcaaac aaacaagctt acttccattg caaaatagaa gaagaggaag | 120 |
| ttagagataa ttctgatcaa tcattttgga ggctttgtta taaggcaacc cccggtatat | 180 |
| catggaattt ccattgacat ttgaatttgg acttggatct tcccttggtc ccattagctg | 240 |
| aggtttagta atctaaagtc cctatagtat atgattataa tgctatttta aaaaatatat | 300 |
| atataaaata ttttttttctt tttaaaatag acactatagt tttacccata agtaaatttt | 360 |
| aaagattata gctcccaaaa gaatggacca accactttcg tatcataatt tcttttttggt | 420 |
| aaatatgaga ctattatgaa atcatagtat atgattgtat ttaaaggtac aatcaaagga | 480 |
| tcttttgtcc attccattaa taactgaata aaaaataaat aaaatggata gaaaaaaact | 540 |
| aaagttgaaa atacattctt aaactagttg tctgaattga gaaaagagtg agaactaggt | 600 |
| gtgcaagaac caaacgtatt ttattttatt ttttaaatgg gagcaacata tcagtcgtgt | 660 |
| caccagctgg tatattgtgt aaatattaaa gctccattgg gactgatttt tcatggcaac | 720 |
| atcagctttc taatgttcta aattctataa aaccaccca caaagaaaca agcaaattt | 780 |
| cattatctaa tgagttgctg gaaaatcata ttgagaataa ttatttcaga ttcctcagtt | 840 |
| gttaacttct acattcaagg cttatctctg cccccattga tttttaacct caaaatggtg | 900 |
| ttgagattta cgtggaaccc taaagcagta aaataaaaaa cctggttgca gcacattcac | 960 |
| actgttgtcc ttaaaattcc cctttttttct ctatgtacga taaagtaaca gtatgtcaga | 1020 |
| taagccggtg gggggatgag attaggctga ggcagtgcta gtcaactggg gaaaaggatg | 1080 |
| atggaaaaat cacccagttg tgctatattt ttaaagaagg aggtcgttta tgtgtgcaga | 1140 |
| caattctccc tgaggttagc ccaatgga | 1168 |

<210> SEQ ID NO 477
<211> LENGTH: 109
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Affymetrix ID 3088320

<400> SEQUENCE: 477

-continued cgtgcgaaca aaccaacctg aaattctgca tgaactgccg gaacttgtcc accctttttg    60
ctagaggcac gataacattg ataagcgtgt tggccatgtt gagcttttc              109

<210> SEQ ID NO 478
<211> LENGTH: 79
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Affymetrix ID 3095470

<400> SEQUENCE: 478
gagcccctcc tactggccaa cccagtctcc atccctcccc aaacataccc caggctctag    60
ccctgcttcg cagcaccct                                                79

<210> SEQ ID NO 479
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Affymetrix ID 3142384

<400> SEQUENCE: 479
gaatgcgtca tgaaaggcgt cacttccacg agagtttatg agagagcata             50

<210> SEQ ID NO 480
<211> LENGTH: 226
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Affymetrix ID 2721315

<400> SEQUENCE: 480
actactaagc gaccaatttt gctgaagatt ttaagaggag atgacaattg tagacattat    60
atgttgcact gcatttcaag cccagaatat ctctagagaa aaaacaaatc tccctcaatc   120
tcctctttat gttattctcc aggaaggttc caaactttac cttctagcct cattcagcat   180
ctttcaagtc ctcatctcct tgctttccaa agctctaaat cacttc                 226

<210> SEQ ID NO 481
<211> LENGTH: 88
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Affymetrix ID 3933546

<400> SEQUENCE: 481
ccaagcaaac aatccagagc agctgtgcaa acaacggtgc ataaatgagg cctcctggac    60
catgaagcga gtcctgagct gcgtcccg                                     88

<210> SEQ ID NO 482
<211> LENGTH: 1083
<212> TYPE: DNA

<213> ORGANISM: Artificial Sequence
<220> FEATURE:
<223> OTHER INFORMATION: Description of Artificial Sequence: Synthetic
     polynucleotide
<220> FEATURE:
<223> OTHER INFORMATION: Affymetrix ID 2608677

<400> SEQUENCE: 482

```
agttctgatt cacccacgaa ggttacattt atgctgaata catttgtaaa tactcagttt      60
tatactgtat gtatatgatt gctactctaa aggtttggat atatgtattg taattagaat     120
tgttggcatg atgacatttc atttgtgcca aaaatattaa aaatgccttt tttggaagga     180
ctaacagaaa gcacctgatt tgcacttgaa ccagattata gatttaaaag tatatgacat     240
gtattttgta tttaaaacta gaatagccag tatttatgtt ttttataaaa ctgtgcaata     300
cgaattatgc aatcacaata catttgtagc tcccgagtgt cctaaaggga gtgcacttct     360
ttgaagctgg tgtgttaata ctatgtaata aatggttaac tttcaaatga tgctgctgcc     420
aaaattatat taatagtgag tttcaggccc ctgggcattt tgtaccatgt aattatcctc     480
tggtgatgct gtttctcgtt agtggcagta gtgcctccgt ctcctagtga taatgctcca     540
agtctatgaa ctgttaaatc agcattcatt ttaagaaaag caactttagt ttcaaagata     600
cttttaagct tctaaattga tcatttaaac tatttcttta aataagagag ccaaattaga     660
ggctcatact ttagcttgtg aagaagataa tgaattttt aaagggaact ttctatgcaa      720
tgttcaggat aaatgcatac tgctggccaa tcagtgtcat ctcctgggta aattttgatg     780
tcgcattata aagacatgca taattgatgg tttctagatt atctagtcca acaatagag      840
tttatttttt cttcatctga accaacatgc tacagtagct aagaagtatt aaaactatat     900
acatccatat aaagatgaaa tatgaactat tcattagaa gtcatagttg accacagaca      960
tgttattctt ctgaaagagc cacattttgg ttttatttct tgtcacatga tttcttttct    1020
tgatggatga aaaatatgaa aggaaacttt tatatctgtt gcctagtttt gtacatggat    1080
ctc                                                                  1083
```

<210> SEQ ID NO 483
<211> LENGTH: 256
<212> TYPE: DNA
<213> ORGANISM: Artificial Sequence
<220> FEATURE:
<223> OTHER INFORMATION: Description of Artificial Sequence: Synthetic
     polynucleotide
<220> FEATURE:
<223> OTHER INFORMATION: Affymetrix ID 3893027

<400> SEQUENCE: 483

```
caaggacgcc cgaagcacag tggacggtca tgaaggagcg ggggtgtggc aggcgggtga      60
cgtccaggag agggagcgcc cctggctgcc cctcggccgc cgactggacg cgcgggcctt     120
gccagcgagc accctcatcg ggctgtcgcc tgacagcata cctcaaaagg ccctagctaa     180
taaacctgta agcccagcat ttgagagaag gtagggtgtg tatatataaa aggttgtgta     240
caactccacg aggtga                                                     256
```

<210> SEQ ID NO 484
<211> LENGTH: 297
<212> TYPE: DNA
<213> ORGANISM: Artificial Sequence
<220> FEATURE:
<223> OTHER INFORMATION: Description of Artificial Sequence: Synthetic
     polynucleotide
<220> FEATURE:

<223> OTHER INFORMATION: Affymetrix ID 3811420

<400> SEQUENCE: 484
gagtttgtga tgaatccttc cagtatttttt ctgaaaacca gtgaactatt ttgtaggttt    60
ctgtgtcgtt agaaacatgc aaacctatcc actaaaacca ctccagttga tctattaagt   120
cattcgttag gtcttacctg gactctcttc actgtcacta tcatgatctg tccacatcac   180
tggccctttc tcctatcacc tagctctcct gtgagcccag cactgatata aagtggtttc   240
tagtcttctt ggactctcaa tttaacttgc ttcccatggg aatcttctaa ctgtttc      297

<210> SEQ ID NO 485
<211> LENGTH: 104
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Affymetrix ID 2608644

<400> SEQUENCE: 485
ttggctcggc ataacaaaga acttcagagc atgctgaaac ctggtggcca agtggacgga    60
gatgaagccc tggagtttta tgccaagcac acggcgcaga taga                   104

<210> SEQ ID NO 486
<211> LENGTH: 156
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Affymetrix ID 3811357

<400> SEQUENCE: 486
gaccttggac aatcatgaaa tatgcatctc actggatgca aagaaaatca gatggagcat    60
gaatggtact gtaccggttc atctggactg ccccagaaaa ataacttcaa gcaaacatcc   120
tatcaacaac aaggttgttc tgcataccaa gctgag                            156

<210> SEQ ID NO 487
<211> LENGTH: 56
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Affymetrix ID 2932274

<400> SEQUENCE: 487
atggcccaga tctttacacg atatcctcct ccgactcatc gtgagaaaac ctgcaa        56

<210> SEQ ID NO 488
<211> LENGTH: 358
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Affymetrix ID 3811424

<400> SEQUENCE: 488
ttgggtttcg taaatgcagg gatacaaaag ctattggatc ttgagatagc tttgtatttt    60

```
gtagagaatc atcccaggag cacattccct cactgagggt tccagccacc tcttccgcct    120
cattatactt tgcttagcac cgagaagtct ggcatcgttt ctgttggaat gaaaagattg    180
gcagagctgc cctggacaac agcactgcaa aacactgtgg cagaaggttt ggtctacata    240
ccaaggcagc caaagtatta attgcattct ctgtgatcac aaaataaggc gctgaattat    300
tctcttcatg ttttaagaat gacaggcttt tgctctgcca gctccaagca tagtgcat     358

<210> SEQ ID NO 489
<211> LENGTH: 113
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Affymetrix ID 3354786

<400> SEQUENCE: 489
cgaaggtcat gtcctggtgg gattatggct atcagattac agctatggca aaccgaacaa     60
ttttagtgga caataacaca tggaataata cccatatttc tcgagtaggg cag           113

<210> SEQ ID NO 490
<211> LENGTH: 234
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Affymetrix ID 2740186

<400> SEQUENCE: 490
agccctgtca gcagagtcag ttttaacaac tgagaagagt ggcatgaaat ttagtacctg     60
ctttggacat gagcataccc attctcttgc tagttttgtt tttgcctgaa aattcactcc    120
aagtgtgagg tgtaccagta actcaatcac gtatagacat tttttttta actgaaaatc    180 tccttttcca gaaggtttat taatacgctt tgaaacttag aatgccgaac tgcc         234

<210> SEQ ID NO 491
<211> LENGTH: 367
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Affymetrix ID 2586104

<400> SEQUENCE: 491
gtctggatca atgtacacac ttttcatagc agcttctgaa agagcctgtt tcttgttact     60
gttatgatat aggctgtgtc tttatcagtt gcaactatac tttctcttgc cttaggctaa    120
ttccagggtc ccctgggttt gggagcctat gacaccttca ttagttaaat aggaacatgt    180
ggggttaggg ttagagcatc tgaatcagtg atggctaatt tgaagtagaa gagtgactta    240
ttttaattca gtatttattg aacagtggtg ttctaggaac ttttgggctg tgtcagtgaa    300
taagacaaca atccctaccc acatggagct aaatattctaa agaggggaga caggcaacca    360
atcagta                                                              367

<210> SEQ ID NO 492
<211> LENGTH: 142
```

```
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Affymetrix ID 3046236

<400> SEQUENCE: 492
gcagcgagga aaggacgcat tgatcttgaa gttgtagaga taatgtctca gcaccctgct    60
tggggtgcca tccttttagt ggcatggcaa aaccaagcac aaaatatttt ttattgtcct   120
ttccagaata gatcccttc tc                                             142

<210> SEQ ID NO 493
<211> LENGTH: 222
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Affymetrix ID 3126509

<400> SEQUENCE: 493
tgtgcacctt tatcgcaagt atctccacag caacctcata gtggtacgga cgcctgtgcg    60
aggactcttc cacctctggc atgagaagcg ctgcatggac gagctgaccc ccgagcagta   120
caagatgtgc atgcagtcca aggccatgaa cgaggcatcc cacggccagc tgggcatgct   180
ggtgttcagg cacgagatag aggctcacct tcgcaaacag aa                      222

<210> SEQ ID NO 494
<211> LENGTH: 102
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Affymetrix ID 2608546

<400> SEQUENCE: 494
ggagggacag caacaaagag attcgcagca agagtgtgag ggaattggct caggatgcta    60
aagaagggca gaaggaggac cgagacgttc tcagctacta ca                      102

<210> SEQ ID NO 495
<211> LENGTH: 64
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Affymetrix ID 3108613

<400> SEQUENCE: 495
agactccgat ggaagacagg actctccagc aggggaactg ccaaaaacgg tccaacagcc    60
aaca                                                                 64

<210> SEQ ID NO 496
<211> LENGTH: 37
<212> TYPE: DNA
<213> ORGANISM: Artificial Sequence
<220> FEATURE:
<223> OTHER INFORMATION: Description of Artificial Sequence: Synthetic
      oligonucleotide
```

<220> FEATURE:
<223> OTHER INFORMATION: Affymetrix ID 2997541

<400> SEQUENCE: 496
tatgaaccaa atgaacctgc gcatacacaa cgcatac                            37

<210> SEQ ID NO 497
<211> LENGTH: 81
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Affymetrix ID 3088362

<400> SEQUENCE: 497
ttcaagtgtt caagcttttc caggtaccac aacgccagcc tcacccaatc cctctatgcc   60
cacaatccct acccgtcctg g                                             81

<210> SEQ ID NO 498
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Affymetrix ID 3662157

<400> SEQUENCE: 498
tttttcaata cgatactgag ccatttgctg                                    30

<210> SEQ ID NO 499
<211> LENGTH: 34
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Affymetrix ID 2586125

<400> SEQUENCE: 499
atgacccatt caaaagggca ggatcagatc ttac                               34

<210> SEQ ID NO 500
<211> LENGTH: 84
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Affymetrix ID 2608612

<400> SEQUENCE: 500
ggggcttcca atctagttat cgacctcatc atgaacgcat ccagtgaccg agtgttccat   60
gaaagcattc tcctggccat tgcc                                          84

<210> SEQ ID NO 501
<211> LENGTH: 29
<212> TYPE: DNA
<213> ORGANISM: Artificial Sequence
<220> FEATURE:
<223> OTHER INFORMATION: Description of Artificial Sequence: Synthetic
      oligonucleotide

```
<220> FEATURE:
<223> OTHER INFORMATION: Affymetrix ID 2608627

<400> SEQUENCE: 501
gtagctgaag ttgcatgtcg acgatggaa                                          29

<210> SEQ ID NO 502
<211> LENGTH: 367
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Affymetrix ID 2586096

<400> SEQUENCE: 502
acccttcaat cagtggctgc gatcacaact gcacagacac cttaaccagt ttctattgtt         60
cctgtcgtcc tggttacaag ctcatgtctg acaagcggac ttgtgttgat attgatgaat        120
gcacagagat gccttttgtc tgtagccaga agtgtgagaa tgtaataggc tcctacatct        180
gtaagtgtgc cccaggctac ctccgagaac cagatggaaa gacctgccgg caaaacagta        240
acatcgaacc ctatctcatt tttagcaacc gttactattt gagaaattta actatagatg        300
gctattttta ctccctcatc ttggaaggac tggacaatgt tgtggcatta gattttgacc        360
gagtaga                                                                  367

<210> SEQ ID NO 503
<211> LENGTH: 267
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Affymetrix ID 3811405

<400> SEQUENCE: 503
ccacgtccct caacagagaa aggtgagagt ctgttatttg ttaggtttcc ttgtccatat         60
ttcttggtgg gtcccacaaa agtctcatga atctctacaa gtgggaaaat aaattgccca        120
tttcttggca caccgaactt tccatgtcat attttaaaac tgtaagtcca tactttacat        180
agctaaagac caatgggcca aagcatggtg ggtcacacct ataatctcag cattttggga        240
ggccgatgtg gtaggattaa ttgagcc                                            267

<210> SEQ ID NO 504
<211> LENGTH: 228
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Affymetrix ID 3862194

<400> SEQUENCE: 504
atctgtctgg tacaaaatgc ttcccccacc gactttgggg tgttgtgtag atccatgggt         60
acgtctctcc atccctccac tctccatcct tttatccgtc tatccagatc tctagctatc        120
ttctcatgta tccattgctc caaatagtgc aaacatccag gtcttcatct ctttcagcac        180
ctgcctcttt gatttagctc catgaactta tcttgtttgg ggtctcca                     228
```

```
<210> SEQ ID NO 505
<211> LENGTH: 44
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Affymetrix ID 3126514

<400> SEQUENCE: 505
atttgggatg acgtgtcagt atcggtcaga cttcatcaat atag                44

<210> SEQ ID NO 506
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Affymetrix ID 3992437

<400> SEQUENCE: 506
ctgtcagtgg ggctatccaa ttgcttccct ct                             32

<210> SEQ ID NO 507
<211> LENGTH: 846
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Affymetrix ID 2702151

<400> SEQUENCE: 507
caggcctgct tgctcgtttt gtcaaagagg gatggctttg cagatggcta agtttccttc    60
aggctctgac atctgcctca tgactttggc actcttgtca tgaagatgaa gtgacagttc   120
ttttaaagtg ggaagccaga cacagggttt ctagtttgcc tgagatttcc atatagggat   180
ggctggtacc caggttacct tttggaatga tagattctct gccagggaat tcttttttgga  240 agagaaaaga aaataataag agtgcgtgga attttttctt aaggacataa ctaactaact   300
aactaactgt gaaatacatt agtatattta ccatgacaga ttcgcatata aaaaactggc   360
tgttcccaca gctaagccat aatatttata tttggttttg atttgcaagt aagttttaa    420 aagtgaattt gtgaagcctt aaccttagtg cggagtgttc taaaacccag tgagaaatgg   480
tatcttcagt agttaatctc cattgattga ttgatgatag aatatgtttg gattgcaatt    540
taaatctcag acttttgatc actactattt ctgttgagta ttcagtgcag cttagctgcc    600
aatataattt ttatttagat gattattgcc taatttatgg ccacatatat tttacatgtg   660
tatgttttac atatatggaa aatacacata agccttacag tgaaagatca gataaaatct   720
attgtaagat tgaatgcaca aaatgctttt attactctaa gcaataaaat caatcaaatc   780
acatttccca ttagacagca cctcagctcc tctatacata cagcagttcg ctggattgaa   840
tacaca                                                             846

<210> SEQ ID NO 508
<211> LENGTH: 126
<212> TYPE: DNA
<213> ORGANISM: Artificial Sequence
<220> FEATURE:
<223> OTHER INFORMATION: Description of Artificial Sequence: Synthetic
```

-continued

```
      polynucleotide
<220> FEATURE:
<223> OTHER INFORMATION: Affymetrix ID 2649018

<400> SEQUENCE: 508
catatgtcta agaatccatg gaaggatatt aaccgcttta atatcagata ataagttcct      60
aaacccaaag attccgtttc agtgggcctg ggatggtttt gagtgattct gagcaacatg     120
gtccga                                                                126

<210> SEQ ID NO 509
<211> LENGTH: 62
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Affymetrix ID 2908192

<400> SEQUENCE: 509
atgcggatca aacctcacca aggccagcac ataggagaga tgagcttcct acagcacaac      60
aa                                                                     62

<210> SEQ ID NO 510
<211> LENGTH: 405
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Affymetrix ID 3573883

<400> SEQUENCE: 510
agggaagcta ctgtctacgt taagataaag ggtattgcct tggctctatt tggcatggat      60
ggagcccagt tggaaaattc ccaaatatta caacaagtcc ttgaacccag gccatgtggt     120
tagacgttgg tgttaaggtt agaccttatg ttagagtcat ttctgatgtt ccagcttcta     180
gccatgtagt gctctcagtc ttcatacccc agaaattatt ggtatatttg tagataccga     240
gaatgatccc tcagtctgag aggttagaat gatcatctgt aatctgaggg ttaatttcta     300
ggcaggtgga gagagtggta aaaaagaaat gaaattgaca agctaggaaa gaggaggcag     360
aaagatttgg aaaattcaca gagtttcacc cttaagctgt agaga                     405

<210> SEQ ID NO 511
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Affymetrix ID 2608610

<400> SEQUENCE: 511
ggggaggttc cggatccagc tctatgagca                                       30

<210> SEQ ID NO 512
<211> LENGTH: 1687
<212> TYPE: DNA
<213> ORGANISM: Artificial Sequence
<220> FEATURE:
<223> OTHER INFORMATION: Description of Artificial Sequence: Synthetic
      polynucleotide
```

```
<220> FEATURE:
<223> OTHER INFORMATION: Affymetrix ID 3126563

<400> SEQUENCE: 512
cacctgtgta gttgcttctg ttgtaagtgg tgaactttta tccaaactgc tgacgtcaaa      60
tatgtaccct cagctcaaac cactcctctg agatgcacac tcctgaccat cttcatggca     120
tattccacca gcaccctcaa ttcatgatgt ccccagctga gttctgatat tctgtctcca     180
agtcaccatt ccagtccttc tccttccatc ctgaagcagc ctagagggag agacagggaa     240
ggaaaattaa gtttcagcac aaggttgaga agggtcttga cacagatggg cttgtggagc     300
aataagtggg ctctcatcca gccctcaagg gaaggaatgt aggaatcagt cccaaaaagt     360
gatgcttgag cagaattctt ggagcatgtg taggaatttt ctgggcagaa tgagaggagc     420
tgcacagtgt cctttaacct caaggatctt tttctctgta ctgagtcttc agctcatttg     480
atttaagatg aaaaccaccc ttcctgatgt tattcatacc ctgtaaagaa atctacagac     540
ttcctcaaaa gaacaaatca ttgtacatta atgggagctg gggcttccca gcatgcaaag     600
ggtcatctag aacctgcaga tggccctagt gtagtccgtg ggccatctgc agctatcttc     660
tggggcactt gagagccatt gggccccagg ccccactcca gacctacaga gcagaatcat     720
ttgaggagcc tagctgttgt ggtgccccag gaggaccaca aaatgatgca gacttcactt     780
gcatatggtg aaccttacca gtaaggtccc tatatatctt gttcatttaa gtttggtatc     840
ttcagttctt ttcactgttc ctgcacatca cttagtgcac agtcttcagc aggctgatga     900
ctgagaactt gcgtttatgt gctttggtac catcacacta ttgattgaca gtgaacatcc     960
tgtcattaag cccacgtatt tctgatacat atcgtacatt ctttagctgt ggtgcaggca    1020
tcctatttag ttactgaagc agttagcttc ttgtactcca gagtgccaca tagacatttt    1080
acttactgaa aatatttgga aataatttca aattacagat gttctttgac ttaatgatgc    1140
tgttatatct ggataagcct attgtaagtc aaaaatattg taagtcaaaa agcatttaat    1200
accctgttaa acccaatgta agtagaaaa attgtaattt gaaccactgt agtggggtat     1260
ggtctgtata agaaagttgc aaaaataaga atagtacaaa gaacttatgt gttctttact    1320
tagattgacc tgttgttaac attttacatc atttcccttt ttttaaattt tttttttcatt   1380 agagacaggg tctgtctttg tcccccaggc cagagtgcag tggtgcagtg gcacagtggt    1440
gcgatcttgg ctcactgcag cctctgcctt ccaggctcat gagatcctcc cacccctagcc   1500 tcctaagtag ctgggacagc aggtgtgtac cactacatct gcctaaattt tttgtatctt    1560
ttgtagagac tgagttttgc catggtgccc acgctggtct caaactcctg ggctcaagtg    1620
atccacctgc cttgaagtcc tggaatgctg ggattacagg catgggccac tataccctgc    1680
tcatttg                                                              1687

<210> SEQ ID NO 513
<211> LENGTH: 614
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Affymetrix ID 2897465

<400> SEQUENCE: 513
cagagctctt gatatcttga atgtcttttc tgtttggcct ggctcttaat ttgcttttgt      60
tttgcccagt atagactcgg aagtaacagt tatagctagt ggtcttgcat gattgcatga     120
```

```
gatgtttaat cacaaattaa acttgttctg agtccattca aatgtgtttt tttaaatgta      180
gattgaaatc tttgtatttg aagcatacat gttgaaaata caccttatca gtttttaagt      240
acagggtttt atagtgtaat atatacagag taagtgtttg ttttgtttt tcaactgagg       300 tcaaaatgga ttctgaatga ttttgcatat gggatgagga aatgcttgga tccttaagga     360
gtttacgaaa tctgctgttt tatcaaagtg aaaaaaatt gcttattact cttcatttta      420
cactaaagct taatgtcact aagtttcatg tctgtacaga ttatttaaat catggaaatg     480
aaaaaaatgt tctctgcttg ctaccaaagg acaaactctt ggaaatgaac actttctgct    540
ttccttcctc caaagaatta ataggcaaca gtgggagaaa aaaaggcat aatggcaaat      600 ccttcaagca ggga                                                       614
```

<210> SEQ ID NO 514
<211> LENGTH: 320
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: Affymetrix ID 2649054

<400> SEQUENCE: 514

```
agggcactag ccgtggactg taatgtggtt cagtttggat aaataatgaa gttagaggca     60
acggaagttc ctggtgaatt agatatgagc gtgactgaaa gaaagagtg aagaatgact     120 ccaaggtttt aggcctgagt caccaaaagg atggagttgc catcagttga tatgggattc    180
atagctgata tggaaccagc tgtggggaag ctcaggggtt tgagtttagt catcttgagt    240
ttgaaatgtt tattaggtgg ccaagtgaag atgctgagta gggagttaga caccaaagct    300
gaaactccat cttgggatga                                                320
```

<210> SEQ ID NO 515
<211> LENGTH: 27
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Affymetrix ID 2608569

<400> SEQUENCE: 515

```
gagggaaata acaagccaca aaagcat                                         27
```

<210> SEQ ID NO 516
<211> LENGTH: 347
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: Affymetrix ID 2897464

<400> SEQUENCE: 516

```
agcccgagcc aggagcacta gagagggagg gggaagagca gaagttagag aaaaaaagcc    60
accggaggaa aggaaaaaac atcggccaac ctagaaacgt tttcattcgt cattccaaga    120
gagagagagg aaagaaaaat acaactttca ttctttcttt gcacgttcat aaacattcta    180
catacgtatt ctcttttgtc tcttcattta taactgctgt gaattgtaca tttctgtgtt    240
```

```
ttttggaggt gcagttaaac ttttaagctt aagtgtgaca ggactgataa atagaagatc    300
aagagtagat ccgactttag aagcctactt tgtgaccaag gagctca                 347
```

<210> SEQ ID NO 517
<211> LENGTH: 146
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Affymetrix ID 2980483

<400> SEQUENCE: 517

```
tgagagaacc tactgattta cctttaata gtggtcaggg catttccaga ggctgttgga    60
aagattggac gctgatggag cttggcatgt ctgtgggaag taataaagct cagatagaag   120
gaggatgttc atcttctccg ggaatc                                        146
```

<210> SEQ ID NO 518
<211> LENGTH: 140
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Affymetrix ID 3791695

<400> SEQUENCE: 518

```
gcaggtgcac tgtcattttg gtaactcaac actgtctgca ttttattttg gtgcatgggc    60 gggggctct ggcttcgatt tagtccttca gacacataca gtgaaataaa taggtactcg    120
acgatagtat gtgttgttgc                                                140
```

<210> SEQ ID NO 519
<211> LENGTH: 184
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Affymetrix ID 3603305

<400> SEQUENCE: 519

```
ccctgaggaa tatgtcatag ttctgagctg ccagtggacc gccctttttcc cctaccaata    60 ttaggtgatc ccgttttccc catgacaatg ttgtagtgtc ccccaccccc accccccagg   120
ccttggtgcc tcttgtatcc ctagtgctcc atagtttggc atttgcacgg tttcgaagtc   180
atta                                                                184
```

<210> SEQ ID NO 520
<211> LENGTH: 142
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Affymetrix ID 2608568

<400> SEQUENCE: 520

```
gttcaactgc tggttaccag ccaagatgtg gacaactaca aacagatcaa acaagacttg    60
```

```
gatcaactga ggtccatcgt ggaaaagtca gagctttggg tgtacaaagg gcagggcccc      120
gatgagacta tggatggtgc at                                              142
```

<210> SEQ ID NO 521
<211> LENGTH: 455
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Affymetrix ID 2586115

<400> SEQUENCE: 521

```
cctaggcata ttgttgtaga tcccaagaac agatacctct tctgggctga ctatgggcag       60
agaccaaaga ttgagcgttc tttccttgac tgtaccaatc gaacagtgct tgtgtcagag      120
ggcattgtca caccacgggg cttggcagtg gaccgaagtg atggctacgt ttattgggtt      180
gatgattctt tagatataat tgcaaggatt cgtatcaatg gagagaactc tgaagtgatt      240
cgttatggca gtcgttaccc aactccttat ggcatcactg ttttttgaaaa ttctatcata      300 tgggtagata ggaatttgaa aaagatcttc caagccagca aggaaccaga gaacacagag      360
ccacccacag tgataagaga caatatcaac tggctaagag atgtgaccat ctttgacaag      420
caagtccagc cccggtcacc agcagaggtc aacaa                                 455
```

<210> SEQ ID NO 522
<211> LENGTH: 2178
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Affymetrix ID 3811408

<400> SEQUENCE: 522

```
tcacaggtat gtctcactcc aaagcctatg atctcatgca gtttggcatg gatactcttc       60 tatcttttg atttatgatt ttccttcatt taaaaaatct tttatttaga agtataataa       120 ataccaaa atgtaaataa aatataaatg tatatcccat tgggctattt taaagtaaac       180
actttgtagc catcatgcag gtaaaagaaa cagggcattg ccagccccca taaggccatg      240 tccctgaca atcatagccc tgtatcttcc accaaaggta gaaattatgt taagttttat      300
ggtagccaat tccttacttt ccttacacat ttaccaccta agtatgtcac cctaaatgat      360
ataaattagt tgtgcttgtt atttaacttc atgtagatga aattgtagtg tatgtagttt      420
gtgttttggg cttcatttgc tcatagttac gtttgtgaga tttcatgaag ctaaagtttg      480 ttcatttttcc ttgttgtatt ttattgtgaa agttcaccca ctgtatttat tcatcctgtt      540 gttttttgtta tgatatataa tgctgctgtg aacattattg tacctgttct ttggtgcctt      600
gtgcatatat ttctattggg aacacaccaa atagtgaaat tgttgtagat gtaatgccat      660
gtatgagagt tcctgttgtt ttgtatactc tccaaactta gaactgtcag tctctttaat      720
tttagccatt ctggcatgtt cacaggagta tcacattgtg ggtttaattt gcatttccct      780
gattacttat tactaataat cttttcatat gcttattttc ttttagaacg tgcctatgca      840
agtctcttgt ccattttca actgtttct atttcttatg aatttgtagg agttctttgc      900
agcttctggc tatgcatcct tcattaattt tgtgtgttgc aaatatattc ttccattttg      960
tgacttgtct ttttagtctc aaaacagaat cttttgatga aaagaatttc ttaattttga     1020
```

```
tgtaacctca tttatcactc ttttccttca tggttggcac ttgttgtgtc ttgtttgaca   1080
atgttgccta tcccaaagtc atgaagattt tctcttatgt taacttctaa aagttgtatc   1140
atttgtcttt tatatttata tctacataat gcacctggaa ttgagttata tgaatgctgt   1200
gaatttggga ggggcgtgtt tccttttttt cccacatgga tatccaatca actcagccac   1260
atttactggg ggaagacatc ttttttttcta atgcgctgta gtgttaggtt tttcaaaact   1320
taggtgtctg tatatgtgtg ggtctgttta tgagtctgtc tattcttttc cactggtctg   1380
tttcctacac ttgtgccaat gccacactgt cttacttata gctctataag tcttggtatt   1440
gttaaggaaa atatttgta acatttgtta aaaatggcag agaagacttt attcaaggag   1500
gggaacattg tgataggtag agggactgct gcaacgaggt cttgctgtgg tgaggagaga   1560
gattgggctg gagtccaact tctacaagga caagagggga tttatagtca agcagcaggg   1620
tggggtcagt ggatggaaga ggaaacatca gagacagggg tattcttgct agaccaactc   1680
aacagaattc ttgctgaagg caggccaggg tgataagata tcaagagtta ggggtgagga   1740
cagataccaa gggtggagaa ttttcactaa aactagtagg attcttgctt aaactggatt   1800
ctataagaca gaaaaggaag cccaaggtca gggtctagtg gaagagaagg ctccggggag   1860
cccgacctga gtttgatcta ggagagtctt tgtcaatatc ctgtagaata tgaccttcac   1920
ctcattttct tttcctcaag tgtatctgga ctgtatttgg ccttttgggc ttccaggtga   1980
cttttagagt aagtttatca agatctacaa aaatagctac tgagattttg atttgaatag   2040
tatttcttcc tgataatttc tgagtaaaat tcattttaag gaagtaggag gggcagtggc   2100
ctgatgaaaa gcaaaatga agaaaagaat aaggaaagac acagttttgc catcaccagc   2160
cagtgtttag tgatctta                                                  2178

<210> SEQ ID NO 523
<211> LENGTH: 134
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Affymetrix ID 2466604

<400> SEQUENCE: 523
cccactaata cgaggccttc ttgcaagacc agccaaactg caggtgcagg atcagctgat   60
gaacgaggag ctgacggaaa ggctctttgt gctgtccaat tccagcacct tggatctggc   120
gtccatcaac ctgc                                                       134

<210> SEQ ID NO 524
<211> LENGTH: 108
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Affymetrix ID 2586166

<400> SEQUENCE: 524
tatgcttgca caatgagttt tcatgtggca atggagagtg tatccctcgt gcttatgtct   60
gtgaccatga caatgattgc caagacggca gtgacgaaca tgcttgca               108

<210> SEQ ID NO 525
```

```
<211> LENGTH: 75
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Affymetrix ID 3018611

<400> SEQUENCE: 525
gtgatcccgt tctttctgtt cctcgctctt cccctccgat cgtcctcgct taccgcgtgt    60
cctccctcct cgctg                                                     75

<210> SEQ ID NO 526
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Affymetrix ID 3693008

<400> SEQUENCE: 526
ttgggaactc tagtctcgcc tcggttgca                                      30

<210> SEQ ID NO 527
<211> LENGTH: 126
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Affymetrix ID 3862192

<400> SEQUENCE: 527
tcagcaatga ccatgctggg aaactgtgtg gggcctgtgg aaactttgac ggggaccaga    60
ccaatgattg gcatgactcc caggagaagc cagcgatgga gaaatggaga gcgcaggact   120
tctccc                                                              126

<210> SEQ ID NO 528
<211> LENGTH: 41
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Affymetrix ID 2649046

<400> SEQUENCE: 528
gaggtccagt ctggtcataa caaccaaact ctactggggt g                        41

<210> SEQ ID NO 529
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Affymetrix ID 2763600

<400> SEQUENCE: 529
tttaaaacga caatcagagg agagtg                                         26
```

<210> SEQ ID NO 530
<211> LENGTH: 516
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Affymetrix ID 3546098

<400> SEQUENCE: 530
gctgaatggc catggtacct acctcccgca gcagctgaga atatatatac atatatttgt    60
atgtatgtat gtatgtgtgt atgtacgtat aatttcttca gctcagcatt cagagagaac   120
actgctatag agaccaagat taggaatgac ttgggccaca tagaaattgt aggaatgggg   180
aggaaaagac cagcaccacc agacccactg gtttcctttt aataggtatc atggggtata   240
attaacccac tgaaaatata cataccacat acatggttca aaagtaatta tttccaaaag   300 aaaccctca caattacaaa tatttaagta tttttttttc tttcaatcac ccctttctcc    360
tctctaggag catatgacaa atatattgtt tttatatgtg tattctctat gccactttta   420
gttgagctcc ttcttctttt tctggccttg tgtatgtttc tatgtttccg tggctaacaa   480
atgtgaccca ctctctacag cttaagggtg aaactc                             516

<210> SEQ ID NO 531
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Affymetrix ID 3385513

<400> SEQUENCE: 531
aagtatgtct gcatcgatgt ctgtactgta aatttc                              36

<210> SEQ ID NO 532
<211> LENGTH: 150
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Affymetrix ID 2586141

<400> SEQUENCE: 532
ttcatcttcg gcgttcacct gtggccatgg ggagtgcatt cctgcacact ggcgctgtga    60
caaacgcaac gactgtgtgg atggcagtga tgagcacaac tgccccaccc acgcacctgc   120
ttcctgcctt gacacccaat acacctgtga                                    150

<210> SEQ ID NO 533
<211> LENGTH: 320
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Affymetrix ID 3046243

<400> SEQUENCE: 533
ccaagttgga ataggatcta ctctgtgtag acttgctgga agtgaaacac acagagcctg    60

-continued

```
cgggaagagt tgttctatga gtacttgagc ccccagcctg actaggttaa gtcttctatg    120
agtacatgaa cccctagcct gactaggtta agtcttctat gagtacatga acccctagcc    180
tgactaggtt aagtcttcta tgagtacttg agcccccagc ctgactaggt taagtcttct    240
atgagtactt gagcccccag cctgactagg ttaagtcttg agcagatct tagactctgt     300 cttcggtaag tggccaagtc                                                320
```

<210> SEQ ID NO 534
<211> LENGTH: 133
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Affymetrix ID 3046224

<400> SEQUENCE: 534

```
atgagagcac ttacaaccaa gcctagctcc ctggaccagt tcaagagcaa actgcagaac    60
ctgagctaca ctgagatcct gaaaatccgc cagtccgaga ggatgaacca ggaagatttc    120
cagtcccgcc cga                                                       133
```

<210> SEQ ID NO 535
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Affymetrix ID 4023361

<400> SEQUENCE: 535

```
aatattttca tgcaagtttc caaaccca                                       28
```

<210> SEQ ID NO 536
<211> LENGTH: 429
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Affymetrix ID 3546096

<400> SEQUENCE: 536

```
catctgctgg gtcttcgaag tctcagtaaa tattgaataa gctccctgga gctctgctgt    60
tgctgcctaa gacgggtagc cagccccgac ttgcatgagc agtcttgttt ggatatctgc    120
acatgtttgc tttctattgg ttcagactca ccttggaaca gagctgggtc tgttaagtct    180
gagaccttgc ttctggtact atacacatag ggcattagga agtggcccaa tgttttgctc    240
atcctaaagt cactcaatga cttgcagcag ccttcagcct tccttcagtt gcgagaagtt    300
tgttttcaaa tcttcccaga ttggtagacc aagccctcag ggccttgttc ttcccagtta    360
gcaactttct agctctccca tcctagatcc tctctttttct tagagagcct caggacatga    420
ccaagattg                                                            429
```

<210> SEQ ID NO 537
<211> LENGTH: 185
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Affymetrix ID 3046199

<400> SEQUENCE: 537
atctggacgg atggactgaa tgcgctactc gggaaggaca tgatgagcga cctgacgcgg     60
aatgacctgg acaccctgct cagcatggaa atcaagctcc gcctcctgga cctggaaaac    120
atccagatcc ctgacgcacc tccgccgatt cccaaggagc ccagcaacta tgacttcgtc    180
tatga                                                                185

<210> SEQ ID NO 538
<211> LENGTH: 544
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Affymetrix ID 2740233

<400> SEQUENCE: 538
ggaagctctc acatggcaat ctataggtgg atgcagaagt tgtcagtgtc tatataacag     60
gttgggaagg gtgatgagtg gtgactgctg agacctggag gggaagtagg aatatattta    120
aaatcctaaa tcttgacatc acaaaacaaa aaagtcctat acttcttttt ccccaccaca    180
gttgttaaat tttatatttg cttaatgaat tattcttgta aatagagatc agccatctag    240
agaaaagctc atagcattag gtttgacatt gtaaattttt attaaatgaa taaaataaaa    300
tattatttgt atatttaaat atacatgtta ttccaagaat taaaatatag aaatgggtat    360
atcaacccaa atgagcataa tttcattgta ttttgatggt gcagaatgta ttttgggggtt    420 tgtattgctg attagtagtg agtcagtgga ggcagtatgc caataagaac gacaaagaaa    480
tatgtactgc tgcgggcaag ccacctgagt gttaaagaaa gatgactgag ctttggctga    540
tttc                                                                 544

<210> SEQ ID NO 539
<211> LENGTH: 31
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Affymetrix ID 2980484

<400> SEQUENCE: 539
ttgtggcaag cgatagtcct ctacatcttt t                                    31

<210> SEQ ID NO 540
<211> LENGTH: 80
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Affymetrix ID 2980450

<400> SEQUENCE: 540
tggctgcgtt ttgatcgtct acaacaaggt tacagtgccc tctggtggca gtcatcaaaa     60
tcgcttctag acttgttttt                                               80

<210> SEQ ID NO 541
<211> LENGTH: 124
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Affymetrix ID 2763628

<400> SEQUENCE: 541
tcacctctgg atggaatcaa cacacaaagc agataaaaag ctgaacatta aagaccacat     60
tgttaaagca gagagccaaa ttgttcctcc accattccct atcccagact tcacatctaa    120
caag                                                                 124

<210> SEQ ID NO 542
<211> LENGTH: 37
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Affymetrix ID 2649009

<400> SEQUENCE: 542
gagagcattc acacaggcca tctggtctag ccctcat                              37

<210> SEQ ID NO 543
<211> LENGTH: 416
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Affymetrix ID 3791690

<400> SEQUENCE: 543
ggggaagtcc ctgcgatata taatggtctc aatttaaatt ctgtgctgtt tttatttag      60 ctgtgtaatt tggaaacttc aaataaaaag cctgaaagga agttggact atttaagctt     120 acacagactc tattaatgct atatggttat tctaccctg actttggaag aaggagaaac    180
tggcatggga atacactttt ctaaaaaaaa tactatttaa aaatatgaaa gtttatttaa    240
catctaagga aaggtactta attagaggga cactcaacaa gaagaattga ggatctaagt    300
aaatagtccc catctgctcc tggtcctacc acctggcgat tacttcctct tcttctctga    360
tagattttag ccaaccaatt ttgttttatt tgtgcaagtt gagaggccac ctgtta       416

<210> SEQ ID NO 544
<211> LENGTH: 149
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Affymetrix ID 2980485

<400> SEQUENCE: 544
cggaggagga tatcgtgtaa agatctgggc catgctgact gccaagggtg gctgtataag     60
aaaaaggaaa agggaagttt cctaagcaac aaatggaaaa agttctgggt gatactgaag    120

<210> SEQ ID NO 545
<211> LENGTH: 154
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: Affymetrix ID 3811446

<400> SEQUENCE: 545

```
tgtaactttc aatggaaacc tttgagattt tttacttaaa gtgcattcga gtaaatttaa      60
tttccaggca gcttaataca ttcttttag ccgtgttact tgtagtgtgt atgccctgct     120
ttcactcagt gtgtacaggg aaacgcacct gatt                                154
```

<210> SEQ ID NO 546
<211> LENGTH: 1832
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: Affymetrix ID 3811358

<400> SEQUENCE: 546

```
cctgtgctgc tatcctgcca aaatcatttt aatggagtca gtttgcagta tgctccacgt      60
ggtaagatcc tccaagctgc tttagaagta acaatgaaga acgtggacgt ttttaatata     120
aagcctgttt tgtcttttgt tgttgttcaa acgggattca cagagtattt gaaaaatgta     180
tatatattaa gaggtcacgg gggctaattg ctggctggct gccttttgct gtggggtttt     240
gttacctggt tttaataaca gtaaatgtgc ccagcctctt ggccccagaa ctgtacagta     300
ttgtggctgc acttgctcta agagtagttg atgttgcatt ttccttattg ttaaaaacat     360
gttagaagca atgaatgtat ataaaagcct caactagtca ttttttttctc ctcttctttt     420
ttttcattat atctaattat tttgcagttg ggcaacagag aaccatccct attttgtatt     480
gaagagggat tcacatctgc atcttaactg ctctttatga atgaaaaaac agtcctctgt     540
atgtactcct ctttacactg gccagggtca gagttaaata gagtatatgc actttccaaa     600
ttggggacaa gggctctaaa aaaagcccca aaggagaag aacatctgag aacctcctcg     660
gccctcccag tccctcgctg cacaaatact ccgcaagaga ggccgaatg acagctgaca     720
gggtctatgg ccatcgggtc gtctccgaag atttggcagg ggcagaaaac tctggcaggc     780
ttaagatttg gaataaagtc acagaattaa ggaagcacct caatttagtt caaacaagac     840
gccaacattc tctccacagc tcacttacct ctctgtgttc agatgtggcc ttccatttat     900
atgtgatctt tgttttatta gtaaatgctt atcatctaaa gatgtagctc tggcccagtg     960
ggaaaaatta ggaagtgatt ataaatcgag aggagttata ataatcaaga ttaaatgtaa    1020
ataatcaggg caatcccaac acatgtctag cttctcacctc caggatctat tgagtgaaca    1080
gaattgcaaa tagtctctat ttgtaattga acttatccta aaacaaatag tttataaatg    1140
tgaacttaaa ctctaattaa ttccaactgt acttttaagg cagtggctgt ttttagactt    1200
tcttatcact tatagttagt aatgtacacc tactctatca gagaaaaaca ggaaaggctc    1260
gaaatacaag ccattctaag gaaattaggg agtcagttga aattctattc tgatcttatt    1320
```

```
ctgtggtgtc ttttgcagcc cagacaaatg tggttacaca cttttttaaga aatacaattc    1380 tacattgtca agcttatgaa ggttccaatc agatctttat tgttattcaa tttggatctt    1440
tcagggattt ttttttttaaa ttattatggg acaaaggaca tttgttggag gggtgggagg    1500
gaggaagaat ttttaaatgt aaaacattcc caagtttgga tcagggagtt ggaagttttc    1560
agaataacca gaactaaggg tatgaaggac ctgtattggg gtcgatgtga tgcctctgcg    1620
aagaaccttg tgtgacaaat gagaaacatt ttgaagtttg tggtacgacc tttagattcc    1680
agagacatca gcatggctca aagtgcagct ccgtttggca gtgcaatggt ataaatttca    1740
agctggatat gtctaatggg tatttaaaca ataaatgtgc agttttaact aacaggatat    1800
ttaatgacaa ccttctggtt ggtagggaca tc                                  1832

<210> SEQ ID NO 547
<211> LENGTH: 214
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Affymetrix ID 3573884

<400> SEQUENCE: 547
ccaggaagat cgatgtgcag cagcccagca gcttctggag cgtttctcct tgccgcccca      60
gtgccgagtt gtggctgacc gcatggacaa taacgccaac atagcttacg gggtagcctt     120
tgaacgtgtg tgcattgtgc agagacagaa aattgcttat ctgggaggaa agggccccctt    180 ctcctacaac cttcaagaag tccggcattg gctg                                 214

<210> SEQ ID NO 548
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Affymetrix ID 2925965

<400> SEQUENCE: 548
agaaaagttg ggtagaagaa ccatgtgaga gcattaatga gccacagtgc                 50

<210> SEQ ID NO 549
<211> LENGTH: 258
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Affymetrix ID 2608614

<400> SEQUENCE: 549
agctcattct gagggcacaa aattctgttt tgaaaaatga gttctgctag tatcctgctg      60
tgatcatttg gtcataaaatc agacttggtt ccagaacatg agttacattt gaaaactgat    120
aaaacactga gaatacgcaa aggaaactgg cctaagatct ggcacatagt gggcactcca    180
taaatgtttg ttgaataagt aaatgattgc atgaagttta tttacagttt ttatccaaga    240
ttgtagggga tctcatca                                                  258

<210> SEQ ID NO 550
```

```
<211> LENGTH: 73
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Affymetrix ID 3787876

<400> SEQUENCE: 550
cagttacaag aacatgggag aaattgagcc cacctttac gtcacccttt atggcactaa       60
tgcagattcc cag                                                         73

<210> SEQ ID NO 551
<211> LENGTH: 218
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Affymetrix ID 2331561

<400> SEQUENCE: 551
ctggggccat tggtgcaga acaaccccca acccagtggc catcttcaca actgcagcac       60
agtgctggcc ctaatgccag gtgagcgtgc aaagtcctgt ttctttgtct ttacataggg     120
accgggcgat gcgctttaga gaaattccct attatttcac aggaaaggag gctgtgaaaa     180
ggagagggca ggttttggag ccaagtcgac ctggcatc                             218

<210> SEQ ID NO 552
<211> LENGTH: 250
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Affymetrix ID 2661102

<400> SEQUENCE: 552
taattcttag actgcctcct tgggaccctg ctttcctcag tttacctgtc ctctactgcc      60
aggtgtatag tcctccgtta cagctccaaa gccccttgga gggctgcact gctcctatat    120
atgaacccca accccatcc aaggcccttc acttctacat agcactcctc ggtctgaaag     180
acccaaccgc tgttctggaa acccaactgc tgctctcaca cctctgggcc ctctctacca    240
tggaatatga                                                           250

<210> SEQ ID NO 553
<211> LENGTH: 58
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Affymetrix ID 2586047

<400> SEQUENCE: 553
tgaaaaccca atgtactcag ccagagacag tgctgtcaaa gtggttcagc caatccag        58

<210> SEQ ID NO 554
<211> LENGTH: 64
<212> TYPE: DNA
<213> ORGANISM: Artificial Sequence
```

```
<220> FEATURE:
<223> OTHER INFORMATION: Description of Artificial Sequence: Synthetic
      oligonucleotide
<220> FEATURE:
<223> OTHER INFORMATION: Affymetrix ID 3787860

<400> SEQUENCE: 554
tgagcaactc cgttcctctg ctctgtttct ggagcctctg ctattgcttt gctgcgggga    60
gccc                                                                 64

<210> SEQ ID NO 555
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Affymetrix ID 3791668

<400> SEQUENCE: 555
atgggtcctt cagcggagac tacaagac                                       28

<210> SEQ ID NO 556
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Affymetrix ID 3126507

<400> SEQUENCE: 556
tattgcacag ctaataaaat atgatt                                         26

<210> SEQ ID NO 557
<211> LENGTH: 101
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Affymetrix ID 2608643

<400> SEQUENCE: 557
gaaagcctac atgcaaggtg aagtggaatt tgaggatgga gaaaacggtg aggatggggc    60
ggcgtccccc aggaacgtgg ggcacaacat ctacatatta g                       101

<210> SEQ ID NO 558
<211> LENGTH: 339
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Affymetrix ID 3807530

<400> SEQUENCE: 558
tgcgctgttc cgctcagcct tagaacctct gaaggaaaga gttaatgatg ctctgaaaat    60
cagatgctgg ggaaaaccag ctcccccac agacctcatc catcccacag acaggcatct   120
gtctccccca aactcctagc ctcttcctgt ctgtccctct catttggctt ggcctcatct   180
gccttgccct acctgtgtgt aagtgtgcac gtgcgtgtac aaacctggtc tcccagctag   240
```

```
actgtgagcc ctgagaagtg agctactttg atgatgtttc atcacaatcc caacattact    300
tggcatgatg ctttgtccct ggtggatact caacaaaca                            339

<210> SEQ ID NO 559
<211> LENGTH: 432
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Affymetrix ID 2763570

<400> SEQUENCE: 559
tttgtactat ctactcaggt gctgaaaatt gtggtaggta tgtatgtgga tattgtgtgt     60
ttccacatgt gttcatgatt tctgtatgtg tgttgtgtgt gcatgcagct ttatattttg   120
tgagtgcatg tattgtgtgt atctctgtgg atattgtgtg tgtctgtgtg tgttgtgtga   180
atattaaaca tgtatgtgtg tagtattgtg ctttgtgtgt gcgtgtgtta tgcagatgtg   240
tgtggctatc atgtgtcttt gtgtgtgtat gtatgcaggt attgtatgtg tctacatgtg   300
tttatgattc atgtgtgtgt gtgtgtgtgt gtgtttgtaa cctgattttg ccttccaggc   360
ctaccctgaa tcctttcacg aaccatagca ttgccatcat tgttttatgg aacagaatat   420
gcaagtctca tt                                                        432

<210> SEQ ID NO 560
<211> LENGTH: 102
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Affymetrix ID 2925993

<400> SEQUENCE: 560
ccctactgcg aaagtatgct gaagaaagaa atggtgtcaa tgtcgtcagt ggtcctgtgt     60
ttgactttga ttatgatgga cgttgtgatt ccttagagaa tc                      102

<210> SEQ ID NO 561
<211> LENGTH: 147
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Affymetrix ID 2908205

<400> SEQUENCE: 561
gaattctaca tactaaatct ctctccttt ttaattttaa tatttgttat catttattta     60
ttggtgctac tgtttatccg taataattgt ggggaaaaga tattaacatc acgtctttgt   120
ctctagtgca gttttttcgag atattcc                                      147

<210> SEQ ID NO 562
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
```

<223> OTHER INFORMATION: Affymetrix ID 2586123

<400> SEQUENCE: 562
gatggcacca acaggacagt atttgcttct atatctatgg tggggccttc tatgaacctg    60
gccttagatt ggatttcaag aaacctttat tctaccaatc                         100

<210> SEQ ID NO 563
<211> LENGTH: 283
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Affymetrix ID 3791749

<400> SEQUENCE: 563
ccaggtaaga cctaacgaat gacttaatag atcaactgga gtggttttag tggataggtt    60
tgcatgtttc taacgacaca gaaacctaca aaatagttca ctggttttca gaaaaatact   120
ggaaggattc atcacaaact cctagcccca gccaacccca gtgcaaaaaa aaaaaaaaaa   180
aaaaatcatg cccaatcctt caaaagattc atatgtgcag gttattact ctagacatca    240 gcttgcctgg gaccatcctg gcctacccta ttgtcccaga ata                    283

<210> SEQ ID NO 564
<211> LENGTH: 135
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Affymetrix ID 2586195

<400> SEQUENCE: 564
agggattcat cagtgagggc atttcacacc ctcatgtggc atttcacttg gtagtgtcca    60
gatcggattg ggtttttttt cctctggtta gtcacggtcc ttggaaagaa agatatgctg   120
gctcatgttg ttatg                                                    135

<210> SEQ ID NO 565
<211> LENGTH: 103
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Affymetrix ID 2763627

<400> SEQUENCE: 565
tcaaggagga gcaatcaggc tggtagggca gagaggagga aggagactca gtagtcaaat    60
ccctggtggc cgatgcccct ccctgcgcca aatcagcatg att                    103

<210> SEQ ID NO 566
<211> LENGTH: 53
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Affymetrix ID 2608559

<400> SEQUENCE: 566
ttcagaaaca tcctccggaa acagcagcca agaagggcca agtaatgtac cag        53

<210> SEQ ID NO 567
<211> LENGTH: 132
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Affymetrix ID 3126535

<400> SEQUENCE: 567
ggctcatctt atttcgacca ttcggcccca tcatgaaagt gaaaaatgaa aagctcaaca        60
tggccaacac gcttatcaat gttatcgtgc ctctagcaaa aagggtggac aagttccggc       120
agttcatgca ga                                                           132

<210> SEQ ID NO 568
<211> LENGTH: 179
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Affymetrix ID 3791743

<400> SEQUENCE: 568
agactcatga gtggggctaa cgccagggtc ggaatgcttt ctcttggtta ggtcttccag        60
caaaaccaat caaccaatac acatggaaaa tgcatcatac aaacttttca gatcagagct       120
ggggctttgc cttgtgtcag ccgacgaaga actcccaagg ccgttctgga ttgaatctc        179

<210> SEQ ID NO 569
<211> LENGTH: 638
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Affymetrix ID 3727623

<400> SEQUENCE: 569
ggtagccctc tcatcgtctt ttagttccaa caaagaaagg tgccatgtct ttactagact        60
gaggagccct ctcgcgggtc tcccatcccc tccctccttc actcctgcct cctcagcttt       120
gcttcatgtt cgagcttacc tactcttcca ggactctctg cttggattca ctaaaaaggg       180
ccctggtaaa atagtggatc tcagttttta agagtacaag ctcttgtttc tgtttagtcc       240
gtaagttacc atgctaatga ggtgcacaca ataacttagc actactccgc agctctagtc       300
ctttataagt tgctttcctc ttactttcag ttttggtgat aatcgtcttc aaattaaagt       360
gctgtttaga tttattagat cccatattta cttactgcta tctactaagt ttccttttaa       420
ttctaccaac cccagataag taagagtact attaatagaa cacagagtgt gttttttgcac      480 tgtctgtacc taaagcaata atcctattgt acgctagagc atgctgcctg agtattacta       540
gtggacgtag gatattttcc ctacctaaga atttcactgt cttttaaaaa acaaaaagta       600
aagtaatgca tttgagcatg gccagactat tccctagg                              638

<210> SEQ ID NO 570
<211> LENGTH: 129

```
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Affymetrix ID 2586057

<400> SEQUENCE: 570
gaacctaaaa tcgagtctgc ctggatgaat ggagaggacc gcaacatcct ggttttcgag      60
gaccttggtt ggccaactgg cctttctatc gattatttga acaatgaccg aatctactgg     120
agtgacttc                                                             129

<210> SEQ ID NO 571
<211> LENGTH: 191
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Affymetrix ID 2763598

<400> SEQUENCE: 571
gtgttcaatc tgatggcagt agtcattgta ataagacttt tggctggcgg gtgttgccat      60
catacactaa agagatttca tgacttaaga catttcatgg actcacaagt actgaaacag     120
ggtatgagtg gtaatggagg agagaactgt gactcaggaa agaagactcc ttcggtcaag     180
gggccagact t                                                          191

<210> SEQ ID NO 572
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Affymetrix ID 2925966

<400> SEQUENCE: 572
tggattcagg gcagaatatt tacacacttg gggtggactt cttcctgt                   48

<210> SEQ ID NO 573
<211> LENGTH: 416
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Affymetrix ID 4016044

<400> SEQUENCE: 573
atgacgtctc tgcaatgcac atgtgtgaaa atctgctact gaaacataga gcaagcaaac      60
actggcaggt gggtcaaaac gctactggta gcaggaggaa cgactaaagc aaagtattac     120
cataaggtta aaacatatgg cctgacaaat gcctgccagg acactacac ataaggaatg      180 tcttcagtgt cccttcgtgg ggccctgcag ccaccccctga attcccttgg acccctagga    240
tagaaggggt cctgtaaatt tctttgcatc cacaaaaacg cccccaattt ctgtttgctt     300
tttctccttt tatcctccac cctagccatg ttgtcaaatt ctcttatcat gtcctcattg     360
ctgaaattca tatcatgtat ggcttcctta tattgcttga ggtactgagc cagccc         416
```

```
<210> SEQ ID NO 574
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Affymetrix ID 2980475

<400> SEQUENCE: 574
aaataaactt ggatcggctg taatccatca ggaatc                                36

<210> SEQ ID NO 575
<211> LENGTH: 112
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Affymetrix ID 2944441

<400> SEQUENCE: 575
tgtaaaagtt acacatcaca agagattgga cagtagctta gcgtaacata gctatagtga        60
aaatcatttt tataaaaaaa taatctagat gcggtcatca gaattttttgg tc              112

<210> SEQ ID NO 576
<211> LENGTH: 328
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Affymetrix ID 2608634

<400> SEQUENCE: 576
ggagtagaat ccctccatga gtgtcagagg tgcagtgcca atgtgcttgt tcccgagctt        60
agctctggtg gtatgggcct gctccgcctt ccctctctcc ctgaccttcc ctccctcgcc      120
cacacaccca cttccttcca ctgtgaaagc ggagtaaggc tttaattgca caggttcatc      180
atttcttgtt tggaagtctt cagattttta gttttatacc ttagctttct gcagaattct      240
ccgttgaatc aatgccctgg gaaccccatg gacagaagca ccttttaatg aagtccttcc      300
aaaactcgtt cctcagtgca ttgctctg                                         328

<210> SEQ ID NO 577
<211> LENGTH: 1186
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Affymetrix ID 2727646

<400> SEQUENCE: 577
ggcctcccta gccagcactt gtatatacgc atctataaat tgtccgtgtt catacatttg        60
aggggaaaac accataaggt ttcgtttctg tatacaaccc tggcattatg tccactgtgt      120
atagaagtag attaagagcc atataagttt gaaggaaaca gttaatacca ttttttaagg      180
aaacaatata accacaaagc acagtttgaa caaaatctcc tcttttagct gatgaactta      240
ttctgtagat tctgtggaac aagcctatca gcttcagaat ggcattgtac tcaatggatt      300
```

```
tgatgctgtt tgacaaagtt actgattcac tgcatggctc ccacaggagt gggaaaacac    360
tgccatctta gtttggattc ttatgtagca ggaaataaag tataggttta gcctccttcg    420
caggcatgtc ctggacaccg ggccagtatc tatatatgtg tatgtacgtt tgtatgtgtg    480
tagacaaata tttggagggg tattttttgcc ctgagtccaa gagggtcctt tagtacctga    540
aaagtaactt ggctttcatt attagtactg ctcttgtttc ttttcacata gctgtctaga    600
gtagcttacc agaagcttcc atagtggtgc agaggaagtg gaaggcatca gtccctatgt    660
atttgcagtt cacctgcact taaggcactc tgttatttag actcatctta ctgtacctgt    720
tccttagacc ttccataatg ctactgtctc actgaaacat ttaaattta ccctttagac     780 tgtagcctgg atattattct tgtagtttac ctctttaaaa acaaaacaaa acaaaacaaa    840
aaactcccct tcctcactgc ccaatataaa aggcaaatgt gtacatggca gagtttgtgt    900
gttgtcttga aagattcagg tatgttgcct ttatggtttc ccccttctac atttcttaga    960
ctacatttag agaactgtgg ccgttatctg gaagtaacca tttgcactgg agttctatgc   1020
tctcgcacct ttccaaagtt aacagatttt ggggttgtgt tgtcacccaa gagattgttg   1080
tttgccatac tttgtctgaa aaattccttt gtgtttctat tgacttcaat gatagtaaga   1140
aaagtggttg ttagttatag atgtctaggt acttcagggg cacttc                  1186

<210> SEQ ID NO 578
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Affymetrix ID 2925978

<400> SEQUENCE: 578
aggaaatatt gtggaagtgg atttcatggc tct                                  33

<210> SEQ ID NO 579
<211> LENGTH: 247
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Affymetrix ID 2608490

<400> SEQUENCE: 579
gcatgtttct gtagtggcat ctcaactatt gcaatggaaa atatgtcctt ggcaagactc     60
ttagaaacac agcctcaaag gtcattggat tgtgcaagct tcttgactat ttacaaggtc    120
acctacctga atgaatagaa atgctccctg cccttaagga atttgcaatt ttatgaagag    180
agatgagtga gaactacttt gtggattatt cttggagaat gttgaatccc agatgagctt    240
ttagtcc                                                              247

<210> SEQ ID NO 580
<211> LENGTH: 34
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Affymetrix ID 3992448
```

```
<400> SEQUENCE: 580
agcaagtgta ttgtcccgac tgtgccaaaa agct                              34

<210> SEQ ID NO 581
<211> LENGTH: 101
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Affymetrix ID 3985030

<400> SEQUENCE: 581
ggctggctca gtacctcaag caatataagg aagccataca tgatatgaat ttcagcaatg   60
aggacatgat aagagaattt gacaacatgg ctagggtgga g                      101

<210> SEQ ID NO 582
<211> LENGTH: 90
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Affymetrix ID 3753968

<400> SEQUENCE: 582
aagagaagat gccaaggccc cctcctccac ccaccgctaa ctctcagccc cagtcaccct   60
cttggagctt ccctgctttg aattaaagac                                   90

<210> SEQ ID NO 583
<211> LENGTH: 103
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Affymetrix ID 3573878

<400> SEQUENCE: 583
tgatgctaag agtcctgggt aaatgtggtg agaatgcacg cgtgcatatg ctacacatat   60
gtgcttctca gttgcagaaa atgaactgct ttgggagatt atc                    103

<210> SEQ ID NO 584
<211> LENGTH: 120
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Affymetrix ID 2586112

<400> SEQUENCE: 584
tgtactgggc tgactgggat acacatgcca aaatcgagag agccacattg ggaggaaact   60
tccgcgtacc cattgtgaac agcagtctgg tcatgcccag tgggctgact ctggactatg   120

<210> SEQ ID NO 585
<211> LENGTH: 211
<212> TYPE: DNA
<213> ORGANISM: Artificial Sequence
<220> FEATURE:
```

<223> OTHER INFORMATION: Description of Artificial Sequence: Synthetic
      polynucleotide
<220> FEATURE:
<223> OTHER INFORMATION: Affymetrix ID 3354794

<400> SEQUENCE: 585
ggaggcaaaa gctatgctag gctgccagaa ggacataagc agaccttgtc cattctctta      60
gctccctaaa ttagccaaat agagacttct ttctcaaatc aggaaaacta tcaaagacca    120
attcagatcc tacatttaca gacagttttg tcataaccct ttgcattgca gcacctagta    180
caattccttg gaaacagcgt ggctcaataa a                                   211

<210> SEQ ID NO 586
<211> LENGTH: 159
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Affymetrix ID 2925981

<400> SEQUENCE: 586
ttgacaccgg ctcctaataa cggaactcat ggaagtctta accaccttct aaagaatcct      60
gtttatacgc caaagcatcc caaagaagtg cacccctgg tacagtgccc cttcacaaga     120
aaccccagag ataaccttgg ctgctcatgt aacccttcg                           159

<210> SEQ ID NO 587
<211> LENGTH: 907
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Affymetrix ID 3787884

<400> SEQUENCE: 587
tccttccgac aggagctgac tcatgtcagg atggcaggcc tggtatcttg ctcgggccct      60
agctgttggg gttctcatgg gttgcactga ccatactgct tacgtcttag ccattccgtc    120
ctgctcccca gctcactctc tgaagcacac atcattggct ttcctatttt tctgttcatt    180
ttttaattga gcaaatgtct attgaacact taaaattaat tagaatgtgg taatggacat    240
attactgagc ctctccattt ggaacccagt ggagttggga tttctagacc ctctttctgt    300
ttggatggtg tatgtgtata tgcatgggga aaggcacctg gggcctgggg gaggctatag    360
gatataagca ttagggaccc tgaggcttta agtggtttct atttcttctt agttattatg    420
tgccaccttc ttagttatta tgtgccacct cccctatgag tgacgtgttt gatcactagc    480
agaatagcaa gcagagtatc attcatgctg gggccagaat gatggccggt tgccagatat    540
aactgctttg gagcaaatct cttctgttta gagagataga agttatgaca tatgtaatac    600
acatctgtgt acacagaaac cggcacctgc cagacagagc tggttctaag atttaataca    660
gtgctttttt tcctctttga aatattttac tttaatacca gtgccttttc ttgttgaact    720
tcttggaaaa gccaccaatt ctagatcttg atttgaatta atacacacaa tatctgagac    780
acttacactt ttcaaaagat ttgtgtatgc attgcctaat tagagtaggg ggagaagggc    840
aactattatt atccctattt tacaaaactg aggcttagtg aggttcagcc acatgcctag    900
acttata                                                              907

<210> SEQ ID NO 588
<211> LENGTH: 45
<212> TYPE: DNA
<213> ORGANISM: Artificial Sequence
<220> FEATURE:
<223> OTHER INFORMATION: Description of Artificial Sequence: Synthetic
    oligonucleotide
<220> FEATURE:
<223> OTHER INFORMATION: Affymetrix ID 3791660

<400> SEQUENCE: 588
agttaggggt cggatgcatg agcagcaatc ggggcactcc tactt                45

<210> SEQ ID NO 589
<211> LENGTH: 79
<212> TYPE: DNA
<213> ORGANISM: Artificial Sequence
<220> FEATURE:
<223> OTHER INFORMATION: Description of Artificial Sequence: Synthetic
    oligonucleotide
<220> FEATURE:
<223> OTHER INFORMATION: Affymetrix ID 3569378

<400> SEQUENCE: 589
ttcaaggatg cactgtatag ccaggctgtg ggaggaggga ggaaagatga aaaccactt   60 aaatgtgaag gaacaacag                                              79

<210> SEQ ID NO 590
<211> LENGTH: 175
<212> TYPE: DNA
<213> ORGANISM: Artificial Sequence
<220> FEATURE:
<223> OTHER INFORMATION: Description of Artificial Sequence: Synthetic
    polynucleotide
<220> FEATURE:
<223> OTHER INFORMATION: Affymetrix ID 2932285

<400> SEQUENCE: 590
gctgacacag gatgagagca cagtaaaact taagctaaga tttccacatt aatatcttgc  60
ccccaaacac catgcagtgc taaaagtcac attcccatca tgcaagcaca ttaaaatata 120
tggcgattaa aactcctggt ttctatttta cggcatttgc tctttccacg aggca       175

<210> SEQ ID NO 591
<211> LENGTH: 65
<212> TYPE: DNA
<213> ORGANISM: Artificial Sequence
<220> FEATURE:
<223> OTHER INFORMATION: Description of Artificial Sequence: Synthetic
    oligonucleotide
<220> FEATURE:
<223> OTHER INFORMATION: Affymetrix ID 2586165

<400> SEQUENCE: 591
gtgaggtgag agcactttca gttttccccg gtgatttgtg tctttggagt gcagctgttg  60
cttta                                                             65

<210> SEQ ID NO 592
<211> LENGTH: 103
<212> TYPE: DNA
<213> ORGANISM: Artificial Sequence
<220> FEATURE:
<223> OTHER INFORMATION: Description of Artificial Sequence: Synthetic
    polynucleotide
<220> FEATURE:
<223> OTHER INFORMATION: Affymetrix ID 3787881

<400> SEQUENCE: 592
gtaaccagga ctttctcaca cgttccaccc aggacacgtt gacatgatga tctcctagca    60
tgtgctgggg atggatctgg gtgccaggga catagcatga aca                      103

<210> SEQ ID NO 593
<211> LENGTH: 103
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Affymetrix ID 2925998

<400> SEQUENCE: 593
ctgcttctct taaaggagaa gtagctgtga acattgtctg gataccagat atttgaatct    60
ttcttactat tggtaataaa ccttgatggc attgggcaaa cag                      103

<210> SEQ ID NO 594
<211> LENGTH: 129
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Affymetrix ID 2925975

<400> SEQUENCE: 594
catggaacaa ggcagttgta agaaatacat atatctgaat aaatatttgg gggatgttaa    60
aaatattaaa gttatctatg gacctgcagc tcgattgaga ccctctgatg tcccagataa    120
atactattc                                                            129

<210> SEQ ID NO 595
<211> LENGTH: 198
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Affymetrix ID 3126541

<400> SEQUENCE: 595
cgtgttctca ccaataagtg gtagctaaat gatgaaaaca catggacaca tagagggcaa    60
caacacacac tggtgcctac ctctgagggt ggaggatggg aggaaggaga ggaccaggaa    120
aaataatagg tactaggctt aatactgggg tgatgaaata atctgtacaa taaattcctg    180
gggcagaagt ttacctat                                                  198

<210> SEQ ID NO 596
<211> LENGTH: 284
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Affymetrix ID 2782529

<400> SEQUENCE: 596
tcagattgtt acagtcccctt ctttgagaca aacaaacaga agtgcacaaa tgcacttaag    60
agtttccaag ggagtgtgga tttcaaataa ataaaccaaa aattttaacc aaaaccaaat    120

```
tttcaaggat tctctcaatct tgtctgcaag ctgaaaaaca gacctagctg gaaagtgaaa      180
agtgctcact cagggtaaaa agaatggaaa caattaatgt gattagaaga ggggtttgac      240
cgtggtcttg attttaaac gccacatgca ggtattagag aaga                        284
```

<210> SEQ ID NO 597
<211> LENGTH: 88
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Affymetrix ID 2763596

<400> SEQUENCE: 597

```
acattaattg tttaacagag tcctctttgt cacatccatt gccttctccg gggtgtttga      60
ttgttgaaac tcatgctaaa ctaattga                                         88
```

<210> SEQ ID NO 598
<211> LENGTH: 1076
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Affymetrix ID 2649079

<400> SEQUENCE: 598

```
ggccttgtac aacttatcca gaatgtctat taggattcta atgttatgtc cacttacaag      60
tagagacagt aaaaggatga atacccaatc tttagtgaca atgcagctga tttatgaaag     120
agagggctac actgctatgg aaacttagct tcaaagaaaa tgcaatgtat ctgcaattag     180
gtgttcattt tttactacat tttattaaaa cctgctttat actttcaact gcttgtaggc     240
acaacttctg caagtttaaa tatttgagct ttacaaataa acatacacat gctcagtttt     300
ttaagtaaac ctgtaaaata cccaggaagg caaatgttca ttgtttaatt agcactggga     360
ttttataata taatgtttgg tatttttgag gcattgttaa catgaaagtc aaccactggc     420
tttgtgaaaa atgctatgtc actattcaga atatgctggg taaattgact tgcctagtga     480
aaagcaaaat gttaaagaaa gaacttctgg ttctataatc atattatatg cactaaacta     540
tatgcatgaa agttctttgc atggattaat ggggcttacc cttgttgcac tcgaaatctg     600
aggtgtatct agccctgcca ctattggcta cttaccctca ttaatatccc acttgagaaa     660
aattgtgaga ctatactgtg tcaatatctg taaaaagaga gaaaacatgt tttgtttttt     720
tttgaagggg gtggtgtggg agtggccctt taactctatt tggctatctg aggatgtaca     780
aaattctcat ttaattttct ggtcagcaag ttccccacac agaaatcact ctgaggttta     840
cagaagaact gtaatattat tttaaaatgc gattttttctg tcattagttc tagatatgta     900
cttcatggtt aaattctaaa tctgaaaatg ctagtgggag atatcaagaa attttctttt     960
tgattactag tacctgtatt ctaacagaga gtttgaattt tttgcccgtg ttatcagaat    1020
gatggaaatt gatcattttc agttgttcat tgtgtattca atccagcgaa ctgctg        1076
```

<210> SEQ ID NO 599
<211> LENGTH: 87
<212> TYPE: DNA
<213> ORGANISM: Artificial Sequence
<220> FEATURE:

```
<223> OTHER INFORMATION: Description of Artificial Sequence: Synthetic
      oligonucleotide
<220> FEATURE:
<223> OTHER INFORMATION: Affymetrix ID 2925973

<400> SEQUENCE: 599
agagggttga tggtatggtt ggtatgctga tggatggtct gaaagagctg aacttgcaca    60
gatgcctgaa cctcatcctt atttcag                                       87

<210> SEQ ID NO 600
<211> LENGTH: 268
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Affymetrix ID 2925999

<400> SEQUENCE: 600 gttgggtag cccatgttat gtgactatct ttatgagaat tttaaagtgg ttctggatat     60
cttttaactt ggagtttcat ttcttttcat tgtaatcaaa aaaaaaatta acagaagcca   120
aaatacttct gagaccttgt ttcaatcttt gctgtatatc ccctcaaaat ccaagttatt   180
aatcttatgt gttttctttt taatttttg attggatttc tttagattta atggttcaaa   240
tgagttcaac tttgagggac gatctttg                                     268

<210> SEQ ID NO 601
<211> LENGTH: 1122
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Affymetrix ID 3126508

<400> SEQUENCE: 601
tttgcctgca aaagtaaccc agttgcaccc tgtgaagtgt ctgacaaagg cagaatgctt    60
gtgagattat aagcctaatg gtgtggaggt tttgatggtg tttacaacac actgagacct   120
gttgttttgt gtgctcattg aaatattcat gatttaagag cagttttgta aaaaattcat   180
tagcatgaaa ggcaagcata tttctcctca tatgaatgag cctatcagca gggctctagt   240
ttctaggaat gctaaaatat cagaaggcag gagaggagat aggcttatta tgatactagt   300
gagtacatta agtaaaataa aatggaccag aaaagaaaag aaaccataaa tatcgtgtca   360
tattttcccc aagattaacc aaaaataatc tgcttatctt tttggttgtc cttttaactg   420
tctccgtttt tttctttat ttaaaaatgc acttttttc ccttgtgagt tatagtctgc    480
ttatttaatt accactttgc aagccttaca agagagcaca agttggccta catttttata   540
ttttttaaga agatactttg agatgcatta tgagaacttt cagttcaaag catcaaattg   600
atgccatatc caaggacatg ccaaatgctg attctgtcag gcactgaatg tcaggcattg   660
agacataggg aaggaatggt ttgtactaat acagacgtac agatactttc tctgaagagt   720
attttcgaag aggagcaact gaacactgga ggaaaagaaa atgacacttt ctgctttaca   780
gaaaaggaaa ctcattcaga ctggtgatat cgtgatgtac ctaaaagtca gaaaccacat   840
tttctcctca gaagtaggga ccgctttctt acctgtttaa ataaaccaaa gtataccgtg   900
tgaaccaaac aatctctttt caaaacaggg tgctcctcct ggcttctggc ttccataaga   960
```

```
agaaatggag aaaaaaatat atatatatat attgtgaaag atcaatccat ctgccagaat    1020
ctagtgggat ggaagttttt gctacatgtt atccacccca ggccaggtgg aagtaactga    1080
attatttttt aaattaagca gttctactcg atcaccaaga tg                       1122
```

<210> SEQ ID NO 602
<211> LENGTH: 87
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Affymetrix ID 2586072

<400> SEQUENCE: 602

```
tcagtgtaca agtggacatt gtgtacacag tgaactgaaa tgcgatggat ccgctgactg    60
tttggatgcg tctgatgaag ctgattg                                        87
```

<210> SEQ ID NO 603
<211> LENGTH: 636
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Affymetrix ID 2661165

<400> SEQUENCE: 603

```
acaggagatt tagtagggcg ctcccgacag cctggctggc agtcactaat ccagaagaat    60
gaatgaatgt tgtactaaat actccccaat gtttgttcta ataattctcc tcagagctgt    120
cataacaaca gcaagtgttt ttttaaataa tcaggtaaac attttctgaa ttaacctggt    180
aatcaaaccg actgtacttc aaactgatcc taaagaaagt acataaatgg aatagcagtt    240
aagtcacaaa tgccaaatga aagccaccaa ccagtcactg tatattctgc atcatttatt    300 aaatatttttt atatatgcat ttacaaactt tactcatttc agaactctgc tttcaatgca    360
tttttaaact gttttttttt ttttttgcaga gagattctct tgtaaaatga gatccatgta    420
caaaactagg caacagatat aaaagttttcc tttcatattt ttcatccatc aagaaaagaa    480
atcatgtgac aagaaataaa accaaaatgt ggctctttca gaagaataac atgtctgtgg    540
tcaactatga cttctaatga gatagttcat atttcatctt tatatggatg tatatagttt    600
taatacttct tagctactgt agcatgttgg ttcaga                              636
```

<210> SEQ ID NO 604
<211> LENGTH: 94
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Affymetrix ID 3018623

<400> SEQUENCE: 604

```
tgcctttggg atcagcaaca tcttctcagg attcttctct tgttttgtgg ccaccactgc    60
tctttcccgc acggccgtcc aggagagcac tgga                                94
```

<210> SEQ ID NO 605
<211> LENGTH: 462
<212> TYPE: DNA

<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Affymetrix ID 2944443

<400> SEQUENCE: 605

```
ctgactcttt ggttgtgcct atacaatgaa aagtctacaa atgaaatgag agaagtcagg      60
atattttcct ttgttaaact aagtagctga ataattagaa ctacctagat aaaagactca     120
aaatgttttt gttatctggt tgcctggtta ggacatagcc aacatttcaa tggaatgtag     180
tatcttgtac aactgcatat aattttttaa aaaataaaca atgactttgt ttctttagat     240
acatcaaatg ctgcttgagt ggccaaaggg aaaatgccaa ctcttttgaaa tgtagtatct    300
gtagcacttt tcttctttca gtagttttc atgccccaaa tacaaacttt aaggagtaac     360
atctatcctc aaaacccaaa aatacccatt tgttttgagg ttcacagtcc accagtataa    420
gttttaaact gcgccaaaag cttaggtag ggttcagcag tc                        462
```

<210> SEQ ID NO 606
<211> LENGTH: 109
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Affymetrix ID 3573881

<400> SEQUENCE: 606

```
gttcaataga acatgcaaga atttctggaa gaaaggctgt ggaagggcca atggagaaaa      60
tgaatggaca aagctcagga atcctacgct atgtagaatg tcttggtgt                 109
```

<210> SEQ ID NO 607
<211> LENGTH: 140
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Affymetrix ID 3573895

<400> SEQUENCE: 607

```
gtaactggat tagggacgag tacgccagct tttttttttt tttttttttt tttttttaa      60
catcttaaat cctgaaaaaa aaaaaaaaaa aaaaaaaag gcagcagctc cgaattgaat     120
gaattgatgg gcacactcca                                                 140
```

<210> SEQ ID NO 608
<211> LENGTH: 211
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Affymetrix ID 3811395

<400> SEQUENCE: 608

```
tgactggagc agtctggttt cttcccttt tatcgagttc tgtcattgtg ttcctcaaac      60
tgtggtttgt tccagaaagg aagaggttgt cttcttcacc cgcctgccct aagttgcgtc    120
aagttccagt tccctgtatt aagtaaatta ctaaatgagt ggaatgaaca tcataatgtc    180
```
aagggtaggg cgttgacatt atgggacaat a                                    211

<210> SEQ ID NO 609
<211> LENGTH: 394
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Affymetrix ID 3787879

<400> SEQUENCE: 609
tatcagctcc taacaccgtg cctggactcc ctgagcaggc ttttttctaa acagaagcca     60
gggaagcctg cgagaccttt gtcaagaagg gagagtttcc ttaaccaagt ccttcagctg    120
acctctacag aggtcactgc cagccttggc atgggaggag gcagctgcct ccctctttgt    180
ccctcctctg gcattttctc cattataatt cctgccatgt ctggtttaca ttcgtcatct    240
atgacacagc ttggcagcag agggaagtga agtggaggct tggagccctc agctgaatga    300
ttctagtcta gaaacctgtg aactgggggt gctggcctgt ggtctagact gtgtatgttt    360
ttacttctct gggcccttgc aggtacaaac tata                                394

<210> SEQ ID NO 610
<211> LENGTH: 71
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Affymetrix ID 2608590

<400> SEQUENCE: 610
aatttgtggt tgacgctggc cattaaccta tctctgaaag tcagttttga aattggccta     60
aagaacttct c                                                          71

<210> SEQ ID NO 611
<211> LENGTH: 97
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Affymetrix ID 2763629

<400> SEQUENCE: 611
tttaagagtg ataatgctga cagtcgtaag aggtgtaggc aagtaggaaa tacggaaaat     60
cagacagcag gcagtgctgc attccaaacc caatgtg                              97

<210> SEQ ID NO 612
<211> LENGTH: 565
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Affymetrix ID 3992441

<400> SEQUENCE: 612
aaagagtcct tgctaagtct gccaggctag gttttgcgca tggtaaccat ctctcatttt     60

```
cctgtcgtcg gtttcatcca caaaggcccc cagagaatgc ccttctcccc ctgctattgt    120
ggtcccaaag gccccccaag agtttggatt cgtccccagg ccaggttagc ctttgcaata    180
cagaacactt cctgactgtt gactaacaat gctgagagtt cacaagcctg agacctgcca    240
gccaacaccg gcaggcactg ccactttgca gggggattct ggggggaggg gtgggaggag    300
ggtagaaaga aggggggtggg ggagggtggg gaagggggtaa gggaggccga agagtgataa    360
cccgggattg taatacccca tagctgaagg ctagttcaga gatgcctgtt ggcagggttt    420
cttttttttt tggtttgctg tttatttgtt tttgcgatca gcaaagctaa tcacttcatt    480
cctcatctcg cggccgcgat ccacgtgccc tgggcccttt ccttgcctc caattttccc    540 atcttcccgg ggagccttga aatgt                                         565
```

<210> SEQ ID NO 613
<211> LENGTH: 406
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Affymetrix ID 3727625

<400> SEQUENCE: 613

```
cctttaatga tctggtggtc tcctcgtcaa tccatcagca atgcttctct catagtgtca    60
tagacttggg aaacccaacc agtaggatat ttctacaagg tgttcatttt gtcacaagct    120
gtagataaca gcaagagatg ggggtgtatt ggaattgcaa tacattgttc aggtgaataa    180
taaaatcaaa aacttttgca atcttaagca gagataaata aagatagca atatgagaca    240 caggtggacg tagagttggc cttttttacag gcaaagaggc gaattgtaga attgttagat    300
ggcaatagtc attaaaaaca tagaaaaatg atgtctttaa gtggagaatt gtggaaggat    360
tgtaacatgg accatccaaa tttatggccg tatcaaatgg tagctg                  406
```

<210> SEQ ID NO 614
<211> LENGTH: 477
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Affymetrix ID 2615655

<400> SEQUENCE: 614

```
cctctaattt ggtccctggc acatgcatac ttgtcaatgt ttttattctt ttacaagacc    60
tgcattttat ttgaattacc cgaatagcaa tatgtaaaat acaagtgaca aaatgtgatg    120
agagcttctt gaaccggtaa actagtacag gtctgagaaa gacatattag aagaatcatt    180
atacttcctt gaattatatt tatttttcatg tttctctaat gcaaagaatg tttcatcaaa    240
tgtatatttt ctgttgctta ctgtttgctc tgagaagaag ctgctgtttc aaagatggac    300
ctctgagtag ctaattgatt caagtagttt tttatgttg acacattatt actgctgtta    360
gcagtcgttt tcaccaggta cttacagagc agatttcata catcattcat tcaagggcta    420
aatttatatt ttttggaaat catggcaact acacaggatg ttgcttacca ggacgga      477
```

<210> SEQ ID NO 615
<211> LENGTH: 75
<212> TYPE: DNA
<213> ORGANISM: Artificial Sequence

```
<220> FEATURE:
<223> OTHER INFORMATION: Description of Artificial Sequence: Synthetic
      oligonucleotide
<220> FEATURE:
<223> OTHER INFORMATION: Affymetrix ID 3603302

<400> SEQUENCE: 615
gaatgagaac aagatccact gcacgcaaac tcttcttgaa ggggacggcc ccaaaaccta    60
ctggacccgt gagct                                                    75

<210> SEQ ID NO 616
<211> LENGTH: 103
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Affymetrix ID 2586098

<400> SEQUENCE: 616
tggattcttc tagaattggc gattagtggg gtagacgaag atgatggggg aaagggggatc    60 aaggacactg gtgatcttgt cgaaatggtt gacctggcat tta                    103

<210> SEQ ID NO 617
<211> LENGTH: 135
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Affymetrix ID 2925996

<400> SEQUENCE: 617
gttaatgtta cacagagcac ggatcacaga tgttgagcac atcactggac tcagcttcta    60
tcaacaaaga aaagagccag tttcagacat tttaaagttg aaaacacatt tgccaacctt   120
tagccaagaa gactg                                                   135

<210> SEQ ID NO 618
<211> LENGTH: 160
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Affymetrix ID 3791650

<400> SEQUENCE: 618
aagtgccatt atagctaatg gtggccaact ggagacttac tttaccttaa ccatgtaaag    60
tatccttacc gtatttttta tgtgtacagt gttgcagaat atcagccacc tcttaaaagt   120
atcaatctta aaagagccaa tggaaggtaa aagtatgaaa                        160

<210> SEQ ID NO 619
<211> LENGTH: 52
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Affymetrix ID 2925967

<400> SEQUENCE: 619
```
ctaaaaacat gagaccggta tatccaacaa aaactttccc caatcactac ag    52

<210> SEQ ID NO 620
<211> LENGTH: 175
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Affymetrix ID 2586147

<400> SEQUENCE: 620
ctcgcagcta acagggtgga aaatgttgaa agtttggctt ttgattggat ttcaaagaat    60
ctctattgga cagactctca ttacaagagt atcagtgtca tgaggctagc tgataaaacg   120
agacgcacag tagttcagta tttaaataac ccacggtcgg tggtagttca tcctt        175

<210> SEQ ID NO 621
<211> LENGTH: 392
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Affymetrix ID 3992436

<400> SEQUENCE: 621
cttgcttatc atggtggggc taacgttgct ctgagctgct ttgagatctt agcatatata    60
tgtacacata tacatacacg tatatatgcg tacacatata tgctcgcaca cacgcacaca   120
ctcggagact aaagaacact ggcgagaaca gcctgtggca acagaatgaa gtgaacagta   180
tgtagcgctt tctcatttgg gcgtagtaag tgatgaaagc atgcttcttc ctcagggtgt   240
cattctgggc caggcagtcc ctgatttaat gtctaagtgc acgcagggta tagaggtggg   300
ggagtggggg attcaggcac tggatcctaa aataataatg ctggggtccc cacccatgac   360
agaaatcctg ggttggcaca agcacaagta ga                                 392

<210> SEQ ID NO 622
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Affymetrix ID 2740285

<400> SEQUENCE: 622
ttgaatatat ctatgagggc atgtattagt taatggaaaa aaaaatacaa cactaacaat    60
acatagctgc aatgtgtaca atggctgatt taattaaata                         100

<210> SEQ ID NO 623
<211> LENGTH: 207
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Affymetrix ID 2740135

<400> SEQUENCE: 623

```
ctcggtttgg gaccttagtt cattgtagtg agttgtgggt gctgcagagg ctggagcaag      60
attatgacct agctcggggg cggagtggat tatcttgtga gtgttctggc tgccagccat     120
tgccctggtg gggaaaatca catctccata gagctctgaa atcacctgga ttgctgggga    180
gtggaaactg atcctctgct actgctt                                         207

<210> SEQ ID NO 624
<211> LENGTH: 225
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Affymetrix ID 2586097

<400> SEQUENCE: 624
cggcacaatg actgtggtga ctatagcgac gagaggggct gcttatacca gacttgccaa     60
cagaatcagt ttacctgtca gaacgggcgc tgcattagta aaaccttcgt ctgtgatgag    120
gataatgact gtggagacgg atctgatgag ctgatgcacc tgtgccacac cccagaaccc    180
acgtgtccac ctcacgagtt caagtgtgac aatgggcgct gcatc                   225

<210> SEQ ID NO 625
<211> LENGTH: 116
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Affymetrix ID 3985031

<400> SEQUENCE: 625
gcaggcattt gtcaggccat atgttttaac cttatggtaa tactttgctt tagtcgttcc     60
tcctgctacc agtagcgttt tgacccacct gccagtgttt gcttgctcta tgtttc        116

<210> SEQ ID NO 626
<211> LENGTH: 76
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Affymetrix ID 2954890

<400> SEQUENCE: 626
aaggactgtt ctgtcgatgg tgatggtgtg gtggcggcag cgtggtttct gtatcgatcg     60
ttctgtatca gtcttt                                                     76

<210> SEQ ID NO 627
<211> LENGTH: 130
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Affymetrix ID 2586154

<400> SEQUENCE: 627
ttggcgaggc ctccattatc ttctccaatg gtcgggattt gttaattggt gatattcatg     60
gaaggagctt ccggatccta gtggagtctc agaatcgtgg agtggccgtg ggtgtggctt    120
```

```
tccactatca                                                           130

<210> SEQ ID NO 628
<211> LENGTH: 361
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Affymetrix ID 4013550

<400> SEQUENCE: 628
tcctgacaat aaattccatc cgttgttttt tttgtttgtt tgttttttct tttcctttaa    60
gtaagctctt tattcatctt atggtggagc aattttaaaa tttgaaatat tttaaattgt   120
ttttgaactt tttgtgtaaa atatatcaga tctcaacatt gttggtttct tttgttttc    180 attttgtaca actttcttga atttagaaat tacatctttg cagttctgtt aggtgctctg   240
taattaacct gacttatatg tgaacaattt tcatgagaca gtcattttta actaatgcag   300
tgattctttc tcactactat ctgtattgtg gaatgcacaa aattgtgtag gtgctgaatg   360
c                                                                   361

<210> SEQ ID NO 629
<211> LENGTH: 504
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Affymetrix ID 3811377

<400> SEQUENCE: 629
agctcagtca tgtctagaat ataccaaatg ataagaagtc tgatacaaac aagaagtctt    60
gtcctattag agttcatagt aatagcattt gatctataat aacagaaaaa atattgcatg   120
gacatacatt aatctattcc tgagcttaac tccagatgag gaatcagttt ttatatctca   180
tttgtacagg gtggagagag atgggctttt ttctttcgat ttgttttttcc acgtctattt   240 agagcaacca aaataggaaa actgctgcac aggtcttaaa attcacttcc tccatccgct   300
ttccgaattc tgctccaggt ctgatgacta aacttttta tacatgtcat ttattttat    360 ttttattttta gtctaaatgt ctcttcaaaa acaccaggga aaaacatttt tagcttcact   420
aagaaaacaa acatgtttaa acaacccccca aaatgttcag gtagagtcgg tgttttggc   480 ttgtgtgtat tttaacggtg agcc                                           504

<210> SEQ ID NO 630
<211> LENGTH: 715
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Affymetrix ID 3763258

<400> SEQUENCE: 630
aaggccaact ctacgtccac ctgtgtctca tattgctatc ttttatttat ctctgcttaa    60
gattgcaaaa gttttgatt ttattattca cctgaacaat gtattgcaat tccaatacac    120
ccccatctct tgctgttatc tacagcttgt gacaaaatga acaccttgta gaaatatcct   180
```

```
actggttggg tttcccaagt ctatgacact atgagagaag cattgctgat ggattgacga    240
ggagaccacc agatcattaa aggattagat actctgaagg caggaaacta gaaaatccca    300
ttgatgaaag gatattttaa tctagcgtaa aatgtttctt tgtcgtaaca gcagaatttc    360
ttgacatttt acaacttaat gaaacaaaag aacaatcatc tttaaagtca aacatctatc    420
aaattataaa ccaaacacat agcaccgata tcaacctcat aaaacgtgcg ggcccgcagg    480
gtagaaaaga actgtctggg gcactggcag caacgtgcca ttccaggaac tcagaatttc    540
gaagtgaaca tttttgtggc agatgctttt cctaaaaaac actgtatcat ccaataaata    600
tttgactaaa atccattttg tgcttttggg tgacgttaac tgacttcttt ctgaggccta    660
ataagaaaca agaaagctcc ttgtgtattt tagagcagga ttcgtcatca caagc         715
```

<210> SEQ ID NO 631
<211> LENGTH: 68
<212> TYPE: DNA
<213> ORGANISM: Artificial Sequence
<220> FEATURE:
<223> OTHER INFORMATION: Description of Artificial Sequence: Synthetic
    oligonucleotide
<220> FEATURE:
<223> OTHER INFORMATION: Affymetrix ID 3753974

<400> SEQUENCE: 631

```
atgaagatct ccgtggctgc cattcccttc ttcctcctca tcaccatcgc cctagggacc    60
aagactga                                                              68
```

<210> SEQ ID NO 632
<211> LENGTH: 144
<212> TYPE: DNA
<213> ORGANISM: Artificial Sequence
<220> FEATURE:
<223> OTHER INFORMATION: Description of Artificial Sequence: Synthetic
    polynucleotide
<220> FEATURE:
<223> OTHER INFORMATION: Affymetrix ID 3088318

<400> SEQUENCE: 632

```
agtaggcacc gcatcttcaa ttcatcttct gatcccctgc accttggtag catgtctagc    60
acatgcaaaa ggctctcaaa acatcctctc caggtcacaa gtcttccgcc acccatccct    120
tcctacctcc acgagcaagg gaca                                            144
```

<210> SEQ ID NO 633
<211> LENGTH: 47
<212> TYPE: DNA
<213> ORGANISM: Artificial Sequence
<220> FEATURE:
<223> OTHER INFORMATION: Description of Artificial Sequence: Synthetic
    oligonucleotide
<220> FEATURE:
<223> OTHER INFORMATION: Affymetrix ID 2925979

<400> SEQUENCE: 633

```
gccctctttg ttggctatgg acctggattc aagcatggca ttgaggc                   47
```

<210> SEQ ID NO 634
<211> LENGTH: 295
<212> TYPE: DNA
<213> ORGANISM: Artificial Sequence
<220> FEATURE:
<223> OTHER INFORMATION: Description of Artificial Sequence: Synthetic
    polynucleotide
<220> FEATURE:

<223> OTHER INFORMATION: Affymetrix ID 3811413

<400> SEQUENCE: 634

```
ttgccctgca tggaaacggt gcaccctctc ccgctacaca ctcagagatg agagatgagc      60
ctgtttgtga aaccaaactc aggattctgt ttttgtgtaa gaaccgtacc acatggctga     120
catatgttca gtccatggct ggcagaagcc tcctgaacac atcccccatc cagtacctcc     180
ccggcagtga cccatctcat atttgcatat gttccctgt cacaagattg tggggagggt      240
gcagtttgca gctgactcct tacctagcta cagctccaac taagggcgtg cattc          295
```

<210> SEQ ID NO 635
<211> LENGTH: 343
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Affymetrix ID 2980497

<400> SEQUENCE: 635

```
tgtgctgaca ttctacctgg tgatctctct agtgatttag aagtctgcac agatgggaca      60
gggagagagc actcttaatt agcataggag atgtaggaat tcaagcagaa cctgtataaa     120
atgctggaat ccccagtttt atgtgatgaa ggagagaatc tcttcagttt tcaagatttt     180
ttaattgaaa gttttaaac acaaaaatca cataaaactt gattcttgaa acatagcatc      240
ttcacatata gacttaaact accaggtaag tatttgtcat tcactggttt tcaccagaag     300
atgaatttgt atcataaaaa gttatcaaca tgggccgggt aca                       343
```

<210> SEQ ID NO 636
<211> LENGTH: 414
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Affymetrix ID 3811431

<400> SEQUENCE: 636

```
ctgcacgtgt agaatcaaag gactgacagc aggtcgaatg tgaggaatga gggagggaaa      60
gaatcaggac tcaagtgcca tcctggctgc ctcaaaaaat gatactgtct tccagaggga     120
aaggaaagat aacaacagtt actgctttgt ggcgtacatg tgatgaattt cattttggac     180
attccagtag gatatccaag tggaaatgcc cagtaagcct tagacataag gatctggatc     240
tcaagagaaa aattgaggtt gaaccataat atgtctttcc cctcgaatca tgtaggtttc     300
tcttttgcct tctttcattg ccctaagtgg tcctaaatgc tactgctgat gctgtcttag     360
tttgcgactg ttgtttgcac cccaccttt cccaaggta atctgtagac ttgc             414
```

<210> SEQ ID NO 637
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Affymetrix ID 2608556

<400> SEQUENCE: 637
agcaatcctg ggaaaagtga ccctgtgttg ga                                    32

<210> SEQ ID NO 638
<211> LENGTH: 109
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Affymetrix ID 3108611

<400> SEQUENCE: 638
tatcactatg tatgctgttg gggtaggaaa agccattgag gaggaactac aagagattgc      60
ctctgagccc acaaacaagc atctcttcta tgccgaagac ttcagcaca               109

<210> SEQ ID NO 639
<211> LENGTH: 83
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Affymetrix ID 3160684

<400> SEQUENCE: 639
tgttgctgca ctggattcca acgtatccgg aaaaattggt ctgcgcgctg tcgtgtatta      60
tttctgtacc actctcattg ctg                                             83

<210> SEQ ID NO 640
<211> LENGTH: 87
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Affymetrix ID 4023355

<400> SEQUENCE: 640
ttcaggagca gcacctagac cagtcttccc tcaaccccag ctgataaggc tgtggctcat      60
ttgtgaacat acatttaagg ggaagcg                                         87

<210> SEQ ID NO 641
<211> LENGTH: 119
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Affymetrix ID 3862191

<400> SEQUENCE: 641
gggatgtagt atggaaacca ggcttcttgg ggcaaaggca cctggatcct catgggatga      60
gggcagtcag ggtgggtgtt tagtctgcaa gcggaggtgc taaatgtctg tgtcttgca     119

<210> SEQ ID NO 642
<211> LENGTH: 64
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:

<223> OTHER INFORMATION: Affymetrix ID 2997556

<400> SEQUENCE: 642
cagactggct gcagcgagtt ggattcgtgc agaacatctg ctgccagacc cataatcaac    60
tgca    64

<210> SEQ ID NO 643
<211> LENGTH: 142
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Affymetrix ID 3787882

<400> SEQUENCE: 643
gcccatggag gaaagttact gctgaggacc cacccaatgg aaggattctt ctcagccttg    60
accctggagc actgggaaca actggtctcc tgtgatggct gggactcctc gcgggagggg   120
actgcgctgc tatagctctt gc    142

<210> SEQ ID NO 644
<211> LENGTH: 243
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Affymetrix ID 2483130

<400> SEQUENCE: 644
ttccgccgga tgacaaagtt atttcggcca gtctgcattt cagggcctgc gactgcagca    60
gcactggcca caaaaccacc cccgggcaac actccactgg ttgccatgct gctggcagct   120
acaaccccgg tggttgcccc tgaggttcct tctgctggtt gtgtttcctg ctgaggctgt   180
tcattattga caataatctg ggctgttttc ggaaggcaga ggtatcctcc atagtggttg   240
aca    243

<210> SEQ ID NO 645
<211> LENGTH: 46
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Affymetrix ID 3811426

<400> SEQUENCE: 645
atgagcagcg gctttcccctt tggcagtctg cgagccaaga cttctg    46

<210> SEQ ID NO 646
<211> LENGTH: 185
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Affymetrix ID 3787871

<400> SEQUENCE: 646
cccatgtttg aaggggccga catccacaag aggctctctc cggacgatgc agattttgtg    60

```
gatgtcctcc acacctacac gcgttccttc ggcttgagca ttggtattca gatgcctgtg    120
ggccacattg acatctaccc caatgggggt gacttccagc caggctgtgg actcaacgat    180
gtctt                                                                185

<210> SEQ ID NO 647
<211> LENGTH: 341
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Affymetrix ID 2660997

<400> SEQUENCE: 647
acactcaggg tggattcatg atgccaaagg ataacagaca atggaaagca ttttacaact    60
gttcacagta ccagcaagtc aagcacgtca cctaacaaag gggctacatc acaagctcaa    120
aacttccgat aactttacat tcccctaagg tgagagggtg tatttaaata acatcaatcc    180
aaccaaagcc ttgctccaac ttccacatca actattttcc ttgggcgaaa cagagtattg    240
cattgcatta agtgtattta caaccaactg tctgtgtaaa tataagagat gctaacatac    300
tagtaacaga acgaaattag ccttgctgat tttgccctgc c                        341

<210> SEQ ID NO 648
<211> LENGTH: 215
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Affymetrix ID 3787872

<400> SEQUENCE: 648
atgagcgagc cgtccaccct ctttgttgact ctctggtgaa tcaggacaag ccgagttttg   60
ccttccagtg cactgactcc aatcgcttca aaaaggggat ctgtctgagc tgccgcaaga   120
accgttgtaa tagcattggc tacaatgcca agaaaatgag gaacaagagg aacagcaaaa   180
tgtacctaaa aacccgggca ggcatgcctt tcaga                              215

<210> SEQ ID NO 649
<211> LENGTH: 118
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Affymetrix ID 2763609

<400> SEQUENCE: 649
cttgatcttt ctgaactaga tgtgaacgac ttggatacag acagctttct gggtggactc   60
aagtggtgca gtgaccaatc agaaataata tccaatcagt acaacaatga gccttcaa     118

<210> SEQ ID NO 650
<211> LENGTH: 251
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
```

<223> OTHER INFORMATION: Affymetrix ID 2980500

<400> SEQUENCE: 650

```
agtcctctac tcgagtcttc ctgggcctga tcacttttgc atacaccaca aagcttagac      60
tgctcagagc tagttttctt ctcacattat atagcactga gttcatacat ttgcccttag     120
gtgaaaatag ctttgtttct taacactttt cttcctagcc aacctggttc ctccctcctc     180
ccctttctac cccacaaata acggaaattt gactgtggcc aaatctcttt cctcgttgct     240
gtgcctcttt t                                                          251
```

<210> SEQ ID NO 651
<211> LENGTH: 122
<212> TYPE: DNA
<213> ORGANISM: Artificial Sequence
<220> FEATURE:
<223> OTHER INFORMATION: Description of Artificial Sequence: Synthetic
    polynucleotide
<220> FEATURE:
<223> OTHER INFORMATION: Affymetrix ID 2586129

<400> SEQUENCE: 651

```
tctgtgtact ggactgaccg tgctactcgt cgggttatgc gagccaacaa gtggcatgga      60
gggaaccagt cagttgtaat gtataatatt caatggcccc ttgggattgt tgcggttcat     120
cc                                                                    122
```

<210> SEQ ID NO 652
<211> LENGTH: 109
<212> TYPE: DNA
<213> ORGANISM: Artificial Sequence
<220> FEATURE:
<223> OTHER INFORMATION: Description of Artificial Sequence: Synthetic
    polynucleotide
<220> FEATURE:
<223> OTHER INFORMATION: Affymetrix ID 4023341

<400> SEQUENCE: 652

```
gggaggcaag gtcaaactaa gaatagaagc tcaagtacta tcacctgtcc taagcataaa      60
tctaaaaaac tttccacttt ccgactagcc ataagtacat ggtcccatc                 109
```

<210> SEQ ID NO 653
<211> LENGTH: 942
<212> TYPE: DNA
<213> ORGANISM: Artificial Sequence
<220> FEATURE:
<223> OTHER INFORMATION: Description of Artificial Sequence: Synthetic
    polynucleotide
<220> FEATURE:
<223> OTHER INFORMATION: Affymetrix ID 2897466

<400> SEQUENCE: 653

```
accatggtcc ctagtagtca gttgaagtgg caatgtctaa acagaaatga acaaaactaa      60
tgctagcagg ttaaaatcaa tcaaaatgtt taaaaattga ttctgtcctc agcatgttat     120
ttcctcagct ctgataattt actggtcttg agtattttga gaatttgatg ttgaacgtta     180
taaagtcaaa gaactgcttg tttagatgag gtttattttt attttgata ttattcattc      240 ttgtcacaca tcaagaagaa aacactagag tgctgctgga attccaaatc tgaagaattc     300
taacgactgc attctttgtt attaaaaagg gcacaatcct tcctttttat ttggcagttt     360
aatttcagta ggaagcatgt cacatgtgca ctgttggtta gaattatgca tctgtcatgc     420
ctgactgctg aaccctacct aagccttttg gcgcagttta aaacttatac tggtggactg     480
```

```
tgaacctcaa acaaatgggg tattttttggg ttttgaggat agatgttact ccttaaagtt      540
tgtatttggg gcatgaaaaa ctactgaaag aagaaaagtg ctacagatac tacatttcaa      600
agagttggca ttttcccttt ggccactcaa gcagcatttg atgtatctaa agaaacaaag      660
tcattgttta ttttttaaaa aattatatgc agttgtacaa gatactacat tccattgaaa      720
tgttggctat gtcctaacca ggcaaccaga taacaaaaac attttgagtc ttttatctag      780
gtagttctaa ttattcagct acttagttta acaaaggaaa atatcctgac ttctctcatt      840
tcatttgtag acttttcatt gtataggcac aaccaaagag tcagactggt ttaaaactcc      900
agaaggaaaa aaagtatccc acacagtgga tgttgtttct aa                        942

<210> SEQ ID NO 654
<211> LENGTH: 294
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Affymetrix ID 3791755

<400> SEQUENCE: 654
tttctcacag atacggacaa gctcaagaat cccactgtca ctggatgtat tcattaagaa       60
ggaatctggc agcagcacag gggacagata ctttggagaa caggccaatt atctgggtgt      120
cctttataat ttgaagtttc tgaattcact catagataag ctgcttgaag agggcctggc      180
aatgggaaca taatgcacag atggccactg aagaaacaag agggaggaag ggaggctgga      240
agagagaaga gaatttgctt gtggtttcat tcatggggac aaatctacaa gctg            294

<210> SEQ ID NO 655
<211> LENGTH: 189
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Affymetrix ID 3811429

<400> SEQUENCE: 655
ttgtacggaa tacttaaagg gcatcaccca tgactaaacc agtgctttta aaatatggag       60
aatatgggga aatttaatat gagttgggat acttgactct ttttttaaaac ctctctacct    120 gtttggcaca acagggtatt gataaagagt gggctcattg ttatggcaaa ggattcactt     180
gcatctctg                                                             189

<210> SEQ ID NO 656
<211> LENGTH: 176
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Affymetrix ID 2649081

<400> SEQUENCE: 656
acagggataa gtcagcgaaa agatgatata ttgaaaattc atgaaggcca acgagaagtt       60
agcctctatc gccctgaaaa tttaaaccaa ccccccaaaa gaccctccta atctattaat      120
tcctctgctt gggagtccca aggaagtgaa agagaatccc ttagagctct gataca         176
```

-continued

```
<210> SEQ ID NO 657
<211> LENGTH: 31
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Affymetrix ID 2830194

<400> SEQUENCE: 657
atgaactccc tcgtggcggc cgaaggcctg g                              31

<210> SEQ ID NO 658
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Affymetrix ID 2830301

<400> SEQUENCE: 658
ttatttcgtg tgtgtctctt ggctctgtag                                30

<210> SEQ ID NO 659
<211> LENGTH: 97
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Affymetrix ID 2830378

<400> SEQUENCE: 659
tgcttgcacc cacagtccat agacatccaa ccgcccaatg catatccaac ctcagcaact  60
ttacaatccc caacgccagc ccacaacttg actttta                          97
```

SYSTEMS AND METHODS FOR EXPRESSION-BASED CLASSIFICATION OF THYROID TISSUE

CROSS-REFERENCE TO RELATED APPLICATIONS

This application is a continuation application of U.S. patent application Ser. No. 13/258,429, filed Sep. 21, 2011, which is a National Stage Entry of International Application No. PCT/CA2010/000621, filed Apr. 29, 2010, which claims the benefit of U.S. Provisional Patent Application No. 61/173,738, filed Apr. 29, 2009, each of which is entirely incorporated herein by reference.

SEQUENCE LISTING

The instant application contains a Sequence Listing which has been submitted in ASCII format via EFS-Web and is hereby incorporated by reference in its entirety. Said ASCII copy, created on Nov. 23, 2015, is named 14926349.txt and is 333,785 bytes in size.

FIELD OF THE INVENTION

This invention relates to the field of diagnostics and in particular to systems and methods for diagnosis of thyroid cancer.

BACKGROUND

Thyroid nodule disease is a common clinical problem, found in 4-7% of the living adult population in North America. The occurrence of thyroid nodules increases with age; autopsies reveal the presence of thyroid nodules in 50% of the population. It is estimated that, at 80 years old, 90% of the population will have at least one thyroid nodule. However, the vast majority of solitary thyroid nodules are benign in nature, and would require no further treatment if a correct diagnosis could be obtained without surgery.

A number of techniques can be used to diagnose thyroid conditions, including radioactive thyroid scans, ultrasound, thyroid hormone level and thyroglobulin measurements, and fine needle aspiration biopsy (FNAB). Thyroid scans do not effectively distinguish benign and malignant conditions, however, and are typically used in conjunction with other techniques. Similarly, ultrasound may provide information suggestive of either benign or malignant conditions, but cannot definitively diagnose thyroid status. Measurements of thyroid hormone level and thyroglobulin can be informative, but are nondiagnostic by themselves.

Thyroid FNAB is the only non-surgical method which can by itself differentiate malignant and benign nodules. More than 300,000 fine needle aspiration biopsies (FNAB) of the thyroid are performed annually in the US and evaluated using cytology. The primary purpose of FNAB is to distinguish thyroid nodules that require immediate surgical intervention (e.g., total thyroidectomy in the case of a diagnosis of malignant disease) from nodules that can be treated effectively with less aggressive clinical approaches.

In FNAB, samples of thyroid cells are obtained by inserting a needle into the thyroid and aspirating cells into a syringe. Usually, 2 to 4 aspirations are made from different sites in each nodule. The cells are mounted on a slide (for each aspiration, 2 to 4 slides are prepared), stained, and examined. The sample is then classified as nondiagnostic (indeterminate), benign, suspicious or malignant. Most samples are categorized as benign.

FNAB can be used to successfully diagnose papillary carcinoma, medullary carcinoma, anaplastic carcinoma, thyroid lymphoma and metastases to the thyroid from other sites. Papillary carcinoma accounts for ~60-70% and the follicular variant of papillary carcinoma accounts for ~6% of thyroid cancers. These well differentiated thyroid cancers are usually curable, but they must be found first.

Especially problematic are cases considered 'suspicious', 'inadequate' or 'indeterminate' by cytological diagnosis of FNAB samples. These patients are invariably triaged by invasive surgery, which has a significant morbidity. Overtreatment with total-thyroidectomy frequently occurs as a result; it is estimated that less than 25% of patients with such diagnoses in fact have cancer that warrants removal of the thyroid gland. Approximately 5-10% of samples are classified as nondiagnostic by FNAB. In those cases, FNAB can be repeated; however, only half of repeat biopsies yield a diagnostic result. For the remaining patients, further testing and surgery may be required. Due to the fear of cancer, invasive surgery is chosen, but in most cases is unnecessary. Approximately 10-20% of samples are classified as suspicious by FNAB. Of these, approximately 25% will ultimately prove to be malignant after surgery, typically exhibiting follicular or Hurthle cell cancers, which cannot be diagnosed by FNAB. Follicular carcinoma, which accounts for ~12-15% of all thyroid cancers and the less prevalent Hurthle cell carcinoma cannot be distinguished cytologically from benign follicular or Hurthle cell adenomas. Therefore, most patients with suspicious biopsies are typically subjected to surgery, when in fact ~75% of these patients do not have malignant disease.

A contributing factor to the difficulties with current FNAB cytology-based diagnoses is the variability between different pathologists and cytopathologists in diagnostic agreement between cytological analysis and final histological review, ranging from 40%-90%. The overall accuracy of diagnoses using only FNAB ranges from 60% to >90%, and is dependent on the expertise of the cytologist and whether or not 'suspicious' or 'indeterminate' diagnostic categories are included in the reported accuracy of the study (see http://www.endocrineweb.com/noduleus.html). When factoring the cytology diagnostic categories of 'suspicious' or 'indeterminate', the literature shows that the overall specificity of FNAB cytology for diagnosis of malignant disease decreases dramatically to <60% with false-positive rates of ~40%. Patients with malignant thyroid disease are invariably treated by total removal of the tumor and all of the thyroid gland followed by radioactive iodine treatment, whereas benign thyroid disease can be treated less aggressively with a near-total thyroidectomy, partial thyroidectomy (e.g., 'lobectomy') or a watchful-waiting approach (e.g., observation without surgical intervention). As FNAB and cytology cannot reliably distinguish malignant from benign disease in cases with 'suspicious' cytological findings, such as occurs in the case of follicular and Hurthle cell lesions, these patients are typically all treated as if they were diagnosed with malignant disease (i.e., with aggressive surgery). Since only a small fraction of these patients in fact have malignant disease, over-treatment of thyroid nodule disease patients occurs frequently, with significant consequences for patients. As such, many unnecessary thyroidectomies are therefore performed in patients with what ultimately proves to be benign or non-neoplastic thyroid nodule disease when an FNAB sample is deemed as 'suspicious' or 'indeterminate.' These deficiencies negatively impact patient outcomes, long-term well-being and healthcare efficiencies.

Use of molecular analyses has the potential to increase the sensitivity, specificity and/or overall accuracy of thyroid diagnoses as compared to FNAB cytology alone. Such a result would reduce the number of unnecessary surgeries for patients without malignant disease and avoid inadvertent undertreatment of highly curable thyroid cancers resulting from misdiagnoses. However, prior attempts at using gene expression profiling to develop diagnostic gene expression signatures and identify mRNA biomarkers useful for the differential diagnosis of thyroid nodule disease have not yet yielded new clinical tools to improve the diagnosis of malignant from benign thyroid nodule disease from clinical specimens. Most of these efforts and those of protein immunohistochemistry studies focused on the protein-encoding genome. However, the transcriptome is inherently more complex than this, given that <2% of the genome encodes for protein and recent studies that have shown that more than 90% of the genome undergoes transcription yielding millions of non-coding RNA transcripts that serve regulatory roles over the protein-encoding transcriptome. So, gene-level analysis may provide only a rough estimate of diagnosis as it cannot capture the full differences between the genomes of malignant and benign thyroid nodule disease (e.g., alternative gene splicing, non-coding and functional RNA expression). Recent efforts to validate a 3-gene signature for diagnosis of thyroid nodule disease FNAB with a QRT-PCR approach report a low diagnostic accuracy in a large validation study (see Sibru et al., citation #14). Other prior attempts using gene-biased microarrays showed similar performance characteristics with low diagnostic accuracy for gene-based signatures (see Jiang et al., US 2007/0037186 A1). For example, Jiang et al., (US 2007/0037186 A1) disclosed a 4-gene QRT-PCR panel with a sensitivity of 92% but a specificity of just 61%. In addition, since these signatures were developed and validated from fresh or fresh frozen tissue specimens their applicability to more routine tissues specimens commonly available in the clinic such as formalin-fixed paraffin embedded fine-needle aspirate cell blocks and surgical resections is not assured because of the impact of sample processing on nucleic acid integrity. As a result, diagnoses using these provide results little better than currently available FNAB cytology in widespread clinical use.

This background information is provided for the purpose of making known information believed by the applicant to be of possible relevance to the present invention. No admission is necessarily intended, nor should be construed, that any of the preceding information constitutes prior art against the present invention.

SUMMARY OF THE INVENTION

An object of the present invention is to provide systems and methods for expression-based classification of thyroid tissue. In accordance with one aspect of the present invention, there is provided a system for expression-based classification of thyroid tissue as malignant or benign, said system comprising one or more polynucleotides, each of said polynucleotides capable of specifically hybridizing to a RNA transcript of a gene selected from the group of genes set forth in Table 1.

In accordance with another aspect of the present invention, there is provided a system for expression-based classification of thyroid tissue as malignant or benign, said system comprising a set of polynucleotides for detecting a set of target sequences selected from the group consisting of SEQ ID NOs: 1-7; SEQ ID NOs: 1-12 and 283-306; and SEQ ID NOs: 261, 657, 658, and 659.

In accordance with another aspect of the present invention, there is provided a nucleic acid array for expression-based classification of thyroid tissue as malignant or benign, said array comprising at least ten probes immobilized on a solid support, each of said probes being between about 15 and about 500 nucleotides in length, each of said probes being derived from a sequence corresponding to, or complementary to, a transcript of a gene selected from the group of genes set forth in Table 1, or a portion of said transcript.

In accordance with another aspect of the present invention, there is provided a method of classifying a thyroid nodule in a subject as malignant or benign, said method comprising: (a) determining the expression level of one or more transcripts of one or more genes in a test sample obtained from said subject to provide an expression pattern profile, said one or more genes selected from the group of genes set forth in Table 1, and (c) comparing said expression pattern profile with a reference expression pattern profile.

In accordance with another aspect of the present invention, there is provided a kit for characterizing the expression of one or more nucleic acid sequences depicted in SEQ ID NOs: 1-659 comprising one or more nucleic acids selected from:
(a) a nucleic acid depicted in any of SEQ ID NOs: 1-659;
(b) an RNA form of any of the nucleic acids depicted in SEQ ID NOs: 1-659;
(c) a peptide nucleic acid form of any of the nucleic acids depicted in SEQ ID NOs: 1-659;
(d) a nucleic acid comprising at least 20 consecutive bases of any of (a-c);
(e) a nucleic acid comprising at least 25 consecutive bases having at least 90% sequence identity to any of (a-c); or
(f) a complement to any of (a-e); and
optionally instructions for correlating the expression level of said one or more nucleic acid sequences with the disease state of thyroid tissue.

In accordance with another aspect of the present invention, there is provided an array of probe nucleic acids certified for use in classifying thyroid disease status, wherein said array comprises at least two different probe nucleic acids that specifically hybridize to corresponding different target nucleic acids depicted in one of SEQ ID NOs: 1-659, an RNA form thereof, or a complement to either thereof.

In accordance with another aspect of the present invention, there is provided a device for classifying a biological sample from a thyroid gland as malignant or benign, the device comprising means for measuring the expression level of one or more transcripts of one or more genes selected from the group of genes set forth in Table 1; means for correlating the expression level with a classification of thyroid disease status; and means for outputting the thyroid disease status.

In accordance with another aspect of the present invention, there is provided a computer-readable medium comprising one or more digitally-encoded expression pattern profiles representative of the level of expression of one or more transcripts of one or more genes selected from the group of genes set forth in Table 1, each of said one or more expression pattern profiles being associated with a value wherein each of said values is correlated with the presence of malignant or benign tissue in a thyroid gland sample.

BRIEF DESCRIPTION OF THE DRAWINGS

These and other features of the invention will become more apparent in the following detailed description in which reference is made to the appended drawings.

DETAILED DESCRIPTION OF THE INVENTION

Figure 1:
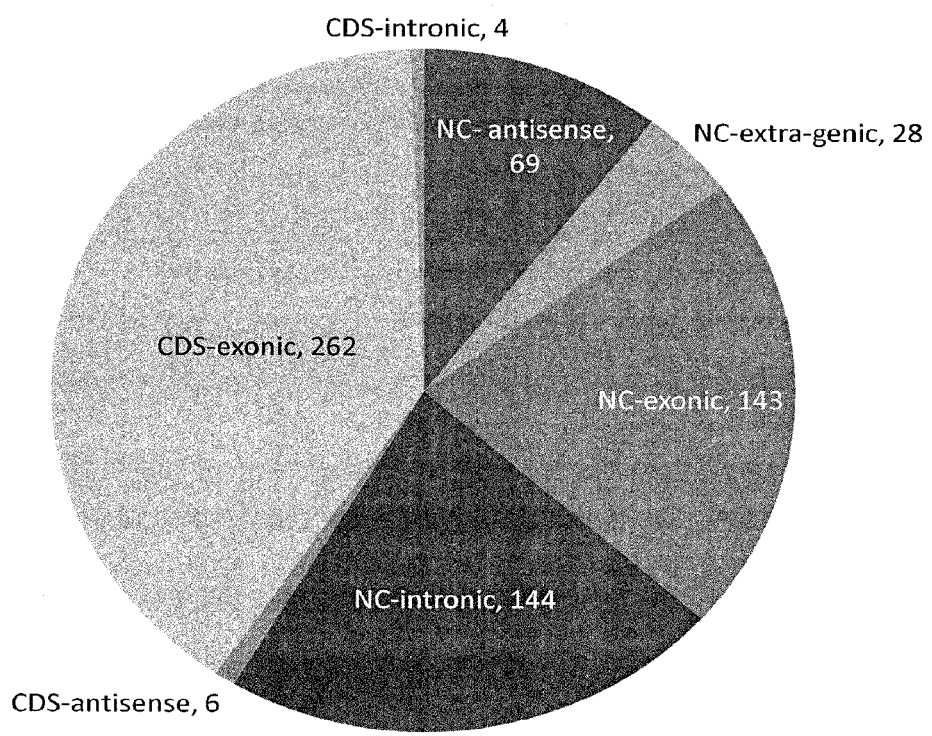
FIG. 1 is a pie chart that depicts the annotations of the 656 selected RNAs from genes previously described in the literature that were identified as differentially expressed in the training subset. Note that more than 60% correspond to non-canonical expressed transcripts (i.e., intronic, antisense and extra-genic) while only a small portion are actually from exonic sequences of protein-encoding genes. The labels in the pie chart indicate the position of the differentially expressed probes relative to the nearest annotated gene. CDS-RNA overlaps with the coding sequence translations of mRNAs in RefSeq or GenBank databases, NC-'non-coding' RNA does not overlap with the CDS.

The present invention provides a system and methods for classifying thyroid tissue from a subject as malignant or benign, which allows for the diagnosis of thyroid cancer in the subject. The system and methods are based on the identification of gene transcripts that are differentially expressed in thyroid cancer relative to benign thyroid nodule disease. These gene transcripts can be considered as a library which can be used as a resource for the identification of sets of specific target sequences ("thyroid classification sets"), which may represent the entire library of gene transcripts or a subset of the library and the detection of which is indicative of the status of the thyroid tissue (for example, malignant or benign). The invention further provides for probes capable of detecting these target sequences and primers that are capable of amplifying the target sequences.

In accordance with one embodiment of the invention, the target sequences comprised by the thyroid classification set are sequences based on or derived from the gene transcripts from the library, or a subset thereof. Such sequences are occasionally referred to herein as "probe selection regions" or "PSRs." In another embodiment of the invention, the target sequences comprised by the thyroid classification set are sequences based on the gene transcripts from the library, or a subset thereof, and include both coding and non-coding sequences.

In one embodiment, the systems and methods provide for the molecular analysis of the expression levels of one or more of the target sequences as set forth in SEQ ID NOs: 1-659 (Table 3). Increased relative expression of one or more target sequences in Group I corresponding to the sequences as set forth in SEQ ID NOs: 1-4, and 8-282, and/or decreased relative expression of one or more target sequences in Group II corresponding to the sequences as set forth in SEQ ID NOs: 5-7, and 283-659, can be correlated with increased likelihood of malignant thyroid nodule disease. Conversely, increased relative expression of one or more target sequences in Group II and/or decreased relative expression of one or more target sequences in Group I can be correlated with an increased likelihood of benign thyroid nodule disease. Subsets and combinations of these target sequences or probes complementary thereto may be used as described herein.

Before the present invention is described in further detail, it is to be understood that this invention is not limited to the particular methodology, compositions, articles or machines described, as such methods, compositions, articles or machines can, of course, vary. It is also to be understood that the terminology used herein is for the purpose of describing particular embodiments only, and is not intended to limit the scope of the present invention.

Definitions

Unless defined otherwise or the context clearly dictates otherwise, all technical and scientific terms used herein have the same meaning as commonly understood by one of ordinary skill in the art to which this invention belongs. In describing the present invention, the following terms will be employed, and are intended to be defined as indicated below.

The term "polynucleotide" as used herein refers to a polymer of greater than one nucleotide in length of ribonucleic acid (RNA), deoxyribonucleic acid (DNA), hybrid RNA/DNA, modified RNA or DNA, or RNA or DNA mimetics, including peptide nucleic acids (PNAs). The polynucleotides may be single- or double-stranded. The term includes polynucleotides composed of naturally-occurring nucleobases, sugars and covalent internucleoside (backbone) linkages as well as polynucleotides having non-naturally-occurring portions which function similarly. Such modified or substituted polynucleotides are well-known in the art and for the purposes of the present invention, are referred to as "analogues."

"Complementary" or "substantially complementary" refers to the ability to hybridize or base pair between nucleotides or nucleic acids, such as, for instance, between a sensor peptide nucleic acid or polynucleotide and a target polynucleotide. Complementary nucleotides are, generally, A and T (or A and U), or C and G. Two single-stranded polynucleotides or PNAs are said to be substantially complementary when the bases of one strand, optimally aligned and compared and with appropriate insertions or deletions, pair with at least about 80% of the bases of the other strand, usually at least about 90% to 95%, and more preferably from about 98 to 100%.

Alternatively, substantial complementarity exists when a polynucleotide will hybridize under selective hybridization conditions to its complement. Typically, selective hybridization will occur when there is at least about 65% complementarity over a stretch of at least 14 to 25 bases, for example at least about 75%, or at least about 90% complementarity. See, M. Kanehisa Nucleic Acids Res. 12:203 (1984).

"Preferential binding" or "preferential hybridization" refers to the increased propensity of one polynucleotide to bind to its complement in a sample as compared to a noncomplementary polymer in the sample.

Hybridization conditions will typically include salt concentrations of less than about 1M, more usually less than about 500 mM, for example less than about 200 mM. In the case of hybridization between a peptide nucleic acid and a polynucleotide, the hybridization can be done in solutions containing little or no salt. Hybridization temperatures can be as low as 5° C., but are typically greater than 22° C., and more typically greater than about 30° C., for example in excess of about 37° C. Longer fragments may require higher hybridization temperatures for specific hybridization as is known in the art. Other factors may affect the stringency of hybridization, including base composition and length of the complementary strands, presence of organic solvents and extent of base mismatching, and the combination of parameters used is more important than the absolute measure of any one alone. Other hybridization conditions which may be controlled include buffer type and concentration, solution pH, presence and concentration of blocking reagents to decrease background binding such as repeat sequences or blocking protein solutions, detergent type(s) and concentrations, molecules such as polymers which increase the relative concentration of the polynucleotides, metal ion(s) and their concentration(s), chelator(s) and their concentrations, and other conditions known in the art.

"Multiplexing" herein refers to an assay or other analytical method in which multiple analytes can be assayed simultaneously.

A "target sequence" as used herein (also occasionally referred to as a "PSR" or "probe selection region") refers to a region of the genome against which one or more probes can be designed. As used herein, a probe is any polynucleotide capable of selectively hybridizing to a target sequence or its complement, or to an RNA version of either. A probe may comprise ribonucleotides, deoxyribonucleotides, peptide nucleic acids, and combinations thereof. A probe may optionally comprise one or more labels. In some embodiments, a probe may be used to amplify one or both strands of a target sequence or an RNA form thereof, acting as a sole primer in an amplification reaction or as a member of a set of primers.

"Having" is an open ended phrase like "comprising" and "including," and includes circumstances where additional elements are included and circumstances where they are not.

"Optional" or "optionally" means that the subsequently described event or circumstance may or may not occur, and that the description includes instances where the event or circumstance occurs and instances in which it does not.

The term "suspected of comprising thyroid cancer," as used in reference to biological samples or purified fractions or components thereof or products derived therefrom, refers to any sample or product that is to analyzed for the expression of the target sequences described herein, and includes samples comprising normal thyroid tissue, as well as samples comprising thyroid tumors, whether benign or malignant. Such tissue may be obtained from the thyroid itself, from another location within a patient that is a suspected metastases, or from a known sample of malignant thyroid cancer or from a known thyroid cancer cell line. Samples known to be malignant can function as positive controls, while samples known to be noncancerous (or of nonthyroid origin) can function as negative controls, but are "suspected" of comprising thyroid cancer in that they are tested to determine whether the assay being performed produces false positives or other abnormal results, indicating a problem with a given assay.

As used herein, the term "about" refers to approximately a +/−10% variation from a given value. It is to be understood that such a variation is always included in any given value provided herein, whether or not it is specifically referred to.

Use of the singular forms "a," "an," and "the" include plural references unless the context clearly dictates otherwise. Thus, for example, reference to "a polynucleotide" includes a plurality of polynucleotides, reference to "a target" includes a plurality of such targets, reference to "a normalization method" includes a plurality of such methods, and the like. Additionally, use of specific plural references, such as "two," "three," etc., read on larger numbers of the same subject, unless the context clearly dictates otherwise.

Terms such as "connected," "attached," "linked" and "conjugated" are used interchangeably herein and encompass direct as well as indirect connection, attachment, linkage or conjugation unless the context clearly dictates otherwise.

Where a range of values is recited, it is to be understood that each intervening integer value, and each fraction thereof, between the recited upper and lower limits of that range is also specifically disclosed, along with each subrange between such values. The upper and lower limits of any range can independently be included in or excluded from the range, and each range where either, neither or both limits are included is also encompassed within the invention. Where a value being discussed has inherent limits, for example where a component can be present at a concentration of from 0 to 100%, or where the pH of an aqueous solution can range from 1 to 14, those inherent limits are specifically disclosed. Where a value is explicitly recited, it is to be understood that values which are about the same quantity or amount as the recited value are also within the scope of the invention, as are ranges based thereon. Where a combination is disclosed, each subcombination of the elements of that combination is also specifically disclosed and is within the scope of the invention. Conversely, where different elements or groups of elements are disclosed, combinations thereof are also disclosed. Where any element of an invention is disclosed as having a plurality of alternatives, examples of that invention in which each alternative is excluded singly or in any combination with the other alternatives are also hereby disclosed; more than one element of an invention can have such exclusions, and all combinations of elements having such exclusions are hereby disclosed.

Thyroid Classification System

The system of the present invention is based on the identification of a library of gene transcripts that are differentially expressed in thyroid cancer relative to benign thyroid nodule disease and thus may be diagnostic for thyroid cancer. For example, relative over and/or under expression of one or more of the gene transcripts in a thyroid nodule sample compared to a reference sample or expression profile or signature there from may be indicative of a malignant condition. The reference sample can be, for example, from one or more benign thyroid nodules from one or more references subject(s). The reference expression profile or signature may optionally be normalized to one or more appropriate reference gene transcripts. Alternatively or in addition to, expression of one or more of the gene transcripts in a thyroid nodule sample may be compared to an expression profile or signature from one or more known thyroid cancer samples such that a substantially similar expression profile or signature may be used to validate a finding of cancer or may be compared to the expression profile or signature from normal thyroid tissue.

Expression profiles or signatures from diagnostic samples may be normalized to one or more house keeping gene transcripts such that normalized over and/or under expression of one or more of the gene transcripts in a thyroid nodule sample may be indicative of a malignant condition.

Thyroid Classification Library

The Thyroid Classification Library in accordance with the present invention comprises one or more gene transcripts whose relative and/or normalized expression is indicative of a thyroid malignancy or of benign thyroid nodule disease. Exemplary genes from which a transcribed RNA or encoded protein shows differential expression in benign and/or malignant thyroid tissue are shown in Table 1. A single gene may give rise to more than one gene transcript. Not all transcripts of a given gene are necessarily indicative of a thyroid malignancy or of benign thyroid nodule disease. A single gene may also give rise to two or more transcripts, where at least one of the two or more transcripts is indicative of a thyroid malignancy while at least one different transcript is indicative of benign thyroid disease. In one embodiment, the library comprises one or more of the gene transcripts of the genes shown in Table 1.

In one embodiment, the library comprises at least one transcript from at least one gene selected from those listed in Table 1. In one embodiment, the library comprises at least one transcript from each of at least 5 genes selected from those listed in Table 1. In another embodiment, the library comprises at least one transcript from each of at least 10 genes selected from those listed in Table 1. In a further embodiment, the library comprises at least one transcript from each of at least 15 genes selected from those listed in Table 1. In other embodiments, the library comprises at least one transcript from each of at least 20, at least 25, at least 30, at least 35, at least 40, at least 45, at least 50, at least 55, at least 60 and at least 65 genes selected from those listed in Table 1. In a further embodiment, the library comprises at least one transcript from all of the genes listed in Table 1. In a further embodiment, the library comprises at all transcripts from all of the genes listed in Table 1.

In one embodiment, the library comprises at least one transcript from at least one gene selected from the group consisting of ABCA8 (ATP-binding cassette, sub-family A (ABC1), member 8); ADORA1 (Adenosine A1 receptor); ALOX5 (Arachidonate 5-lipoxygenase); AMIGO2 (Adhesion molecule with Ig-like domain 2); ANK2 (Ankyrin 2, neuronal); APOE (Apolipoprotein E); ARG2 (Arginase, type II); ARHGAP11A (Rho GTPase activating protein 11A); ARMCX3 (Armadillo repeat containing, X-linked 3); BCL2 (B-cell CLL/lymphoma 2); BEX1 (Brain expressed, X-linked 1); BMP8A (Bone morphogenetic protein 8a); C1orf212 (Chromosome 1 open reading frame 212); C7orf24 (Chromosome 7 open reading frame 24); CA4 (Carbonic anhydrase IV); CAMK2N1 (Calcium/calmodulin-dependent protein kinase II inhibitor 1); CCL14 (Chemokine (C—C motif) ligand 14); CCL21 (Chemokine (C—C motif) ligand 21); CCND1 (Cyclin D1); CD44 (CD44 molecule (Indian blood group)): CD55 (CD55 molecule, decay accelerating factor for complement (Cromer blood group)); CDH16 (Cadherin 16, KSP-cadherin); CDH3 (Cadherin 3, type 1, P-cadherin (placental)); CDKN2A (Cyclin-dependent kinase inhibitor 2A (melanoma, p16, inhibits CDK4)); CFD (Complement factor D (adipsin)); ChGn (Chondroitin beta1,4 N-acetylgalactosaminyltransferase); CHI3L1 (Chitinase 3-like 1 (cartilage glycoprotein-39)); CHRDL1 (Chordin-like 1); CHST2 (Carbohydrate (N-acetylglucosamine-6-O) sulfotransferase 2); CITED1 (Cbp/p300-interacting transactivator, with Glu/Asp-rich carboxy-terminal domain, 1); CKS2 (CDC28 protein kinase regulatory subunit 2): COL9A3 (Collagen, type IX, alpha 3): CRABP1 (Cellular retinoic acid binding protein 1); CSNK1 G2 (Casein kinase 1, gamma 2); CST6 (Cystatin E/M); CTSC (Cathepsin C); CTSH (Cathepsin H); CTSS (Cathepsin S); DDIT3 (DNA-damage-inducible transcript 3); DIO1 (Deiodinase, iodothyronine, type I): DIO2 (Deiodinase, iodothyronine, type II): DLG7 (Discs, large homolog 7 (Drosophila)); DPP4 (Dipeptidyl-peptidase 4 (CD26, adenosine deaminase complexing protein 2)); DUSP5 (Dual specificity phosphatase 5); DUSP6 (Dual specificity phosphatase 6); EFEMP1 (EGF-containing fibulin-like extracellular matrix protein 1); ELMO1 (Engulfment and cell motility 1); ENDOD1 (Endonuclease domain containing 1); ENPP1 (Ectonucleotide pyrophosphatase/phosphodiesterase 1); EPS8 (Epidermal growth factor receptor pathway substrate 8); ETHE1 (Ethylmalonic encephalopathy 1); ETV5 (Ets variant gene 5 (ets-related molecule)); FABP4 (Fatty acid binding protein 4, adipocyte); FAM129A (Family with sequence similarity 129, member A); FAM129B (Family with sequence similarity 129, member B); FAM129C (Family with sequence similarity 129, member C); FBLN1 (Fibulin 1); FCGBP (Fc fragment of IgG binding protein); FHL1 (Four and a half LIM domains 1); FN1 (Fibronectin 1); FZD4 (Frizzled homolog 4 (Drosophila)); GABBR2 (Gamma-aminobutyric acid (GABA) B receptor, 2); GALE (UDP-galactose-4-epimerase); GALNT7 (UDP-N-acetyl-alpha-D-galactosamine:polypeptide N-acetylgalactosaminyltransferase 7 (GalNAc-T7)); GDF15 (Growth differentiation factor 15); GJB3 (Gap junction protein, beta 3, 31 kDa); GPM6A (Glycoprotein M6A); HBA2 (Hemoglobin, alpha 2); HBD (Hemoglobin, delta); HLA-DMB (Major histocompatibility complex, class II, DM beta); HLA-DQA1 (Major histocompatibility complex, class II, DQ alpha 1); HLA-DRA (Major histocompatibility complex, class II, DR alpha); HLF (Hepatic leukemia factor); HMGA2 (High mobility group AT-hook 2): ICAM1 (Intercellular adhesion molecule 1 (CD54), human rhinovirus receptor); ICAM4 (Intercellular adhesion molecule 4 (Landsteiner-Wiener blood group)); ID4 (Inhibitor of DNA binding 4, dominant negative helix-loop-helix protein); IGFBP6 (Insulin-like growth factor binding protein 6); IGSF1 (Immunoglobulin superfamily, member 1); ITM2A (Integral membrane protein 2A); ITPR1 (Inositol 1,4,5-triphosphate receptor, type 1); KCNAB1 (Potassium voltage-gated channel, shaker-related subfamily, beta member 1); KCNJ2 (Potassium inwardly-rectifying channel, subfamily J, member 2); KIAA0746 (KIAA0746 protein): KIT (V-kit Hardy-Zuckerman 4 feline sarcoma viral oncogene homolog); KLK10 (Kallikrein-related peptidase 10); KRT15 (Keratin 15); KRT19 (Keratin 19); LAMB3 (Laminin, beta 3); LCN2

(Lipocalin 2); LGALS3 (Lectin, galactoside-binding, soluble, 3); LIPG (Lipase, endothelial); LPL (Lipoprotein lipase): LRP2 (Low density lipoprotein-related protein 2); LRP4 (Low density lipoprotein receptor-related protein 4); MATN2 (Matrilin 2); MET (Met proto-oncogene (hepatocyte growth factor receptor)); MPPED2 (Metallophosphoesterase domain containing 2); MPZL2 (Myelin protein zero-like 2); MPZL3 (Myelin protein zero-like 3); MRC2 (Mannose receptor, C type 2); MT1F (Metallothioncin 1F); MT1G (Metallothionein 1G); MT1H (Metallothionein 1H); MT1M (Metallothionein 1M); MT1X (Metallothionein 1X); MT2A (Metallothionein 2A); MTF1 (Metal-regulatory transcription factor 1); MUC1 (Mucin 1, cell surface associated); MYBPH (Myosin binding protein H); NELL2 (NEL-like 2 (chicken)); NMU (Neuromedin U); NRCAM (Neuronal cell adhesion molecule); NRIP1 (Nuclear receptor interacting protein 1); OPRM1 (Opioid receptor, mu 1); P4HA2 (Procollagen-proline, 2-oxoglutarate 4-dioxygenase (proline 4-hydroxylase), alpha polypeptide II); PDLIM4 (PDZ and LIM domain 4); PDZK1IP1 (PDZK1 interacting protein 1); PIP3-E (Phosphoinositide-binding protein PIP3-E); PLAU (Plasminogen activator, urokinase); PLXNC1 (Plexin C1); PPARGC1A (Peroxisome proliferator-activated receptor gamma, coactivator 1 alpha); PRIM2 (Primase, DNA, polypeptide 2 (58 kDa)); PRMT8 (Protein arginine methyltransferase 8); PROS1 (Protein S (alpha)); PRSS23 (Protease, serine, 23); PSD3 (Pleckstrin and Sec7 domain containing 3); PTPRE (Protein tyrosine phosphatase, receptor type, E); QPCT (Glutaminyl-peptide cyclotransferase (glutaminyl cyclase)); RAB23 (RAB23, member RAS oncogene family); RCN3 (Reticulocalbin 3, EF-hand calcium binding domain); RET (Ret proto-oncogene); RGS16 (Regulator of G-protein signaling 16): RHOBTB3 (Rho-related BTB domain containing 3); RXRG (Retinoid X receptor, gamma); S100A10 (S100 calcium binding protein A10); SCG5 (Secretogranin V (7B2 protein)); SDC4 (Syndecan 4); SERPINA1 (Serpin peptidase inhibitor, clade A (alpha-1 antiproteinase, antitrypsin), member 1); SFTPB (Surfactant, pulmonary-associated protein B); SLC1A1 (Solute carrier family 1 (neuronal/epithelial high affinity glutamate transporter, system Xag), member 1); SLC26A4 (Solute carrier family 26, member 4); SLC27A6 (Solute carrier family 27 (fatty acid transporter), member 6); SLC34A2 (Solute carrier family 34 (sodium phosphate), member 2): SLC5A5 (Solute carrier family 5 (sodium iodide symporter), member 5); SLP1 (Secretory leukocyte peptidase inhibitor); SOD3 (Superoxide dismutase 3, extracellular); SOX4 (SRY (sex determining region Y)-box 4); SPOCK1 (Sparc/osteonectin, cwcv and kazal-like domains proteoglycan (testican) 1); SPP1 (Secreted phosphoprotein 1 (osteopontin, bone sialoprotein I, early T-lymphocyte activation 1)); ST14 (Suppression of tumorigenicity 14 (colon carcinoma)); STT3A (STT3, subunit of the oligosaccharyltransferase complex, homolog A (*S. cerevisiae*)); STT3B (STT3, subunit of the oligosaccharyltransferase complex, homolog B (*S. cerevisiae*)); SYN1 (Synapsin I); TACSTD2 (Tumor-associated calcium signal transducer 2); TCEAL2 (Transcription elongation factor A (SII)-like 2); TFF3 (Trefoil factor 3 (intestinal)); TGFA (Transforming growth factor, alpha); TIAM1 (T-cell lymphoma invasion and metastasis 1); TIMP1 (TIMP metallopeptidase inhibitor 1); TM7SF4 (Transmembrane 7 superfamily member 4); TNC (Tenascin C (hexabrachion)); TPD52L1 (Tumor protein D52-like 1); TPO (Thyroid peroxidase); TRIM14 (Tripartite motif-containing 14); TUSC3 (Tumor suppressor candidate 3); VEGFA (Vascular endothelial growth factor A) and ZMAT4 (Zinc finger, matrin type 4).

In one embodiment, the library comprises at least one transcript from at least one gene selected from the group consisting of HMGA2 (High mobility group AT-hook 2); CDH3 (Cadherin 3, type 1, P-cadherin (placental)); SERPINA1 (Serpin peptidase inhibitor, clade A (alpha-1 antiproteinase, antitrypsin), member 1); IGFBP6 (Insulin-like growth factor binding protein 6); TPO (Thyroid peroxidase); KIT (V-kit Hardy-Zuckerman 4 feline sarcoma viral oncogene homolog) and MPPED2 (Metallophosphoesterase domain containing 2).

In one embodiment, the library comprises at least one transcript from at least one gene selected from the group consisting of HMGA2 (High mobility group AT-hook 2); CDH3 (Cadherin 3, type 1, P-cadherin (placental)); SERPINA1 (Serpin peptidase inhibitor, clade A (alpha-1 antiproteinase, antitrypsin), member 1); IGFBP6 (Insulin-like growth factor binding protein 6); TPO (Thyroid peroxidase); KIT (V-kit Hardy-Zuckerman 4 feline sarcoma viral oncogene homolog), FN1 (fibronectin 1), HLF (Hepatic leukemia factor), MT1F (Metallothionein 1F), MT1G (Metallothionein 1G), PDLIM4 (PDZ and LIM domain 4), PPARGC1A (Peroxisome proliferator-activated receptor gamma, coactivator 1 alpha), SLC26A4 (Solute carrier family 26, member 4), TFF3 (Trefoil factor 3 (intestinal)), TACSTD2 (Tumor-associated calcium signal transducer 2), ZMAT4 (Zinc finger, matrin type 4) and MPPED2 (Metallophosphoesterase domain containing 2).

In one embodiment, the library comprises at least one transcript from Sparc/osteonectin, cwcv and kazal-like domains proteoglycan (testican) 1.

The invention also contemplates that alternative libraries may be designed that include transcripts of one or more of the genes in Table 1, together with additional gene transcripts that are identified as having differential expression in benign and/or malignant thyroid tissue. As is known in the art, the publication and sequence databases can be mined using a variety of search strategies to identify appropriate candidates for inclusion in the library. For example, currently available scientific and medical publication databases such as Medline, Current Contents, OMIM (online Mendelian inheritance in man), various Biological and Chemical Abstracts, Journal indexes, and the like can be searched using term or key-word searches, or by author, title, or other relevant search parameters. Many such databases are publicly available, and strategies and procedures for identifying publications and their contents, for example, genes, other nucleotide sequences, descriptions, indications, expression pattern, etc, are well known to those skilled in the art. Numerous databases are available through the internet for free or by subscription, see, for example, the National Center Biotechnology Information (NCBI), Infotrieve, Thomson ISI, and Science Magazine (published by the AAAS) websites. Additional or alternative publication or citation databases are also available that provide identical or similar types of information, any of which can be employed in the context of the invention. These databases can be searched for publications describing altered gene expression between malignant thyroid nodule disease and benign thyroid nodule disease. Additional potential candidate genes may be identified by searching the above described databases for differentially expressed proteins and by identifying the nucleotide sequence encoding the differentially expressed proteins.

Thyroid Classification Sets

A Thyroid Classification Set comprises one or more target sequences identified within the gene transcripts in the thyroid classification library, or a subset of these gene transcripts. The target sequences may be within the coding and/or non-coding regions of the gene transcripts. The set can comprise one or a plurality of target sequences from each gene transcript in the library, or subset thereof. The relative and/or normalized level of these target sequences in a sample is indicative of the level of expression of the particular gene transcript and thus of a thyroid malignancy or of benign thyroid nodule disease. For example, the relative and/or normalized expression level of one or more of the target sequences may be indicative of a thyroid malignancy while the relative and/or normalized expression level of one or more other target sequences may be indicative of benign thyroid nodule disease.

Accordingly, one embodiment of the present invention provides for a library or catalog of candidate target sequences derived from the transcripts (both coding and non-coding regions) of at least one gene suitable for classifying thyroid nodules as being malignant or benign. In a further embodiment, the library or catalog of candidate target sequences comprises target sequences derived from the transcripts of one or more of the genes set forth in Table 1. The library or catalog in affect provides a resource list of transcripts from which target sequences appropriate for inclusion in a thyroid classification set can be derived. In one embodiment, an individual thyroid classification set may comprise target sequences derived from the transcripts of one or more genes exhibiting a positive correlation with thyroid cancer. In one embodiment, an individual thyroid classification set may comprise target sequences derived from the transcripts of one or more genes exhibiting a negative correlation with thyroid cancer. In one embodiment, an individual Thyroid Classification Set may comprise target sequences derived from the transcripts of from two or more genes, wherein at least one gene has a transcript that exhibits a positive correlation with thyroid cancer and at least one gene has a transcript that exhibits a negative correlation.

In one embodiment, the Thyroid Classification Set comprises target sequences derived from the transcripts of at least one gene. In one embodiment, the Thyroid Classification set comprises target sequences derived from the transcripts of at least 5 genes. In another embodiment, the Thyroid Classification set comprises target sequences derived from the transcripts of at least 10 genes. In a further embodiment, the Thyroid Classification set comprises target sequences derived from the transcripts of at least 15 genes. In other embodiments, the Thyroid Classification set comprises target sequences derived from the transcripts of at least 20, at least 25, at least 30, at least 35, at least 40, at least 45, at least 50, at least 55, at least 60 and at least 65 genes.

Following the identification of candidate gene transcripts, appropriate target sequences can be identified by screening for target sequences that have been annotated to be associated with each specific gene locus from a number of annotation sources including GenBank, RefSeq, Ensembl, dbEST, GENSCAN, TWINSCAN, Exoniphy, Vega, microRNAs registry and others (see Affymetrix Exon Array design note).

As part of the target sequence selection process, target sequences can be optionally further evaluated for potential cross-hybridization against other putative transcribed sequences in the design (but not the entire genome) to identify only those target sequences that are predicted to uniquely hybridize to a single target.

The set of target sequences that are predicted to uniquely hybridize to a single target can be further filtered using a variety of criteria including, for example, sequence length, for their mean expression levels across a wide selection of human tissues, as being representative of transcripts expressed either as novel alternative (i.e., non-consensus) exons, alternative retained introns, novel exons 5' or 3' of the gene's transcriptional start site or representing transcripts expressed in a manner antisense to the gene, amongst others. Representative, non-limiting examples of filtered candidate target sequences in accordance with the present invention are shown in Table 3.

In one embodiment, the Thyroid Classification Set comprises target sequences derived from intron #3 of High mobility group AT-hook 2; exon #16 of Cadherin 3, type 1, P-cadherin (placental): exon #5 of Serpin peptidase inhibitor, clade A (alpha-1 antiproteinase, antitrypsin), member 1; exon #4 of Insulin-like growth factor binding protein 6; exon #17 of Thyroid peroxidase; exon #22 of V-kit Hardy-Zuckerman 4 feline sarcoma viral oncogene homolog and intron #3 of Metallophosphoesterase domain containing 2.

In one embodiment, the Thyroid Classification Set comprises target sequences derived from exon #16 of Cadherin 3, type 1, P-cadherin (placental); intron #25 of Fibronectin 1; intron #31 of Fibronectin 1; intron #40 of Fibronectin 1; exon #1 of Hepatic leukemia factor; intron #3 of High mobility group AT-hook 2; exon #4 of Insulin-like growth factor binding protein 6; 25 base pairs 3' of Metallophosphoesterase domain containing 2; exon #6 of Metallophosphoesterase domain containing 2; intron #1 of Metallophosphoesterase domain containing 2; intron #3 of Metallophosphoesterase domain containing 2; intron #3 of Metallophosphoesterase domain containing 2; intron #3 of Metallophosphoesterase domain containing 2; exon #3 of Metallothionein 1F; exon #3 of Metallothionein 1 G; exon #7 of PDZ and LIM domain 4; exon #5 of Peroxisome proliferator-activated receptor gamma, coactivator 1 alpha; exon #5 of Serpin peptidase inhibitor, clade A (alpha-1 antiproteinase, antitrypsin), member 1; exon #13 of Solute carrier family 26, member 4; exon #17 of Solute carrier family 26, member 4; exon #5 of Solute carrier family 26, member 4; exon #6 of Solute carrier family 26, member 4; 185 base pairs 3' of Thyroid peroxidase; exon #1 of Thyroid peroxidase; exon #13 of Thyroid peroxidase; exon #17 of Thyroid peroxidase; exon #5 of Thyroid peroxidase; exon #5 of Thyroid peroxidase; exon #7 of Thyroid peroxidase; intron #15 of Thyroid peroxidase; intron #8 of Thyroid peroxidase; exon #3 of Trefoil factor 3 (intestinal): exon #1 of Tumor-associated calcium signal transducer 2; exon #22 of V-kit Hardy-Zuckerman 4 feline sarcoma viral oncogene homolog; exon #6 of Zinc finger, matrin type 4 and exon #7 of Zinc finger, matrin type 4.

In one embodiment, the Thyroid Classification Set comprises target sequences derived from exon #11, intron's #2, 3, and 6 of Sparc/osteonectin, cwcv and kazal-like domains proteoglycan (testican) 1.

In one embodiment, the potential set of target sequences can be filtered for their expression levels using the multi-tissue expression data made publicly available by Affymetrix at (http://www.affymetrix.com/support/technical/sample_data/exon_array_data.affx) such that probes with, for example, expression across numerous tissues or no expression in thyroid tissue can be excluded.

In one embodiment, the thyroid classification set can be specifically designed to be indicative of malignant thyroid cancer in general or alternatively be indicative of one or more individual types of thyroid cancer.

Validation of Target Sequences

Following in silico selection of target sequences or review of the literature for published target sequences, each target sequence suitable for use in the thyroid classification set may be validated to confirm differential relative or normalized expression in thyroid cancer or benign thyroid nodule disease. Validation methods are known in the art and include hybridization techniques such as microarray analysis or Northern blotting using appropriate controls, and may include one or more additional steps, such as reverse transcription, transcription, PCR, RT-PCR and the like. The validation of the target sequences using these methods is well within the abilities of a worker skilled in the art.

Minimal Expression Signature

In one embodiment, individual thyroid classification sets provide for at least a determination of a minimal expression signature, capable of distinguishing malignant from benign thyroid nodule disease. Means for determining the appropriate number of target sequences necessary to obtain a minimal expression signature are known in the art and include the Nearest Shrunken Centroids (NSC) method.

In this method (see US 20070031873), a standardized centroid is computed for each class. This is the average gene expression for each gene in each class divided by the within-class standard deviation for that gene. Nearest centroid classification takes the gene expression profile of a new sample, and compares it to each of these class centroids. The class whose centroid that it is closest to, in squared distance, is the predicted class for that new sample. Nearest shrunken centroid classification "shrinks" each of the class centroids toward the overall centroid for all classes by an amount called the threshold. This shrinkage consists of moving the centroid towards zero by threshold, setting it equal to zero if it hits zero. For example if threshold was 2.0, a centroid of 3.2 would be shrunk to 1.2, a centroid of −3.4 would be shrunk to −1.4, and a centroid of 1.2 would be shrunk to zero. After shrinking the centroids, the new sample is classified by the usual nearest centroid rule, but using the shrunken class centroids. This shrinkage can make the classifier more accurate by reducing the effect of noisy genes and provides an automatic gene selection. In particular, if a gene is shrunk to zero for all classes, then it is eliminated from the prediction rule. Alternatively, it may be set to zero for all classes except one, and it can be learned that the high or low expression for that gene characterizes that class. The user decides on the value to use for threshold. Typically one examines a number of different choices. To guide in this choice, PAM does K-fold cross-validation for a range of threshold values. The samples are divided up at random into K roughly equally sized parts. For each part in turn, the classifier is built on the other K−1 parts then tested on the remaining part. This is done for a range of threshold values, and the cross-validated misclassification error rate is reported for each threshold value. Typically, the user would choose the threshold value giving the minimum cross-validated misclassification error rate.

Alternatively, minimal expression signatures can be established through the use of optimization algorithms such as the mean variance algorithm widely used in establishing stock portfolios. This method is described in detail in US patent publication number 20030194734. Essentially, the method calls for the establishment of a set of inputs (stocks in financial applications, expression as measured by intensity here) that will optimize the return (e.g., signal that is generated) one receives for using it while minimizing the variability of the return. In other words, the method calls for the establishment of a set of inputs (e.g., expression as measured by intensity) that will optimize the signal while minimizing variability. Many commercial software programs are available to conduct such operations. "Wagner Associates Mean-Variance Optimization Application," referred to as "Wagner Software" throughout this specification, is preferred. This software uses functions from the "Wagner Associates Mean-Variance Optimization Library" to determine an efficient frontier and optimal portfolios in the Markowitz sense is preferred. Use of this type of software requires that microarray data be transformed so that it can be treated as an input in the way stock return and risk measurements are used when the software is used for its intended financial analysis purposes.

The process of selecting a minimal expression signature can also include the application of heuristic rules. Preferably, such rules are formulated based on biology and an understanding of the technology used to produce clinical results. More preferably, they are applied to output from the optimization method. For example, the mean variance method of portfolio selection can be applied to microarray data for a number of genes differentially expressed in subjects with cancer. Output from the method would be an optimized set of genes that could include some genes that are expressed in peripheral blood as well as in diseased tissue.

Other heuristic rules can be applied that are not necessarily related to the biology in question. For example, one can apply a rule that only a prescribed percentage of the portfolio can be represented by a particular gene or group of genes. Commercially available software such as the Wagner Software readily accommodates these types of heuristics. This can be useful, for example, when factors other than accuracy and precision (e.g., anticipated licensing fees) have an impact on the desirability of including one or more genes.

In one embodiment, the thyroid classification set for obtaining a minimal expression signature comprises at least one, two, three, four, five, six, eight, 10, 15, 20, 25 or more of target sequences shown to have a positive correlation with malignant thyroid disease, for example those depicted in SEQ ID NOs:1-4, and 8-282 or a subset thereof. In another embodiment, the thyroid classification set for obtaining a minimal expression signature comprises at least one, two, three, four, five, six, eight, 10, 15, 20, 25 or more of those target sequences shown to have a positive correlation with benign thyroid disease, for example those depicted in of SEQ ID NOs:5-7, and 283-659, or a subset thereof. In yet another embodiment, the thyroid classification set for obtaining a minimal expression signature comprises at least one, two, three, four, five, six, eight, 10, 15, 20, 25 or more of target sequences shown to have a positive or negative correlation with malignant thyroid disease, for example those depicted in SEQ ID NOs: 1-659 or a subset thereof.

In some embodiments, the thyroid classification set comprises target sequences for detecting expression products of SEQ IDs: 1-659. In some embodiments, the thyroid classification set comprises probes for detecting expression levels of sequences exhibiting positive and negative correlation with a disease status of interest are employed. For example, a combination useful for identifying a sample as exhibiting malignant or benign disease comprises at least one, two, three, four, five, six, eight, 10, 15, 20, 25 or more of those target sequences shown to have a positive correlation with malignant thyroid disease, for example those depicted in SEQ ID NOs: 1-4, and 8-282 or a subset thereof; and at least one, two, three, four, five, six, eight, 10, 15, 20, 25 or more of those target sequences shown to have a positive correlation with benign thyroid disease, for example those depicted in of SEQ ID NOs: 5-7, and 283-659, or a subset thereof.

Exemplary subsets and combinations of interest also include the target sequences as set forth in SEQ ID NOs: 1-7; SEQ ID NOs: 1-12 and 283-306; and SEQ ID NOs: 261, 657, 658, and 659.

Exemplary subsets of interest include those described herein, including in the examples. Exemplary combinations of interest include those utilizing one or more of the sequences listed in Tables 3, 4 and 5. Of particular interest are those combinations utilizing at least one sequence exhibiting positive correlation with the trait of interest, as well as those combinations utilizing at least one sequence exhibiting negative correlation with the trait of interest. Also of interest are those combinations utilizing at least two, at least three, at least four, at least five or at least six of those sequences exhibiting such a positive correlation, in combination with at least two, at least three, at least four, at least five, or at least six of those sequences exhibiting such a negative correlation. Exemplary combinations include those utilizing at least one, two, three, four, five or six of the target sequences depicted in Tables 3, 4 and 5.

It is to be recognized that those sequences shown as having a positive correlation with malignant disease conversely also possess a negative correlation with benign disease. Correspondingly, those sequences shown as having a positive correlation with benign disease also possess a negative correlation with malignant disease.

The thyroid classification set can optionally include one or more target sequences specifically derived from the transcripts of one or more housekeeping genes and/or one or more internal control target sequences and/or one or more negative control target sequences. In one embodiment, these target sequences can, for example, be used to normalize expression data. Housekeeping genes from which target sequences for inclusion in a Thyroid Classification Set can be derived from are known in the art and include those genes in which are expressed at a constant level in normal, benign and malignant thyroid tissue.

The target sequences described herein may be used alone or in combination with each other or with other known or later identified disease markers.

Thyroid Classification Probes/Primers

The system of the present invention provides for combinations of polynucleotide probes that are capable of detecting the target sequences of the Thyroid classification sets. Individual polynucleotide probes comprise a nucleotide sequence derived from the nucleotide sequence of the target sequences or complementary sequences thereof. The nucleotide sequence of the polynucleotide probe is designed such that it corresponds to, or is complementary to the target sequences. The polynucleotide probe can specifically hybridize under either stringent or lowered stringency hybridization conditions to a region of the target sequences, to the complement thereof, or to a nucleic acid sequence (such as a cDNA) derived therefrom.

The selection of the polynucleotide probe sequences and determination of their uniqueness may be carried out in silico using techniques known in the art, for example, based on a BLASTN search of the polynucleotide sequence in question against gene sequence databases, such as the Human Genome Sequence, UniGene, dbEST or the non-redundant database at NCBI. In one embodiment of the invention, the polynucleotide probe is complementary to a region of a target mRNA derived from a PSR in the thyroid classification set. Computer programs can also be employed to select probe sequences that will not cross hybridize or will not hybridize non-specifically.

One skilled in the art will understand that the nucleotide sequence of the polynucleotide probe need not be identical to its target sequence in order to specifically hybridise thereto. The polynucleotide probes of the present invention, therefore, comprise a nucleotide sequence that is at least about 75% identical to a region of the target gene or mRNA. In another embodiment, the nucleotide sequence of the polynucleotide probe is at least about 90% identical a region of the target gene or mRNA. In a further embodiment, the nucleotide sequence of the polynucleotide probe is at least about 95% identical to a region of the target gene or mRNA. Methods of determining sequence identity are known in the art and can be determined, for example, by using the BLASTN program of the University of Wisconsin Computer Group (GCG) software or provided on the NCBI website. The nucleotide sequence of the polynucleotide probes of the present invention may exhibit variability by differing (e.g. by nucleotide substitution, including transition or transversion) at one, two, three, four or more nucleotides from the sequence of the target gene.

Other criteria known in the art may be employed in the design of the polynucleotide probes of the present invention. For example, the probes can be designed to have <50% G content and/or between about 25% and about 70% G+C content. Strategies to optimize probe hybridization to the target nucleic acid sequence can also be included in the process of probe selection. Hybridization under particular pH, salt, and temperature conditions can be optimized by taking into account melting temperatures and by using empirical rules that correlate with desired hybridization behaviours. Computer models may be used for predicting the intensity and concentration-dependence of probe hybridization.

As is known in the art, in order to represent a unique sequence in the human genome, a probe should be at least 15 nucleotides in length. Accordingly, the polynucleotide probes of the present invention range in length from about 15 nucleotides to the full length of the PSR or target mRNA. In one embodiment of the invention, the polynucleotide probes are at least about 15 nucleotides in length. In another embodiment, the polynucleotide probes are at least about 20 nucleotides in length. In a further embodiment, the polynucleotide probes are at least about 25 nucleotides in length. In another embodiment, the polynucleotide probes are between about 15 nucleotides and about 500 nucleotides in length. In other embodiments, the polynucleotide probes are between about 15 nucleotides and about 450 nucleotides, about 15 nucleotides and about 400 nucleotides, about 15 nucleotides and about 350 nucleotides, about 15 nucleotides and about 300 nucleotides in length.

The polynucleotide probes of a thyroid classification set can comprise RNA, DNA, RNA or DNA mimetics, or combinations thereof, and can be single-stranded or double-stranded. Thus the polynucleotide probes can be composed of naturally-occurring nucleobases, sugars and covalent internucleoside (backbone) linkages as well as polynucleotide probes having non-naturally-occurring portions which function similarly. Such modified or substituted polynucleotide probes may provide desirable properties such as, for example, enhanced affinity for a target gene and increased stability.

The system of the present invention further provides for primers and primer pairs capable of amplifying target sequences defined by the thyroid classification set, or fragments or subsequences or complements thereof. The nucleotide sequences of the thyroid classifying set may be provided in computer-readable media for in silico applications and as a basis for the design of appropriate primers for amplification of one or more target sequences of the thyroid classifying set.

Primers based on the nucleotide sequences of target sequences can be designed for use in amplification of the target sequences. For use in amplification reactions such as PCR, a pair of primers will be used. The exact composition of the primer sequences is not critical to the invention, but for most applications the primers will hybridize to specific sequences of the thyroid classification set under stringent conditions, particularly under conditions of high stringency, as known in the art. The pairs of primers are usually chosen so as to generate an amplification product of at least about 50 nucleotides, more usually at least about 100 nucleotides. Algorithms for the selection of primer sequences are generally known, and are available in commercial software packages. These primers may be used in standard quantitative or qualitative PCR-based assays to assess transcript expression levels of RNAs defined by the thyroid classification set. Alternatively, these primers may be used in combination with probes, such as molecular beacons in amplifications using real-time PCR.

In one embodiment, the primers or primer pairs, when used in an amplification reaction, specifically amplify at least a portion of a nucleic acid depicted in one of SEQ ID NOs: 1-659, an RNA form thereof, or a complement to either thereof. Optionally, when amplified, either stand produced by amplification may be provided in purified and/or isolated form.

As is known in the art, a nucleoside is a base-sugar combination and a nucleotide is a nucleoside that further includes a phosphate group covalently linked to the sugar portion of the nucleoside. In forming oligonucleotides, the phosphate groups covalently link adjacent nucleosides to one another to form a linear polymeric compound, with the normal linkage or backbone of RNA and DNA being a 3' to 5' phosphodiester linkage. Specific examples of polynucleotide probes or primers useful in this invention include oligonucleotides containing modified backbones or non-natural internucleoside linkages. As defined in this specification, oligonucleotides having modified backbones include both those that retain a phosphorus atom in the backbone and those that lack a phosphorus atom in the backbone. For the purposes of the present invention, and as sometimes referenced in the art, modified oligonucleotides that do not have a phosphorus atom in their internucleoside backbone can also be considered to be oligonucleotides.

Exemplary polynucleotide probes or primers having modified oligonucleotide backbones include, for example, those with one or more modified internucleotide linkages that are phosphorothioates, chiral phosphorothioates, phosphorodithioates, phosphotriesters, aminoalkylphosphotriesters, methyl and other alkyl phosphonates including 3'-alkylene phosphonates and chiral phosphonates, phosphinates, phosphoramidates including 3'amino phosphoramidate and aminoalkylphosphoramidates, thionophosphoramidates, thionoalkyl-phosphonates, thionoalkylphosphotriesters, and boranophosphates having normal 3'-5' linkages, 2'-5' linked analogs of these, and those having inverted polarity wherein the adjacent pairs of nucleoside units are linked 3'-5' to 5'-3' or 2'-5' to 5'-2'. Various salts, mixed salts and free acid forms are also included.

Exemplary modified oligonucleotide backbones that do not include a phosphorus atom are formed by short chain alkyl or cycloalkyl internucleoside linkages, mixed heteroatom and alkyl or cycloalkyl internucleoside linkages, or one or more short chain heteroatomic or heterocyclic internucleoside linkages. Such backbones include morpholino linkages (formed in part from the sugar portion of a nucleoside); siloxane backbones; sulfide, sulfoxide and sulphone backbones; formacetyl and thioformacetyl backbones; methylene formacetyl and thioformacetyl backbones; alkene containing backbones; sulphamate backbones; methyleneimino and methylenehydrazino backbones; sulphonate and sulfonamide backbones; amide backbones; and others having mixed N, O, S and $CH_2$ component parts.

The present invention also contemplates oligonucleotide mimetics in which both the sugar and the internucleoside linkage of the nucleotide units are replaced with novel groups. The base units are maintained for hybridization with an appropriate nucleic acid target compound. An example of such an oligonucleotide mimetic, which has been shown to have excellent hybridization properties, is a peptide nucleic acid (PNA) [Nielsen et al., *Science,* 254:1497-1500 (1991)]. In PNA compounds, the sugar-backbone of an oligonucleotide is replaced with an amide containing backbone, in particular an aminoethylglycine backbone. The nucleobases are retained and are bound directly or indirectly to aza-nitrogen atoms of the amide portion of the backbone.

The present invention also contemplates polynucleotide probes or primers comprising "locked nucleic acids" (LNAs), which are novel conformationally restricted oligonucleotide analogues containing a methylene bridge that connects the 2'-O of ribose with the 4'-C (see, Singh et al., *Chem. Commun.,* 1998, 4:455-456). LNA and LNA analogues display very high duplex thermal stabilities with complementary DNA and RNA, stability towards 3'-exonuclease degradation, and good solubility properties. Synthesis of the LNA analogues of adenine, cytosine, guanine, 5-methylcytosine, thymine and uracil, their oligomerization, and nucleic acid recognition properties have been described (see Koshkin et al., *Tetrahedron,* 1998, 54:3607-3630). Studies of mis-matched sequences show that LNA obey the Watson-Crick base pairing rules with generally improved selectivity compared to the corresponding unmodified reference strands.

LNAs form duplexes with complementary DNA or RNA or with complementary LNA, with high thermal affinities. The universality of LNA-mediated hybridization has been emphasized by the formation of exceedingly stable LNA: LNA duplexes (Koshkin et al., *J. Am. Chem. Soc.,* 1998, 120:13252-13253). LNA:LNA hybridization was shown to be the most thermally stable nucleic acid type duplex system, and the RNA-mimicking character of LNA was established at the duplex level. Introduction of three LNA monomers (T or A) resulted in significantly increased melting points toward DNA complements.

Synthesis of 2'-amino-LNA (Singh et al., J. Org. Chem., 1998, 63, 10035-10039) and 2'-methylamino-LNA has been described and thermal stability of their duplexes with complementary RNA and DNA strands reported. Preparation of phosphorothioate-LNA and 2'-thio-LNA have also been described (Kumar et al., *Bioorg. Med. Chem. Lett.,* 1998, 8:2219-2222).

Modified polynucleotide probes or primers may also contain one or more substituted sugar moieties. For example, oligonucleotides may comprise sugars with one of the following substituents at the 2' position: OH; F; O-, S-, or N-alkyl; O-, S-, or N-alkenyl: O-, S- or N-alkynyl: or O-alkyl-O-alkyl, wherein the alkyl, alkenyl and alkynyl may be substituted or unsubstituted $C_1$ to $C_{10}$ alkyl or $C_2$ to $C_{10}$ alkenyl and alkynyl. Examples of such groups are: $O[(CH_2)_nO]_mCH_3$, $O(CH_2)_nOCH_3$, $O(CH_2)_n NH_2$, $O(CH_2)_nCH_3$, $O(CH_2)_nONH_2$, and $O(CH_2)_nON[(CH_2)_nCH_3)]_2$, where n and m are from 1 to about 10. Alternatively, the oligonucleotides may comprise one of the following substituents at the 2' position: $C_1$ to $C_{10}$ lower alkyl, substituted lower alkyl, alkaryl, aralkyl, O-alkaryl or O-aralkyl, SH, $SCH_3$, OCN, Cl, Br, CN, CF$_3$, OCF$_3$, SOCH$_3$, SO$_2$CH$_3$, ONO$_2$, NO$_2$, N$_3$, NH$_2$, heterocycloalkyl, heterocycloalkaryl, aminoalkylamino, polyalkylamino, substituted silyl, an RNA cleaving group, a reporter group, an intercalator, a group for improving the pharmacokinetic properties of an oligonucleotide, or a group for improving the pharmacodynamic properties of an oligonucleotide, and other substituents having similar properties. Specific examples include 2'-methoxyethoxy (2'-O—CH$_2$CH$_2$OCH$_3$, also known as 2'-O-(2-methoxyethyl) or 2'-MOE) [Martin et al., *Helv. Chim. Acta*, 78:486-504 (1995)], 2'-dimethylaminooxyethoxy (O(CH$_2$)$_2$ON(CH$_3$)$_2$ group, also known as 2'-DMAOE), 2'-methoxy (2'-O—CH$_3$), 2'-aminopropoxy (2'-OCH$_2$CH$_2$CH$_2$NH$_2$) and 2'-fluoro (2'-F).

Similar modifications may also be made at other positions on the polynucleotide probes or primers, particularly the 3' position of the sugar on the 3' terminal nucleotide or in 2'-5' linked oligonucleotides and the 5' position of 5' terminal nucleotide. Polynucleotide probes or primers may also have sugar mimetics such as cyclobutyl moieties in place of the pentofuranosyl sugar.

Polynucleotide probes or primers may also include modifications or substitutions to the nucleobase. As used herein, "unmodified" or "natural" nucleobases include the purine bases adenine (A) and guanine (G), and the pyrimidine bases thymine (T), cytosine (C) and uracil (U). Modified nucleobases include other synthetic and natural nucleobases such as 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl uracil and cytosine, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 8-azaguanine and 8-azaadenine, 7-deazaguanine and 7-deazaadenine and 3-deazaguanine and 3-deazaadenine. Further nucleobases include those disclosed in U.S. Pat. No. 3,687,808: The Concise Encyclopedia Of Polymer Science And Engineering, (1990) pp 858-859, Kroschwitz, J. I., ed. John Wiley & Sons; Englisch et al., *Angewandte Chemie, Int. Ed.*, 30:613 (1991); and Sanghvi, Y. S., (1993) *Antisense Research and Applications*, pp 289-302, Crooke, S. T. and Lebleu, B., ed., CRC Press. Certain of these nucleobases are particularly useful for increasing the binding affinity of the polynucleotide probes of the invention. These include 5-substituted pyrimidines, 6-azapyrimidines and N-2, N-6 and O-6 substituted purines, including 2-aminopropyladenine, 5-propynyluracil and 5-propynylcytosine. 5-methylcytosine substitutions have been shown to increase nucleic acid duplex stability by 0.6-1.2° C. [Sanghvi, Y. S., (1993) *Antisense Research and Applications*, pp 276-278, Crooke, S. T. and Lebleu, B., ed., CRC Press, Boca Raton].

One skilled in the art will recognize that it is not necessary for all positions in a given polynucleotide probe or primer to be uniformly modified. The present invention, therefore, contemplates the incorporation of more than one of the aforementioned modifications into a single polynucleotide probe or even at a single nucleoside within the probe or primer.

One skilled in the art will also appreciate that the nucleotide sequence of the entire length of the polynucleotide probe or primer does not need to be derived from the target sequence. Thus, for example, the polynucleotide probe may comprise nucleotide sequences at the 5' and/or 3' to the transcription start and stop sites, respectively that are not derived from the target sequences. Nucleotide sequences which are not derived from the nucleotide sequence of the target sequence may provide additional functionality to the polynucleotide probe. For example, they may provide a restriction enzyme recognition sequence or a "tag" that facilitates detection, isolation, purification or immobilisation onto a solid support. Alternatively, the additional nucleotides may provide a self-complementary sequence that allows the primer/probe to adopt a hairpin configuration. Such configurations are necessary for certain probes, for example, molecular beacon and Scorpion probes, which can be used in solution hybridization techniques.

The polynucleotide probes or primers can incorporate moieties useful in detection, isolation, purification, or immobilisation, if desired. Such moieties are well-known in the art (see, for example, Ausubel et al., (1997 & updates) *Current Protocols in Molecular Biology*, Wiley & Sons, New York) and are chosen such that the ability of the probe to hybridize with its target sequence is not affected.

Examples of suitable moieties are detectable labels, such as radioisotopes, fluorophores, chemiluminophores, enzymes, colloidal particles, and fluorescent microparticles, as well as antigens, antibodies, haptens, avidin/streptavidin, biotin, haptens, enzyme cofactors/substrates, enzymes, and the like.

A label can optionally be attached to or incorporated into a probe or primer polynucleotide to allow detection and/or quantitation of a target polynucleotide representing the target sequence of interest. The target polynucleotide may be the expressed target sequence RNA itself, a cDNA copy thereof, or an amplification product derived therefrom, and may be the positive or negative strand, so long as it can be specifically detected in the assay being used. Similarly, an antibody may be labeled.

In certain multiplex formats, labels used for detecting different targets may be distinguishable. The label can be attached directly (e.g., via covalent linkage) or indirectly, e.g., via a bridging molecule or series of molecules (e.g., a molecule or complex that can bind to an assay component, or via members of a binding pair that can be incorporated into assay components, e.g. biotin-avidin or streptavidin). Many labels are commercially available in activated forms which can readily be used for such conjugation (for example through amine acylation), or labels may be attached through known or determinable conjugation schemes, many of which are known in the art.

Labels useful in the invention described herein include any substance which can be detected when bound to or incorporated into the biomolecule of interest. Any effective detection method can be used, including optical, spectroscopic, electrical, piezoelectrical, magnetic, Raman scattering, surface plasmon resonance, colorimetric, calorimetric, etc. A label is typically selected from a chromophore, a lumiphore, a fluorophore, one member of a quenching system, a chromogen, a hapten, an antigen, a magnetic particle, a material exhibiting nonlinear optics, a semiconductor nanocrystal, a metal nanoparticle, an enzyme, an antibody or binding portion or equivalent thereof, an aptamer, and one member of a binding pair, and combinations thereof. Quenching schemes may be used, wherein a quencher and a fluorophore as members of a quenching pair may be used on a probe, such that a change in optical parameters occurs upon binding to the target introduce or quench the signal from the fluorophore. One example of such a system is a molecular beacon. Suitable quencher/ fluorophore systems are known in the art. The label may be bound through a variety of intermediate linkages. For example, a polynucleotide may comprise a biotin-binding species, and an optically detectable label may be conjugated to biotin and then bound to the labeled polynucleotide. Similarly, a polynucleotide sensor may comprise an immunological species such as an antibody or fragment, and a secondary antibody containing an optically detectable label may be added.

Chromophores useful in the methods described herein include any substance which can absorb energy and emit light. For multiplexed assays, a plurality of different signaling chromophores can be used with detectably different emission spectra. The chromophore can be a lumophore or a fluorophore. Typical fluorophores include fluorescent dyes, semiconductor nanocrystals, lanthanide chelates, polynucleotide-specific dyes and green fluorescent protein.

Coding schemes may optionally be used, comprising encoded particles and/or encoded tags associated with different polynucleotides of the invention. A variety of different coding schemes are known in the art, including fluorophores, including SCNCs, deposited metals, and RF tags.

Polynucleotides from the described target sequences may be employed as probes for detecting target sequences expression, for ligation amplification schemes, or may be used as primers for amplification schemes of all or a portion of a target sequences. When amplified, either strand produced by amplification may be provided in purified and/or isolated form.

In one embodiment, polynucleotides of the invention include a nucleic acid depicted in (a) any of SEQ ID NOs: 1-659; (b) an RNA form of any of the nucleic acids depicted in SEQ ID NOs: 1-659; (c) a peptide nucleic acid form of any of the nucleic acids depicted in SEQ ID NOs: 1-659; (d) a nucleic acid comprising at least 20 consecutive bases of any of (a-c); (e) a nucleic acid comprising at least 25 consecutive bases having at least 90% sequence identity to any of (a-c); and a complement to any of (a-e).

Complements may take any polymeric form capable of base pairing to the species recited in (a)-(e), including nucleic acid such as RNA or DNA, or may be a neutral polymer such as a peptide nucleic acid. Polynucleotides of the invention can be selected from the subsets of the recited nucleic acids described herein, as well as their complements.

In some embodiments, polynucleotides of the invention comprise at least 20 consecutive bases as depicted in SEQ ID NOs:1-659, or a complement thereto. The polynucleotides may comprise at least 21, 22, 23, 24, 25, 27, 30, 32, 35 or more consecutive bases as depicted in SEQ ID NOs: 1-659.

The polynucleotides may be provided in a variety of formats, including as solids, in solution, or in an array. The polynucleotides may optionally comprise one or more labels, which may be chemically and/or enzymatically incorporated into the polynucleotide.

In one embodiment, solutions comprising polynucleotide and a solvent are also provided. In some embodiments, the solvent may be water or may be predominantly aqueous. In some embodiments, the solution may comprise at least two, three, four, five, six, seven, eight, nine, ten, twelve, fifteen, seventeen, twenty or more different polynucleotides, including primers and primer pairs, of the invention. Additional substances may be included in the solution, alone or in combination, including one or more labels, additional solvents, buffers, biomolecules, polynucleotides, and one or more enzymes useful for performing methods described herein, including polymerases and ligases. The solution may further comprise a primer or primer pair capable of amplifying a polynucleotide of the invention present in the solution.

In some embodiments, one or more polynucleotides provided herein can be provided on a substrate. The substrate can comprise a wide range of material, either biological, nonbiological, organic, inorganic, or a combination of any of these. For example, the substrate may be a polymerized Langmuir Blodgett film, functionalized glass, Si, Ge, GaAs, GaP, $SiO_2$, $SiN_4$, modified silicon, or any one of a wide variety of gels or polymers such as (poly)tetrafluoroethylene, (poly)vinylidenedifluoride, polystyrene, cross-linked polystyrene, polyacrylic, polylactic acid, polyglycolic acid, poly(lactide coglycolide), polyanhydrides, poly(methyl methacrylate), poly(ethylene-co-vinyl acetate), polysiloxanes, polymeric silica, latexes, dextran polymers, epoxies, polycarbonates, or combinations thereof. Conducting polymers and photoconductive materials can be used.

Substrates can be planar crystalline substrates such as silica based substrates (e.g. glass, quartz, or the like), or crystalline substrates used in, e.g., the semiconductor and microprocessor industries, such as silicon, gallium arsenide, indium doped GaN and the like, and includes semiconductor nanocrystals.

The substrate can take the form of an array, a photodiode, an optoelectronic sensor such as an optoelectronic semiconductor chip or optoelectronic thin-film semiconductor, or a biochip. The location(s) of probe(s) on the substrate can be addressable; this can be done in highly dense formats, and the location(s) can be microaddressable or nanoaddressable.

Silica aerogels can also be used as substrates, and can be prepared by methods known in the art. Aerogel substrates may be used as free standing substrates or as a surface coating for another substrate material.

The substrate can take any form and typically is a plate, slide, bead, pellet, disk, particle, microparticle, nanoparticle, strand, precipitate, optionally porous gel, sheets, tube, sphere, container, capillary, pad, slice, film, chip, multiwell plate or dish, optical fiber, etc. The substrate can be any form that is rigid or semi-rigid. The substrate may contain raised or depressed regions on which an assay component is located. The surface of the substrate can be etched using known techniques to provide for desired surface features, for example trenches, v-grooves, mesa structures, or the like.

Surfaces on the substrate can be composed of the same material as the substrate or can be made from a different material, and can be coupled to the substrate by chemical or physical means. Such coupled surfaces may be composed of any of a wide variety of materials, for example, polymers, plastics, resins, polysaccharides, silica or silica-based materials, carbon, metals, inorganic glasses, membranes, or any of the above-listed substrate materials. The surface can be optically transparent and can have surface Si—OH functionalities, such as those found on silica surfaces.

The substrate and/or its optional surface can be chosen to provide appropriate characteristics for the synthetic and/or detection methods used. The substrate and/or surface can be transparent to allow the exposure of the substrate by light applied from multiple directions. The substrate and/or surface may be provided with reflective "mirror" structures to increase the recovery of light.

The substrate and/or its surface is generally resistant to, or is treated to resist, the conditions to which it is to be exposed in use, and can be optionally treated to remove any resistant material after exposure to such conditions.

The substrate or a region thereof may be encoded so that the identity of the sensor located in the substrate or region being queried may be determined. Any suitable coding scheme can be used, for example optical codes, RFID tags, magnetic codes, physical codes, fluorescent codes, and combinations of codes.

Preparation of Probes and Primers

The polynucleotide probes or primers of the present invention can be prepared by conventional techniques well-known to those skilled in the art. For example, the polynucleotide probes can be prepared using solid-phase synthesis using commercially available equipment. As is well-known in the art, modified oligonucleotides can also be readily prepared by similar methods. The polynucleotide probes can also be synthesized directly on a solid support according to methods standard in the art. This method of synthesizing polynucleotides is particularly useful when the polynucleotide probes are part of a nucleic acid array.

Polynucleotide probes or primers can be fabricated on or attached to the substrate by any suitable method, for example the methods described in U.S. Pat. No. 5,143,854, PCT Publ. No. WO 92/10092, U.S. patent application Ser. No. 07/624,120, filed Dec. 6, 1990 (now abandoned), Fodor et al., Science, 251: 767-777 (1991), and PCT Publ. No. WO 90/15070). Techniques for the synthesis of these arrays using mechanical synthesis strategies are described in, e.g., PCT Publication No. WO 93/09668 and U.S. Pat. No. 5,384,261. Still further techniques include bead based techniques such as those described in PCT Appl. No. PCT/US93/04145 and pin based methods such as those described in U.S. Pat. No. 5,288,514. Additional flow channel or spotting methods applicable to attachment of sensor polynucleotides to a substrate are described in U.S. patent application Ser. No. 07/980,523, filed Nov. 20, 1992, and U.S. Pat. No. 5,384,261.

Alternatively, the polynucleotide probes of the present invention can be prepared by enzymatic digestion of the naturally occurring target gene, or mRNA or cDNA derived therefrom, by methods known in the art.

Thyroid Classification Methods

The present invention further provides methods for characterizing thyroid samples for the presence of malignant or benign thyroid nodule disease. The methods use the thyroid classification sets, probes and primers described herein to provide expression signatures or profiles from a test sample derived from a subject having or suspected of having thyroid cancer. In some embodiments, such methods involve contacting a test sample with thyroid classifying probes (either in solution or immobilized) under conditions that permit hybridization of the probe(s) to any target nucleic acid(s) present in the test sample and then detecting any probe:target duplexes formed as an indication of the presence of the target nucleic acid in the sample. Expression patterns thus determined are then compared to one or more reference profiles or signatures.

Optionally, the expression pattern can be normalized. The methods use the thyroid classification sets, probes and primers described herein to provide expression signatures or profiles from a test sample derived from a subject to classify thyroid nodule tissue as malignant or benign.

In some embodiments, such methods involve the specific amplification of target sequences nucleic acid(s) present in the test sample using methods known in the art to generate an expression profile or signature which is then compared to a reference profile or signature.

In some embodiments, the invention further provides for diagnosing thyroid cancer, for prognosing patient outcome, and/or for designating treatment modalities.

In one embodiment, the methods generate expression profiles or signatures detailing the expression of the 659 target sequences having altered relative expression in malignant and benign thyroid disease disclosed herein. In one embodiment, the methods generate expression profiles or signatures detailing the expression of the subsets of these target sequences having 7 or 36 target sequences as described in the examples.

In one embodiment, the methods generate expression profiles or signatures detailing the expression of the target sequences as set forth in SEQ ID NOs: 1-7; the target sequences as set forth in SEQ ID NOs: 1-12 and 283-306; or the target sequences as set forth in SEQ ID NOs: 261, 657, 658, and 659.

In some embodiments, the methods detect increased relative expression of one or more target sequences in Group I corresponding to the expression products of SEQ IDs:1-4 and 8-282, and/or decreased relative expression of one or more target sequences in Group II corresponding to the expression products of SEQ ID NOs: 5-7, and 283-659, and thereby designate a sample as comprising malignant thyroid nodule disease. In some embodiments, increased relative expression of one or more target sequences in Group II and/or decreased relative expression of one or more target sequences in Group 1 and thereby designate a sample as comprising benign thyroid nodule disease.

In some embodiments, the methods detect combinations of expression levels of sequences exhibiting positive and negative correlation with a disease status. In one embodiment, the methods detect a minimal expression signature.

Any method of detecting and/or quantitating the expression of the encoded target sequences can in principle be used in the invention. Such methods can include Northern blotting, array or microarray hybridization, by enzymatic cleavage of specific structures (e.g., an Invader® assay, Third Wave Technologies, e.g. as described in U.S. Pat. Nos. 5,846,717, 6,090,543; 6,001,567; 5,985,557; and 5,994,069) and amplification methods, e.g. RT-PCR, including in a TaqMan® assay (PE Biosystems, Foster City, Calif., e.g. as described in U.S. Pat. Nos. 5,962,233 and 5,538,848), and may be quantitative or semi-quantitative, and may vary depending on the origin, amount and condition of the available biological sample. Combinations of these methods may also be used. For example, nucleic acids may be amplified, labeled and subjected to microarray analysis. Single-molecule sequencing (e.g., Illumina, Helicos, PacBio, ABI SOLID), in situ hybridization, bead-array technologies (e.g., Luminex xMAP, Illumina BeadChips), branched DNA technology (e.g., Panomics, Genisphere).

The expressed target sequences can be directly detected and/or quantitated, or may be copied and/or amplified to allow detection of amplified copies of the expressed target sequences or its complement. In some embodiments, degraded and/or fragmented RNA can be usefully analyzed for expression levels of target sequences, for example RNA having an RNA integrity number of less than 8.

In some embodiments, quantitative RT-PCR assays are used to measure the expression level of target sequences depicted in SEQ IDs: 1-659. In other embodiments, a GeneChip or microarray can be used to measure the expression of one or more of the target sequences.

Molecular assays measure the relative expression levels of the target sequences, which can be normalized to the expression levels of one or more control sequences, for example array control sequences and/or one or more housekeeping genes, for example GAPDH. Increased (or decreased) relative expression of the target sequences as described herein, including any of SEQ ID NOs: 1-659, may thus be used alone or in any combination with each other in the methods described herein. In addition, negative control probes may be included.

Diagnostic Samples

Diagnostic samples for use with the systems and in the methods of the present invention comprise nucleic acids suitable for providing RNAs expression information. In principle, the biological sample from which the expressed RNA is obtained and analyzed for target sequence expression can be any material suspected of comprising thyroid cancer. The diagnostic sample can be a biological sample used directly in a method of the invention. Alternatively, the diagnostic sample can be a sample prepared from a biological sample.

In one embodiments, the sample or portion of the sample comprising or suspected of comprising thyroid cancer can be any source of biological material, including cells, tissue or fluid, including bodily fluids. Non-limiting examples of the source of the sample include an aspirate, a needle biopsy, a cytology pellet, a bulk tissue preparation or a section thereof obtained for example by surgery or autopsy, lymph fluid, blood, plasma, serum, tumors, and organs.

The samples may be archival samples, having a known and documented medical outcome, or may be samples from current patients whose ultimate medical outcome is not yet known. Samples to be analyzed for thyroid cancer are typically obtained as fine needle aspirates, a cytology smear, a liquid-based preparation (e.g., ThinPrep®), a cytology pellet, or as bulk samples obtained, for example, from a thyroidectomy. Where samples of a bodily fluid are obtained, cells or cell types may be isolated and/or purified therefrom. For example, circulating epithelial cells can be obtained from peripheral blood and analyzed as described herein. In some embodiments, magnetic separation can be used to obtain circulating epithelial cells (U.S. Pat. No. 6,136,182).

In some embodiments, the sample may be dissected prior to molecular analysis. The sample may be prepared via macrodissection of a bulk tumor specimen or portion thereof, or may be treated via microdissection, for example via Laser Capture Microdissection (LCM).

The sample may initially be provided in a variety of states, as fresh tissue, fresh frozen tissue, fine needle aspirates, and may be fixed or unfixed. Frequently, medical laboratories routinely prepare medical samples in a fixed state, which facilitates tissue storage. A variety of fixatives can be used to fix tissue to stabilize the morphology of cells, and may be used alone or in combination with other agents. Exemplary fixatives include crosslinking agents, alcohols, acetone, Bouin's solution, Zenker solution, Hely solution, osmic acid solution and Carnoy solution.

Crosslinking fixatives can comprise any agent suitable for forming two or more covalent bonds, for example an aldehyde. Sources of aldehydes typically used for fixation include formaldehyde, paraformaldehyde, glutaraldehyde or formalin. Preferably, the crosslinking agent comprises formaldehyde, which may be included in its native form or in the form of paraformaldehyde or formalin. One of skill in the art would appreciate that for samples in which crosslinking fixatives have been used special preparatory steps may be necessary including for example heating steps and proteinase-k digestion; see methods One or more alcohols may be used to fix tissue, alone or in combination with other fixatives. Exemplary alcohols used for fixation include methanol, ethanol and isopropanol.

Formalin fixation is frequently used in medical laboratories. Formalin comprises both an alcohol, typically methanol, and formaldehyde, both of which can act to fix a biological sample.

Whether fixed or unfixed, the biological sample may optionally be embedded in an embedding medium. Exemplary embedding media used in histology including paraffin, Tissue-Tek® V.I.P.™, Paramat, Paramat Extra, Paraplast, Paraplast X-tra, Paraplast Plus, Peel Away Paraffin Embedding Wax, Polyester Wax, Carbowax Polyethylene Glycol, Polyfin™, Tissue Freezing Medium TFM™, Cryo-Gel™, and OCT Compound (Electron Microscopy Sciences, Hatfield, Pa.). Prior to molecular analysis, the embedding material may be removed via any suitable techniques, as known in the art. For example, where the sample is embedded in wax, the embedding material may be removed by extraction with organic solvent(s), for example xylenes. Kits are commercially available for removing embedding media from tissues. Samples or sections thereof may be subjected to further processing steps as needed, for example serial hydration or dehydration steps.

In some embodiments, the sample is a fixed, wax-embedded biological sample. Frequently, samples from medical laboratories are provided as fixed, wax-embedded samples, most commonly as formalin-fixed, paraffin embedded (FFPE) tissues.

Whatever the source of the biological sample, the target polynucleotide that is ultimately assayed can be prepared synthetically (in the case of control sequences), but typically is purified from the biological source and subjected to one or more preparative steps. The RNA may be purified to remove or diminish one or more undesired components from the biological sample or to concentrate it. Conversely, where the RNA is too concentrated for the particular assay, it may be diluted.

RNA Extraction

RNA can be extracted and purified from biological samples using any suitable technique. A number of techniques are known in the art, and several are commercially available (e.g., FormaPure™ nucleic acid extraction kit, Agencourt Biosciences, Beverly Mass., High Pure FFPE RNA Micro Kit™, Roche Applied Science, Indianapolis, Ind.). RNA can be extracted from frozen tissue sections using TRIzol (Invitrogen, Carlsbad, Calif.) and purified using RNeasy Protect kit (Qiagen, Valencia, Calif.). RNA can be further purified using DNAse I treatment (Ambion, Austin, Tex.) to eliminate any contaminating DNA. RNA concentrations can be made using a Nanodrop ND-1000 spectrophotometer (Nanodrop Technologies, Rockland, Del.). RNA integrity can be evaluated by running electropherograms, and RNA integrity number (RIN, a correlative measure that indicates intactness of mRNA) can be determined using the RNA 6000 PicoAssay for the Bioanalyzer 2100 (Agilent Technologies, Santa Clara, Calif.).

Amplification and Hybridization

Following sample collection and nucleic acid extraction, the nucleic acid portion of the sample comprising RNA that is or can be used to prepare the target polynucleotide(s) of interest can be subjected to one or more preparative reactions. These preparative reactions can include in vitro transcription (IVT), labeling, fragmentation, amplification and other reactions. mRNA can first be treated with reverse transcriptase and a primer to create cDNA prior to detection, quantitation and/or amplification; this can be done in vitro with purified mRNA or in situ, e.g., in cells or tissues affixed to a slide.

By "amplification" is meant any process of producing at least one copy of a nucleic acid, in this case an expressed RNA, and in many cases produces multiple copies. An amplification product can be RNA or DNA, and may include a complementary strand to the expressed target sequence. DNA amplification products can be produced initially through reverse translation and then optionally from further amplification reactions. The amplification product may include all or a portion of a PSR, and may optionally be labeled. A variety of amplification methods are suitable for use, including polymerase-based methods and ligation-based methods. Exemplary amplification techniques include the polymerase chain reaction method (PCR), the ligase chain reaction (LCR), ribozyme-based methods, self sustained sequence replication (3SR), nucleic acid sequence-based amplification (NASBA), the use of Q Beta replicase, reverse transcription, nick translation, and the like.

Asymmetric amplification reactions may be used to preferentially amplify one strand representing the PSR that is used for detection as the target polynucleotide. In some cases, the presence and/or amount of the amplification product itself may be used to determine the expression level of a given PSR. In other instances, the amplification product may be used to hybridize to an array or other substrate comprising sensor polynucleotides which are used to detect and/or quantitate PSR expression.

The first cycle of amplification in polymerase-based methods typically forms a primer extension product complementary to the template strand. If the template is single-stranded RNA, a polymerase with reverse transcriptase activity is used in the first amplification to reverse transcribe the RNA to DNA, and additional amplification cycles can be performed to copy the primer extension products. The primers for a PCR must, of course, be designed to hybridize to regions in their corresponding template that will produce an amplifiable segment; thus, each primer must hybridize so that its 3' nucleotide is paired to a nucleotide in its complementary template strand that is located 3' from the 3' nucleotide of the primer used to replicate that complementary template strand in the PCR.

The target polynucleotide can be amplified by contacting one or more strands of the target polynucleotide with a primer and a polymerase having suitable activity to extend the primer and copy the target polynucleotide to produce a full-length complementary polynucleotide or a smaller portion thereof. Any enzyme having a polymerase activity that can copy the target polynucleotide can be used, including DNA polymerases, RNA polymerases, reverse transcriptases, enzymes having more than one type of polymerase or enzyme activity. The enzyme can be thermolabile or thermostable. Mixtures of enzymes can also be used. Exemplary enzymes include: DNA polymerases such as DNA Polymerase I ("Pol I"), the Klenow fragment of Pol I, T4, T7, Sequenase® T7, Sequenase® Version 2.0 T7, Tub, Taq, Tth, Pfx, Pfu, Tsp, Tfl, Tli and *Pyrococcus* sp GB-D DNA polymerases; RNA polymerases such as *E. coli*, SP6, T3 and T7 RNA polymerases; and reverse transcriptases such as AMV, M-MuLV, MMLV, RNAse H⁻ MMLV (SuperScript®), SuperScript® II, ThermoScript®, HIV-1, and RAV2 reverse transcriptases. All of these enzymes are commercially available. Exemplary polymerases with multiple specificities include RAV2 and Tli (exo-) polymerases. Exemplary thermostable polymerases include Tub, Taq, Tth, Pfx, Pfu, Tsp, Tfl, Tli and *Pyrococcus* sp. GB-D DNA polymerases.

Suitable reaction conditions are chosen to permit amplification of the target polynucleotide, including pH, buffer, ionic strength, presence and concentration of one or more salts, presence and concentration of reactants and cofactors such as nucleotides and magnesium and/or other metal ions (e.g., manganese), optional cosolvents, temperature, thermal cycling profile for amplification schemes comprising a polymerase chain reaction, and may depend in part on the polymerase being used as well as the nature of the sample. Cosolvents include formamide (typically at from about 2 to about 10%), glycerol (typically at from about 5 to about 10%), and DMSO (typically at from about 0.9 to about 10%). Techniques may be used in the amplification scheme in order to minimize the production of false positives or artifacts produced during amplification. These include "touchdown" PCR, hot-start techniques, use of nested primers, or designing PCR primers so that they form stem-loop structures in the event of primer-dimer formation and thus are not amplified. Techniques to accelerate PCR can be used, for example centrifugal PCR, which allows for greater convection within the sample, and comprising infrared heating steps for rapid heating and cooling of the sample. One or more cycles of amplification can be performed. An excess of one primer can be used to produce an excess of one primer extension product during PCR; preferably, the primer extension product produced in excess is the amplification product to be detected. A plurality of different primers may be used to amplify different target polynucleotides or different regions of a particular target polynucleotide within the sample.

An amplification reaction can be performed under conditions which allow an optionally labeled sensor polynucleotide to hybridize to the amplification product during at least part of an amplification cycle. When the assay is performed in this manner, real-time detection of this hybridization event can take place by monitoring for light emission or fluorescence during amplification, as known in the art.

Where the amplification product is to be used for hybridization to an array or microarray, a number of suitable commercially available amplification products are available. These include amplification kits available from NuGEN, Inc. (San Carlos, Calif.), including the WT-Ovation™ System, WT-Ovation™ System v2, WT-Ovation™ Pico System, WT-Ovation™ FFPE Exon Module, WT-Ovation™ FFPE Exon Module RiboAmp and RiboAmp$^{Plus}$ RNA Amplification Kits (MDS Analytical Technologies (formerly Arcturus) (Mountain View, Calif.), Genisphere, Inc. (Hatfield, Pa.), including the RampUp Plus™ and SenseAmp™ RNA Amplification kits, alone or in combination. Amplified nucleic acids may be subjected to one or more purification reactions after amplification and labeling, for example using magnetic beads (e.g., RNAClean magnetic beads, Agencourt Biosciences).

Multiple RNA biomarkers can be analyzed using real-time quantitative multiplex RT-PCR platforms and other multiplexing technologies such as GenomeLab GeXP Genetic Analysis System (Beckman Coulter, Foster City, Calif.), SmartCycler® 9600 or GeneXpert® Systems (Cepheid, Sunnyvale, Calif.), ABI 7900 HT Fast Real Time PCR system (Applied Biosystems, Foster City, Calif.), LightCycler® 480 System (Roche Molecular Systems, Pleasanton, Calif.), xMAP 100 System (Luminex, Austin, Tex.) Solexa Genome Analysis System (Illumina, Hayward, Calif.), OpenArray Real Time qPCR (BioTrove, Woburn, Mass.) and BeadXpress System (Illumina, Hayward, Calif.).

Thyroid Classification Arrays

The present invention contemplates that a thyroid classification set or probes derived therefrom may be provided in an array format. In the context of the present invention, an "array" is a spatially or logically organized collection of polynucleotide probes. Any array comprising sensor probes specific for two or more of the target sequences depicted in SEQ ID NOs: 1-659 or a product derived from the target sequences depicted therein can be used. Desirably, an array will be specific for 5, 10, 15, 20, 25, 30, 50, 75, 100, 150, 200, 250, 300, 350, 400, 450, 500, 600, or more of SEQ ID NOs: 1-659. Expression of these sequences may be detected alone or in combination with other transcripts. In some embodiments, an array is used which comprises a wide range of sensor probes for thyroid-specific expression products, along with appropriate control sequences. An array of interest is the Human Exon 1.0 ST Array (HuEx 1.0 ST, Affymetrix, Inc., Santa Clara, Calif.).

In one embodiment, the array comprising sensor probes specific for the target sequences as set forth in SEQ ID NOs: 1-7; the target sequences as set forth in SEQ ID NOs: 1-12 and 283-306; or the target sequences as set forth in SEQ ID NOs: 261, 657, 658, and 659.

Typically the polynucleotide probes are attached to a solid substrate and are ordered so that the location (on the substrate) and the identity of each are known. The polynucleotide probes can be attached to one of a variety of solid substrates capable of withstanding the reagents and conditions necessary for use of the array. Examples include, but are not limited to, polymers, such as (poly)tetrafluoroethylene, (poly)vinylidenedifluoride, polystyrene, polycarbonate, polypropylene and polystyrene; ceramic; silicon; silicon dioxide; modified silicon; (fused) silica, quartz or glass; functionalized glass; paper, such as filter paper; diazotized cellulose; nitrocellulose filter; nylon membrane; and polyacrylamide gel pad. Substrates that are transparent to light are useful for arrays that will be used in an assay that involves optical detection.

Examples of array formats include membrane or filter arrays (for example, nitrocellulose, nylon arrays), plate arrays (for example, multiwell, such as a 24-, 96-, 256-, 384-, 864- or 1536-well, microtitre plate arrays), pin arrays, and bead arrays (for example, in a liquid "slurry"). Arrays on substrates such as glass or ceramic slides are often referred to as chip arrays or "chips." Such arrays are well known in the art. In one embodiment of the present invention, the thyroid classification array is a chip.

Data Analysis

Array data can be managed and analyzed using techniques known in the art. The Genetrix suite of tools can be used for microarray analysis (Epicenter Software, Pasadena, Calif.). Probe set modeling and data pre-processing can be derived using the Robust Multi-Array (RMA) algorithm or variant GC-RMA, Probe Logarithmic Intensity Error (PLIER) algorithm or variant iterPLIER. Variance or intensity filters can be applied to pre-process data using the RMA algorithm, for example by removing target sequences with a standard deviation of <10 or a mean intensity of <100 intensity units of a normalized data range, respectively.

In some embodiments, one or more pattern recognition methods can be used in analyzing the expression level of target sequences. The pattern recognition method can comprise a linear combination of expression levels, or a nonlinear combination of expression levels. In some embodiments, expression measurements for RNA transcripts or combinations of RNA transcript levels are formulated into linear or non-linear models or algorithms (i.e., an 'expression signature') and converted into a likelihood score. This likelihood score indicates the probability that a biological sample is from malignant thyroid nodule disease or benign disease. The likelihood score can be used to distinguish malignant from benign thyroid nodule disease. The models and/or algorithms can be provided in machine readable format, and may be used to correlate expression levels or an expression profile with a disease state, and/or to designate a treatment modality for a patient or class of patients.

Thus, results of the expression level analysis can be used to correlate increased expression of one or more target sequences in group I (or a subset thereof) and/or decreased expression of one or more target sequences in group II (or a subset thereof) with thyroid cancer, and to designate a treatment modality selected from total thyroidectomy, radioactive iodine treatment, and a combination thereof. Patients with benign disease would be candidates for watchful waiting (careful monitoring at regular intervals), thyroid hormone suppression therapy (treating with levothyroxine or other synthetic forms of thyroxine) to shrink the nodule, radioactive iodine to treat hyperfunctioning adenomas or multinodular goiters and surgery. For benign patients surgical management is much more limited to either cosmetic debulking procedures or only partial thyroidectomy leaving thyroid function largely intact. In contrast, the usual treatment for malignant nodules is surgical removal using more aggressive approaches such as near-total or total thyroidectomy followed by radioactive iodine ablation therapy and permanent thyroid hormone replacement therapy. Results of the expression level analysis can be used to correlate increased expression of one or more target sequences in group II (or a subset thereof) and/or decreased expression of one or more target sequences in group I (or a subset thereof) with benign disease, and to designate a treatment modality selected from near-total thyroidectomy, partial thyroidectomy, or watchful-waiting. The preferred treatment regimen for benign or non-neoplastic disease is observation.

Factors known in the art for diagnosing and/or suggesting, selecting, designating, recommending or otherwise determining a course of treatment for a patient or class of patients suspected of having thyroid disease can be employed in combination with measurements of the target sequence expression. These techniques include FNAB cytology and classification, ultrasound analysis, MRI results, CT scan results, thyroid scans, and measurements of thyroid hormone levels.

For example, factors which may be used to indicate a benign condition include a family history of Hashimoto's thyroiditis, of benign thyroid nodule, or of goiter, symptoms of hyper- or hypothyroidism, pain or tenderness associated with a nodule, a nodule that is soft, smooth and mobile, a multinodular goiter without a predominant nodule, a nodule that is "warm" on a thyroid scan, or an ultrasound indication of a simple cyst structure.

Factors which may be used to indicate a malignant thyroid condition include patient age less than 20 or greater than seventy, male gender, new onset of swallowing difficulties or hoarseness, a history of external neck irradiation, a nodule that is firm, irregular and fixed, cervical lymphadenopathy, a history of thyroid cancer, a nodule that is "cold" on a thyroid scan, and a solid or complex morphology seen on ultrasound.

Certified tests for classifying thyroid disease status and/or designating treatment modalities are also provided. A certified test comprises a means for characterizing the expression levels of one or more of the target sequences of interest, and a certification from a government regulatory agency endorsing use of the test for classifying the thyroid disease status of a biological sample.

In some embodiments, the certified test may comprise reagents for amplification reactions used to detect and/or quantitate expression of the target sequences to be characterized in the test. An array of probe nucleic acids can be used, with or without prior target amplification, for use in measuring target sequence expression.

The test is submitted to an agency having authority to certify the test for use in distinguishing benign from malignant thyroid tissues. Results of detection of expression levels of the target sequences used in the test and correlation with disease status and/or outcome are submitted to the agency. A certification authorizing the diagnostic and/or prognostic use of the test is obtained.

Also provided are portfolios of expression levels comprising a plurality of normalized expression levels of the target sequences described herein, including SEQ ID NOs: 1-659. Such portfolios may be provided by performing the methods described herein to obtain expression levels from an individual patient or from a group of patients. The expression levels can be normalized by any method known in the art; exemplary normalization methods that can be used in various embodiments include Robust Multichip Average (RMA), probe logarithmic intensity error estimation (PLIER), non-linear fit (NLFIT) quantile-based and nonlinear normalization, and combinations thereof. Background correction can also be performed on the expression data; exemplary techniques useful for background correction include mode of intensities, normalized using median polish probe modeling and sketch-normalization.

In some embodiments, portfolios are established such that the combination of genes in the portfolio exhibit improved sensitivity and specificity relative to known methods. In considering a group of genes for inclusion in a portfolio, a small standard deviation in expression measurements correlates with greater specificity. Other measurements of variation such as correlation coefficients can also be used in this capacity. The invention also encompasses the above methods where the specificity is at least about 50% and at least about 60%. The invention also encompasses the above methods where the sensitivity is at least about 90%.

The gene expression profiles of each of the target sequences comprising the portfolio can fixed in a medium such as a computer readable medium. This can take a number of forms. For example, a table can be established into which the range of signals (e.g., intensity measurements) indicative of disease is input. Actual patient data can then be compared to the values in the table to determine whether the patient samples are normal, benign or diseased. In a more sophisticated embodiment, patterns of the expression signals (e.g., fluorescent intensity) are recorded digitally or graphically.

Comparisons can also be used to determine whether the patient is not likely to experience the disease. The expression profiles of the samples are then compared to a control portfolio. If the sample expression patterns are consistent with the expression pattern for cancer then (in the absence of countervailing medical considerations) the patient is treated as one would treat a thyroid cancer patient. If the sample expression patterns are consistent with the expression pattern from the normal/control cell then the patient is diagnosed negative for cancer.

Genes can be grouped so that information obtained about the set of genes in the group can be used to make or assist in making a clinically relevant judgment such as a diagnosis, prognosis, or treatment choice.

A patient report is also provided comprising a representation of measured expression levels of a plurality of target sequences in a biological sample from the patient, wherein the representation comprises expression levels of target sequences corresponding to any one, two, three, four, five, six, eight, ten, twenty, thirty, fifty or more of the target sequences depicted in SEQ ID NOs: 1-659, or of the subsets described herein, or of a combination thereof. In some embodiments, the representation of the measured expression level(s) may take the form of a linear or nonlinear combination of expression levels of the target sequences of interest. The patient report may be provided in a machine (e.g., a computer) readable format and/or in a hard (paper) copy. The report can also include standard measurements of expression levels of said plurality of target sequences from one or more sets of patients with known thyroid status and/or outcome. The report can be used to inform the patient and/or treating physician of the expression levels of the expressed target sequences, the likely medical diagnosis and/or implications, and optionally may recommend a treatment modality for the patient.

Also provided are representations of the gene expression profiles useful for treating, diagnosing, prognosticating, and otherwise assessing disease. In some embodiments, these profile representations are reduced to a medium that can be automatically read by a machine such as computer readable media (magnetic, optical, and the like). The articles can also include instructions for assessing the gene expression profiles in such media. For example, the articles may comprise a readable storage form having computer instructions for comparing gene expression profiles of the portfolios of genes described above. The articles may also have gene expression profiles digitally recorded therein so that they may be compared with gene expression data from patient samples. Alternatively, the profiles can be recorded in different representational format. A graphical recordation is one such format. Clustering algorithms can assist in the visualization of such data.

Kits

Kits for performing the desired method(s) are also provided, and comprise a container or housing for holding the components of the kit, one or more vessels containing one or more nucleic acid(s), and optionally one or more vessels containing one or more reagents. The reagents include those described in the composition of matter section above, and those reagents useful for performing the methods described, including amplification reagents, and may include one or more probes, primers or primer pairs, enzymes (including polymerases and ligases), intercalating dyes, labeled probes, and labels that can be incorporated into amplification products.

In some embodiments, the kit comprises primers or primer pairs specific for those subsets and combinations of target sequences described herein. At least two, three, four or five primers or pairs of primers suitable for selectively amplifying the same number of target sequence-specific polynucleotides can be provided in kit form. In some embodiments, the kit comprises from five to fifty primers or pairs of primers suitable for amplifying the same number of target sequence-representative polynucleotides of interest.

The reagents may independently be in liquid or solid form. The reagents may be provided in mixtures. Control samples and/or nucleic acids may optionally be provided in the kit. Control samples may include tissue and/or nucleic acids obtained from or representative of benign thyroid tissue, as well as tissue and/or nucleic acids obtained from or representative of malignant thyroid tissue.

The nucleic acids may be provided in an array format, and thus an array or microarray may be included in the kit. The kit optionally may be certified by a government agency for use in classifying the disease status of thyroid tissue and/or for designating a treatment modality.

Instructions for using the kit to perform one or more methods of the invention can be provided with the container, and can be provided in any fixed medium. The instructions may be located inside or outside the container or housing, and/or may be printed on the interior or exterior of any surface thereof. A kit may be in multiplex form for concurrently detecting and/or quantitating one or more different target polynucleotides representing the expressed target sequences.

Devices

Devices useful for performing methods of the invention are also provided. The devices can comprise means for characterizing the expression level of a target sequence of the invention, for example components for performing one or more methods of nucleic acid extraction, amplification, and/or detection. Such components may include one or more of an amplification chamber (for example a thermal cycler), a plate reader, a spectrophotometer, capillary electrophoresis apparatus, a chip reader, and or robotic sample handling components. These components ultimately can obtain data that reflects the expression level of the target sequences used in the assay being employed.

The devices may include an excitation and/or a detection means. Any instrument that provides a wavelength that can excite a species of interest and is shorter than the emission wavelength(s) to be detected can be used for excitation. Commercially available devices can provide suitable excitation wavelengths as well as suitable detection components.

Exemplary excitation sources include a broadband UV light source such as a deuterium lamp with an appropriate filter, the output of a white light source such as a xenon lamp or a deuterium lamp after passing through a monochromator to extract out the desired wavelength(s), a continuous wave (cw) gas laser, a solid state diode laser, or any of the pulsed lasers. Emitted light can be detected through any suitable device or technique; many suitable approaches are known in the art. For example, a fluorimeter or spectrophotometer may be used to detect whether the test sample emits light of a wavelength characteristic of a label used in an assay.

The devices typically comprise a means for identifying a given sample, and of linking the results obtained to that sample. Such means can include manual labels, barcodes, and other indicators which can be linked to a sample vessel, and/or may optionally be included in the sample itself, for example where an encoded particle is added to the sample. The results may be linked to the sample, for example in a computer memory that contains a sample designation and a record of expression levels obtained from the sample. Linkage of the results to the sample can also include a linkage to a particular sample receptacle in the device, which is also linked to the sample identity.

The devices also comprise a means for correlating the expression levels of the target sequences being studied with a classification of thyroid disease. Such means may comprise one or more of a variety of correlative techniques, including lookup tables, algorithms, multivariate models, and linear or nonlinear combinations of expression models or algorithms. The expression levels may be converted to one or more likelihood scores, reflecting the likelihood that the sample comprises malignant tissue and/or the likelihood that the sample comprises benign tissue. The models and/or algorithms can be provided in machine readable format, and can optionally further designate a treatment modality for a patient or class of patients The device also comprises output means for outputting the thyroid disease status and/or a treatment modality. Such output means can take any form which transmits the results to a patient and/or a healthcare provider, and may include a monitor, a printed format, or both. The device may use a computer system for performing one or more of the steps provided.

CITATIONS

1: Griffith O L, et al., "Meta-analysis and meta-review of thyroid cancer gene expression profiling studies identifies important diagnostic biomarkers," J Clin Oncol. 2006 Nov. 1, 24(31):5043-51.

2: Puskas L G, et al., "Gene profiling identifies genes specific for well-differentiated epithelial thyroid tumors," Cell Mol Biol (Noisy-le-grand), 2005 Sep. 5, 51(2):177-86.

3: Fujarewicz K, et al., "A multi-gene approach to differentiate papillary thyroid carcinoma from benign lesions: gene selection using support vector machines with bootstrapping," Endocr Relat Cancer. 2007 September, 14(3): 809-26.

4: Kebebew E, et al., "Diagnostic and extent of disease multigene assay for malignant thyroid neoplasms," Cancer. 2006 Jun. 15, 106(12):2592-7.

5: Finley D J, et al., "Discrimination of benign and malignant thyroid nodules by molecular profiling," Ann Surg. 2004 September, 240(3):425-36; discussion 436-7.

6: Mazzanti C, et al., "Using gene expression profiling to differentiate benign versus malignant thyroid tumors," Cancer Res. 2004 Apr. 15:64(8):2898-903. Erratum in: Cancer Res. 2004 Jul. 15, 64(14):5028.

7: Finley D J, et al., "Advancing the molecular diagnosis of thyroid nodules: defining benign lesions by molecular profiling," Thyroid. 2005 June; 15(6):562-8.

8: Cerutti J M, et al., "Diagnosis of suspicious thyroid nodules using four protein biomarkers," Clin Cancer Res. 2006 Jun. 1; 12(11 Pt 1):3311-8.

9: Fryknäs M, et al., "Molecular markers for discrimination of benign and malignant follicular thyroid tumors," Tumour Biol. 2006; 27(4):211-20.

10: Hamada A, et al., "Diagnostic usefulness of PCR profiling of the differentially expressed marker genes in thyroid papillary carcinomas," Cancer Lett. 2005 Jun. 28, 224(2):289-301.

11: Yukinawa N, et al., "A multi-class predictor based on a probabilistic model: application to gene expression profiling-based diagnosis of thyroid tumors," BMC Genomics. 2006 Jul. 27, 7:190.

12: Griffiths O L, et al., "Biomarker panel diagnosis of thyroid cancer: a critical review," Expert Rev. Anticancer Therapy. 2008 September, 8(9): 1399-1413.

13. Prasad N B, et al., "Identification of Genes Differentially Expressed in Benign versus Malignant Thyroid Tumors," Clinical Cancer Res. 2008 Jun. 1, 14(11):3327-37.

14. Shibru D, et al., "Does the 3-gene diagnostic assay accurately distinguish benign from malignant thyroid neoplasms?" Cancer. 2008 Sep. 1; 113(5):930-5.

15. Fontaine J F, et al., "Increasing the number of thyroid lesions classes in microarray analysis improves the relevance of diagnostic markers," PLoS One. 2009 Oct. 29; 4(10):e7632.

PATENT DOCUMENTS

1. US 2005/0042222
2. US 2007/0037186
3. U.S. Pat. No. 7,319,011
4. WO 2005/085471
5. WO 2005/085471
6. WO 2005/100608
7. WO 2005/100608
8. WO 2006/047484
9. WO 2006/127537

EXAMPLES

To gain a better understanding of the invention described herein, the following examples are set forth. It will be understood that these examples are intended to describe illustrative embodiments of the invention and are not intended to limit the scope of the invention in any way. Efforts have been made to ensure accuracy with respect to numbers used (e.g., amounts, temperature, etc.) but some experimental error and deviation should be accounted for. Unless otherwise indicated, parts are parts by weight, temperature is degree centigrade and pressure is at or near atmospheric, and all materials are commercially available.

Example 1

Identification of Target Sequences Differentially Expressed in Benign and Malignant Thyroid One hundred and ten genes were identified as having increased expression in malignant thyroid nodule disease tissue relative to benign thyroid nodule disease tissue, and fifty eight genes were identified as having increased relative expression in benign thyroid disease relative to malignant thyroid nodule disease from a detailed literature review (see citations #1-15) (Table 1). The 110 and 58 gene lists were used to identify 5491 and 3651 respective target sequences (i.e., probesets) from these genomic regions on the Affymetrix Human Exon 1.0 ST GeneChip microarray, totaling 9,142 candidate target sequences.

These candidate 9,149 target sequences were further analyzed through several rounds of technical and biological data filtering to select those most likely to provide a selective, reproducible assay. The candidate target sequences were evaluated for potential cross-hybridization with transcribed sequences that would interfere with unique detection. Only those target sequences that were predicted to uniquely hybridize to a single target were considered further, reducing the candidate target sequences to 7,826 (i.e., removing 1,252 probeset)). Probesets with known cross-hybridization properties (i.e., probesets that map to multiple locations in the human genome) were obtained from the supporting annotation files downloaded from the Affymetrix website (www.affymetrix.com). Further biological filtering of probesets was performed using a microarray dataset of whole-transcriptome expression profiles from 48 thyroid nodule disease specimens (formalin-fixed paraffin embedded thyroidectomy samples with pathological characteristics as indicated in Table 2). Affymetrix HuEx 1.0 ST microarray expression data was modeled and normalized using the iterPLIER algorithm and log transformation. A background expression filter removed probesets whose maximal expression was lower than the background expression level (100 units of a normalized data range) in all 48 samples leaving 4,917 probesets for differential expression analysis. Differentially expressed probesets between malignant (n=23) and benign (n=25) (based on the 'gold-standard' pathology review diagnosis) thyroid nodule disease were determined based on three probeset selection criteria; a) at least 2-fold mean difference in expression, b) a student's t-test p<0.001 (with a Benjamini-Hochberg false discovery correction) and c) mean expression of >100 units (i.e., above background) in either the malignant or benign groups of thyroid nodule disease. With these probeset selection criteria, 279 (from 58 genes) and 377 (from 43 genes) probesets were found at increased expression in malignant and benign thyroid nodule disease samples, respectively (Table 3). Intriguingly, the majority of the probesets (59%) identified in this analysis do not overlap with the protein coding sequence (CDS) as indicated by the start point of initiation codon to the end point termination codon location of the translated protein from the mRNA (FIG. 1). Therefore, this data suggests that in the formalin-fixed paraffin embedded thyroidectomy specimens non-coding target sequences from thyroid nodule disease diagnostic genes identified in the literature are more likely to be detectable as differentially expressed between malignant and benign clinical samples than are the target sequences from protein coding sequence.

By applying the selection criteria from genes identified in literature as described above, we defined target sequences that are detectable and differentially expressed in routine thyroid nodule disease clinical samples (e.g., FFPE thyroidectomies) and therefore may be of diagnostic value for thyroid nodule disease. Increased relative expression of one or more encoded sequences from the 279 target sequences representing 58 genes in Table 3 having increased expression in thyroid cancer can be used to designate a sample as malignant thyroid cancer. Additionally, a decreased relative level of expression of one or more encoded sequences from the 377 target sequences representing the 43 genes in Table 3 can also be used to designate the sample as malignant thyroid cancer, alone or in combination with one or more increased expression levels from the 58 gene set.

Conversely, increased relative expression of one or more encoded sequences from the 377 target sequences representing the 43 genes in Table 3 having increased expression in benign disease can be used to designate a sample as benign. Similarly, a decreased relative level of expression of one or more encoded sequences from the 279 target sequences representing the 58 genes in Table 3 can also be used to designate the sample as benign, alone or in combination with one or more increased expression levels from the 43 gene set.

The data can be used to designate disease state, and/or to recommend or designate one or more treatment modalities for patients, to produce patient reports, and to prepare expression profiles. By measuring the expression level of each transcript in a patient sample and multiplying it by a weighting factor a linear combination of the expression signature (reduced to one variable) can be determined for each patient. Thresholds will be applied to determine whether or not the weighted expression signature score is indicative of malignant or benign thyroid nodule disease. Similarly, such expression data from the filtered subsets described below may also be employed in these techniques.

Example 2

Identification of Minimal Thyroid Nodule Disease Expression Signatures and Evaluation in Pre-Operative Patient Specimens In order to determine the appropriate number of target sequences necessary to obtain a minimal expression signature we used the Nearest Shrunken Centroids (NSC) method. In this method (see US 20070031873), a standardized centroid is computed for each class. This is the average gene expression for each gene in each class divided by the within-class standard deviation for that gene. Nearest centroid classification was done under cross-validation, so that on each iteration, 5 out of 48 samples was removed for class centroid computation (~10% cross-validation). In this manner, we identified a 36 target sequence signature (Table 4) with an estimated cross-validated error rate of 6.3%. We also identified a subset of 7 target sequences (Table 5), a minimal expression signature that maintained the overall cross-validated error rate of 6.3%. With both signatures, three samples were misclassified by the centroid classification approach of which all were follicular lesions: two follicular carcinomas had a predicted class of benign and one follicular adenoma had a predicted class of malignant.

Figure 2:
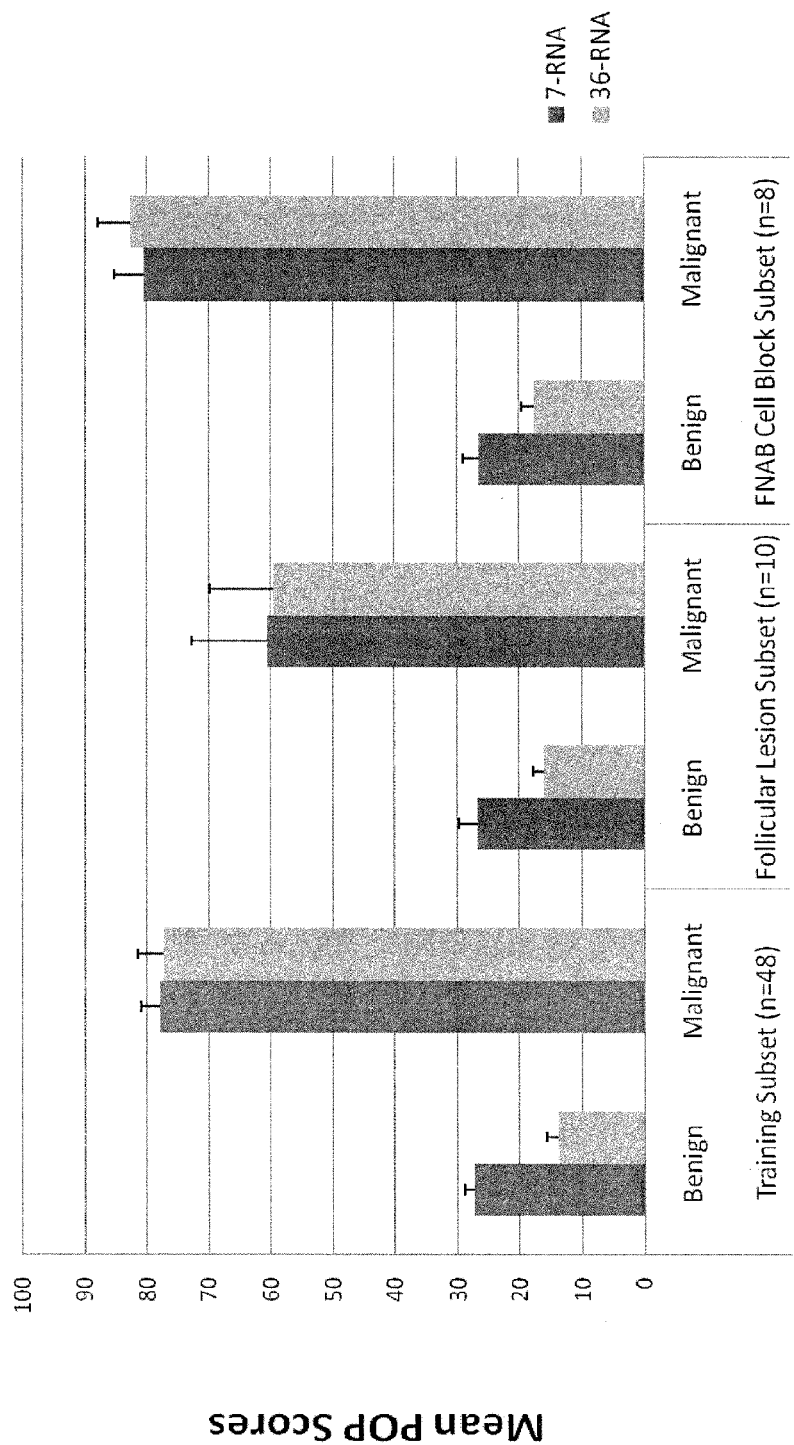
FIG. 2 depicts mean POP scores for pathological diagnostic categories of malignant and benign patient specimens in the three subsets of patient specimens evaluated. 'POP' (patient outcome predictor) scores for thyroid nodule disease benign and malignant sample groups were derived using 7- and 36-RNA target sequence metagenes to generate patient outcome predictor scores normalized on a data range of 0-100 points. Differences in POP scores between benign and malignant thyroid nodule disease groups were highly significant as evaluated by t-tests for significance (p<1E-6). Error bars indicate the standard error of the mean.
Figure 3:
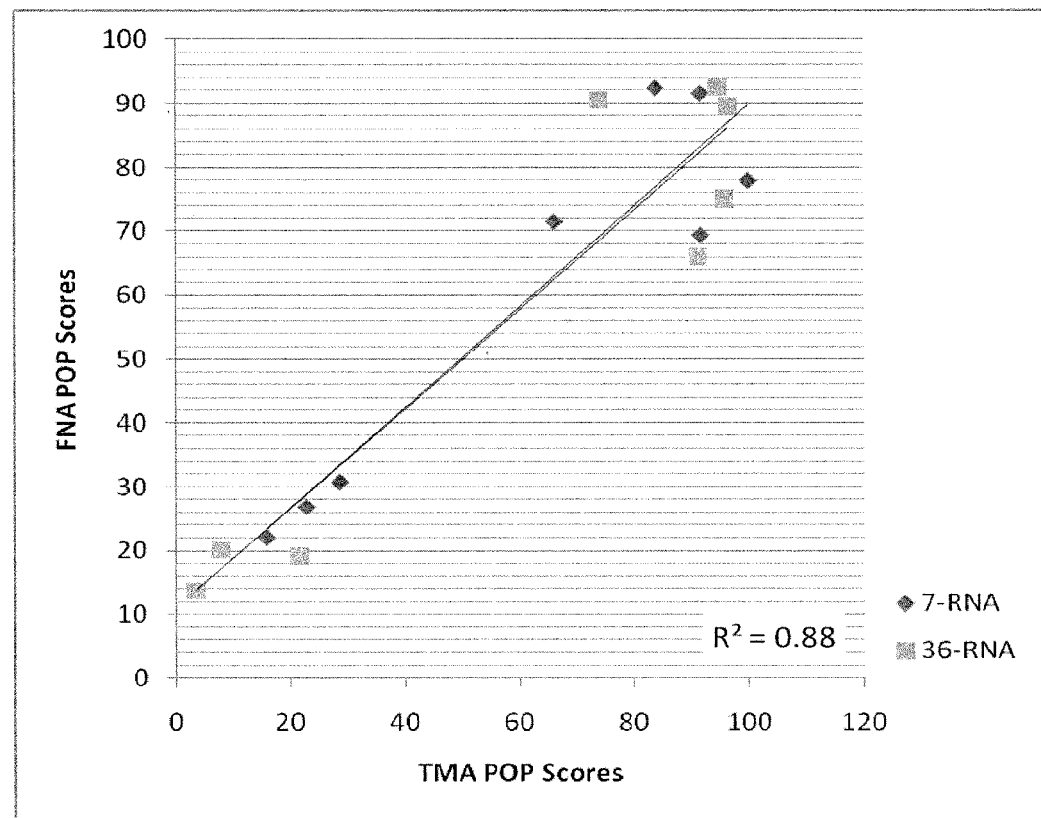
FIG. 3 shows the correlation between POP scores generated using the 7- and 36-RNA metagenes in analysis of pre-operative and post-operative specimens for a subset of eight patients. The correlation coefficient $R^2$ value is 0.88 for both of target sequence metagenes.
Figure 4:
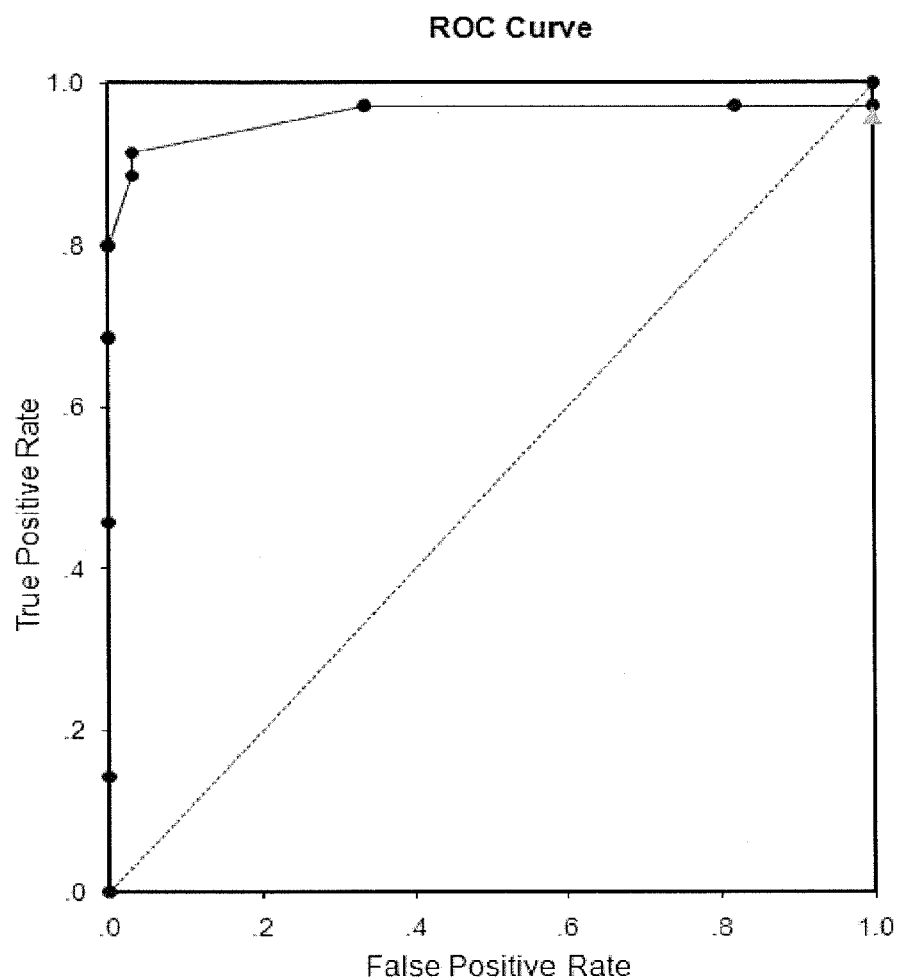
FIG. 4 depicts receiver-operator curves (ROC) of the POP scores derived from the 7-RNA metagene. The area-under-the curve is indicated below the ROC curve and show that the POP scores as a continuous variable (i.e., without setting an arbitrary cut-points) are excellent discriminators of malignant and benign disease.
Figure 5:
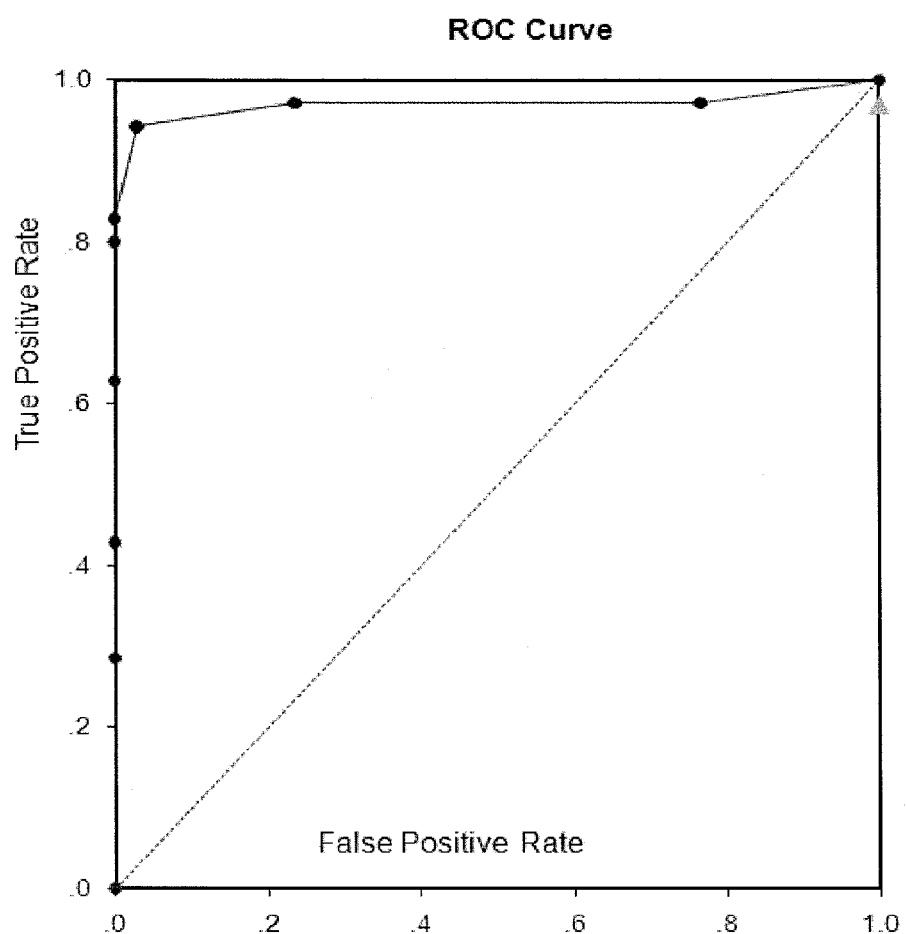
FIG. 5 depicts receiver-operator curves (ROC) of the POP scores derived from the 36-RNA metagene. The area-under-the curve is indicated below the ROC curve and show that the POP scores as a continuous variable (i.e., without setting an arbitrary cut-points) are excellent discriminators of malignant and benign disease.

Next, 36- and 7-target sequence 'metagenes' were created with the target sequences in Table 4 and 5 using a simple linear combination by measuring the expression levels of the corresponding RNAs for each patient and multiplying each measurement by a corresponding weighting factor and combining these values into a single variable. Weighting factors were derived from the test statistic coefficients from a t-test for significance when comparing malignant and benign pathology review diagnoses (Table 4). Patient outcome predictor ('POP') scores were generated from the metagene values for each patient by scaling and normalizing the metagene scores within a range of 0 to 100. We used arbitrary cut-points to establish a diagnostic criteria—a value of between 0-40 points was used to indicate a patient with benign thyroid nodule disease and 40-100 points a patient with malignant thyroid nodule disease (FIG. 2). Using these cut-point criteria, the evaluation of the 7-RNA target sequence metagene in the training subset revealed that 22/23 patients with malignant thyroid nodule disease had POP scores above 40 points and 24/25 patients with benign thyroid nodule disease had scores below 40 points (Table 6). Using the same cut-point criteria, the 36-RNA target sequence metagene in the training subset revealed that 20/23 patients with malignant thyroid nodule disease had POP scores above 40 points and 24/25 patients with benign thyroid nodule disease had scores below 40 points (Table 6). The 7- and 36-RNA target sequence metagenes were further validated on two independent subsets of ten and eight patient specimens (see Table 2) that were not used to identify or select the target sequences described in Table 3. The ten specimen 'follicular lesion only' subset were from patients diagnosed with follicular pattern lesions, that were all indeterminate or 'suspicious for cancer' based on cytology fine-needle aspirate diagnosis. All ten of these patients were treated with total-thyroidectomy however, pathology review diagnosis revealed that only five of these patients actually had a malignant thyroid nodule disease lesion warranting total thyroidectomy. For the 7-RNA target sequence metagene, all five of the follicular adenoma (i.e., patients diagnosed with benign disease) specimens had POP scores of less than 40 points and 4/5 patients with follicular carcinoma or follicular variant of papillary carcinoma had scores of greater than 40 points (Table 6). For the 7-RNA target sequence metagene, all five of the follicular adenoma (i.e., patients diagnosed with benign disease) specimens had POP scores of less than 40 points and 4/5 patients with follicular carcinoma or follicular variant of papillary carcinoma had scores of greater than 40 points (Table 6). For the 36-RNA target sequence metagene, all five of the follicular adenoma (i.e., patients diagnosed with benign disease) specimens had POP scores of less than 40 points and 3/5 patients with follicular carcinoma or follicular variant of papillary carcinoma had scores of greater than 40 points (Table 6). In the second validation subset of specimens, eight samples were from cell blocks prepared from pre-operative fine-needle aspirates. These samples were from a subset of eight patients whose post-operative FFPE thyroidectomy specimens were profiled in the training subset. POP scores for these specimens showed that 3/3 patients with pathology review benign diagnoses had scores of less than 40 points and 5/5 patients with pathology review malignant diagnoses had scores of greater than 40 points. POP scores derived from pre- (i.e., FNA cell blocks) and post-operative (i.e., TMA FFPE thyroidectomy) specimens from the 7- and 36-RNA target sequence metagenes were highly correlated, both with an $R^2$ value of 0.88 (FIG. 3). This data suggests that the 7- and 36-RNA target sequence metagene expression signatures and derived POP scores can be applied to exact an identical diagnosis from patients either before the surgery via a fine-needle aspiration of thyroid cells or after the thyroid is removed from the patient. In order to evaluate the diagnostic accuracy of the 7- and 36-RNA metagene POP scores in comparison to the 'gold-standard' review pathology diagnosis in a manner where no a priori cut-points are pre-determined, receiver-operator characteristic (ROC) curves were generated. ROC curves for the 7- and 36-RNA metagene POP scores are depicted in FIGS. 4 and 5 and show that the area-under-the curve was above 96% and 97%, respectively demonstrating that both expression signatures and the POP specimen scoring method are performing extremely well as a diagnostic test.

Example 3

Differential Expression of SPOCK1 Target Sequences

Intriguingly, several of target sequences showed the reverse correlation in terms of differential expression than a gene-level analysis would suggest. For example, the gene SPOCK1 has been previously reported as found at increased expression in malignant than benign thyroid nodule disease (see Prasad N B et al., citation #13).

Figure 6:
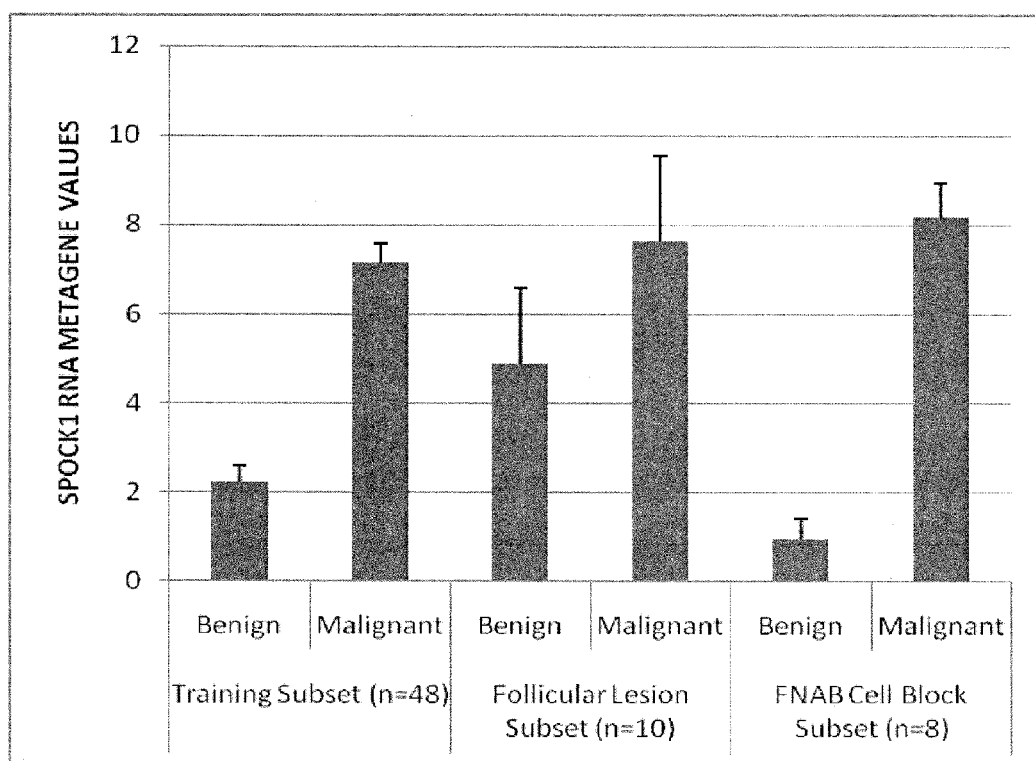
FIG. 6 depicts mean SPOCK1 RNA metagene values for pathological diagnostic categories of malignant and benign patient specimens in the three subsets of patient specimens evaluated. SPOCK1 RNA metagene was generated by a weighted linear combination of expression values for exon 11, intron 2, 3 and 6 RNA target sequences. Error bars indicate the standard error of the mean.

However, on the individual RNA transcript level over 2- and 1.8-fold mean increased expression of exon 11 and intron 2 RNAs, respectively was observed in malignant (rel. to benign) thyroid nodule disease samples, whereas nearly 8.6- and 1.2-fold mean increased expression of intron 6 and intron 3 RNAs, respectively was observed in benign (rel. to malignant) thyroid nodule disease samples (Table 7). Furthermore, the protein-coding strand of the SPOCK1 by convention occurs of the negative (or alternatively, 'bottom') strand and while the RNAs representing the target sequence for the protein-encoding exon 11 RNA is transcribed in this sense direction, the target sequences for introns 2, 3 and 6 are transcribed in an antisense direction to transcription, that is off the positive (or alternatively, 'top') strand of the gene. Using these four SPOCK1 RNAs, a SPOCK1-target sequence metagene was generated as described in Example #1. FIG. 6 shows the mean metagene values for of these SPOCK1 RNAs in the three subsets of patient specimens analyzed. The differences in mean overall expression for SPOCK1 RNAs clearly distinguish malignant from benign thyroid nodule disease in the training subset and the FNAB subset. In the follicular lesion subset, the mean metagene values did show some overlap. In summary, this data suggests that gene-level analysis (e.g., using 3' biased microarrays such as U133 Plus 2.0) can miss important differences in transcription such as intron retention, antisense transcription, alternative splicing or exon usage and non-coding (i.e., translated into protein) RNA expression observed in this whole-transcriptome analysis. In particular, non-coding RNA the predominant RNA species (over 90% of the transcription in the genome) represent functional RNA molecules that are thought to convey key differences between pathological conditions through regulatory roles of protein-encoding gene expression. This is a potentially rich source of diagnostic information that cannot be captured by solely observing differences in protein-encoding gene expression or protein biomarker expression and may improve the diagnosis of specific pathological conditions of clinical importance such as malignant vs. benign in thyroid nodule disease.

These scoring systems can be used to select or guide the selection of treatment modalities such as observation and/or thyroid lobectomy for benign thyroid nodule disease patients, and total thyroid resection for malignant thyroid nodule disease. Other metagenes can similarly be created using other combinations of target sequence expression, for example using one or more of the target sequences depicted in any of the Tables.

Materials and Methods:

Tissue Samples.

Sixty (60) formalin-fixed paraffin embedded (FFPE) surgical specimens of human thyroid nodule disease were collected from patients at the Department of Surgery, St. Paul's Hospital (Vancouver, BC, Canada) according to an institutional review board-approved protocol. For a subset of 8 surgical specimens, fine-needle aspirate cell blocks were also available. For surgical specimens, a tissue microarrayer (Beecher Instruments, Silver Spring, Md.) was used to core each FFPE surgical resected specimen once with either a 0.6 mm or 1.0 diameter cylinder ('FFPE TMA'). Surgical resected samples from 60 patients were evaluated. These samples were divided into three subsets consisting of a training (n=48) and a validation (n=10) subset of patients. Table 1 shows the composition of the subsets including the original cytology diagnosis as well as the 'gold-standard' pathology review diagnosis (obtained from careful dissection and histopathological analysis of specimens after thyroidectomy procedures). From cell blocks, 3 ten micron sections were obtained using a microtome. Cell block specimens were matched to 8 of the FFPE TMA surgical specimen samples evaluated.

Extraction of RNA.

RNA was extracted and purified from the FFPE TMA cores using a modified protocol for the commercially available Formapure nucleic acid extraction kit (Agencourt Biosciences, Beverly Mass.). Principal modifications to the kit protocol included preheating the lysis buffer to 70° C. before immersing the FFPE sections in lysis buffer and then subjecting FFPE lysates to incubation at 99° C. for 1 min. In addition, FFPE samples were incubated with Proteinase K (20 ul of 40 mg/mL) for 16 hrs in a water bath at 55° C. RNA was further purified using DNAse I treatment (Ambion, Austin, Tex.) to eliminate any contaminating DNA. RNA was eluted with 300 ul of RNAse-free water and subsequently concentrated and purified using sodium acetate precipitation and a series of ethanol washes and resuspended in 15 ul of water. RNA concentrations were calculated using a Nanodrop ND-1000 spectrophotometer (Nanodrop Technologies, Rockland, Del.). These additional purification steps significantly improved the yield of amplified material in subsequent steps described below (data not shown). RNA integrity was evaluated by running electropherograms and RNA integrity number, RIN (a correlative measure that indicates intactness of mRNA) was determined using the RNA 6000 PicoAssay for the Bioanalyzer 2100 (Agilent Technologies, Santa Clara, Calif.). Sufficient RNA (75 ng) was obtained using these procedures from all 60 FFPE TMA cores and 8 cell block microtome sections.

Nucleic Acid Amplification and GeneChip Hybridization.

Purified RNA was subjected to whole-transcriptome amplification using the WT-Ovation FFPE system including the WT-Ovation Exon and FL-Ovation Biotin V2 labeling modules, with the following modifications. Seventy-five (75) nanograms of RNA extracted from FFPE TMA cores or FNAB cell blocks was used to generate amplified Ribo-SPIA product. For the WT-Ovation Exon sense-target strand conversion kit 4 ug of Ribo-SPIA product were used. Between 2.5 and 5 micrograms of WT-Ovation Exon product were used to fragment and label using the FL-Ovation Biotin V2 labeling module and labeled product was hybridized to Affymetrix Human Exon 1.0 ST GeneChips following manufacturer's recommendations (Affymetrix, Santa Clara, Calif.).

Microarray Analysis.

All data management and analysis was conducted using the Genetrix suite of tools for microarray analysis (Epicenter Software, Pasadena, Calif.). Probe set modeling and data pre-processing were derived using the iterPlier algorithm (Affymetrix, Santa Clarita, Calif.). The mode of intensity values was used for background correction and sketch was used for normalization and probe modeling used a median polish routine. Outlier samples were identified by evaluating the median absolute deviation of the normalized expression values in each sample and $25^{th}$ percentile outlier samples. Two samples from the testing cohort were removed from further analysis because they were clearly outliers using both quality control metrics described above. A variance filter was applied to data pre-processed using the iterPlier algorithm, by removing probe set regions (PSRs) with a mean intensity of <10 intensity units of a normalized data range. PSRs are comprised of an average of four individual probes that interrogate the expression of RNA transcripts or portions thereof. PSR annotations and the sequences (RNAs) that they interrogate were downloaded from the Affymetrix website (www.netaffx.com). An additional filter employed was to remove PSRs with known cross-hybridization properties (i.e., significant homology to more than one transcript from different genes or loci), leaving 1,134,588 PSRs for further analysis. Cross-hybridization properties of PSRs were downloaded from the Affymetrix website. Supervised analysis of differentially expressed RNA transcripts was determined based on the fold difference in the average expression (at least 2 fold difference) and the associated t-test, with a p-value cut-off of $p<0.001$ between malignant and benign thyroid nodule disease samples using the final pathology review diagnosis obtained from analysis of surgical specimens as the benchmark diagnosis.

Although the invention has been described with reference to certain specific embodiments, various modifications thereof will be apparent to those skilled in the art without departing from the spirit and scope of the invention. All such modifications as would be apparent to one skilled in the art are intended to be included within the scope of the claims.

TABLE 1

Examples of Suitable Genes for Inclusion in a Thyroid Classification Library

| Gene Symbol | Gene |
|---|---|
| | Thyroid Malignant- Increased Expression |
| ADORA1 | Adenosine A1 receptor |
| ALOX5 | Arachidonate 5-lipoxygenase |
| AMIGO2 | Adhesion molecule with Ig-like domain 2 |
| APOE | Apolipoprotein E |
| ARHGAP11A | Rho GTPase activating protein 11A |
| ARMCX3 | Armadillo repeat containing, X-linked 3 |
| C7orf24 | Chromosome 7 open reading frame 24 |
| CA4 | Carbonic anhydrase IV |
| CAMK2N1 | Calcium/calmodulin-dependent protein kinase II inhibitor 1 |
| CCND1 | Cyclin D1 |
| CD44 | CD44 molecule (Indian blood group) |
| CD55 | CD55 molecule, decay accelerating factor for complement (Cromer blood group) |
| CDH16 | Cadherin 16, KSP-cadherin |
| CDH3 | Cadherin 3, type 1, P-cadherin (placental) |
| CDKN2A | Cyclin-dependent kinase inhibitor 2A (melanoma, p16, inhibits CDK4) |
| CHI3L1 | Chitinase 3-like 1 (cartilage glycoprotein-39) |
| CHRDL1 | Chordin-like 1 |
| CHST2 | Carbohydrate (N-acetylglucosamine-6-O) sulfotransferase 2 |
| CITED1 | Cbp/p300-interacting transactivator, with Glu/Asp-rich carboxy-terminal domain, 1 |
| CKS2 | CDC28 protein kinase regulatory subunit 2 |
| CSNK1G2 | Casein kinase 1, gamma 2 |
| CST6 | Cystatin E/M |
| CTSC | Cathepsin C |
| CTSH | Cathepsin H |
| CTSS | Cathepsin S |
| DLG7 | Discs, large homolog 7 (*Drosophila*) |
| DPP4 | Dipeptidyl-peptidase 4 (CD26, adenosine deaminase complexing protein 2) |
| DUSP5 | Dual specificity phosphatase 5 |
| DUSP6 | Dual specificity phosphatase 6 |
| ENDOD1 | Endonuclease domain containing 1 |
| EPS8 | Epidermal growth factor receptor pathway substrate 8 |
| ETHE1 | Ethylmalonic encephalopathy 1 |
| ETV5 | Ets variant gene 5 (ets-related molecule) |
| FAM129A | Family with sequence similarity 129, member A |
| FAM129B | Family with sequence similarity 129, member B |
| FAM129C | Family with sequence similarity 129, member C |
| FBLN1 | Fibulin 1 |
| FN1 | Fibronectin 1 |
| GABBR2 | Gamma-aminobutyric acid (GABA) B receptor, 2 |
| GALE | UDP-galactose-4-epimerase |
| GALNT7 | UDP-N-acetyl-alpha-D-galactosamine: polypeptide N-acetylgalactosaminyltransferase 7 (GalNAc-T7) |
| GDF15 | Growth differentiation factor 15 |
| GJB3 | Gap junction protein, beta 3, 31 kDa |
| GPM6A | Glycoprotein M6A |
| HBD | Hemoglobin, delta |
| HLA-DMB | Major histocompatibility complex, class II, DM beta |
| HLA-DQA1 | Major histocompatibility complex, class II, DQ alpha 1 |
| HLA-DRA | Major histocompatibility complex, class II, DR alpha |
| HMGA2 | High mobility group AT-hook 2 |
| ICAM1 | Intercellular adhesion molecule 1 (CD54), human rhinovirus receptor |
| ICAM4 | Intercellular adhesion molecule 4 (Landsteiner-Wiener blood group) |
| IGFBP6 | Insulin-like growth factor binding protein 6 |
| IGSF1 | Immunoglobulin superfamily, member 1 |
| KCNJ2 | Potassium inwardly-rectifying channel, subfamily J, member 2 |
| KIAA0746 | KIAA0746 protein |
| KLK10 | Kallikrein-related peptidase 10 |
| KRT15 | Keratin 15 |
| KRT19 | Keratin 19 |
| LAMB3 | Laminin, beta 3 |
| LCN2 | Lipocalin 2 |
| LGALS3 | Lectin, galactoside-binding, soluble, 3 |
| LPL | Lipoprotein lipase |
| LRP4 | Low density lipoprotein receptor-related protein 4 |
| MET | Met proto-oncogene (hepatocyte growth factor receptor) |
| MPZL2 | Myelin protein zero-like 2 |
| MPZL3 | Myelin protein zero-like 3 |
| MRC2 | Mannose receptor, C type 2 |
| MUC1 | Mucin 1, cell surface associated |
| MYBPH | Myosin binding protein H |
| NELL2 | NEL-like 2 (chicken) |
| NMU | Neuromedin U |
| NRCAM | Neuronal cell adhesion molecule |
| NRIP1 | Nuclear receptor interacting protein 1 |
| P4HA2 | Procollagen-proline, 2-oxoglutarate 4-dioxygenase (proline 4-hydroxylase), alpha polypeptide II |
| PDLIM4 | PDZ and LIM domain 4 |
| PDZK1IP1 | PDZK1 interacting protein 1 |
| PLAU | Plasminogen activator, urokinase |
| PLXNC1 | Plexin C1 |
| PRMT8 | Protein arginine methyltransferase 8 |
| PROS1 | Protein S (alpha) |
| PRSS23 | Protease, serine, 23 |
| PSD3 | Pleckstrin and Sec7 domain containing 3 |
| PTPRE | Protein tyrosine phosphatase, receptor type, E |
| QPCT | Glutaminyl-peptide cyclotransferase (glutaminyl cyclase) |
| RCN3 | Reticulocalbin 3, EF-hand calcium binding domain |
| RET | Ret proto-oncogene |
| RXRG | Retinoid X receptor, gamma |
| S100A10 | S100 calcium binding protein A10 |
| SCG5 | Secretogranin V (7B2 protein) |
| SDC4 | Syndecan 4 |
| SERPINA1 | Serpin peptidase inhibitor, clade A (alpha-1 antiproteinase, antitrypsin), member 1 |
| SFTPB | Surfactant, pulmonary-associated protein B |
| SLC27A6 | Solute carrier family 27 (fatty acid transporter), member 6 |
| SLC34A2 | Solute carrier family 34 (sodium phosphate), member 2 |
| SLC5A5 | Solute carrier family 5 (sodium iodide symporter), member 5 |
| SLPI | Secretory leukocyte peptidase inhibitor |
| SOX4 | SRY (sex determining region Y)-box 4 |
| SPOCK1 | Sparc/osteonectin, cwcv and kazal-like domains proteoglycan (testican) 1 |
| SPP1 | Secreted phosphoprotein 1 (osteopontin, bone sialoprotein I, early T-lymphocyte activation 1) |
| ST14 | Suppression of tumorigenicity 14 (colon carcinoma) |
| SYN1 | Synapsin I |
| TACSTD2 | Tumor-associated calcium signal transducer 2 |
| TGFA | Transforming growth factor, alpha |
| TIAM1 | T-cell lymphoma invasion and metastasis 1 |
| TIMP1 | TIMP metallopeptidase inhibitor 1 |
| TM7SF4 | Transmembrane 7 superfamily member 4 |
| TNC | Tenascin C (hexabrachion) |
| TPD52L1 | Tumor protein D52-like 1 |
| TRIM14 | Tripartite motif-containing 14 |
| TUSC3 | Tumor suppressor candidate 3 |
| | Thyroid Benign- Increased Expression |
| ABCA8 | ATP-binding cassette, sub-family A (ABC1), member 8 |
| ANK2 | Ankyrin 2, neuronal |
| ARG2 | Arginase, type II |
| BCL2 | B-cell CLL/lymphoma 2 |
| BEX1 | Brain expressed, X-linked 1 |
| BMP8A | Bone morphogenetic protein 8a |
| C1orf212 | Chromosome 1 open reading frame 212 |
| CCL14 | Chemokine (C-C motif) ligand 14 |
| CCL21 | Chemokine (C-C motif) ligand 21 |
| CFD | Complement factor D (adipsin) |
| ChGn | Chondroitin beta1,4 N-acetylgalactosaminyltransferase |
| COL9A3 | Collagen, type IX, alpha 3 |
| CRABP1 | Cellular retinoic acid binding protein 1 |
| DDIT3 | DNA-damage-inducible transcript 3 |
| DIO1 | Deiodinase, iodothyronine, type I |

TABLE 1-continued

Examples of Suitable Genes for Inclusion in a Thyroid Classification Library

| Gene Symbol | Gene |
|---|---|
| DIO2 | Deiodinase, iodothyronine, type II |
| EFEMP1 | EGF-containing fibulin-like extracellular matrix protein 1 |
| ELMO1 | Engulfment and cell motility 1 |
| ENPP1 | Ectonucleotide pyrophosphatase/phosphodiesterase 1 |
| FABP4 | Fatty acid binding protein 4, adipocyte |
| FCGBP | Fc fragment of IgG binding protein |
| FHL1 | Four and a half LIM domains 1 |
| FZD4 | Frizzled homolog 4 (*Drosophila*) |
| HBA2 | Hemoglobin, alpha 2 |
| HLF | Hepatic leukemia factor |
| ID4 | Inhibitor of DNA binding 4, dominant negative helix-loop-helix protein |
| ITM2A | Integral membrane protein 2A |
| ITPR1 | Inositol 1,4,5-triphosphate receptor, type 1 |
| KCNAB1 | Potassium voltage-gated channel, shaker-related subfamily, beta member 1 |
| KIT | V-kit Hardy-Zuckerman 4 feline sarcoma viral oncogene homolog |
| LIPG | Lipase, endothelial |
| LRP2 | Low density lipoprotein-related protein 2 |
| MATN2 | Matrilin 2 |
| MPPED2 | Metallophosphoesterase domain containing 2 |
| MT1F | Metallothionein 1F |
| MT1G | Metallothionein 1G |
| MT1H | Metallothionein 1H |
| MT1M | Metallothionein 1M |
| MT1X | Metallothionein 1X |
| MT2A | Metallothionein 2A |
| MTF1 | Metal-regulatory transcription factor 1 |
| OPRM1 | Opioid receptor, mu 1 |
| PIP3-E | Phosphoinositide-binding protein PIP3-E |
| PPARGC1A | Peroxisome proliferator-activated receptor gamma, coactivator 1 alpha |
| PRIM2 | Primase, DNA, polypeptide 2 (58 kDa) |
| RAB23 | RAB23, member RAS oncogene family |
| RGS16 | Regulator of G-protein signaling 16 |
| RHOBTB3 | Rho-related BTB domain containing 3 |
| SLC1A1 | Solute carrier family 1 (neuronal/epithelial high affinity glutamate transporter, system Xag), member 1 |
| SLC26A4 | Solute carrier family 26, member 4 |
| SOD3 | Superoxide dismutase 3, extracellular |
| STT3A | STT3, subunit of the oligosaccharyltransferase complex, homolog A (*S. cerevisiae*) |
| STT3B | STT3, subunit of the oligosaccharyltransferase complex, homolog B (*S. cerevisiae*) |
| TCEAL2 | Transcription elongation factor A (SII)-like 2 |
| TFF3 | Trefoil factor 3 (intestinal) |
| TPO | Thyroid peroxidase |
| VEGFA | Vascular endothelial growth factor A |
| ZMAT4 | Zinc finger, matrin type 4 |

TABLE 2

Pathological Characteristics of Thyroid Nodule Disease Specimens Used for Data Filtering and Validation of Candidate Target Sequences

| Training Subset | | N |
|---|---|---|
| Fine-Needle Aspirate Cytology Diagnosis | Goiter | 14 |
| | Suspicious for Cancer | 20 |
| | Cancer | 14 |
| Pathology Diagnosis | Benign | 25 |
| | Malignant | 23 |
| Review Histology Diagnosis | Goiter | 15 |
| | Thyroiditis | 1 |
| | Hashimoto's Disease | 1 |
| | Hurthle Cell Adenoma | 4 |
| | Follicular Adenoma | 4 |
| | Follicular Carcinoma | 3 |
| | Papillary Carcinoma | 20 |

| Follicular Lesion Subset | | n |
|---|---|---|
| Fine-Needle Aspirate Cytology Diagnosis | Suspicious for Cancer | 10 |
| Pathology Diagnosis | Benign | 5 |
| | Malignant | 5 |
| Review Histology Diagnosis | Follicular Adenoma | 5 |
| | Follicular Carcinoma | 3 |
| | Papillary Carcinoma | 2 |

| Pre-operative Cell Block Subset | | n |
|---|---|---|
| Fine-Needle Aspirate Cytology Diagnosis | Goiter | 2 |
| | Suspicious for Cancer | 1 |
| | Cancer | 5 |
| Pathology Diagnosis | Benign | 3 |
| | Malignant | 5 |
| Review Histology Diagnosis | Goiter | 2 |
| | Hurthle Cell Adenoma | 1 |
| | Papillary Carcinoma | 5 |

TABLE 3

Thyroid Nodule Disease Candidate Gene RNA Sequences

| SEQ ID | ID | MFD | Weights | Gene | Probeset Overlaps CDS | Target Sequence Subtype |
|---|---|---|---|---|---|---|
| 1 | 3420365 | 14 | 8.75 | High mobility group AT-hook 2 | NO | intronic |
| 2 | 3696401 | 11 | 8.59 | Cadherin 3, type 1, P-cadherin (placental) | NO | exonic |
| 3 | 3577628 | 3 | 8.12 | Serpin peptidase inhibitor, clade A (alpha-1 antiproteinase, antitrypsin), member 1 | YES | exonic |
| 4 | 3415760 | 4 | 5.94 | Insulin-like growth factor binding protein 6 | NO | exonic |
| 5 | 2537615 | −14 | −11.03 | Thyroid peroxidase | NO | antisense |
| 6 | 2727648 | −5 | −9.09 | V-kit Hardy-Zuckerman 4 feline sarcoma viral oncogene homolog | NO | exonic |
| 7 | 3367706 | −31 | −8.23 | Metallophosphoesterase domain containing 2 | NO | intronic |
| 8 | 2828473 | 8 | 10.26 | PDZ and LIM domain 4 | NO | exonic |
| 9 | 2414960 | 24 | 8.9 | Tumor-associated calcium signal transducer 2 | NO | exonic |

TABLE 3-continued

Thyroid Nodule Disease Candidate Gene RNA Sequences

| SEQ ID | ID | MFD | Weights | Gene | Probeset Overlaps CDS | Target Sequence Subtype |
|---|---|---|---|---|---|---|
| 10 | 2526829 | 6 | 8.69 | Fibronectin 1 | NO | antisense |
| 11 | 2526817 | 13 | 8.66 | Fibronectin 1 | NO | antisense |
| 12 | 2598305 | 17 | 8.61 | Fibronectin 1 | NO | intronic |
| 13 | 2338243 | 28 | 8.2 | Tumor-associated calcium signal transducer 2 | NO | exonic |
| 14 | 2598348 | 35 | 8.16 | Fibronectin 1 | NO | intronic |
| 15 | 2598349 | 21 | 8.15 | Fibronectin 1 | NO | intronic |
| 16 | 2598307 | 10 | 8.11 | Fibronectin 1 | YES | exonic |
| 17 | 2562439 | 24 | 7.98 | Surfactant, pulmonary-associated protein B | NO | exonic |
| 18 | 3577632 | 17 | 7.92 | Serpin peptidase inhibitor, clade A (alpha-1 antiproteinase, antitrypsin), member 1 | YES | exonic |
| 19 | 2401582 | 4 | 7.82 | UDP-galactose-4-epimerase | NO | exonic |
| 20 | 2598368 | 32 | 7.78 | Fibronectin 1 | NO | intronic |
| 21 | 2598282 | 8 | 7.77 | Fibronectin 1 | NO | intronic |
| 22 | 3549675 | 12 | 7.77 | Serpin peptidase inhibitor, clade A (alpha-1 antiproteinase, antitrypsin), member 1 | NO | antisense |
| 23 | 2526824 | 16 | 7.7 | Fibronectin 1 | NO | antisense |
| 24 | 2598340 | 15 | 7.67 | Fibronectin 1 | YES | exonic |
| 25 | 2598328 | 13 | 7.65 | Fibronectin 1 | YES | exonic |
| 26 | 3460512 | 4 | 7.64 | High mobility group AT-hook 2 | NO | antisense |
| 27 | 2598278 | 10 | 7.63 | Fibronectin 1 | NO | intronic |
| 28 | 3976357 | 2 | 7.58 | Synapsin I | YES | antisense |
| 29 | 3335899 | 8 | 7.56 | Cystatin E/M | NO | exonic |
| 30 | 2598367 | 10 | 7.55 | Fibronectin 1 | YES | exonic |
| 31 | 2598338 | 8 | 7.54 | Fibronectin 1 | YES | exonic |
| 32 | 2598326 | 10 | 7.51 | Fibronectin 1 | NO | intronic |
| 33 | 2598299 | 8 | 7.49 | Fibronectin 1 | YES | exonic |
| 34 | 3549673 | 9 | 7.45 | Serpin peptidase inhibitor, clade A (alpha-1 antiproteinase, antitrypsin), member 1 | NO | antisense |
| 35 | 2598346 | 7 | 7.35 | Fibronectin 1 | YES | exonic |
| 36 | 2598372 | 9 | 7.31 | Fibronectin 1 | YES | exonic |
| 37 | 2598281 | 10 | 7.3 | Fibronectin 1 | YES | exonic |
| 38 | 2598374 | 11 | 7.27 | Fibronectin 1 | YES | exonic |
| 39 | 2598329 | 9 | 7.25 | Fibronectin 1 | YES | exonic |
| 40 | 2598352 | 10 | 7.2 | Fibronectin 1 | YES | exonic |
| 41 | 2400179 | 5 | 7.19 | Calcium/calmodulin-dependent protein kinase II inhibitor 1 | YES | exonic |
| 42 | 2324040 | 5 | 7.19 | Calcium/calmodulin-dependent protein kinase II inhibitor 1 | NO | exonic |
| 43 | 2375629 | 51 | 7.19 | Chitinase 3-like 1 (cartilage glycoprotein-39) | NO | exonic |
| 44 | 2598342 | 10 | 7.16 | Fibronectin 1 | YES | exonic |
| 45 | 3577630 | 12 | 7.15 | Serpin peptidase inhibitor, clade A (alpha-1 antiproteinase, antitrypsin), member 1 | YES | exonic |
| 46 | 2526820 | 9 | 7.13 | Fibronectin 1 | NO | antisense |
| 47 | 2598358 | 17 | 7.12 | Fibronectin 1 | YES | exonic |
| 48 | 2598321 | 16 | 7.1 | Fibronectin 1 | YES | intronic |
| 49 | 2598302 | 10 | 7.09 | Fibronectin 1 | YES | exonic |
| 50 | 3536718 | 13 | 7.09 | Lectin, galactoside-binding, soluble, 3 | NO | intronic |
| 51 | 2598289 | 19 | 7.09 | Fibronectin 1 | YES | exonic |
| 52 | 3976358 | 7 | 7.07 | Synapsin I | YES | antisense |
| 53 | 3335898 | 7 | 7.07 | Cystatin E/M | YES | exonic |
| 54 | 2598296 | 14 | 7.06 | Fibronectin 1 | YES | exonic |
| 55 | 2598271 | 8 | 7.05 | Fibronectin 1 | YES | exonic |
| 56 | 2526809 | 10 | 7.05 | Fibronectin 1 | NO | exonic |
| 57 | 2598277 | 10 | 7.04 | Fibronectin 1 | YES | exonic |
| 58 | 2598280 | 8 | 7.01 | Fibronectin 1 | YES | exonic |
| 59 | 2562441 | 32 | 7.01 | Surfactant, pulmonary-associated protein B | NO | intronic |
| 60 | 2598320 | 10 | 7 | Fibronectin 1 | NO | intronic |
| 61 | 3460465 | 18 | 7 | High mobility group AT-hook 2 | NO | antisense |
| 62 | 2598313 | 8 | 6.98 | Fibronectin 1 | YES | exonic |
| 63 | 2598354 | 10 | 6.97 | Fibronectin 1 | YES | exonic |
| 64 | 2598286 | 10 | 6.96 | Fibronectin 1 | YES | exonic |
| 65 | 2526813 | 6 | 6.94 | Fibronectin 1 | NO | antisense |
| 66 | 2598332 | 8 | 6.93 | Fibronectin 1 | NO | intronic |
| 67 | 2598356 | 11 | 6.93 | Fibronectin 1 | YES | exonic |
| 68 | 2598267 | 18 | 6.9 | Fibronectin 1 | NO | exonic |
| 69 | 2598365 | 15 | 6.88 | Fibronectin 1 | NO | intronic |

TABLE 3-continued

Thyroid Nodule Disease Candidate Gene RNA Sequences

| SEQ ID | ID | MFD | Weights | Gene | Probeset Overlaps CDS | Target Sequence Subtype |
|---|---|---|---|---|---|---|
| 70 | 3270357 | 6 | 6.86 | Protein tyrosine phosphatase, receptor type, E | NO | exonic |
| 71 | 2598301 | 9 | 6.85 | Fibronectin 1 | YES | exonic |
| 72 | 2598371 | 8 | 6.84 | Fibronectin 1 | YES | exonic |
| 73 | 2685324 | 5 | 6.83 | Protein S (alpha) | YES | exonic |
| 74 | 3536724 | 8 | 6.83 | Lectin, galactoside-binding, soluble, 3 | NO | extra-genic |
| 75 | 3451841 | 9 | 6.82 | NEL-like 2 (chicken) | YES | exonic |
| 76 | 2598270 | 11 | 6.82 | Fibronectin 1 | YES | exonic |
| 77 | 2598288 | 8 | 6.81 | Fibronectin 1 | YES | exonic |
| 78 | 2827683 | 41 | 6.8 | Solute carrier family 27 (fatty acid transporter), member 6 | YES | exonic |
| 79 | 2598324 | 7 | 6.79 | Fibronectin 1 | YES | exonic |
| 80 | 2598303 | 9 | 6.79 | Fibronectin 1 | NO | intronic |
| 81 | 2562442 | 21 | 6.73 | Surfactant, pulmonary-associated protein B | NO | intronic |
| 82 | 2598363 | 10 | 6.71 | Fibronectin 1 | YES | exonic |
| 83 | 2598273 | 9 | 6.7 | Fibronectin 1 | YES | exonic |
| 84 | 2598304 | 2 | 6.66 | Fibronectin 1 | YES | exonic |
| 85 | 3020344 | 2 | 6.64 | Met proto-oncogene (hepatocyte growth factor receptor) | NO | exonic |
| 86 | 2325319 | 3 | 6.64 | UDP-galactose-4-epimerase | NO | exonic |
| 87 | 3460510 | 2 | 6.63 | High mobility group AT-hook 2 | NO | antisense |
| 88 | 2598339 | 8 | 6.61 | Fibronectin 1 | YES | exonic |
| 89 | 3371816 | 3 | 6.59 | Low density lipoprotein receptor-related protein 4 | NO | extra-genic |
| 90 | 2400181 | 4 | 6.59 | Calcium/calmodulin-dependent protein kinase II inhibitor 1 | YES | exonic |
| 91 | 3536743 | 4 | 6.58 | Lectin, galactoside-binding, soluble, 3 | YES | exonic |
| 92 | 3536736 | 9 | 6.54 | Lectin, galactoside-binding, soluble, 3 | NO | intronic |
| 93 | 3634838 | 2 | 6.51 | Cathepsin H | YES | exonic |
| 94 | 3976359 | 3 | 6.46 | Synapsin I | NO | antisense |
| 95 | 2598268 | 10 | 6.46 | Fibronectin 1 | NO | exonic |
| 96 | 3451865 | 3 | 6.42 | NEL-like 2 (chicken) | NO | intronic |
| 97 | 2526825 | 8 | 6.41 | Fibronectin 1 | NO | antisense |
| 98 | 2721993 | 10 | 6.4 | Solute carrier family 34 (sodium phosphate), member 2 | YES | exonic |
| 99 | 2827693 | 32 | 6.39 | Solute carrier family 27 (fatty acid transporter), member 6 | NO | exonic |
| 100 | 2598309 | 12 | 6.38 | Fibronectin 1 | NO | intronic |
| 101 | 2722006 | 11 | 6.37 | Solute carrier family 34 (sodium phosphate), member 2 | NO | exonic |
| 102 | 2598330 | 19 | 6.37 | Fibronectin 1 | YES | exonic |
| 103 | 2598283 | 4 | 6.35 | Fibronectin 1 | NO | intronic |
| 104 | 2685316 | 3 | 6.34 | Protein S (alpha) | YES | exonic |
| 105 | 3666402 | 8 | 6.34 | Cadherin 3, type 1, P-cadherin (placental) | NO | exonic |
| 106 | 2685306 | 5 | 6.33 | Protein S (alpha) | NO | exonic |
| 107 | 2526814 | 8 | 6.31 | Fibronectin 1 | NO | antisense |
| 108 | 2598344 | 7 | 6.3 | Fibronectin 1 | YES | exonic |
| 109 | 2491742 | 4 | 6.28 | Surfactant, pulmonary-associated protein B | NO | exonic |
| 110 | 2598318 | 11 | 6.28 | Fibronectin 1 | YES | exonic |
| 111 | 3839605 | 3 | 6.27 | Kallikrein-related peptidase 10 | NO | exonic |
| 112 | 2598325 | 11 | 6.27 | Fibronectin 1 | YES | exonic |
| 113 | 2451595 | 13 | 6.27 | Chitinase 3-like 1 (cartilage glycoprotein-39) | NO | exonic |
| 114 | 2721980 | 3 | 6.24 | Solute carrier family 34 (sodium phosphate), member 2 | YES | exonic |
| 115 | 2721989 | 5 | 6.24 | Solute carrier family 34 (sodium phosphate), member 2 | YES | exonic |
| 116 | 2722000 | 9 | 6.24 | Solute carrier family 34 (sodium phosphate), member 2 | NO | exonic |
| 117 | 3087187 | 4 | 6.23 | Tumor suppressor candidate 3 | YES | exonic |
| 118 | 2526818 | 5 | 6.22 | Fibronectin 1 | NO | antisense |
| 119 | 2598331 | 3 | 6.21 | Fibronectin 1 | YES | exonic |
| 120 | 2721991 | 18 | 6.21 | Solute carrier family 34 (sodium phosphate), member 2 | YES | exonic |
| 121 | 2400180 | 6 | 6.2 | Calcium/calmodulin-dependent protein kinase II inhibitor 1 | NO | exonic |
| 122 | 2598287 | 5 | 6.19 | Fibronectin 1 | YES | intronic |
| 123 | 2584026 | 4 | 6.18 | Dipeptidyl-peptidase 4 (CD26, adenosine deaminase complexing protein 2) | YES | exonic |

TABLE 3-continued

Thyroid Nodule Disease Candidate Gene RNA Sequences

| SEQ ID | ID | MFD | Weights | Gene | Probeset Overlaps CDS | Target Sequence Subtype |
|---|---|---|---|---|---|---|
| 124 | 3536744 | 6 | 6.17 | Lectin, galactoside-binding, soluble, 3 | YES | exonic |
| 125 | 2598284 | 8 | 6.17 | Fibronectin 1 | YES | exonic |
| 126 | 2598294 | 4 | 6.15 | Fibronectin 1 | YES | exonic |
| 127 | 3451875 | 3 | 6.14 | NEL-like 2 (chicken) | YES | exonic |
| 128 | 2598308 | 11 | 6.14 | Fibronectin 1 | YES | exonic |
| 129 | 3825011 | 5 | 6.08 | Growth differentiation factor 15 | NO | exonic |
| 130 | 3464873 | 4 | 6.07 | Dual specificity phosphatase 6 | NO | exonic |
| 131 | 3263765 | 5 | 6.07 | Dual specificity phosphatase 5 | NO | intronic |
| 132 | 2562440 | 30 | 6.07 | Surfactant, pulmonary-associated protein B | NO | intronic |
| 133 | 3536745 | 7 | 5.99 | Lectin, galactoside-binding, soluble, 3 | YES | exonic |
| 134 | 2598290 | 10 | 5.98 | Fibronectin 1 | YES | exonic |
| 135 | 2526822 | 14 | 5.98 | Fibronectin 1 | NO | antisense |
| 136 | 2526816 | 7 | 5.94 | Fibronectin 1 | NO | antisense |
| 137 | 2584027 | 4 | 5.92 | Dipeptidyl-peptidase 4 (CD26, adenosine deaminase complexing protein 2) | YES | exonic |
| 138 | 3329530 | 4 | 5.91 | Low density lipoprotein receptor-related protein 4 | NO | exonic |
| 139 | 3020368 | 2 | 5.88 | Met proto-oncogene (hepatocyte growth factor receptor) | NO | intronic |
| 140 | 3451912 | 5 | 5.86 | NEL-like 2 (chicken) | YES | exonic |
| 141 | 3917691 | 4 | 5.83 | T-cell lymphoma invasion and metastasis 1 | NO | intronic |
| 142 | 3420343 | 10 | 5.82 | High mobility group AT-hook 2 | NO | intronic |
| 143 | 3343460 | 3 | 5.81 | Protease, serine, 23 | NO | exonic |
| 144 | 2721982 | 8 | 5.8 | Solute carrier family 34 (sodium phosphate), member 2 | YES | exonic |
| 145 | 2598310 | 9 | 5.79 | Fibronectin 1 | YES | exonic |
| 146 | 3270278 | 7 | 5.76 | Protein tyrosine phosphatase, receptor type, E | NO | intronic |
| 147 | 3577627 | 2 | 5.75 | Serpin peptidase inhibitor, clade A (alpha-1 antiproteinase, antitrypsin), member 1 | YES | exonic |
| 148 | 2598276 | 10 | 5.74 | Fibronectin 1 | YES | exonic |
| 149 | 3907236 | 4 | 5.71 | Syndecan 4 | YES | exonic |
| 150 | 3464882 | 3 | 5.69 | Dual specificity phosphatase 6 | NO | extra-genic |
| 151 | 2598295 | 4 | 5.68 | Fibronectin 1 | NO | intronic |
| 152 | 2477461 | 4 | 5.67 | Glutaminyl-peptide cyclotransferase (glutaminyl cyclase) | NO | exonic |
| 153 | 2562463 | 10 | 5.67 | Surfactant, pulmonary-associated protein B | YES | exonic |
| 154 | 3907239 | 4 | 5.66 | Syndecan 4 | YES | exonic |
| 155 | 2944958 | 3 | 5.65 | SRY (sex determining region Y)-box 4 | NO | antisense |
| 156 | 2512878 | 8 | 5.65 | Dipeptidyl-peptidase 4 (CD26, adenosine deaminase complexing protein 2) | NO | exonic |
| 157 | 3020350 | 3 | 5.64 | Met proto-oncogene (hepatocyte growth factor receptor) | YES | exonic |
| 158 | 3928670 | 6 | 5.64 | T-cell lymphoma invasion and metastasis 1 | NO | intronic |
| 159 | 3460452 | 4 | 5.61 | High mobility group AT-hook 2 | NO | antisense |
| 160 | 2721987 | 5 | 5.61 | Solute carrier family 34 (sodium phosphate), member 2 | NO | intronic |
| 161 | 2598357 | 9 | 5.61 | Fibronectin 1 | YES | exonic |
| 162 | 2722004 | 12 | 5.59 | Solute carrier family 34 (sodium phosphate), member 2 | NO | exonic |
| 163 | 3420360 | 6 | 5.58 | High mobility group AT-hook 2 | NO | intronic |
| 164 | 2721988 | 6 | 5.54 | Solute carrier family 34 (sodium phosphate), member 2 | YES | exonic |
| 165 | 2721976 | 8 | 5.54 | Solute carrier family 34 (sodium phosphate), member 2 | YES | exonic |
| 166 | 3634817 | 4 | 5.5 | Cathepsin H | NO | exonic |
| 167 | 2584025 | 4 | 5.5 | Dipeptidyl-peptidase 4 (CD26, adenosine deaminase complexing protein 2) | NO | exonic |
| 168 | 2722002 | 3 | 5.47 | Solute carrier family 34 (sodium phosphate), member 2 | NO | exonic |
| 169 | 3312464 | 7 | 5.47 | Protein tyrosine phosphatase, receptor type, E | NO | intronic |
| 170 | 3263773 | 5 | 5.44 | Dual specificity phosphatase 5 | NO | exonic |
| 171 | 3460456 | 5 | 5.43 | High mobility group AT-hook 2 | NO | antisense |
| 172 | 2598373 | 15 | 5.41 | Fibronectin 1 | YES | exonic |

TABLE 3-continued

Thyroid Nodule Disease Candidate Gene RNA Sequences

| SEQ ID | ID | MFD | Weights | Gene | Probeset Overlaps CDS | Target Sequence Subtype |
|---|---|---|---|---|---|---|
| 173 | 3730395 | 3 | 5.39 | Mannose receptor, C type 2 | NO | exonic |
| 174 | 2377256 | 3 | 5.38 | CD55 molecule, decay accelerating factor for complement (Cromer blood group) | NO | exonic |
| 175 | 3312484 | 5 | 5.38 | Protein tyrosine phosphatase, receptor type, E | NO | exonic |
| 176 | 3451913 | 7 | 5.38 | NEL-like 2 (chicken) | NO | extra-genic |
| 177 | 2400178 | 7 | 5.38 | Calcium/calmodulin-dependent protein kinase II inhibitor 1 | NO | exonic |
| 178 | 2451596 | 20 | 5.38 | Chitinase 3-like 1 (cartilage glycoprotein-39) | NO | exonic |
| 179 | 2827686 | 7 | 5.37 | Solute carrier family 27 (fatty acid transporter), member 6 | YES | exonic |
| 180 | 2685329 | 6 | 5.34 | Protein S (alpha) | NO | intronic |
| 181 | 2584058 | 9 | 5.33 | Dipeptidyl-peptidase 4 (CD26, adenosine deaminase complexing protein 2) | YES | exonic |
| 182 | 2598306 | 8 | 5.32 | Fibronectin 1 | YES | exonic |
| 183 | 3928671 | 2 | 5.3 | T-cell lymphoma invasion and metastasis 1 | NO | intronic |
| 184 | 3069235 | 2 | 5.3 | Met proto-oncogene (hepatocyte growth factor receptor) | NO | exonic |
| 185 | 2562462 | 3 | 5.29 | Surfactant, pulmonary-associated protein B | NO | intronic |
| 186 | 2632440 | 4 | 5.29 | Protein S (alpha) | NO | exonic |
| 187 | 3420356 | 4 | 5.29 | High mobility group AT-hook 2 | NO | intronic |
| 188 | 3263784 | 4 | 5.24 | Dual specificity phosphatase 5 | NO | intronic |
| 189 | 3769232 | 3 | 5.23 | Potassium inwardly-rectifying channel, subfamily J, member 2 | NO | exonic |
| 190 | 2377249 | 4 | 5.23 | CD55 molecule, decay accelerating factor for complement (Cromer blood group) | NO | intronic |
| 191 | 2377248 | 3 | 5.18 | CD55 molecule, decay accelerating factor for complement (Cromer blood group) | NO | exonic |
| 192 | 3067479 | 3 | 5.17 | Neuronal cell adhesion molecule | NO | exonic |
| 193 | 3020359 | 6 | 5.16 | Met proto-oncogene (hepatocyte growth factor receptor) | NO | intronic |
| 194 | 3451874 | 7 | 5.16 | NEL-like 2 (chicken) | YES | exonic |
| 195 | 2491744 | 9 | 5.16 | Surfactant, pulmonary-associated protein B | NO | intronic |
| 196 | 3464875 | 3 | 5.08 | Dual specificity phosphatase 6 | NO | intronic |
| 197 | 2584067 | 3 | 5.06 | Dipeptidyl-peptidase 4 (CD26, adenosine deaminase complexing protein 2) | YES | exonic |
| 198 | 2722005 | 10 | 5.06 | Solute carrier family 34 (sodium phosphate), member 2 | NO | exonic |
| 199 | 3721357 | 7 | 5.05 | Keratin 19 | NO | antisense |
| 200 | 3020391 | 3 | 5.04 | Met proto-oncogene (hepatocyte growth factor receptor) | YES | exonic |
| 201 | 3868840 | 5 | 5.04 | Kallikrein-related peptidase 10 | NO | extra-genic |
| 202 | 3306643 | 3 | 5.02 | Dual specificity phosphatase 5 | NO | extra-genic |
| 203 | 2721994 | 3 | 5.02 | Solute carrier family 34 (sodium phosphate), member 2 | YES | exonic |
| 204 | 3329532 | 3 | 5.01 | Low density lipoprotein receptor-related protein 4 | NO | antisense |
| 205 | 2377247 | 3 | 5 | CD55 molecule, decay accelerating factor for complement (Cromer blood group) | YES | exonic |
| 206 | 2558642 | 3 | 5 | Transforming growth factor, alpha | NO | exonic |
| 207 | 2830378 | 2 | 4.99 | Sparc/osteonectin, cwcv and kazal-like domains proteoglycan (testican) 1 | NO | antisense |
| 208 | 2477456 | 4 | 4.98 | Glutaminyl-peptide cyclotransferase (glutaminyl cyclase) | YES | exonic |
| 209 | 3451868 | 6 | 4.98 | NEL-like 2 (chicken) | YES | exonic |
| 210 | 3087225 | 6 | 4.98 | Tumor suppressor candidate 3 | NO | extra-genic |
| 211 | 3020384 | 3 | 4.89 | Met proto-oncogene (hepatocyte growth factor receptor) | YES | exonic |

TABLE 3-continued

Thyroid Nodule Disease Candidate Gene RNA Sequences

| SEQ ID | ID | MFD | Weights | Gene | Probeset Overlaps CDS | Target Sequence Subtype |
|---|---|---|---|---|---|---|
| 212 | 2735072 | 5 | 4.87 | Secreted phosphoprotein 1 (osteopontin, bone sialoprotein I, early T-lymphocyte activation 1) | NO | exonic |
| 213 | 2598353 | 8 | 4.87 | Fibronectin 1 | YES | exonic |
| 214 | 3385809 | 3 | 4.85 | Cathepsin C | NO | intronic |
| 215 | 2721985 | 9 | 4.85 | Solute carrier family 34 (sodium phosphate), member 2 | YES | exonic |
| 216 | 3020363 | 4 | 4.77 | Met proto-oncogene (hepatocyte growth factor receptor) | YES | exonic |
| 217 | 2437139 | 3 | 4.76 | Mucin 1, cell surface associated | YES | intronic |
| 218 | 3460453 | 3 | 4.72 | High mobility group AT-hook 2 | NO | antisense |
| 219 | 3020356 | 3 | 4.72 | Met proto-oncogene (hepatocyte growth factor receptor) | NO | intronic |
| 220 | 2830183 | 9 | 4.72 | Sparc/osteonectin, cwcv and kazal-like domains proteoglycan (testican) 1 | NO | exonic |
| 221 | 2562444 | 2 | 4.7 | Surfactant, pulmonary-associated protein B | NO | intronic |
| 222 | 2830181 | 4 | 4.68 | Sparc/osteonectin, cwcv and kazal-like domains proteoglycan (testican) 1 | NO | exonic |
| 223 | 2764175 | 13 | 4.68 | Solute carrier family 34 (sodium phosphate), member 2 | NO | exonic |
| 224 | 3907240 | 3 | 4.66 | Syndecan 4 | YES | exonic |
| 225 | 3917721 | 5 | 4.66 | T-cell lymphoma invasion and metastasis 1 | NO | intronic |
| 226 | 2442021 | 9 | 4.65 | Retinoid X receptor, gamma | YES | exonic |
| 227 | 3907235 | 3 | 4.64 | Syndecan 4 | NO | exonic |
| 228 | 3451838 | 3 | 4.64 | NEL-like 2 (chicken) | YES | exonic |
| 229 | 3769234 | 5 | 4.64 | Potassium inwardly-rectifying channel, subfamily J, member 2 | NO | exonic |
| 230 | 3577636 | 4 | 4.63 | Serpin peptidase inhibitor, clade A (alpha-1 antiproteinase, antitrypsin), member 1 | YES | exonic |
| 231 | 2377236 | 3 | 4.61 | CD55 molecule, decay accelerating factor for complement (Cromer blood group) | YES | exonic |
| 232 | 2435391 | 4 | 4.61 | S100 calcium binding protein A10 | NO | exonic |
| 233 | 2400186 | 3 | 4.6 | Calcium/calmodulin-dependent protein kinase II inhibitor 1 | NO | extra-genic |
| 234 | 2751991 | 3 | 4.59 | UDP-N-acetyl-alpha-D-galactosamine: polypeptide N-acetylgalactosaminyltransferase 7 (GalNAc-T7) | NO | intronic |
| 235 | 2377265 | 3 | 4.53 | CD55 molecule, decay accelerating factor for complement (Cromer blood group) | NO | intronic |
| 236 | 3464878 | 4 | 4.53 | Dual specificity phosphatase 6 | NO | intronic |
| 237 | 3835890 | 6 | 4.53 | Apolipoprotein E | NO | exonic |
| 238 | 2721999 | 15 | 4.53 | Solute carrier family 34 (sodium phosphate), member 2 | NO | exonic |
| 239 | 3125505 | 3 | 4.5 | Tumor suppressor candidate 3 | NO | antisense |
| 240 | 2562443 | 5 | 4.5 | Surfactant, pulmonary-associated protein B | NO | intronic |
| 241 | 2453163 | 3 | 4.45 | CD55 molecule, decay accelerating factor for complement (Cromer blood group) | NO | antisense |
| 242 | 3263752 | 6 | 4.43 | Dual specificity phosphatase 5 | NO | extra-genic |
| 243 | 3825012 | 3 | 4.4 | Growth differentiation factor 15 | NO | exonic |
| 244 | 2377237 | 3 | 4.39 | CD55 molecule, decay accelerating factor for complement (Cromer blood group) | NO | intronic |
| 245 | 3907194 | 6 | 4.39 | Secretory leukocyte peptidase inhibitor | NO | exonic |
| 246 | 2377268 | 3 | 4.36 | CD55 molecule, decay accelerating factor for complement (Cromer blood group) | YES | exonic |
| 247 | 3343458 | 3 | 4.36 | Protease, serine, 23 | NO | exonic |
| 248 | 2377271 | 4 | 4.36 | CD55 molecule, decay accelerating factor for complement (Cromer blood group) | NO | exonic |
| 249 | 2359172 | 5 | 4.36 | S100 calcium binding protein A10 | NO | exonic |
| 250 | 3733280 | 3 | 4.35 | Potassium inwardly-rectifying channel, subfamily J, member 2 | NO | exonic |

TABLE 3-continued

Thyroid Nodule Disease Candidate Gene RNA Sequences

| SEQ ID | ID | MFD | Weights | Gene | Probeset Overlaps CDS | Target Sequence Subtype |
|---|---|---|---|---|---|---|
| 251 | 3020355 | 3 | 4.34 | Met proto-oncogene (hepatocyte growth factor receptor) | NO | intronic |
| 252 | 2453796 | 3 | 4.32 | Laminin, beta 3 | YES | exonic |
| 253 | 3460455 | 3 | 4.31 | High mobility group AT-hook 2 | NO | antisense |
| 254 | 3928709 | 2 | 4.3 | T-cell lymphoma invasion and metastasis 1 | YES | exonic |
| 255 | 3351275 | 3 | 4.3 | Myelin protein zero-like 2 | NO | exonic |
| 256 | 3217301 | 2 | 4.21 | Gamma-aminobutyric acid (GABA) B receptor, 2 | NO | intronic |
| 257 | 2377263 | 2 | 4.18 | CD55 molecule, decay accelerating factor for complement (Cromer blood group) | NO | intronic |
| 258 | 3976345 | 3 | 4.18 | Synapsin I | YES | antisense |
| 259 | 2377245 | 5 | 4.16 | CD55 molecule, decay accelerating factor for complement (Cromer blood group) | YES | exonic |
| 260 | 2414961 | 4 | 4.14 | Tumor-associated calcium signal transducer 2 | NO | exonic |
| 261 | 2876911 | 2 | 4.12 | Sparc/osteonectin, cwcv and kazal-like domains proteoglycan (testican) 1 | YES | exonic |
| 262 | 2764272 | 4 | 4.12 | KIAA0746 protein | YES | exonic |
| 263 | 3406425 | 3 | 4.08 | Epidermal growth factor receptor pathway substrate 8 | NO | intronic |
| 264 | 3222204 | 7 | 4.06 | Tenascin C (hexabrachion) | NO | intronic |
| 265 | 3928687 | 3 | 4.05 | T-cell lymphoma invasion and metastasis 1 | YES | exonic |
| 266 | 3067480 | 4 | 4.04 | Neuronal cell adhesion molecule | NO | exonic |
| 267 | 3451908 | 7 | 3.99 | NEL-like 2 (chicken) | YES | exonic |
| 268 | 3928672 | 5 | 3.98 | T-cell lymphoma invasion and metastasis 1 | NO | intronic |
| 269 | 2437119 | 4 | 3.97 | Mucin 1, cell surface associated | NO | exonic |
| 270 | 3252064 | 3 | 3.93 | Plasminogen activator, urokinase | NO | exonic |
| 271 | 2751985 | 2 | 3.92 | UDP-N-acetyl-alpha-D-galactosamine: polypeptide N-acetylgalactosaminyltransferase 7 (GalNAc-T7) | NO | exonic |
| 272 | 2830201 | 2 | 3.9 | Sparc/osteonectin, cwcv and kazal-like domains proteoglycan (testican) 1 | NO | antisense |
| 273 | 3126229 | 3 | 3.9 | Pleckstrin and Sec7 domain containing 3 | NO | intronic |
| 274 | 3252057 | 2 | 3.83 | Plasminogen activator, urokinase | NO | intronic |
| 275 | 3222218 | 3 | 3.82 | Tenascin C (hexabrachion) | NO | intronic |
| 276 | 3217284 | 3 | 3.8 | Gamma-aminobutyric acid (GABA) B receptor, 2 | YES | exonic |
| 277 | 3401511 | 3 | 3.76 | Protein arginine methyltransferase 8 | NO | exonic |
| 278 | 3020380 | 3 | 3.74 | Met proto-oncogene (hepatocyte growth factor receptor) | YES | exonic |
| 279 | 3371817 | 2 | 3.71 | Low density lipoprotein receptor-related protein 4 | NO | exonic |
| 280 | 2377242 | 2 | 3.7 | CD55 molecule, decay accelerating factor for complement (Cromer blood group) | YES | exonic |
| 281 | 2558708 | 2 | 3.7 | Transforming growth factor, alpha | NO | intronic |
| 282 | 3351271 | 2 | 3.63 | Myelin protein zero-like 3 | NO | antisense |
| 283 | 2466609 | −8 | −10.87 | Thyroid peroxidase | YES | exonic |
| 284 | 2537610 | −6 | −9.87 | Thyroid peroxidase | NO | antisense |
| 285 | 3727592 | −3 | −9.81 | Hepatic leukemia factor | YES | exonic |
| 286 | 3367674 | −11 | −9.45 | Metallophoesterase domain containing 2 | NO | extra-genic |
| 287 | 2537568 | −19 | −9.37 | Thyroid peroxidase | NO | antisense |
| 288 | 2466585 | −26 | −9.14 | Thyroid peroxidase | YES | exonic |
| 289 | 3095405 | −9 | −9.07 | Zinc finger, matrin type 4 | NO | exonic |
| 290 | 3933538 | −16 | −8.91 | Trefoil factor 3 (intestinal) | NO | exonic |
| 291 | 2763591 | −3 | −8.86 | Peroxisome proliferator-activated receptor gamma, coactivator 1 alpha | YES | exonic |
| 292 | 2466562 | −30 | −8.84 | Thyroid peroxidase | NO | extra-genic |
| 293 | 3662208 | −6 | −8.84 | Metallothionein 1F | YES | exonic |
| 294 | 2466570 | −55 | −8.64 | Thyroid peroxidase | YES | exonic |
| 295 | 2466631 | −19 | −8.52 | Thyroid peroxidase | NO | extra-genic |
| 296 | 3367675 | −14 | −8.49 | Metallophoesterase domain containing 2 | NO | exonic |

TABLE 3-continued

Thyroid Nodule Disease Candidate Gene RNA Sequences

| SEQ ID | ID | MFD | Weights | Gene | Probeset Overlaps CDS | Target Sequence Subtype |
|---|---|---|---|---|---|---|
| 297 | 3367709 | −24 | −8.39 | Metallophosphoesterase domain containing 2 | NO | intronic |
| 298 | 2466600 | −5 | −8.37 | Thyroid peroxidase | NO | intronic |
| 299 | 3367737 | −9 | −8.35 | Metallophosphoesterase domain containing 2 | NO | intronic |
| 300 | 3018629 | −8 | −8.35 | Solute carrier family 26, member 4 | YES | exonic |
| 301 | 3132624 | −6 | −8.35 | Zinc finger, matrin type 4 | YES | exonic |
| 302 | 3018633 | −7 | −8.33 | Solute carrier family 26, member 4 | YES | exonic |
| 303 | 3367689 | −13 | −8.27 | Metallophosphoesterase domain containing 2 | NO | intronic |
| 304 | 3693001 | −14 | −8.22 | Metallothionein 1G | NO | exonic |
| 305 | 3018617 | −6 | −8.21 | Solute carrier family 26, member 4 | YES | exonic |
| 306 | 3018618 | −8 | −8.16 | Solute carrier family 26, member 4 | YES | exonic |
| 307 | 2763563 | −6 | −8.12 | Peroxisome proliferator-activated receptor gamma, coactivator 1 alpha | NO | exonic |
| 308 | 3862190 | −3 | −8.03 | Fc fragment of IgG binding protein | NO | exonic |
| 309 | 2721305 | −4 | −8 | Peroxisome proliferator-activated receptor gamma, coactivator 1 alpha | NO | exonic |
| 310 | 2466569 | −26 | −7.98 | Thyroid peroxidase | YES | exonic |
| 311 | 3367712 | −15 | −7.98 | Metallophosphoesterase domain containing 2 | YES | exonic |
| 312 | 3833280 | −2 | −7.97 | Fc fragment of IgG binding protein | NO | exonic |
| 313 | 3018642 | −10 | −7.93 | Solute carrier family 26, member 4 | NO | exonic |
| 314 | 3367697 | −16 | −7.85 | Metallophosphoesterase domain containing 2 | NO | intronic |
| 315 | 3018616 | −13 | −7.79 | Solute carrier family 26, member 4 | YES | exonic |
| 316 | 3367743 | −28 | −7.77 | Metallophosphoesterase domain containing 2 | NO | extra-genic |
| 317 | 2537609 | −12 | −7.73 | Thyroid peroxidase | NO | antisense |
| 318 | 3933539 | −19 | −7.71 | Trefoil factor 3 (intestinal) | NO | exonic |
| 319 | 2586066 | −4 | −7.7 | Low density lipoprotein-related protein 2 | YES | exonic |
| 320 | 3132617 | −13 | −7.68 | Zinc finger, matrin type 4 | NO | extra-genic |
| 321 | 2727647 | −11 | −7.6 | V-kit Hardy-Zuckerman 4 feline sarcoma viral oncogene homolog | NO | intronic |
| 322 | 3067233 | −20 | −7.53 | Solute carrier family 26, member 4 | NO | extra-genic |
| 323 | 2763565 | −5 | −7.53 | Peroxisome proliferator-activated receptor gamma, coactivator 1 alpha | NO | exonic |
| 324 | 3018631 | −13 | −7.51 | Solute carrier family 26, member 4 | YES | exonic |
| 325 | 2586118 | −7 | −7.5 | Low density lipoprotein-related protein 2 | YES | exonic |
| 326 | 2466608 | −9 | −7.49 | Thyroid peroxidase | YES | exonic |
| 327 | 2586111 | −5 | −7.46 | Low density lipoprotein-related protein 2 | YES | exonic |
| 328 | 3367703 | −9 | −7.44 | Metallophosphoesterase domain containing 2 | NO | intronic |
| 329 | 2586171 | −4 | −7.36 | Low density lipoprotein-related protein 2 | YES | exonic |
| 330 | 2331562 | −3 | −7.34 | Bone morphogenetic protein 8a | NO | exonic |
| 331 | 3108614 | −4 | −7.32 | Matrilin 2 | YES | exonic |
| 332 | 2537604 | −6 | −7.31 | Thyroid peroxidase | NO | antisense |
| 333 | 2466626 | −3 | −7.31 | Thyroid peroxidase | YES | exonic |
| 334 | 3018640 | −7 | −7.28 | Solute carrier family 26, member 4 | NO | exonic |
| 335 | 2466621 | −14 | −7.27 | Thyroid peroxidase | NO | intronic |
| 336 | 2586151 | −3 | −7.27 | Low density lipoprotein-related protein 2 | YES | exonic |
| 337 | 2466629 | −16 | −7.25 | Thyroid peroxidase | NO | exonic |
| 338 | 3367739 | −8 | −7.24 | Metallophosphoesterase domain containing 2 | NO | intronic |
| 339 | 3811356 | −3 | −7.22 | B-cell CLL/lymphoma 2 | NO | exonic |
| 340 | 3108604 | −3 | −7.19 | Matrilin 2 | YES | exonic |
| 341 | 2466601 | −35 | −7.17 | Thyroid peroxidase | NO | intronic |
| 342 | 2466566 | −9 | −7.16 | Thyroid peroxidase | YES | exonic |
| 343 | 2586065 | −5 | −7.14 | Low density lipoprotein-related protein 2 | YES | exonic |
| 344 | 3095521 | −5 | −7.14 | Zinc finger, matrin type 4 | NO | intronic |
| 345 | 2586168 | −4 | −7.14 | Low density lipoprotein-related protein 2 | YES | exonic |
| 346 | 2466628 | −21 | −7.13 | Thyroid peroxidase | YES | exonic |
| 347 | 2466564 | −13 | −7.1 | Thyroid peroxidase | YES | exonic |
| 348 | 3160700 | −5 | −7.04 | Chromosome 9 open reading frame 68 | NO | intronic |

TABLE 3-continued

Thyroid Nodule Disease Candidate Gene RNA Sequences

| SEQ ID | ID | MFD | Weights | Gene | Probeset Overlaps CDS | Target Sequence Subtype |
|---|---|---|---|---|---|---|
| 349 | 3325106 | −9 | −7 | Metallophosphoesterase domain containing 2 | NO | antisense |
| 350 | 2721311 | −7 | −6.99 | Peroxisome proliferator-activated receptor gamma, coactivator 1 alpha | NO | antisense |
| 351 | 3018619 | −6 | −6.98 | Solute carrier family 26, member 4 | YES | exonic |
| 352 | 2586130 | −6 | −6.9 | Low density lipoprotein-related protein 2 | YES | exonic |
| 353 | 3018636 | −12 | −6.87 | Solute carrier family 26, member 4 | YES | exonic |
| 354 | 3108616 | −8 | −6.86 | Matrilin 2 | YES | exonic |
| 355 | 3862193 | −4 | −6.86 | Fc fragment of IgG binding protein | YES | exonic |
| 356 | 2586039 | −4 | −6.84 | Low density lipoprotein-related protein 2 | NO | extra-genic |
| 357 | 3833286 | −4 | −6.83 | Fc fragment of IgG binding protein | NO | antisense |
| 358 | 2586132 | −2 | −6.83 | Low density lipoprotein-related protein 2 | YES | exonic |
| 359 | 2763561 | −6 | −6.82 | Peroxisome proliferator-activated receptor gamma, coactivator 1 alpha | NO | exonic |
| 360 | 2466620 | −15 | −6.8 | Thyroid peroxidase | YES | exonic |
| 361 | 2586145 | −5 | −6.79 | Low density lipoprotein-related protein 2 | YES | exonic |
| 362 | 3018615 | −7 | −6.78 | Solute carrier family 26, member 4 | YES | exonic |
| 363 | 4023363 | −6 | −6.77 | Four and a half LIM domains 1 | NO | exonic |
| 364 | 2537578 | −6 | −6.76 | Thyroid peroxidase | NO | antisense |
| 365 | 2763557 | −6 | −6.74 | Peroxisome proliferator-activated receptor gamma, coactivator 1 alpha | NO | exonic |
| 366 | 2586159 | −4 | −6.74 | Low density lipoprotein-related protein 2 | YES | exonic |
| 367 | 3862199 | −4 | −6.74 | Fc fragment of IgG binding protein | YES | exonic |
| 368 | 3811391 | −2 | −6.74 | B-cell CLL/lymphoma 2 | NO | intronic |
| 369 | 3046252 | −4 | −6.73 | Engulfment and cell motility 1 | NO | intronic |
| 370 | 2466563 | −7 | −6.72 | Thyroid peroxidase | NO | extra-genic |
| 371 | 2721641 | −5 | −6.72 | Superoxide dismutase 3, extracellular | NO | exonic |
| 372 | 3108607 | −3 | −6.71 | Matrilin 2 | NO | intronic |
| 373 | 2721309 | −5 | −6.7 | Peroxisome proliferator-activated receptor gamma, coactivator 1 alpha | NO | exonic |
| 374 | 2586135 | −4 | −6.7 | Low density lipoprotein-related protein 2 | YES | exonic |
| 375 | 2537607 | −9 | −6.69 | Thyroid peroxidase | NO | antisense |
| 376 | 3018628 | −8 | −6.67 | Solute carrier family 26, member 4 | YES | exonic |
| 377 | 2466583 | −8 | −6.66 | Thyroid peroxidase | NO | intronic |
| 378 | 2586149 | −5 | −6.65 | Low density lipoprotein-related protein 2 | YES | exonic |
| 379 | 3662230 | −16 | −6.63 | Metallothionein 1G | NO | exonic |
| 380 | 2586140 | −3 | −6.61 | Low density lipoprotein-related protein 2 | YES | exonic |
| 381 | 3367740 | −6 | −6.53 | Metallophosphoesterase domain containing 2 | NO | intronic |
| 382 | 2466598 | −5 | −6.53 | Thyroid peroxidase | NO | intronic |
| 383 | 3367691 | −6 | −6.52 | Metallophosphoesterase domain containing 2 | NO | intronic |
| 384 | 3367679 | −4 | −6.49 | Metallophosphoesterase domain containing 2 | YES | exonic |
| 385 | 2763590 | −3 | −6.47 | Peroxisome proliferator-activated receptor gamma, coactivator 1 alpha | NO | intronic |
| 386 | 2586102 | −3 | −6.46 | Low density lipoprotein-related protein 2 | YES | exonic |
| 387 | 3367693 | −12 | −6.44 | Metallophosphoesterase domain containing 2 | NO | intronic |
| 388 | 2586067 | −4 | −6.44 | Low density lipoprotein-related protein 2 | YES | exonic |
| 389 | 3095516 | −3 | −6.42 | Zinc finger, matrin type 4 | NO | intronic |
| 390 | 2466573 | −10 | −6.41 | Thyroid peroxidase | YES | intronic |
| 391 | 3145950 | −5 | −6.41 | Matrilin 2 | NO | antisense |
| 392 | 2586043 | −3 | −6.41 | Low density lipoprotein-related protein 2 | YES | exonic |
| 393 | 3104982 | −23 | −6.37 | Fatty acid binding protein 4, adipocyte | NO | exonic |
| 394 | 2336909 | −7 | −6.37 | Deiodinase, iodothyronine, type I | NO | exonic |
| 395 | 3108620 | −6 | −6.37 | Matrilin 2 | NO | exonic |
| 396 | 3095473 | −4 | −6.31 | Zinc finger, matrin type 4 | NO | antisense |
| 397 | 2763580 | −4 | −6.31 | Peroxisome proliferator-activated receptor gamma, coactivator 1 alpha | YES | exonic |
| 398 | 3367742 | −3 | −6.31 | Metallophosphoesterase domain containing 2 | NO | extra-genic |

TABLE 3-continued

Thyroid Nodule Disease Candidate Gene RNA Sequences

| SEQ ID | ID | MFD | Weights | Gene | Probeset Overlaps CDS | Target Sequence Subtype |
|---|---|---|---|---|---|---|
| 399 | 3662219 | −17 | −6.29 | Metallothionein 1H | NO | exonic |
| 400 | 2331563 | −11 | −6.29 | Bone morphogenetic protein 8a | NO | exonic |
| 401 | 3727624 | −9 | −6.29 | Hepatic leukemia factor | NO | exonic |
| 402 | 2586061 | −4 | −6.29 | Low density lipoprotein-related protein 2 | NO | intronic |
| 403 | 2997517 | −4 | −6.28 | Engulfment and cell motility 1 | NO | exonic |
| 404 | 2586088 | −3 | −6.28 | Low density lipoprotein-related protein 2 | YES | exonic |
| 405 | 3992449 | −5 | −6.27 | Four and a half LIM domains 1 | NO | exonic |
| 406 | 2586155 | −9 | −6.25 | Low density lipoprotein-related protein 2 | YES | exonic |
| 407 | 2586139 | −4 | −6.25 | Low density lipoprotein-related protein 2 | YES | exonic |
| 408 | 3126609 | −3 | −6.25 | Chondroitin beta1,4 N-acetylgalactosaminyltransferase | NO | intronic |
| 409 | 2586113 | −4 | −6.2 | Low density lipoprotein-related protein 2 | YES | exonic |
| 410 | 2586160 | −4 | −6.2 | Low density lipoprotein-related protein 2 | YES | exonic |
| 411 | 2608611 | −3 | −6.2 | Inositol 1,4,5-triphosphate receptor, type 1 | YES | exonic |
| 412 | 2586152 | −3 | −6.19 | Low density lipoprotein-related protein 2 | YES | exonic |
| 413 | 2466574 | −10 | −6.17 | Thyroid peroxidase | NO | intronic |
| 414 | 2763558 | −4 | −6.14 | Peroxisome proliferator-activated receptor gamma, coactivator 1 alpha | NO | exonic |
| 415 | 3662224 | −4 | −6.13 | Metallothionein 1F | NO | extra-genic |
| 416 | 3367741 | −3 | −6.13 | Metallophosphoesterase domain containing 2 | YES | exonic |
| 417 | 2466582 | −3 | −6.12 | Thyroid peroxidase | YES | exonic |
| 418 | 3108615 | −5 | −6.08 | Matrilin 2 | YES | exonic |
| 419 | 2721643 | −2 | −6.08 | Superoxide dismutase 3, extracellular | NO | exonic |
| 420 | 2586153 | −4 | −6.07 | Low density lipoprotein-related protein 2 | YES | exonic |
| 421 | 2537572 | −8 | −6.05 | Thyroid peroxidase | NO | antisense |
| 422 | 2586068 | −3 | −6.04 | Low density lipoprotein-related protein 2 | YES | exonic |
| 423 | 2586143 | −5 | −6.03 | Low density lipoprotein-related protein 2 | YES | exonic |
| 424 | 3893028 | −15 | −6.01 | Collagen, type IX, alpha 3 | YES | exonic |
| 425 | 3367676 | −7 | −6.01 | Metallophosphoesterase domain containing 2 | YES | exonic |
| 426 | 2586172 | −5 | −6.01 | Low density lipoprotein-related protein 2 | YES | exonic |
| 427 | 3142383 | −25 | −6 | Fatty acid binding protein 4, adipocyte | NO | exonic |
| 428 | 3367677 | −3 | −5.97 | Metallophosphoesterase domain containing 2 | NO | intronic |
| 429 | 2763566 | −7 | −5.96 | Peroxisome proliferator-activated receptor gamma, coactivator 1 alpha | NO | exonic |
| 430 | 3763228 | −5 | −5.94 | Hepatic leukemia factor | NO | extra-genic |
| 431 | 3108580 | −4 | −5.92 | Matrilin 2 | YES | exonic |
| 432 | 2608485 | −3 | −5.92 | Inositol 1,4,5-triphosphate receptor, type 1 | YES | exonic |
| 433 | 2331560 | −3 | −5.91 | Bone morphogenetic protein 8a | YES | exonic |
| 434 | 2763602 | −3 | −5.89 | Peroxisome proliferator-activated receptor gamma, coactivator 1 alpha | NO | intronic |
| 435 | 3811360 | −2 | −5.89 | B-cell CLL/lymphoma 2 | NO | exonic |
| 436 | 2586150 | −4 | −5.86 | Low density lipoprotein-related protein 2 | YES | exonic |
| 437 | 2586050 | −7 | −5.84 | Low density lipoprotein-related protein 2 | YES | exonic |
| 438 | 2586041 | −3 | −5.84 | Low density lipoprotein-related protein 2 | YES | exonic |
| 439 | 3811354 | −3 | −5.84 | B-cell CLL/lymphoma 2 | NO | exonic |
| 440 | 3088273 | −5 | −5.82 | Chondroitin beta1,4 N-acetylgalactosaminyltransferase | NO | exonic |
| 441 | 3046251 | −3 | −5.81 | Engulfment and cell motility 1 | NO | intronic |
| 442 | 2336897 | −5 | −5.8 | Deiodinase, iodothyronine, type I | YES | exonic |
| 443 | 3108574 | −5 | −5.8 | Matrilin 2 | YES | exonic |

TABLE 3-continued

Thyroid Nodule Disease Candidate Gene RNA Sequences

| SEQ ID | ID | MFD | Weights | Gene | Probeset Overlaps CDS | Target Sequence Subtype |
|---|---|---|---|---|---|---|
| 444 | 3354771 | −2 | −5.8 | STT3, subunit of the oligosaccharyltransferase complex, homolog A (S. cerevisiae) | YES | exonic |
| 445 | 3367705 | −7 | −5.77 | Metallophosphoesterase domain containing 2 | NO | intronic |
| 446 | 3791751 | −5 | −5.77 | B-cell CLL/lymphoma 2 | NO | antisense |
| 447 | 2514350 | −4 | −5.77 | Low density lipoprotein-related protein 2 | NO | extra-genic |
| 448 | 2586107 | −5 | −5.75 | Low density lipoprotein-related protein 2 | YES | exonic |
| 449 | 3108602 | −9 | −5.74 | Matrilin 2 | YES | exonic |
| 450 | 2980482 | −4 | −5.73 | Opioid receptor, mu 1 | NO | antisense |
| 451 | 3126512 | −3 | −5.72 | Chondroitin beta1,4 N-acetylgalactosaminyltransferase | NO | intronic |
| 452 | 3913484 | −22 | −5.71 | Collagen, type IX, alpha 3 | NO | exonic |
| 453 | 2763571 | −4 | −5.71 | Peroxisome proliferator-activated receptor gamma, coactivator 1 alpha | YES | exonic |
| 454 | 2980481 | −10 | −5.7 | Opioid receptor, mu 1 | NO | antisense |
| 455 | 2608604 | −6 | −5.68 | Inositol 1,4,5-triphosphate receptor, type 1 | NO | intronic |
| 456 | 2586064 | −6 | −5.66 | Low density lipoprotein-related protein 2 | YES | exonic |
| 457 | 3018621 | −4 | −5.66 | Solute carrier family 26, member 4 | YES | exonic |
| 458 | 3126626 | −4 | −5.66 | Chondroitin beta1,4 N-acetylgalactosaminyltransferase | NO | intronic |
| 459 | 2649002 | −6 | −5.65 | Potassium voltage-gated channel, shaker-related subfamily, beta member 1 | NO | intronic |
| 460 | 2763573 | −4 | −5.65 | Peroxisome proliferator-activated receptor gamma, coactivator 1 alpha | YES | exonic |
| 461 | 3396651 | −2 | −5.65 | STT3, subunit of the oligosaccharyltransferase complex, homolog A (S. cerevisiae) | NO | antisense |
| 462 | 3893026 | −12 | −5.64 | Collagen, type IX, alpha 3 | YES | exonic |
| 463 | 3046250 | −4 | −5.64 | Engulfment and cell motility 1 | NO | intronic |
| 464 | 2586114 | −3 | −5.62 | Low density lipoprotein-related protein 2 | YES | exonic |
| 465 | 3573880 | −6 | −5.61 | Deiodinase, iodothyronine, type II | YES | exonic |
| 466 | 2586101 | −4 | −5.61 | Low density lipoprotein-related protein 2 | YES | exonic |
| 467 | 3126515 | −3 | −5.57 | Chondroitin beta1,4 N-acetylgalactosaminyltransferase | NO | intronic |
| 468 | 2608689 | −3 | −5.57 | Inositol 1,4,5-triphosphate receptor, type 1 | NO | intronic |
| 469 | 4023359 | −4 | −5.55 | Four and a half LIM domains 1 | NO | exonic |
| 470 | 3046202 | −2 | −5.55 | Engulfment and cell motility 1 | YES | exonic |
| 471 | 2586075 | −5 | −5.53 | Low density lipoprotein-related protein 2 | YES | exonic |
| 472 | 3046247 | −6 | −5.52 | Engulfment and cell motility 1 | NO | intronic |
| 473 | 2608629 | −2 | −5.51 | Inositol 1,4,5-triphosphate receptor, type 1 | YES | exonic |
| 474 | 3126548 | −3 | −5.49 | Chondroitin beta1,4 N-acetylgalactosaminyltransferase | YES | exonic |
| 475 | 3046198 | −3 | −5.46 | Engulfment and cell motility 1 | NO | exonic |
| 476 | 3573882 | −3 | −5.45 | Deiodinase, iodothyronine, type II | YES | exonic |
| 477 | 3088320 | −3 | −5.43 | Chondroitin beta1,4 N-acetylgalactosaminyltransferase | NO | antisense |
| 478 | 3095470 | −2 | −5.43 | Zinc finger, matrin type 4 | NO | antisense |
| 479 | 3142384 | −13 | −5.42 | Fatty acid binding protein 4, adipocyte | YES | exonic |
| 480 | 2721315 | −5 | −5.42 | Peroxisome proliferator-activated receptor gamma, coactivator 1 alpha | NO | antisense |
| 481 | 3933546 | −3 | −5.42 | Trefoil factor 3 (intestinal) | YES | exonic |
| 482 | 2608677 | −3 | −5.42 | Inositol 1,4,5-triphosphate receptor, type 1 | NO | exonic |
| 483 | 3893027 | −8 | −5.41 | Collagen, type IX, alpha 3 | YES | exonic |
| 484 | 3811420 | −4 | −5.41 | B-cell CLL/lymphoma 2 | NO | intronic |
| 485 | 2608644 | −3 | −5.41 | Inositol 1,4,5-triphosphate receptor, type 1 | YES | exonic |
| 486 | 3811357 | −2 | −5.41 | B-cell CLL/lymphoma 2 | NO | exonic |
| 487 | 2932274 | −6 | −5.38 | Opioid receptor, mu 1 | YES | exonic |
| 488 | 3811424 | −3 | −5.37 | B-cell CLL/lymphoma 2 | NO | intronic |

TABLE 3-continued

Thyroid Nodule Disease Candidate Gene RNA Sequences

| SEQ ID | ID | MFD | Weights | Gene | Probeset Overlaps CDS | Target Sequence Subtype |
|---|---|---|---|---|---|---|
| 489 | 3354786 | −2 | −5.37 | STT3, subunit of the oligosaccharyltransferase complex, homolog A (S. cerevisiae) | YES | exonic |
| 490 | 2740186 | −5 | −5.35 | Ankyrin 2, neuronal | NO | intronic |
| 491 | 2586104 | −3 | −5.33 | Low density lipoprotein-related protein 2 | NO | intronic |
| 492 | 3046236 | −5 | −5.32 | Engulfment and cell motility 1 | NO | intronic |
| 493 | 3126509 | −4 | −5.31 | Chondroitin beta1,4 N-acetylgalactosaminyltransferase | YES | exonic |
| 494 | 2608546 | −4 | −5.3 | Inositol 1,4,5-triphosphate receptor, type 1 | YES | exonic |
| 495 | 3108613 | −5 | −5.29 | Matrilin 2 | YES | exonic |
| 496 | 2997541 | −3 | −5.29 | Engulfment and cell motility 1 | NO | antisense |
| 497 | 3088362 | −2 | −5.29 | Chondroitin beta1,4 N-acetylgalactosaminyltransferase | NO | intronic |
| 498 | 3662157 | −5 | −5.28 | Metallothionein 1M | NO | exonic |
| 499 | 2586125 | −3 | −5.28 | Low density lipoprotein-related protein 2 | NO | intronic |
| 500 | 2608612 | −7 | −5.27 | Inositol 1,4,5-triphosphate receptor, type 1 | YES | exonic |
| 501 | 2608627 | −7 | −5.25 | Inositol 1,4,5-triphosphate receptor, type 1 | NO | intronic |
| 502 | 2586096 | −5 | −5.25 | Low density lipoprotein-related protein 2 | YES | exonic |
| 503 | 3811405 | −3 | −5.25 | B-cell CLL/lymphoma 2 | NO | intronic |
| 504 | 3862194 | −3 | −5.25 | Fc fragment of IgG binding protein | NO | intronic |
| 505 | 3126514 | −4 | −5.24 | Chondroitin beta1,4 N-acetylgalactosaminyltransferase | YES | exonic |
| 506 | 3992437 | −4 | −5.23 | Four and a half LIM domains 1 | NO | intronic |
| 507 | 2702151 | −3 | −5.22 | Potassium voltage-gated channel, shaker-related subfamily, beta member 1 | NO | exonic |
| 508 | 2649018 | −7 | −5.21 | Potassium voltage-gated channel, shaker-related subfamily, beta member 1 | NO | intronic |
| 509 | 2908192 | −2 | −5.19 | Vascular endothelial growth factor A | YES | exonic |
| 510 | 3573883 | −4 | −5.18 | Deiodinase, iodothyronine, type II | YES | exonic |
| 511 | 2608610 | −4 | −5.17 | Inositol 1,4,5-triphosphate receptor, type 1 | YES | exonic |
| 512 | 3126563 | −3 | −5.17 | Chondroitin beta1,4 N-acetylgalactosaminyltransferase | NO | intronic |
| 513 | 2897465 | −2 | −5.17 | Inhibitor of DNA binding 4, dominant negative helix-loop-helix protein | NO | exonic |
| 514 | 2649054 | −6 | −5.16 | Potassium voltage-gated channel, shaker-related subfamily, beta member 1 | NO | intronic |
| 515 | 2608569 | −3 | −5.16 | Inositol 1,4,5-triphosphate receptor, type 1 | YES | exonic |
| 516 | 2897464 | −2 | −5.16 | Inhibitor of DNA binding 4, dominant negative helix-loop-helix protein | NO | exonic |
| 517 | 2980483 | −3 | −5.14 | Opioid receptor, mu 1 | NO | antisense |
| 518 | 3791695 | −3 | −5.14 | B-cell CLL/lymphoma 2 | NO | antisense |
| 519 | 3603305 | −10 | −5.13 | Cellular retinoic acid binding protein 1 | NO | exonic |
| 520 | 2608568 | −4 | −5.11 | Inositol 1,4,5-triphosphate receptor, type 1 | YES | exonic |
| 521 | 2586115 | −3 | −5.11 | Low density lipoprotein-related protein 2 | YES | exonic |
| 522 | 3811408 | −2 | −5.11 | B-cell CLL/lymphoma 2 | NO | intronic |
| 523 | 2466604 | −2 | −5.11 | Thyroid peroxidase | YES | exonic |
| 524 | 2586166 | −3 | −5.09 | Low density lipoprotein-related protein 2 | YES | exonic |
| 525 | 3018611 | −4 | −5.08 | Solute carrier family 26, member 4 | NO | extra-genic |
| 526 | 3693008 | −4 | −5.07 | Metallothionein 1G | YES | exonic |
| 527 | 3862192 | −4 | −5.07 | Fc fragment of IgG binding protein | YES | exonic |
| 528 | 2649046 | −3 | −5.07 | Potassium voltage-gated channel, shaker-related subfamily, beta member 1 | YES | exonic |
| 529 | 2763600 | −4 | −5.05 | Peroxisome proliferator-activated receptor gamma, coactivator 1 alpha | NO | intronic |
| 530 | 3546098 | −3 | −5.05 | Deiodinase, iodothyronine, type II | NO | exonic |
| 531 | 3385513 | −2 | −5.05 | Frizzled homolog 4 (Drosophila) | NO | exonic |
| 532 | 2586141 | −3 | −5.02 | Low density lipoprotein-related protein 2 | YES | exonic |

TABLE 3-continued

Thyroid Nodule Disease Candidate Gene RNA Sequences

| SEQ ID | ID | MFD | Weights | Gene | Probeset Overlaps CDS | Target Sequence Subtype |
|---|---|---|---|---|---|---|
| 533 | 3046243 | −5 | −5 | Engulfment and cell motility 1 | NO | intronic |
| 534 | 3046224 | −2 | −5 | Engulfment and cell motility 1 | YES | exonic |
| 535 | 4023361 | −2 | −5 | Four and a half LIM domains 1 | NO | exonic |
| 536 | 3546096 | −5 | −4.99 | Deiodinase, iodothyronine, type II | NO | antisense |
| 537 | 3046199 | −5 | −4.98 | Engulfment and cell motility 1 | YES | exonic |
| 538 | 2740233 | −4 | −4.97 | Ankyrin 2, neuronal | NO | intronic |
| 539 | 2980484 | −9 | −4.96 | Opioid receptor, mu 1 | NO | antisense |
| 540 | 2980450 | −7 | −4.96 | Opioid receptor, mu 1 | YES | antisense |
| 541 | 2763628 | −3 | −4.96 | Peroxisome proliferator-activated receptor gamma, coactivator 1 alpha | NO | intronic |
| 542 | 2649009 | −4 | −4.95 | Potassium voltage-gated channel, shaker-related subfamily, beta member 1 | NO | intronic |
| 543 | 3791690 | −4 | −4.94 | B-cell CLL/lymphoma 2 | NO | antisense |
| 544 | 2980485 | −7 | −4.93 | Opioid receptor, mu 1 | YES | antisense |
| 545 | 3811446 | −3 | −4.9 | B-cell CLL/lymphoma 2 | NO | extra-genic |
| 546 | 3811358 | −3 | −4.89 | B-cell CLL/lymphoma 2 | NO | exonic |
| 547 | 3573884 | −8 | −4.88 | Deiodinase, iodothyronine, type II | YES | exonic |
| 548 | 2925965 | −5 | −4.88 | Ectonucleotide pyrophosphatase/phosphodiesterase 1 | YES | exonic |
| 549 | 2608614 | −5 | −4.87 | Inositol 1,4,5-triphosphate receptor, type 1 | NO | intronic |
| 550 | 3787876 | −3 | −4.86 | Lipase, endothelial | YES | exonic |
| 551 | 2331561 | −4 | −4.85 | Bone morphogenetic protein 8a | NO | exonic |
| 552 | 2661102 | −2 | −4.85 | Inositol 1,4,5-triphosphate receptor, type 1 | NO | antisense |
| 553 | 2586047 | −3 | −4.84 | Low density lipoprotein-related protein 2 | YES | exonic |
| 554 | 3787860 | −2 | −4.84 | Lipase, endothelial | YES | exonic |
| 555 | 3791668 | −2 | −4.84 | B-cell CLL/lymphoma 2 | NO | antisense |
| 556 | 3126507 | −3 | −4.83 | Chondroitin beta1,4 N-acetylgalactosaminyltransferase | NO | exonic |
| 557 | 2608643 | −3 | −4.82 | Inositol 1,4,5-triphosphate receptor, type 1 | YES | exonic |
| 558 | 3807530 | −2 | −4.82 | Lipase, endothelial | NO | antisense |
| 559 | 2763570 | −4 | −4.81 | Peroxisome proliferator-activated receptor gamma, coactivator 1 alpha | NO | intronic |
| 560 | 2925993 | −4 | −4.81 | Ectonucleotide pyrophosphatase/phosphodiesterase 1 | YES | exonic |
| 561 | 2908205 | −2 | −4.81 | Vascular endothelial growth factor A | YES | exonic |
| 562 | 2586123 | −4 | −4.8 | Low density lipoprotein-related protein 2 | YES | exonic |
| 563 | 3791749 | −4 | −4.79 | B-cell CLL/lymphoma 2 | NO | antisense |
| 564 | 2586195 | −6 | −4.78 | Low density lipoprotein-related protein 2 | NO | intronic |
| 565 | 2763627 | −3 | −4.78 | Peroxisome proliferator-activated receptor gamma, coactivator 1 alpha | NO | intronic |
| 566 | 2608559 | −4 | −4.74 | Inositol 1,4,5-triphosphate receptor, type 1 | YES | exonic |
| 567 | 3126535 | −4 | −4.74 | Chondroitin beta1,4 N-acetylgalactosaminyltransferase | YES | exonic |
| 568 | 3791743 | −4 | −4.74 | B-cell CLL/lymphoma 2 | NO | antisense |
| 569 | 3727623 | −5 | −4.73 | Hepatic leukemia factor | NO | exonic |
| 570 | 2586057 | −5 | −4.73 | Low density lipoprotein-related protein 2 | YES | exonic |
| 571 | 2763598 | −3 | −4.73 | Peroxisome proliferator-activated receptor gamma, coactivator 1 alpha | NO | intronic |
| 572 | 2925966 | −3 | −4.72 | Ectonucleotide pyrophosphatase/phosphodiesterase 1 | YES | exonic |
| 573 | 4016044 | −3 | −4.7 | Transcription elongation factor A (SII)-like 2 | NO | antisense |
| 574 | 2980475 | −8 | −4.69 | Opioid receptor, mu 1 | YES | antisense |
| 575 | 2944441 | −2 | −4.68 | Inhibitor of DNA binding 4, dominant negative helix-loop-helix protein | NO | exonic |
| 576 | 2608634 | −3 | −4.66 | Inositol 1,4,5-triphosphate receptor, type 1 | NO | intronic |
| 577 | 2727646 | −6 | −4.64 | V-kit Hardy-Zuckerman 4 feline sarcoma viral oncogene homolog | NO | exonic |
| 578 | 2925978 | −3 | −4.63 | Ectonucleotide pyrophosphatase/phosphodiesterase 1 | YES | exonic |
| 579 | 2608490 | −3 | −4.58 | Inositol 1,4,5-triphosphate receptor, type 1 | NO | intronic |
| 580 | 3992448 | −3 | −4.58 | Four and a half LIM domains 1 | YES | exonic |

TABLE 3-continued

Thyroid Nodule Disease Candidate Gene RNA Sequences

| SEQ ID | ID | MFD | Weights | Gene | Probeset Overlaps CDS | Target Sequence Subtype |
|---|---|---|---|---|---|---|
| 581 | 3985030 | −4 | −4.57 | Transcription elongation factor A (SII)-like 2 | YES | exonic |
| 582 | 3753968 | −2 | −4.57 | Chemokine (C-C motif) ligand 14 | NO | exonic |
| 583 | 3573878 | −4 | −4.56 | Deiodinase, iodothyronine, type II | YES | exonic |
| 584 | 2586112 | −2 | −4.56 | Low density lipoprotein-related protein 2 | YES | exonic |
| 585 | 3354794 | −2 | −4.56 | STT3, subunit of the oligosaccharyltransferase complex, homolog A (S. cerevisiae) | NO | extra-genic |
| 586 | 2925981 | −5 | −4.55 | Ectonucleotide pyrophosphatase/phosphodiesterase 1 | YES | exonic |
| 587 | 3787884 | −3 | −4.55 | Lipase, endothelial | NO | exonic |
| 588 | 3791660 | −2 | −4.55 | B-cell CLL/lymphoma 2 | NO | antisense |
| 589 | 3569378 | −2 | −4.54 | Arginase, type II | YES | exonic |
| 590 | 2932285 | −7 | −4.53 | Opioid receptor, mu 1 | NO | intronic |
| 591 | 2586165 | −2 | −4.53 | Low density lipoprotein-related protein 2 | NO | intronic |
| 592 | 3787881 | −3 | −4.52 | Lipase, endothelial | NO | intronic |
| 593 | 2925998 | −5 | −4.5 | Ectonucleotide pyrophosphatase/phosphodiesterase 1 | NO | exonic |
| 594 | 2925975 | −4 | −4.5 | Ectonucleotide pyrophosphatase/phosphodiesterase 1 | YES | exonic |
| 595 | 3126541 | −3 | −4.5 | Chondroitin beta1,4 N-acetylgalactosaminyltransferase | NO | intronic |
| 596 | 2782529 | −2 | −4.5 | Ankyrin 2, neuronal | NO | exonic |
| 597 | 2763596 | −3 | −4.47 | Peroxisome proliferator-activated receptor gamma, coactivator 1 alpha | NO | intronic |
| 598 | 2649079 | −5 | −4.45 | Potassium voltage-gated channel, shaker-related subfamily, beta member 1 | NO | exonic |
| 599 | 2925973 | −2 | −4.44 | Ectonucleotide pyrophosphatase/phosphodiesterase 1 | YES | exonic |
| 600 | 2925999 | −4 | −4.43 | Ectonucleotide pyrophosphatase/phosphodiesterase 1 | NO | exonic |
| 601 | 3126508 | −3 | −4.43 | Chondroitin beta1,4 N-acetylgalactosaminyltransferase | NO | exonic |
| 602 | 2586072 | −4 | −4.42 | Low density lipoprotein-related protein 2 | YES | exonic |
| 603 | 2661165 | −3 | −4.41 | Inositol 1,4,5-triphosphate receptor, type 1 | NO | exonic |
| 604 | 3018623 | −3 | −4.4 | Solute carrier family 26, member 4 | YES | exonic |
| 605 | 2944443 | −2 | −4.4 | Inhibitor of DNA binding 4, dominant negative helix-loop-helix protein | NO | extra-genic |
| 606 | 3573881 | −6 | −4.38 | Deiodinase, iodothyronine, type II | YES | exonic |
| 607 | 3573895 | −4 | −4.38 | Deiodinase, iodothyronine, type II | YES | exonic |
| 608 | 3811395 | −3 | −4.38 | B-cell CLL/lymphoma 2 | NO | intronic |
| 609 | 3787879 | −4 | −4.36 | Lipase, endothelial | NO | intronic |
| 610 | 2608590 | −4 | −4.35 | Inositol 1,4,5-triphosphate receptor, type 1 | NO | intronic |
| 611 | 2763629 | −5 | −4.34 | Peroxisome proliferator-activated receptor gamma, coactivator 1 alpha | NO | intronic |
| 612 | 3992441 | −4 | −4.34 | Four and a half LIM domains 1 | NO | intronic |
| 613 | 3727625 | −4 | −4.33 | Hepatic leukemia factor | NO | exonic |
| 614 | 2615655 | −2 | −4.33 | STT3, subunit of the oligosaccharyltransferase complex, homolog B (S. cerevisiae) | NO | extra-genic |
| 615 | 3603302 | −3 | −4.27 | Cellular retinoic acid binding protein 1 | YES | exonic |
| 616 | 2586098 | −3 | −4.24 | Low density lipoprotein-related protein 2 | NO | intronic |
| 617 | 2925996 | −5 | −4.22 | Ectonucleotide pyrophosphatase/phosphodiesterase 1 | YES | exonic |
| 618 | 3791650 | −3 | −4.21 | B-cell CLL/lymphoma 2 | NO | exonic |
| 619 | 2925967 | −4 | −4.19 | Ectonucleotide pyrophosphatase/phosphodiesterase 1 | YES | exonic |
| 620 | 2586147 | −3 | −4.17 | Low density lipoprotein-related protein 2 | YES | exonic |
| 621 | 3992436 | −4 | −4.14 | Four and a half LIM domains 1 | NO | intronic |
| 622 | 2740285 | −3 | −4.13 | Ankyrin 2, neuronal | NO | exonic |
| 623 | 2740135 | −2 | −4.13 | Ankyrin 2, neuronal | NO | intronic |
| 624 | 2586097 | −3 | −4.08 | Low density lipoprotein-related protein 2 | YES | exonic |
| 625 | 3985031 | −3 | −4.07 | Transcription elongation factor A (SII)-like 2 | NO | exonic |
| 626 | 2954890 | −2 | −4.07 | Vascular endothelial growth factor A | NO | antisense |

TABLE 3-continued

Thyroid Nodule Disease Candidate Gene RNA Sequences

| SEQ ID | ID | MFD | Weights | Gene | Probeset Overlaps CDS | Target Sequence Subtype |
|---|---|---|---|---|---|---|
| 627 | 2586154 | −4 | −4.06 | Low density lipoprotein-related protein 2 | YES | exonic |
| 628 | 4013550 | −2 | −4.06 | Integral membrane protein 2A | NO | exonic |
| 629 | 3811377 | −3 | −4.03 | B-cell CLL/lymphoma 2 | NO | intronic |
| 630 | 3763258 | −4 | −3.99 | Hepatic leukemia factor | NO | exonic |
| 631 | 3753974 | −2 | −3.98 | Chemokine (C-C motif) ligand 14 | YES | exonic |
| 632 | 3088318 | −2 | −3.97 | Chondroitin beta1,4 N-acetylgalactosaminyltransferase | NO | antisense |
| 633 | 2925979 | −4 | −3.94 | Ectonucleotide pyrophosphatase/phosphodiesterase 1 | YES | exonic |
| 634 | 3811413 | −3 | −3.94 | B-cell CLL/lymphoma 2 | NO | intronic |
| 635 | 2980497 | −3 | −3.91 | Phosphoinositide-binding protein PIP3-E | NO | intronic |
| 636 | 3811431 | −4 | −3.9 | B-cell CLL/lymphoma 2 | NO | intronic |
| 637 | 2608556 | −3 | −3.9 | Inositol 1,4,5-triphosphate receptor, type 1 | NO | intronic |
| 638 | 3108611 | −3 | −3.9 | Matrilin 2 | YES | exonic |
| 639 | 3160684 | −3 | −3.9 | Chromosome 9 open reading frame 68 | YES | exonic |
| 640 | 4023355 | −2 | −3.87 | Four and a half LIM domains 1 | NO | antisense |
| 641 | 3862191 | −3 | −3.83 | Fc fragment of IgG binding protein | NO | exonic |
| 642 | 2997556 | −3 | −3.83 | Engulfment and cell motility 1 | NO | antisense |
| 643 | 3787882 | −3 | −3.79 | Lipase, endothelial | NO | exonic |
| 644 | 2483130 | −2 | −3.79 | EGF-containing fibulin-like extracellular matrix protein 1 | NO | antisense |
| 645 | 3811426 | −3 | −3.78 | B-cell CLL/lymphoma 2 | NO | intronic |
| 646 | 3787871 | −2 | −3.78 | Lipase, endothelial | YES | exonic |
| 647 | 2660997 | −3 | −3.74 | Inositol 1,4,5-triphosphate receptor, type 1 | NO | antisense |
| 648 | 3787872 | −3 | −3.72 | Lipase, endothelial | YES | exonic |
| 649 | 2763609 | −3 | −3.7 | Peroxisome proliferator-activated receptor gamma, coactivator 1 alpha | YES | exonic |
| 650 | 2980500 | −3 | −3.68 | Phosphoinositide-binding protein PIP3-E | NO | intronic |
| 651 | 2586129 | −4 | −3.66 | Low density lipoprotein-related protein 2 | YES | exonic |
| 652 | 4023341 | −3 | −3.65 | Four and a half LIM domains 1 | NO | antisense |
| 653 | 2897466 | −2 | −3.64 | Inhibitor of DNA binding 4, dominant negative helix-loop-helix protein | NO | extra-genic |
| 654 | 3791755 | −3 | −3.63 | B-cell CLL/lymphoma 2 | NO | antisense |
| 655 | 3811429 | −3 | −3.62 | B-cell CLL/lymphoma 2 | NO | intronic |
| 656 | 2649081 | −2 | −3.59 | Potassium voltage-gated channel, shaker-related subfamily, beta member 1 | NO | extra-genic |
| 657 | 2830194 | −8.6 | −7.06 | Sparc/osteonectin, cwcv and kazal-like domains proteoglycan (testican) 1 | NO | antisense |
| 658 | 2830301 | −1.2 | −3.02 | Sparc/osteonectin, cwcv and kazal-like domains proteoglycan (testican) 1 | NO | antisense |
| 659 | 2830378 | 1.8 | 4.94 | Sparc/osteonectin, cwcv and kazal-like domains proteoglycan (testican) 1 | NO | antisense |

TABLE 4

Thyroid Nodule Disease 7-RNA Expression Signature

| SEQ ID | MFD | Weights | Gene | Probeset Overlaps CDS | Target Sequence Subtype | Probeset Sequence |
|---|---|---|---|---|---|---|
| 1 | 14 | 8.75 | High mobility group AT-hook 2 | NO | intronic | attctttggagttgcgtcattaggagctttacagt aagatatcttactagccaatattagcctgccac agg |
| 2 | 11 | 8.59 | Cadherin 3, type 1, P-cadherin (placental) | NO | exonic | gggcaacctaggcacactcagtataaaaac gcagagatccatccgaatgggaggcattggg gtctggaaaccagaaatgcaggacggccagt |
| 3 | 3 | 8.12 | Serpin peptidase inhibitor, clade A | YES | exonic | ctgcctctcgctcctcaaccccctccc |

TABLE 4 -continued

Thyroid Nodule Disease 7-RNA Expression Signature

| SEQ ID | MFD | Weights | Gene | Probeset Overlaps CDS | Target Sequence Subtype | Probeset Sequence |
|---|---|---|---|---|---|---|
| | | | (alpha-1 antiproteinase, antitrypsin), member 1 | | | |
| 4 | 4 | 5.94 | Insulin-like growth factor binding protein 6 | NO | exonic | tggagctgtcatcactcaacaaaaaccgag gccctcaatccaccttcaggccccgccccatg ggcccctaccgctggttggaaagagtgttgg tgttggctggggtgtcaataaagctgt |
| 5 | -14 | -11.03 | Thyroid peroxidase | NO | anti-sense | agcctgtgagtatcccggccttccatcccagc actctcctgcaaaaatgcagaacaaacatta ataacgtctgaattctgactgctccagtaacag cacacacttgatacaagacagaagggcctg gacaggagctcttttcacaaaggaccgctggc gagatgagccatccttcttgcttgtcatgctgga gggaagtttctggcttccggacaaatgcttgttt gcaggaggccacagaggatccacgtggca aaggttcctactcacagagtgggatctgcaat ccgcaggcagggtccttcaggaagaagccgt gctgagcacacaggtccctgcgaccacagat gaacagaacgcctggccttgcccctggtgtca gtcagactaattaggggcccaggggacttgct ggcactgcccttgctgtggctggaaaagctatt taaattcacaaagagcctcacttccaggccag gtccttttggttccatgcgtgggagccaggtgc aaagacgaatgtgctctcagcagaacgaccc tgggctctgcttatctccgaggacaggatctaa tctcacactgaatttcagaagggagaccgatc atgttggcaatgccccctcctgtatgcaagta agtgact |
| 6 | -5 | -9.09 | V-kit Hardy-Zuckerman 4 feline sarcoma viral oncogene homolog | NO | exonic | aagcccatgagtccttgaaaatattttttatatat acagtaactttatgtgtaaatacataagcggcg taagtttaaaggatgttggtgttccacgtgttttat tcctgtatgttgtccaattgttgaca |
| 7 | -31 | -8.23 | Metallophos-phoesterase domain containing 2 | NO | intronic | tttttgcctgcacattctgagagagccatttggca aacaacaataataaatttacatttggatggtgt atttcactcagagaactttcatatgtattatctcat ttggggctcacaacaattctttaaccagggtat gtattactaataataattaacaatagccagcatt tacagtgtttatatgtcaactgctgttcattattgc ctccttttgacagagaccaaca |

TABLE 5

Thyroid Nodule Disease 36-RNA Expression Signature

| SEQ ID | MFD | Weights | Gene | Probeset Overlaps CDS | Target Sequence Subtype | Probeset Sequence |
|---|---|---|---|---|---|---|
| 1 | 14 | 8.75 | High mobility group AT-hook 2 | NO | intronic | attctttggagttgcgtcattaggagcttta cagtaagatatcttactagccaatattag cctgccacagg |
| 2 | 11 | 8.59 | Cadherin 3, type 1, P-cadherin (placental) | NO | exonic | gggcaacctaggcacactcagtataaa aacgcagagatccatccgaatgggag gcattgggtctggaaaccgaaatgc aggacggccagt |
| 3 | 3 | 8.12 | Serpin peptidase inhibitor, clade A (alpha-1 antiproteinase, | YES | exonic | ctgcctctcgctcctcaacccctccc |

TABLE 5 -continued

Thyroid Nodule Disease 36-RNA Expression Signature

| SEQ ID | MFD | Weights | Gene | Probeset Overlaps CDS | Target Sequence Subtype | Probeset Sequence |
|---|---|---|---|---|---|---|
| | | | antitrypsin), member 1 | | | |
| 4 | 4 | 5.94 | Insulin-like growth factor binding protein 6 | NO | exonic | tggagctgtcatcactcaacaaaaaacc gaggccctcaatccaccttcaggccccg ccccatgggcccctcaccgctggttgga aagagtgttggtgttggctggggtgtcaa taaagctgt |
| 5 | -14 | -11.03 | Thyroid peroxidase | NO | antisense | agcctgtgagtatcccggccttccatccc agcactctcctgcaaaaatgcagaaca aacattaataacgtctgaattctgactgct ccagtaacagcacacacttgatacaag acagaagggcctggacaggagctctttt cacaaaggaccgctggcgagatgagc catccttcttgcttgtcatgctggagggaa gtttctggcttccggacaaatgcttgtttgc aggaggccacagaggatccacgtggc aaaggttcctactcacagagtgggatct gcaatccgcaggcagggtccttcagga agaagccgtgctgagcacacaggtccc tgcgaccacagatgaacagaacgcctg gccttgcccctggtgtcagtcagactaatt aggggcccaggggacttgctggcactg cccttgctgtggctggaaaagctatttaa attcacaaagagcctcacttccaggcca ggtccttttggttccatgcgtgggagcca ggtgcaaagacgaatgtgctctcagca gaacgaccctgggctctgcttatctccga ggacaggatctaatctcacactgaattttc agaagggagaccgatcatgttggcaat gccccccctcctgtatgcaagtaagtgact |
| 6 | -5 | -9.09 | V-kit Hardy-Zukerman 4 feline sarcoma viral oncogene homolog | NO | exonic | aagcccatgagtccttgaaaatatttttat atatacagtaactttatgtgtaaatacata agcggcgtaagttttaaaggatgttggtgt tccacgtgttttattcctgtatgttgtccaatt gttgaca |
| 7 | -31 | -8.23 | Metallophos-phoesterase domain containing 2 | NO | intronic | ttttgcctgcacattctgagagagccattt ggcaaacaacaataataaatttacatttg gatggtgtatttcactcagagaactttcat atgtattatctcatttggggctcacaacaa ttctttaaccagggtatgtattactaataat aattaacaatagccagcatttacagtgttt atatgtcaactgctgttcattattgcctccttt tgacagagaccaaca |
| 8 | 8 | 10.26 | PDZ and LIM domain 4 | NO | exonic | tgctcccacgcctgcttcttaaggtccctg ctcggccggtgtaaatatgtttcaccctgt ccctctaataaagctcctctgc |
| 9 | 24 | 8.9 | Tumor-associated calcium signal transducer 2 | NO | exonic | gacaacccgggatcgtttgcaagtaact gaatccattgcgacattgtgaaggcttaa atgagtttagatgggaaatagcgttgttat cgccttgggtttaaattatttgatgagttcc acttgtatcatggcctacccgaggagaa gaggagtttgttaactgggcctatgtagta gcctcatttaccatcgtttgtattactgacc acatatgcttgtcactgggaaagaagcc tgtttcagctgcctgaacgcagtttgatg tctttgaggacagacattgcccggaaac tcagtctattta |
| 10 | 6 | 8.69 | Fibronectin 1 | NO | antisense | acgcccaggactatttgaactgatgaaa tatccaaatgtccagtcctatagcctactt acacctaagtgaacactacagcgaagt gttcagtgaacagaccttgagaaggtct gtaattagatgataaggaagggtcacctt gccccatggcctctcgaagccctccattc cacctgtgagtgtgactcagctggatttc gagtgggatgaagttgctgcaacagctg gatatttctcgcatccacctgagagtatgt ctctggagggcacatgataatccttgctg |

TABLE 5 -continued

Thyroid Nodule Disease 36-RNA Expression Signature

| SEQ ID | MFD | Weights | Gene | Probeset Overlaps CDS | Target Sequence Subtype | Probeset Sequence |
|---|---|---|---|---|---|---|
| | | | | | | tggtgctgtggattgccatttatgcctcac aacaaccctggaaggtagtttgctcctttt aaaagcaatttcttgtcatacaacgtact gcatatctttaaagtgatgggtttttacatat gtgtgacttgggagaccatcaccgcattc |
| 11 | 13 | 8.66 | Fibronectin 1 | NO | antisense | cttcaaggacaaatcgtaaaggtagtgtt ttagacttctgcacacaaatggaaattca ggtagaatatctttcttttctagaatcatcta tcttactcaaaaagg |
| 12 | 17 | 8.61 | Fibronectin 1 | NO | intronic | gtctgaatgccacgacatgtcttttgcaa ttcacatagggaaagtgaacttgttggtt agtttatgtcttgagctgagccctttacga acatctttttttccttctcagtgccaagcgag gaatttacagagaaagaagttgtgaaa ccaccatagttagttgctgtgctttgaattt cttttgctcaaatggcctcagcgaaatctt atttgc |
| 283 | -8 | -10.87 | Thyroid peroxidase | YES | exonic | cgacaagtgtggcttcccagagagcgt ggagaatggggactttgtgcactgtgag gagtctgggaggcgcgtgctggtgtattc ctgc |
| 284 | -6 | -9.87 | Thyroid peroxidase | NO | antisense | ggaggttgcacagattgcgggggatttg gggaga |
| 285 | -3 | -9.81 | Hepatic leukemia factor | YES | exonic | atggagaaaatgtcccgaccgctcccc ctgaatcccaccttttatcccgcctcccctac ggcgtgctcaggtccctg |
| 286 | -11 | -9.45 | Metallophos-phoesterase domain containing 2 | NO | extra-genic | atggtggaggatggtagtttcgtcctggg gaaggagggatttattcatatgcaacatc agttatgcctttcaga |
| 287 | -19 | -9.37 | Thyroid peroxidase | NO | antisense | tccaactttcacgagaagattaagaaaa tccacaaacaatacctgttgttgcaagct cctgtgatgggcctgtatttgttcgccagg ca |
| 288 | -26 | -9.14 | Thyroid peroxidase | YES | exonic | cgctattctgacctcctgatggcatgggg acaatacatcgaccacgacatcgcgttc acaccacagagcaccagcaaagctgc cttcggggggaggggctgactgccagat gacttgtgagaacca |
| 289 | -9 | -9.07 | Zinc finger, martin type 4 | NO | exonic | cttattttacacatccgaagaaacaccat caca |
| 290 | -19 | -8.91 | Trefoil factor 3 (intestinal) | NO | exonic | agttcatatctggagcctgatgtcttaacg aataaaggtcccatgctc |
| 291 | -3 | -8.86 | Peroxisome proliferator-activated receptor gamma, coactivator 1 alpha | YES | exonic | aagacgtccctgctcggagcttctcaaat atctgaccacaaacgatgaccctcctca caccaaacccacagagaacagaaac agcagcagagacaaatgcacctccaa aaagaagtcccacacacagtcgcagtc acaacacttacaag |
| 292 | -30 | -8.84 | Thyroid peroxidase | NO | extra-genic | gtccctggaaggcaattaaggcgcccat ttcagaagagttacagccgtgaaaatta ctcagc |
| 293 | -6 | -8.84 | Metallothionein 1F | YES | exonic | gctgtgtttgcaaaggggcgtcagagaag |
| 294 | -55 | -8.64 | Thyroid peroxidase | YES | exonic | tgctgagcatcattgcaaacatgtctgga tgtctcccttacatgctgcccccaaaatg cccaaacacttgcctggcgaacaaata caggcccatcacaggagcttgcaacaaca |

TABLE 5-continued

Thyroid Nodule Disease 36-RNA Expression Signature

| SEQ ID | MFD | Weights | Gene | Probeset Overlaps CDS | Target Sequence Subtype | Probeset Sequence |
|---|---|---|---|---|---|---|
| 295 | -19 | -8.52 | Thyroid peroxidase | NO | extra-genic | ctcctgggaagagcactcctggcttcctg cagggccggtgggaggaggaaagtga ttctgagggagaggctggagccttaagg accaacaaggcaaagtgacttgtctcat cctccagagattcaccaacacatgagc ctcagaccccaggcttctgcctccagca gccgccctgccgcacactgctcttactcc tccttatacectcactcacggggaacac agcccagtgatcccggaggaaactcac tccctccctgactcaacaaggcagtctc gggggcaccgttagccacgcgaccctg taaagctgccgtcctcatttcacatgtgaa gcagctgaattccagagtgctgggtccc agcccaggcagccctcagcctcacgca aggcaatagttaggagtccttcggcattg aaagcaaactcagacacatctgacctg gagttctacctgcactaagagaagaga gtggtaactaattcatggataaaacaga ccatcgaggcagcactgaatgatctcac ccacgaatgacaacagtggcacagga gggctatgaacattttgcttcaggatgtttt atttcgctctactgttatgtagagaaaagca tggtttgcttttttataactttttgtgacccaaa aataccagactgtt |
| 296 | -14 | -8.49 | Metallophos-phoesterase domain containing 2 | NO | exonic | gttagtgttcgccaaaggacagccaag cttctttttaaaaagtgataaaagtcttatttt aatatgctttaagctgaaagaaaaaaa aataagaaacaggcagtgttttaaaac caacacagatttgcacaactgtttaaga gtattgtttgaaatattttaattttcaatgtttt gttgttgttgttttcttggtaatgcttcttttttgc agatgtggtcccaatttatagcaatcttct caacagaagtaggcatggaaaagactt cttttcatactctcactataaagaaagctg cattgagaagaaaatggctgtcatttaaa ggatggtttaactagtgagattcctattgtg gttatacaaggtctcattgtttgtttgtttctttt aaattatttcagctttaaaaatacagaaat ggaatctgtcaagagcaggtatttcatac ggttaaaaaaatgaacatgcagactcct tttcaatatgggtttatatatataagtattttt gtgtattatgactacgttaggagtttattatt gtcaaggacagtacaactgcaaaggg atgctgtatagcaacacatcagaagtcg gaaggaactgacacattctctcagagct caaggtcttaaagagcttgagttaaatct aggtacagttacaggcatgtatagactta aatggatgcaatggaagctaactaaaat aaggcttagttgtcctttctatttaaatacc ccaagttgtcttcttacttcctctcccctctc ccattttgcactgtgtgtcgatgcaatcttcg |
| 297 | -24 | -8.39 | Metallophos-phoesterase domain containing 2 | NO | intronic | gttctgcattgctgataccgctagtggtttt aaaaatagaaatcaaaataagaaccct gatattaaggattcacag |
| 298 | -5 | -8.37 | Thyroid peroxidase | NO | intronic | cccaggccacacaagactcacggctct ccctggtctc |
| 299 | -9 | -8.35 | Metallophos-phoesterase domain containing 2 | NO | intronic | gagctacccagtctacgctattttgttaat agcatctcaaacagcccaaggcaggta ggcagggaatataatgggaagatgaat tttatagagggaacaagaggagaaatg ggcgtatttgtgaaggagagagggaaa aagtaggagggaatatatagcagatgt gttttgtgagatcataactcttccttgtcagtt acgatgtcctgaccttgggcttgactttag caccgggagcaggtcagcatccctaga cttcagtcaacagggagatg |

TABLE 5-continued

Thyroid Nodule Disease 36-RNA Expression Signature

| SEQ ID | MFD | Weights | Gene | Probeset Overlaps CDS | Target Sequence Subtype | Probeset Sequence |
|---|---|---|---|---|---|---|
| 300 | -8 | -8.35 | Solute carrier family 26, member 4 | YES | exonic | |
| 304 | -14 | -8.22 | Metallothionein 1G | NO | exonic | ccctgctcccaagtacaaatagagtgac ccgtaaaatccaggat |
| 305 | -6 | -8.21 | Solute carrier family 26, member 4 | YES | exonic | acctttccagtggtgagtttaatggtggg atctgttgttctgagcatggcccccgacg aacactttctcgtatccagcagcaatgga actgtattaaatactactatgatagacact gcagctagagatacagctagagtcctg attgccagtgccctgactctgctggttg |
| 306 | -8 | -8.16 | Solute carrier family 26, member 4 | YES | exonic | tggtggcttgcagattggattcatagtgag gtacttggcagatcctttggttggtggcttc acaacagctgctgccttccaagtgctggt ctcacagctaaagattgtc |

TABLE 6

7-RNA and 36-RNA POP scores for each of the samples
evaluated in the three subsets of patient specimens

| Specimen Number | Study | Cytology Diagnosis | Pathology Diagnosis | Final Review Histology | 7-RNA POP Score | 36-RNA POP Score |
|---|---|---|---|---|---|---|
| 1 | Training Subset | Benign | Benign | Goiter | 21.9 | 0.0 |
| 2 | Training Subset | Benign | Benign | Goiter | 15.9 | 4.1 |
| 3 | Training Subset | Benign | Benign | Goiter | 28.4 | 5.8 |
| 4 | Training Subset | Benign | Benign | Goiter | 22.4 | 7.6 |
| 5 | Training Subset | Benign | Benign | Goiter | 15.9 | 7.8 |
| 6 | Training Subset | Benign | Benign | Goiter | 25.7 | 7.8 |
| 7 | Training Subset | Benign | Benign | Goiter | 12.4 | 8.1 |
| 8 | Training Subset | Benign | Benign | Goiter | 19.9 | 10.8 |
| 9 | Training Subset | Benign | Benign | Goiter | 34.2 | 11.6 |
| 10 | Training Subset | Benign | Benign | Goiter | 27.5 | 11.9 |
| 11 | Training Subset | Benign | Benign | Goiter | 27.3 | 13.1 |
| 12 | Training Subset | Benign | Benign | Goiter | 31.7 | 15.1 |
| 13 | Training Subset | Benign | Benign | Goiter | 30.4 | 18.9 |
| 14 | Training Subset | Benign | Benign | Goiter | 28.6 | 21.5 |
| 15 | Training Subset | Benign | Benign | Hashimoto's | 28.3 | 26.7 |
| 16 | Training Subset | Suspicious for Cancer | Benign | Follicular Adenoma | 34.3 | 16.9 |
| 17 | Training Subset | Suspicious for Cancer | Benign | Follicular Adenoma | 37.6 | 21.8 |
| 18 | Training Subset | Suspicious for Cancer | Benign | Follicular Adenoma | 31.5 | 21.8 |
| 19 | Training Subset | Suspicious for Cancer | Benign | Follicular Adenoma | 52.9 | 40.4 |
| 20 | Training Subset | Suspicious for Cancer | Benign | Goiter | 17.0 | 13.1 |
| 21 | Training Subset | Suspicious for Cancer | Benign | Hurthle Cell Adenoma | 22.8 | 3.5 |

TABLE 6-continued

7-RNA and 36-RNA POP scores for each of the samples
evaluated in the three subsets of patient specimens

| Specimen Number | Study | Cytology Diagnosis | Pathology Diagnosis | Final Review Histology | 7-RNA POP Score | 36-RNA POP Score |
|---|---|---|---|---|---|---|
| 22 | Training Subset | Suspicious for Cancer | Benign | Hurthle Cell Adenoma | 28.2 | 11.3 |
| 23 | Training Subset | Suspicious for Cancer | Benign | Hurthle Cell Adenoma | 30.8 | 16.6 |
| 24 | Training Subset | Suspicious for Cancer | Benign | Hurthle Cell Adenoma | 31.6 | 19.8 |
| 25 | Training Subset | Suspicious for Cancer | Benign | Thyroiditis | 25.0 | 11.3 |
| 26 | Training Subset | Cancer | Malignant | Papillary Carcinoma | 73.9 | 63.1 |
| 27 | Training Subset | Cancer | Malignant | Papillary Carcinoma | 64.5 | 63.1 |
| 28 | Training Subset | Cancer | Malignant | Papillary Carcinoma | 72.0 | 71.8 |
| 29 | Training Subset | Cancer | Malignant | Papillary Carcinoma | 82.5 | 77.6 |
| 30 | Training Subset | Cancer | Malignant | Papillary Carcinoma | 78.7 | 79.4 |
| 31 | Training Subset | Cancer | Malignant | Papillary Carcinoma | 84.7 | 84.6 |
| 32 | Training Subset | Cancer | Malignant | Papillary Carcinoma | 86.6 | 90.1 |
| 33 | Training Subset | Cancer | Malignant | Papillary Carcinoma | 100.0 | 91.3 |
| 34 | Training Subset | Cancer | Malignant | Papillary Carcinoma | 83.7 | 94.8 |
| 35 | Training Subset | Cancer | Malignant | Papillary Carcinoma | 85.6 | 94.8 |
| 36 | Training Subset | Cancer | Malignant | Papillary Carcinoma | 91.7 | 95.9 |
| 37 | Training Subset | Cancer | Malignant | Papillary Carcinoma | 91.7 | 96.5 |
| 38 | Training Subset | Cancer | Malignant | Papillary Carcinoma | 86.0 | 100.0 |
| 39 | Training Subset | Suspicious for Cancer | Malignant | Follicular Carcinoma | 52.7 | 34.9 |
| 40 | Training Subset | Suspicious for Cancer | Malignant | Follicular Carcinoma | 58.0 | 38.1 |
| 41 | Training Subset | Suspicious for Cancer | Malignant | Follicular Carcinoma | 68.4 | 69.2 |
| 42 | Training Subset | Suspicious for Cancer | Malignant | Papillary Carcinoma | 32.2 | 20.9 |
| 43 | Training Subset | Suspicious for Cancer | Malignant | Papillary Carcinoma | 77.7 | 69.5 |
| 44 | Training Subset | Suspicious for Cancer | Malignant | Papillary Carcinoma | 88.3 | 77.0 |
| 45 | Training Subset | Suspicious for Cancer | Malignant | Papillary Carcinoma | 73.4 | 79.1 |
| 46 | Training Subset | Suspicious for Cancer | Malignant | Papillary Carcinoma | 87.2 | 89.2 |
| 47 | Training Subset | Suspicious for Cancer | Malignant | Papillary Carcinoma | 87.5 | 93.0 |
| 48 | Training Subset | Suspicious for Cancer | Malignant | Papillary Carcinoma | 85.9 | 96.5 |
| 49 | Follicular Subset | Suspicious for Cancer | Benign | Follicular Adenoma | 26.5 | 12.5 |
| 50 | Follicular Subset | Suspicious for Cancer | Benign | Follicular Adenoma | 21.7 | 13.1 |
| 51 | Follicular Subset | Suspicious for Cancer | Benign | Follicular Adenoma | 19.0 | 14.8 |
| 52 | Follicular Subset | Suspicious for Cancer | Benign | Follicular Adenoma | 32.0 | 17.7 |
| 53 | Follicular Subset | Suspicious for Cancer | Benign | Follicular Adenoma | 34.3 | 22.1 |
| 54 | Follicular Subset | Suspicious for Cancer | Malignant | Follicular Carcinoma | 0.0 | 1.5 |
| 55 | Follicular Subset | Suspicious for Cancer | Malignant | Follicular Carcinoma | 53.1 | 41.0 |
| 56 | Follicular Subset | Suspicious for Cancer | Malignant | Follicular Carcinoma | 75.5 | 65.1 |
| 57 | Follicular Subset | Suspicious for Cancer | Malignant | Papillary Carcinoma | 43.3 | 32.8 |
| 58 | Follicular Subset | Suspicious for Cancer | Malignant | Papillary Carcinoma | 39.9 | 39.5 |

TABLE 6-continued

7-RNA and 36-RNA POP scores for each of the samples
evaluated in the three subsets of patient specimens

| Specimen Number | Study | Cytology Diagnosis | Pathology Diagnosis | Final Review Histology | 7-RNA POP Score | 36-RNA POP Score |
|---|---|---|---|---|---|---|
| 59 | Preoperative Cell Block Subset | Benign | Benign | Goiter | 30.7 | 19.2 |
| 60 | Preoperative Cell Block Subset | Benign | Benign | Goiter | 22.0 | 20.1 |
| 61 | Preoperative Cell Block Subset | Suspicious for Cancer | Benign | Hurthle Cell Adenoma | 26.8 | 13.7 |
| 62 | Preoperative Cell Block Subset | Cancer | Malignant | Papillary Carcinoma | 77.9 | 66.0 |
| 63 | Preoperative Cell Block Subset | Cancer | Malignant | Papillary Carcinoma | 69.4 | 75.0 |
| 64 | Preoperative Cell Block Subset | Cancer | Malignant | Papillary Carcinoma | 91.5 | 89.5 |
| 65 | Preoperative Cell Block Subset | Cancer | Malignant | Papillary Carcinoma | 71.5 | 90.4 |
| 66 | Preoperative Cell Block Subset | Cancer | Malignant | Papillary Carcinoma | 92.3 | 92.4 |

TABLE 7

Thyroid Nodule Disease SPOCK1-RNA Expression Signature

| SEQ ID | ID | MFD | Weights | Probe Location rel. to Gene | Gene | Probeset Overlaps CDS | Target Sequence Subtype | Probeset Sequence |
|---|---|---|---|---|---|---|---|---|
| 261 | 2876911 | 2.0 | 4.24 | In EXON #11 | Sparc/osteonectin, cwcv and kazal-like domains proteoglycan (testican) 1 | YES | exonic | ctgagggtgcacaccgagccgtgacagagg |
| 657 | 2830194 | −8.6 | −7.06 | In INTRON #6 | Sparc/osteonectin, cwcv and kazal-like domains proteoglycan (testican) 1 | NO | anti-sense | atgaactccctcgtggcggccgaaggcctgg |
| 658 | 2830301 | −1.2 | −3.02 | In INTRON #3 | Sparc/osteonectin, cwcv and kazal-like domains proteoglycan (testican) 1 | NO | anti-sense | ttatttcgtgtgtgtctcttggctctgtag |
| 659 | 2830378 | 1.8 | 4.94 | In INTRON #2 | Sparc/osteonectin, cwcv and kazal-like domains proteoglycan (testican) 1 | NO | anti-sense | tgcttgcacccacagtccatagacatccaaccgcccaatgcatatccaacctcagcaactttacaatccccaacgccagcccac |

The embodiments of the invention in which an exclusive property or privilege is claimed are defined as follows:

1. A method, comprising:
   (a) assaying by sequencing, array hybridization or nucleic acid amplification the expression level of one or more transcripts in a fine needle aspirate test sample from a thyroid nodule of a subject, wherein said one or more transcripts includes at least one transcript corresponding to at least one sequence selected from SEQ ID No. 1-12, 261, 283-306, 657, 658, and 659; and
   (b) in a programmed computer, comparing said expression level of each of said one or more transcripts with reference expression levels of transcripts corresponding to sequences as set forth in SEQ ID No. 1-12, 261, 283-306, 657, 658, and 659, to classify said thyroid nodule as malignant or benign.

2. The method of claim 1, wherein an increased relative level of expression of said one or more transcripts, a decreased relative level of expression of said one or more transcripts, or a combination thereof is used to classify the thyroid nodule as malignant.

3. The method of claim 1, wherein an increased relative level of expression of said one or more transcripts, a decreased relative level of expression of said one or more transcripts, or a combination thereof is used to classify the thyroid nodule as benign.

4. The method of claim 1, wherein said assaying comprises determining the expression level by RT-PCR, Northern blotting, ligase chain reaction, or a combination thereof.

5. The method of claim 1, further comprising measuring the expression level of at least one control nucleic acid in the fine needle aspirate test sample.

6. The method of claim 1, wherein the fine needle aspirate test sample is fresh-frozen or fixed.

7. The method of claim 1, wherein the expression level is measured by pattern recognition.

8. The method of claim 1, wherein (b) comprises using said programmed computer to
   (1) classify said thyroid nodule as malignant if there is (i) an increase in an expression level corresponding to at least one transcript corresponding to at least one sequence selected from SEQ ID No. 1-4, 8-12, and 261, or (ii) a decrease in an expression level corresponding to at least one transcript corresponding to at least one sequence selected from SEQ ID No. 5-7, 283-306, 657, 658, and 659, or
   (2) classify said thyroid nodule as benign if there is (i) an increase in said expression level corresponding to at least one transcript corresponding to at least one sequence selected from SEQ ID No. 5-7, 283-306, 657, 658, and 659 or (ii) a decrease in said expression level corresponding to at least one transcript corresponding to at least one sequence selected from SEQ ID No. 1-4, 8-12, and 261.

9. The method of claim 1, wherein said assaying is by nucleic acid amplification using at least two primers that each amplifies a transcript corresponding to a sequence as set forth in any one of SEQ ID No. 1-12, 261, 283-306, 657, 658, and 659.

10. The method of claim 1, further comprising (c) based upon a classification of said thyroid nodule as malignant or benign, (i) designating a treatment modality for said subject or (ii) generating a report that designates said thyroid nodule as malignant or benign.

11. The method of claim 10, wherein said treatment modality is selected from total thyroidectomy, near-total thyroidectomy, partial thyroidectomy, cosmetic debulking, radioactive iodine treatment, watchful waiting, thyroid hormone suppression therapy, total or near-total thyroidectomy followed by radioactive iodine ablation therapy and permanent thyroid hormone replacement therapy, or any combination thereof.

* * * * *